(12) United States Patent
Vidlund et al.

(10) Patent No.: US 11,344,412 B2
(45) Date of Patent: May 31, 2022

(54) DELIVERY AND RETRIEVAL DEVICES AND METHODS FOR SIDE-DELIVERABLE TRANSCATHETER PROSTHETIC VALVES

(71) Applicant: VDyne, Inc., Maple Grove, MN (US)

(72) Inventors: Robert Vidlund, Forest Lake, MN (US); Mark Christianson, Plymouth, MN (US); Neelakantan Saikrishnan, Plymouth, MN (US); Scott Kramer, Minneapolis, MN (US); Lucas Harder, Minneapolis, MN (US); David Holtan, Eden Prairie, MN (US); Craig Ekvall, East Bethel, MN (US); Cameron Vidlund, Forest Lake, MN (US)

(73) Assignee: VDyne, Inc., Maple Grove, MN (US)

( * ) Notice: Subject to any disclaimer, the term of this patent is extended or adjusted under 35 U.S.C. 154(b) by 0 days.

(21) Appl. No.: 17/476,215

(22) Filed: Sep. 15, 2021

(65) Prior Publication Data

US 2022/0000614 A1 Jan. 6, 2022

Related U.S. Application Data

(60) Division of application No. 17/193,946, filed on Mar. 5, 2021, now Pat. No. 11,179,239, which is a
(Continued)

(51) Int. Cl.
*A61F 2/24* (2006.01)
(52) U.S. Cl.
CPC ............ *A61F 2/2427* (2013.01); *A61F 2/243* (2013.01); *A61F 2/2436* (2013.01); *A61F 2/2466* (2013.01); *A61F 2210/0014* (2013.01)

(58) Field of Classification Search
CPC ...... A61F 2/2427; A61F 2/243; A61F 2/2436; A61F 2/2466; A61F 2/9522;
(Continued)

(56) References Cited

U.S. PATENT DOCUMENTS 3,744,060 A 7/1973 Bellhouse et al.
4,079,468 A 3/1978 Liotta et al.
(Continued)

FOREIGN PATENT DOCUMENTS

WO WO-2012035279 A1 3/2012
WO WO-2019195860 A2 10/2019

OTHER PUBLICATIONS

International Search Report and Written Opinion for International Application No. PCT/US2019/028822, dated Oct. 24, 2019, 14 pages.
(Continued)

*Primary Examiner* — Richard G Louis
*Assistant Examiner* — Chima U Igboko
(74) *Attorney, Agent, or Firm* — Cooley LLP

(57) ABSTRACT

A delivery system for side-delivery of a prosthetic valve includes a compression device defining a lumen having a first perimeter at a proximal end that is larger than a second perimeter of the lumen at a distal end. A loading device is coupleable to the compression device and defines a lumen having substantially the second perimeter. A distal end of the loading device includes a first gate that is movable between an open state and a closed state to at least partially occlude the lumen of the loading device. A delivery device defines a lumen having substantially the second perimeter. A proximal end of the delivery device is coupleable to the distal end of the loading device and includes a second gate movable between an open state and a closed state to at least partially occlude the lumen of the delivery device.

12 Claims, 54 Drawing Sheets

Related U.S. Application Data continuation of application No. PCT/US2020/047162, filed on Aug. 20, 2020.

(60) Provisional application No. 63/038,807, filed on Jun. 13, 2020, provisional application No. 63/027,345, filed on May 19, 2020, provisional application No. 62/891,964, filed on Aug. 27, 2019, provisional application No. 62/889,327, filed on Aug. 20, 2019.

(58) Field of Classification Search
CPC ........ A61F 2/9525; A61F 2/2418; A61F 2/95; A61F 2/9517; A61F 2/954; A61F 2/962; A61F 2210/0014; A61F 2002/9505; A61F 2002/9511; A61F 2002/9528; A61F 2002/9534
See application file for complete search history.

(56) References Cited

U.S. PATENT DOCUMENTS

| | | |
|---|---|---|
| 5,509,428 A | 4/1996 | Dunlop |
| 5,554,185 A | 9/1996 | Block et al. |
| 6,006,134 A | 12/1999 | Hill et al. |
| 6,290,719 B1 | 9/2001 | Garberoglio |
| 6,312,464 B1 | 11/2001 | Navia |
| 6,449,507 B1 | 9/2002 | Hill et al. |
| 6,458,153 B1 | 10/2002 | Bailey et al. |
| 6,532,388 B1 | 3/2003 | Hill et al. |
| 6,628,987 B1 | 9/2003 | Hill et al. |
| 6,669,724 B2 | 12/2003 | Park et al. |
| 6,718,208 B2 | 4/2004 | Hill et al. |
| 6,769,434 B2 | 8/2004 | Liddicoat et al. |
| 6,890,330 B2 | 5/2005 | Streeter et al. |
| 6,896,690 B1 | 5/2005 | Lambrecht et al. |
| 6,904,318 B2 | 6/2005 | Hill et al. |
| 6,929,653 B2 | 8/2005 | Strecter |
| 7,175,660 B2 | 2/2007 | Cartledge et al. |
| 7,201,761 B2 | 4/2007 | Woolfson et al. |
| 7,225,019 B2 | 5/2007 | Jahns et al. |
| 7,269,457 B2 | 9/2007 | Shafer et al. |
| 7,361,189 B2 | 4/2008 | Case et al. |
| 7,442,204 B2 | 10/2008 | Schwammenthal et al. |
| 7,621,948 B2 | 11/2009 | Herrmann et al. |
| 7,648,527 B2 | 1/2010 | Agnew |
| 7,749,245 B2 | 7/2010 | Cohn et al. |
| 7,753,949 B2 | 7/2010 | Lamphere et al. |
| 7,811,316 B2 | 10/2010 | Kalmann et al. |
| 8,628,571 B1 | 1/2014 | Hacohen et al. |
| 8,900,295 B2 | 12/2014 | Migliazza et al. |
| 8,986,370 B2 | 3/2015 | Annest |
| 9,232,995 B2 | 1/2016 | Kovalsky et al. |
| 9,308,086 B2 | 4/2016 | Ho |
| 9,414,915 B2 | 8/2016 | Lombardi et al. |
| 9,468,525 B2 | 10/2016 | Kovalsky |
| 9,597,181 B2 | 3/2017 | Christianson et al. |
| 9,662,202 B2 | 5/2017 | Quill et al. |
| 9,788,946 B2 | 10/2017 | Bobo, Jr. et al. |
| 9,895,219 B2 | 2/2018 | Costello |
| 10,321,995 B1 | 6/2019 | Christianson et al. |
| 10,463,489 B2 | 11/2019 | Christianson et al. |
| 10,485,976 B2 | 11/2019 | Streeter et al. |
| 10,595,994 B1 | 3/2020 | Christianson et al. |
| 10,631,983 B1 | 4/2020 | Christianson et al. |
| 10,653,522 B1 | 5/2020 | Vidlund et al. |
| 10,758,346 B1 | 9/2020 | Christianson et al. |
| 10,761,511 B2 | 9/2020 | Chen et al. |
| 10,779,937 B2 | 9/2020 | Vidlund et al. |
| 11,071,627 B2 | 7/2021 | Saikrishnan et al. |
| 11,076,956 B2 | 8/2021 | Christianson et al. |
| 11,109,969 B2 | 9/2021 | Vidlund et al. |
| 11,166,814 B2 | 11/2021 | Vidlund et al. |
| 11,173,027 B2 | 11/2021 | Christianson et al. |
| 11,179,239 B2 | 11/2021 | Vidlund et al. |
| 11,185,409 B2 | 11/2021 | Christianson et al. |
| 11,202,706 B2 | 12/2021 | Christianson et al. |
| 11,234,813 B2 | 2/2022 | Perrin |
| 2003/0040808 A1 | 2/2003 | Stack et al. |
| 2004/0049207 A1 | 3/2004 | Goldfarb et al. |
| 2004/0088047 A1 | 5/2004 | Spence et al. |
| 2004/0093060 A1 | 5/2004 | Seguin et al. |
| 2004/0116996 A1 | 6/2004 | Freitag |
| 2004/0199209 A1 | 10/2004 | Hill et al. |
| 2004/0225352 A1 | 11/2004 | Osborne et al. |
| 2005/0010246 A1 | 1/2005 | Streeter et al. |
| 2005/0075659 A1 | 4/2005 | Realyvasquez et al. |
| 2005/0075725 A1 | 4/2005 | Rowe |
| 2005/0107811 A1 | 5/2005 | Starksen et al. |
| 2005/0137686 A1 | 6/2005 | Salahieh et al. |
| 2005/0228495 A1 | 10/2005 | Macoviak |
| 2006/0190075 A1 | 8/2006 | Jordan et al. |
| 2006/0195180 A1 | 8/2006 | Kheradvar et al. |
| 2006/0229708 A1 | 10/2006 | Powell et al. |
| 2006/0241745 A1 | 10/2006 | Solem |
| 2006/0276887 A1 | 12/2006 | Brady et al. |
| 2007/0016286 A1 | 1/2007 | Herrmann et al. |
| 2007/0100427 A1 | 5/2007 | Perouse |
| 2007/0239271 A1 | 10/2007 | Nguyen |
| 2008/0065204 A1 | 3/2008 | Macoviak et al. |
| 2008/0071287 A1 | 3/2008 | Goto |
| 2008/0140181 A1 | 6/2008 | Reynolds et al. |
| 2008/0154355 A1 | 6/2008 | Benichou et al. |
| 2008/0183279 A1 | 7/2008 | Bailey et al. |
| 2008/0200980 A1 | 8/2008 | Robin et al. |
| 2008/0221672 A1 | 9/2008 | Lamphere et al. |
| 2008/0262592 A1 | 10/2008 | Jordan et al. |
| 2009/0005863 A1 | 1/2009 | Goetz et al. |
| 2009/0054976 A1 | 2/2009 | Tuval et al. |
| 2009/0192601 A1* | 7/2009 | Rafiee ................ A61F 2/2436 623/2.11 |
| 2010/0049294 A1 | 2/2010 | Zukowski et al. |
| 2010/0049313 A1 | 2/2010 | Alon et al. |
| 2010/0087918 A1 | 4/2010 | Vesely et al. |
| 2010/0121434 A1 | 5/2010 | Paul et al. |
| 2010/0280591 A1 | 11/2010 | Shin et al. |
| 2010/0298929 A1 | 11/2010 | Thornton et al. |
| 2011/0004237 A1 | 1/2011 | Schneider et al. |
| 2011/0029072 A1 | 2/2011 | Gabbay |
| 2011/0066233 A1 | 3/2011 | Thornton et al. |
| 2011/0071613 A1 | 3/2011 | Wood et al. |
| 2011/0137397 A1 | 6/2011 | Chau et al. |
| 2011/0160836 A1 | 6/2011 | Behan |
| 2011/0224785 A1 | 9/2011 | Hacohen |
| 2011/0245911 A1 | 10/2011 | Quill et al. |
| 2011/0264191 A1 | 10/2011 | Rothstein |
| 2012/0022605 A1 | 1/2012 | Jahns et al. |
| 2012/0022639 A1 | 1/2012 | Hacohen et al. |
| 2012/0065723 A1 | 3/2012 | Drasler et al. |
| 2012/0083874 A1 | 4/2012 | Dale et al. |
| 2012/0165928 A1 | 6/2012 | Nitzan et al. |
| 2012/0203336 A1 | 8/2012 | Annest |
| 2012/0310327 A1 | 12/2012 | McHugo |
| 2012/0310328 A1 | 12/2012 | Olson et al. |
| 2013/0035759 A1 | 2/2013 | Gross et al. |
| 2013/0166017 A1 | 6/2013 | Cartledge et al. |
| 2013/0190861 A1 | 7/2013 | Chau et al. |
| 2013/0238089 A1 | 9/2013 | Lichtenstein et al. |
| 2013/0282110 A1 | 10/2013 | Schweich, Jr. et al. |
| 2013/0304197 A1 | 11/2013 | Buchbinder et al. |
| 2013/0304200 A1 | 11/2013 | McLean et al. |
| 2013/0338764 A1 | 12/2013 | Thornton et al. |
| 2014/0005778 A1 | 1/2014 | Buchbinder et al. |
| 2014/0012372 A1 | 1/2014 | Chau et al. |
| 2014/0018915 A1 | 1/2014 | Biadillah et al. |
| 2014/0039611 A1 | 2/2014 | Lane et al. |
| 2014/0052237 A1 | 2/2014 | Lane et al. |
| 2014/0121763 A1 | 5/2014 | Duffy et al. |
| 2014/0135908 A1 | 5/2014 | Glozman et al. |
| 2014/0142695 A1 | 5/2014 | Gross et al. |
| 2014/0194983 A1 | 7/2014 | Kovalsky et al. |
| 2014/0207231 A1 | 7/2014 | Hacohen et al. |
| 2014/0222136 A1 | 8/2014 | Geist et al. |
| 2014/0222142 A1 | 8/2014 | Kovalsky et al. |
| 2014/0257466 A1 | 9/2014 | Board et al. |

(56) References Cited

U.S. PATENT DOCUMENTS

| | | |
|---|---|---|
| 2014/0257467 A1 | 9/2014 | Lane et al. |
| 2014/0277342 A1 | 9/2014 | Roeder et al. |
| 2014/0296962 A1 | 10/2014 | Cartledge et al. |
| 2014/0296975 A1 | 10/2014 | Tegels et al. |
| 2014/0350662 A1 | 11/2014 | Vaturi |
| 2014/0358224 A1 | 12/2014 | Tegels et al. |
| 2014/0379076 A1 | 12/2014 | Vidlund et al. |
| 2015/0039081 A1 | 2/2015 | Costello |
| 2015/0045880 A1 | 2/2015 | Hacohen |
| 2015/0142103 A1 | 5/2015 | Vidlund |
| 2015/0157457 A1 | 6/2015 | Hacohen |
| 2015/0173898 A1 | 6/2015 | Drasler et al. |
| 2015/0196390 A1 | 7/2015 | Ma et al. |
| 2015/0216661 A1 | 8/2015 | Hacohen et al. |
| 2015/0257878 A1 | 9/2015 | Lane et al. |
| 2015/0265400 A1 | 9/2015 | Eidenschink et al. |
| 2015/0282922 A1 | 10/2015 | Hingston et al. |
| 2015/0282931 A1 | 10/2015 | Brunnett et al. |
| 2015/0335424 A1 | 11/2015 | McLean et al. |
| 2015/0351906 A1 | 12/2015 | Hammer et al. |
| 2015/0351910 A1 | 12/2015 | Gilmore et al. |
| 2016/0008131 A1 | 1/2016 | Christianson et al. |
| 2016/0038280 A1 | 2/2016 | Morriss et al. |
| 2016/0213473 A1 | 7/2016 | Hacohen et al. |
| 2016/0324633 A1 | 11/2016 | Gross et al. |
| 2016/0367360 A1 | 12/2016 | Cartledge et al. |
| 2017/0020670 A1 | 1/2017 | Murray et al. |
| 2017/0035568 A1 | 2/2017 | Lombardi et al. |
| 2017/0056166 A1 | 3/2017 | Ratz et al. |
| 2017/0071733 A1 | 3/2017 | Ghione et al. |
| 2017/0128208 A1 | 5/2017 | Christianson et al. |
| 2017/0172737 A1 | 6/2017 | Kuetting et al. |
| 2017/0172738 A1 | 6/2017 | Kassas |
| 2017/0181852 A1 | 6/2017 | Kassas |
| 2017/0209268 A1 | 7/2017 | Cunningham et al. |
| 2017/0216023 A1 | 8/2017 | Lane et al. |
| 2017/0216026 A1 | 8/2017 | Quill et al. |
| 2017/0245993 A1 | 8/2017 | Gross et al. |
| 2017/0252163 A1 | 9/2017 | Kheradvar |
| 2017/0273784 A1 | 9/2017 | Racchini et al. |
| 2017/0281341 A1 | 10/2017 | Lim et al. |
| 2017/0325948 A1 | 11/2017 | Wallace et al. |
| 2017/0333240 A1 | 11/2017 | Stangenes et al. |
| 2017/0348099 A1 | 12/2017 | Mendelson et al. |
| 2017/0360557 A1* | 12/2017 | Kheradvar ............ A61F 9/0026 |
| 2017/0360558 A1 | 12/2017 | Ma |
| 2018/0014932 A1 | 1/2018 | Hammer et al. |
| 2018/0021130 A1 | 1/2018 | Danino |
| 2018/0116793 A1 | 5/2018 | Salahieh et al. |
| 2018/0147055 A1 | 5/2018 | Vidlund et al. |
| 2018/0153689 A1 | 6/2018 | Maimon et al. |
| 2018/0200049 A1 | 7/2018 | Chambers et al. |
| 2018/0206983 A1 | 7/2018 | Noe et al. |
| 2018/0256322 A1 | 9/2018 | Zhang et al. |
| 2018/0256329 A1 | 9/2018 | Chambers et al. |
| 2018/0263767 A1 | 9/2018 | Chau et al. |
| 2018/0263773 A1 | 9/2018 | Poppe et al. |
| 2018/0289474 A1 | 10/2018 | Rajagopal et al. |
| 2018/0289475 A1 | 10/2018 | Chung et al. |
| 2018/0296325 A1 | 10/2018 | McLean |
| 2018/0296341 A1 | 10/2018 | Noe et al. |
| 2018/0303612 A1 | 10/2018 | Pasquino et al. |
| 2018/0311037 A1 | 11/2018 | Morriss et al. |
| 2018/0333259 A1 | 11/2018 | Dibie |
| 2018/0344456 A1 | 12/2018 | Barash et al. |
| 2018/0353293 A1 | 12/2018 | Colavito et al. |
| 2019/0000619 A1 | 1/2019 | Quijano et al. |
| 2019/0008636 A1 | 1/2019 | Francis et al. |
| 2019/0029819 A1 | 1/2019 | Huber |
| 2019/0060057 A1 | 2/2019 | Cohen et al. |
| 2019/0069995 A1 | 3/2019 | Levi et al. |
| 2019/0262129 A1 | 8/2019 | Cooper et al. |
| 2019/0365538 A1 | 12/2019 | Chambers et al. |
| 2019/0388219 A1 | 12/2019 | Lane et al. |
| 2020/0121452 A1 | 4/2020 | Saikrishnan et al. |
| 2020/0121458 A1 | 4/2020 | Vidlund et al. |
| 2020/0179146 A1 | 6/2020 | Christianson et al. |
| 2020/0188097 A1 | 6/2020 | Perrin et al. |
| 2020/0237506 A1 | 7/2020 | Christianson et al. |
| 2020/0289259 A1 | 9/2020 | Christianson et al. |
| 2020/0289263 A1 | 9/2020 | Christianson et al. |
| 2021/0000592 A1 | 1/2021 | Christianson et al. |
| 2021/0137677 A1 | 5/2021 | Christianson et al. |
| 2021/0154011 A1 | 5/2021 | Christianson et al. |
| 2021/0186693 A1 | 6/2021 | Vidlund et al. |
| 2021/0220126 A1 | 7/2021 | Perrin |
| 2021/0220127 A1 | 7/2021 | Vidlund et al. |
| 2021/0220134 A1 | 7/2021 | Christianson et al. |
| 2021/0228349 A1 | 7/2021 | Vidlund et al. |
| 2021/0236280 A1 | 8/2021 | Christianson et al. |
| 2021/0244533 A1 | 8/2021 | Vidlund et al. |
| 2021/0244535 A1 | 8/2021 | Iyer et al. |
| 2021/0244536 A1 | 8/2021 | Christianson et al. |
| 2021/0290381 A1 | 9/2021 | Vidlund et al. |
| 2021/0290385 A1 | 9/2021 | Christianson et al. |
| 2021/0315694 A1 | 10/2021 | Vidlund et al. |
| 2021/0330459 A1 | 10/2021 | Christianson et al. |
| 2021/0353412 A1 | 11/2021 | Christianson et al. |

OTHER PUBLICATIONS

International Search Report and Written Opinion for International Application No. PCT/US2019/051615, dated Mar. 2, 2020, 14 pages.

International Search Report and Written Opinion for International Application No. PCT/US2019/051957, dated Apr. 30, 2020, 16 pages.

International Search Report and Written Opinion for International Application No. PCT/US2019/067010, dated Mar. 10, 2020, 17 pages.

International Search Report and Written Opinion for International Application No. PCT/US2020/013240, dated Jun. 3, 2020, 7 pages.

International Search Report and Written Opinion for International Application No. PCT/US2020/015231, dated Apr. 23, 2020, 10 pages.

International Search Report and Written Opinion for International Application No. PCT/US2020/021300, dated Oct. 7, 2020, 6 pages.

International Search Report and Written Opinion for International Application No. PCT/US2020/022828, dated May 19, 2020, 12 pages.

International Search Report and Written Opinion for International Application No. PCT/US2020/031390, dated Aug. 3, 2020, 10 pages.

International Search Report and Written Opinion for International Application No. PCT/US2020/045195, dated Jan. 8, 2021, 18 pages.

International Search Report and Written Opinion for International Application No. PCT/US2020/047162, dated Dec. 30, 2020, 9 pages.

International Search Report and Written Opinion for International Application No. PCT/US2021/013570, dated Apr. 1, 2021, 9 pages.

Office Action for U.S. Appl. No. 16/155,890, dated Feb. 8, 2019, 13 pages.

Office Action for U.S. Appl. No. 16/163,577, dated Mar. 8, 2021, 10 pages.

Office Action for U.S. Appl. No. 16/435,687, dated Aug. 7, 2019, 19 pages.

Office Action for U.S. Appl. No. 16/442,504, dated Jan. 14, 2020, 11 pages.

Office Action for U.S. Appl. No. 16/443,862, dated Nov. 12, 2021, 9 pages.

Office Action for U.S. Appl. No. 16/445,210, dated Jan. 28, 2021, 7 pages.

Office Action for U.S. Appl. No. 16/448,108, dated Jan. 21, 2020, 14 pages.

Office Action for U.S. Appl. No. 16/448,108, dated Mar. 8, 2021, 8 pages.

Office Action for U.S. Appl. No. 16/448,108, dated Sep. 1, 2020, 14 pages.

(56) References Cited

OTHER PUBLICATIONS

Office Action for U.S. Appl. No. 16/449,420, dated Sep. 1, 2021, 16 pages.
Office Action for U.S. Appl. No. 16/455,417, dated Sep. 23, 2019, 11 pages.
Office Action for U.S. Appl. No. 16/455,740, dated Jul. 24, 2020, 7 pages.
Office Action for U.S. Appl. No. 16/711,415, dated Jan. 18, 2022, 7 pages.
Office Action for U.S. Appl. No. 17/154,227, dated Jun. 18, 2021, 8 pages.
Office Action for U.S. Appl. No. 17/154,227, dated Mar. 29, 2021, 6 pages.
Office Action for U.S. Appl. No. 17/154,438, dated May 3, 2021, 16 pages.
Office Action for U.S. Appl. No. 17/167,983, dated Apr. 13, 2021, 20 pages.
Office Action for U.S. Appl. No. 17/167,988, dated Sep. 22, 2021, 19 pages.
Office Action for U.S. Appl. No. 17/193,936, dated May 27, 2021, 6 pages.
Office Action for U.S. Appl. No. 17/221,547, dated Aug. 4, 2021, 11 pages.
Office Action for U.S. Appl. No. 17/221,547, dated Oct. 21, 2021, 9 pages.
Office Action for U.S. Appl. No. 17/222,182, dated Sep. 2, 2021, 23 pages.
Office Action for U.S. Appl. No. 17/222,430, dated Oct. 7, 2021, 17 pages.
Office Action for U.S. Appl. No. 17/236,219, dated Aug. 4, 2021, 17 pages.
Office Action for U.S. Appl. No. 17/388,983, dated Jan. 6, 2022, 11 pages.

\* cited by examiner

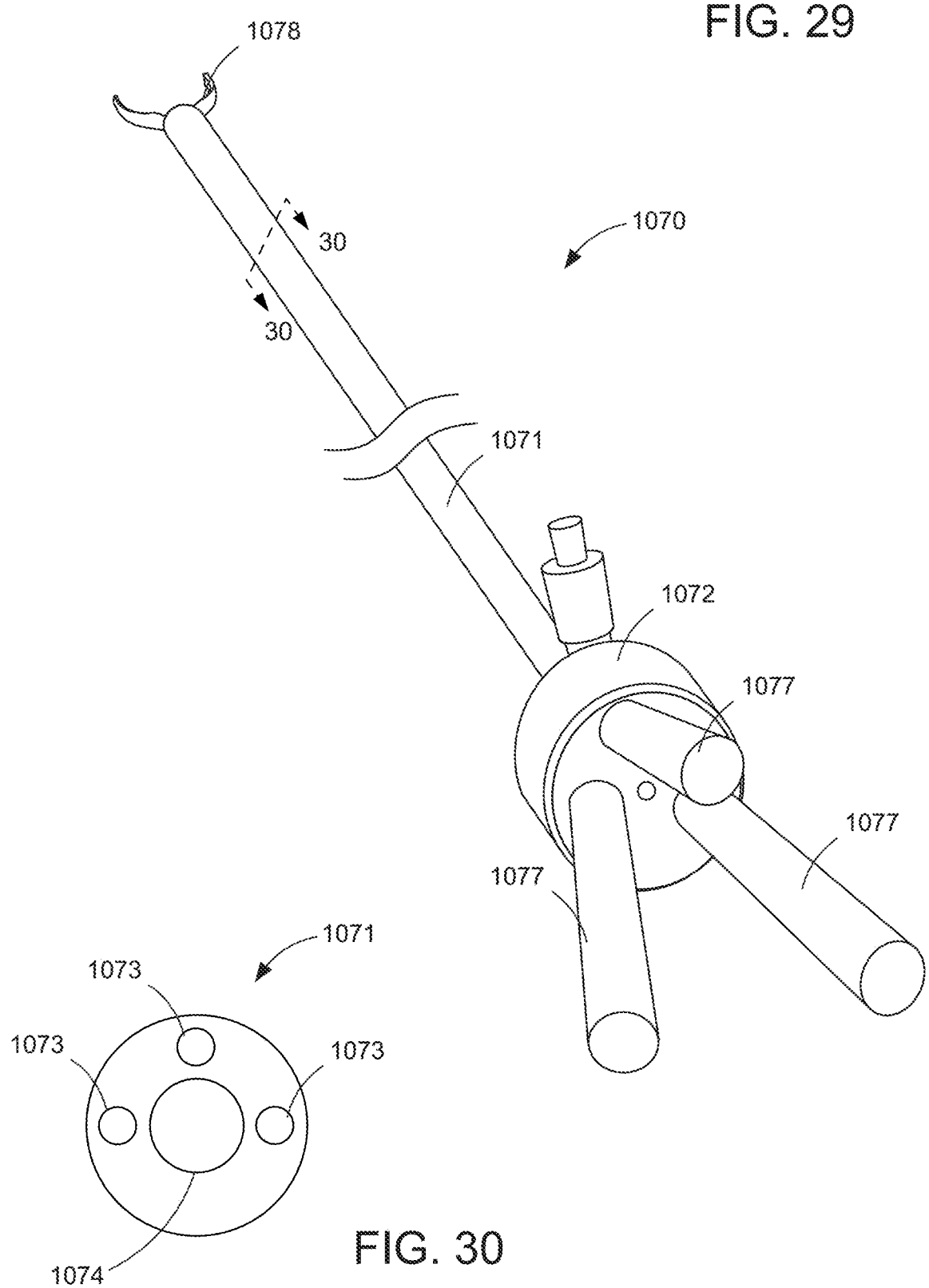

FIG. 48A
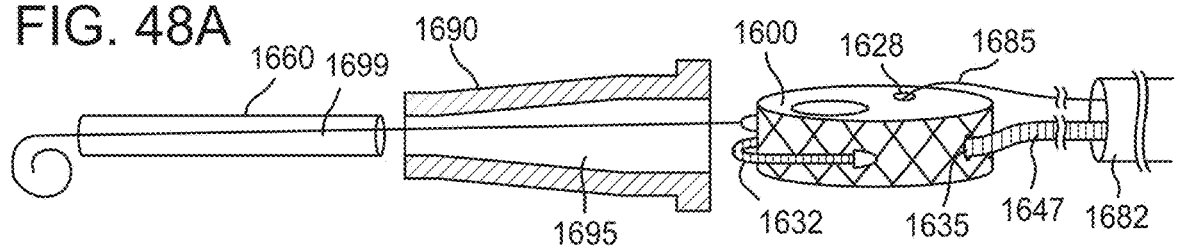
FIG. 48B
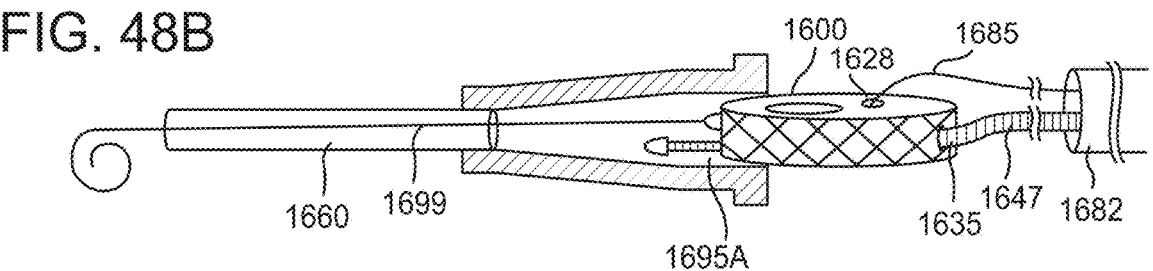
FIG. 48C
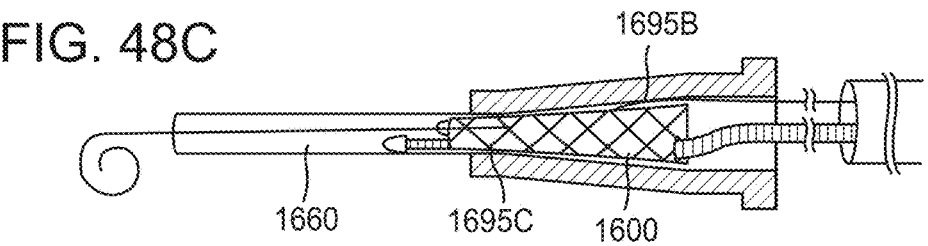
FIG. 48D
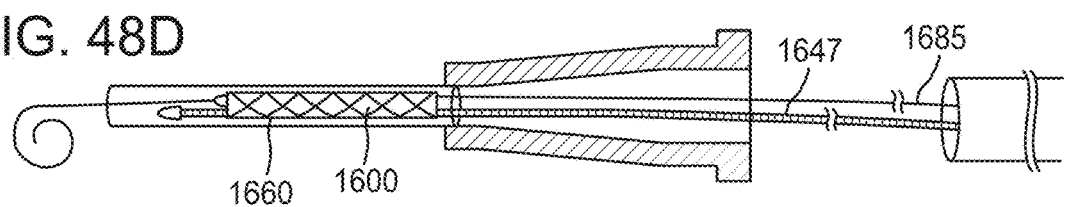
FIG. 48E
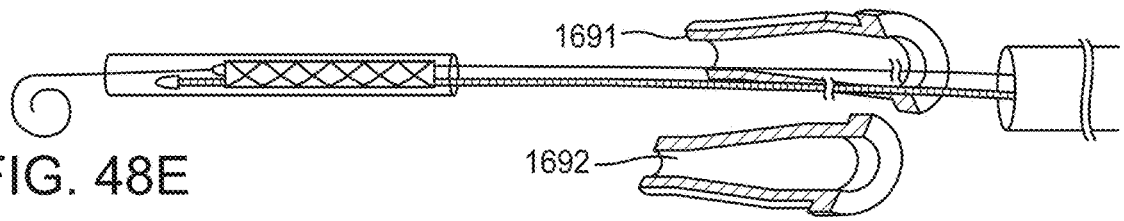
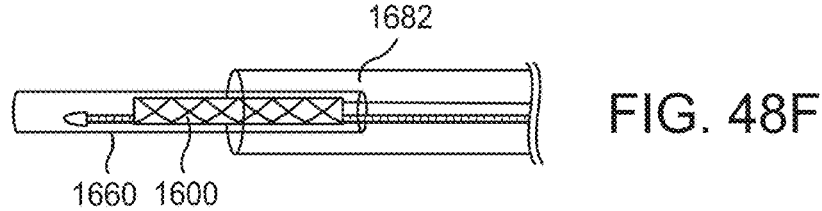
FIG. 48F
FIG. 48G
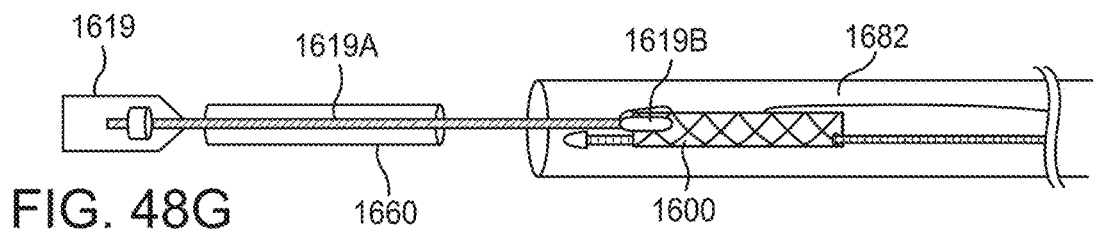

30

Compress the prosthetic valve along a central axis and a lateral axis perpendicular to the central axis to transition the prosthetic valve from an expanded configuration to a delivery configuration
31

Advance the prosthetic valve in the delivery configuration into a lumen of a loading device while a first gate at a distal end of the loading device is in a closed state
32

Couple a distal end portion of the loading device to a handle of the delivery device while the first gate is in the closed state and a second gate at a proximal end of the handle is in a closed state
33

Transition each of the first gate and the second gate from the closed state to an open state
34

```
┌─────────────────────────────────────────────────────────────┐
│ Increase a tension along a first tether and a second tether │
│ to secure a yoke against a surface of a prosthetic valve    │
│                            41                                │
└─────────────────────────────────────────────────────────────┘
                              ↓
┌─────────────────────────────────────────────────────────────┐
│ Advance the prosthetic valve through a lumen of a delivery   │
│ catheter while the yoke is secured against the surface of    │
│ the prosthetic valve                                         │
│                            42                                │
└─────────────────────────────────────────────────────────────┘
                              ↓
┌─────────────────────────────────────────────────────────────┐
│ Release the prosthetic valve from a distal end of the        │
│ delivery catheter                                            │
│                            43                                │
└─────────────────────────────────────────────────────────────┘
                              ↓
┌─────────────────────────────────────────────────────────────┐
│ Increase a tension along a tension member to transition a    │
│ proximal subannular anchoring element from a first           │
│ configuration to a second configuration after releasing the  │
│ prosthetic valve                                             │
│                            44                                │
└─────────────────────────────────────────────────────────────┘
                              ↓
┌─────────────────────────────────────────────────────────────┐
│ Seat the prosthetic valve in an annulus of a native valve in │
│ response to a force exerted by the yoke on the surface of    │
│ the prosthetic valve                                         │
│                            45                                │
└─────────────────────────────────────────────────────────────┘
                              ↓
┌─────────────────────────────────────────────────────────────┐
│ Release the tension along the tension member to allow the    │
│ proximal subannular anchoring element to transition from the │
│ second configuration toward the first configuration after    │
│ the seating the prosthetic valve                             │
│                            46                                │
└─────────────────────────────────────────────────────────────┘
                              ↓
┌─────────────────────────────────────────────────────────────┐
│ Decouple the control device from the prosthetic valve        │
│                            47                                │
└─────────────────────────────────────────────────────────────┘
```

FIG. 68

DELIVERY AND RETRIEVAL DEVICES AND METHODS FOR SIDE-DELIVERABLE TRANSCATHETER PROSTHETIC VALVES

CROSS-REFERENCE TO RELATED APPLICATIONS

This application is a divisional of U.S. patent application Ser. No. 17/193,946, filed Mar. 5, 2021, entitled "Delivery and Retrieval Devices and Method for Side-Deliverable Transcatheter Prosthetic Valves," (now U.S. Pat. No. 11,179,239) which is a continuation of International Patent Application No. PCT/US2020/047162, filed Aug. 20, 2020, entitled "Delivery and Retrieval Devices and Method for Side-Deliverable Transcatheter Prosthetic Valves," which claims priority to and the benefit of U.S. Provisional Patent Application No. 63/038,807, filed Jun. 13, 2020, entitled "Retrieval Device and Method for Side-Deliverable Transcatheter Prosthetic Valves;" U.S. Provisional Patent Application No. 63/027,345, filed May 19, 2020, entitled "Side-Deliverable Transcatheter Prosthetic Valves and Method for Delivering and Anchoring the Same;" U.S. Provisional Patent Application No. 62/891,964, filed Aug. 27, 2019, entitled "Wrap Around Anchor Arm and Catheter Delivery System for Side-Delivered Transcatheter Heart Valve Prosthesis;" and U.S. Provisional Patent Application No. 62/889,327, filed Aug. 20, 2019, entitled "Loader System for Side-Delivered Transcatheter Heart Valve Prosthesis," the disclosure of each of which is incorporated herein by reference in its entirety.

BACKGROUND

The embodiments described herein relate generally to transcatheter prosthetic valves and more particularly, to delivery and/or retrieval devices and methods for side-deliverable transcatheter prosthetic valves.

Prosthetic heart valves can pose challenges for delivery, deployment, and/or retrieval within a heart, particularly for delivery by catheters through the patient's vasculature rather than through a surgical approach. Delivery of traditional transcatheter prosthetic valves generally includes compressing the valve in a radial direction and loading the valve into a delivery catheter such that a central annular axis of the valve is parallel to a lengthwise or longitudinal axis of the delivery catheter. The valves are deployed from an end of the delivery catheter and expanded outwardly in a radial direction from the central annular axis. The expanded size (e.g., diameter) of traditional valves, however, can be limited by the internal diameter of the delivery catheter. The competing interest of minimizing delivery catheter size presents challenges to increasing the expanded diameter of traditional valves (e.g., trying to compress too much material and structure into too little space). Moreover, the orientation of the traditional valves during deployment can create additional challenges when trying to align the valves with the native valve annulus.

Some transcatheter prosthetic valves can be configured for side and/or orthogonal delivery, which can allow for an increase in an expanded diameter of the side-delivered valve relative to traditional valves. For example, in a side (or-thogonal) delivery, the valve can be placed in a compressed or delivery configuration and loaded into a delivery catheter such that a central annular axis of the valve is substantially perpendicular and/or orthogonal to a lengthwise or longitudinal axis of the delivery catheter. More particularly, the valve can be compressed axially (e.g., along the central annular axis) and laterally (e.g., perpendicular to each of the central annular axis and a longitudinal axis of the valve), and uncompressed or elongated longitudinally (e.g., in a direction parallel to the lengthwise or longitudinal axis of the delivery catheter). The compressed valve (e.g., the valve in a delivery configuration) can be loaded into the delivery catheter, advanced through a lumen thereof, and deployed from the end of the delivery catheter. Moreover, the side-delivered valve is generally in a desired orientation relative to the native valve annulus when deployed from the end of the delivery catheter.

In some implementations, however, challenges associated with compressing the side-deliverable valve and/or the loading of the valve into a delivery system may persist. In addition, in some instances, it may be desirable to retrieve or at least partially retrieve the valve after deployment of valve from the end of the delivery catheter.

Accordingly, a need exists for delivery and/or retrieval devices and methods for side-deliverable transcatheter prosthetic valves.

SUMMARY

The embodiments described herein are directed to side-deliverable prosthetic valves and devices and/or methods for delivering and/or retrieving the side-deliverable prosthetic valves. In some embodiments, a delivery system for side-delivery of a transcatheter prosthetic valve includes a compression device, a loading device, and a delivery device. The compression device defines a lumen that extends through a proximal end and a distal end, with a perimeter of the lumen at the proximal end being larger than a perimeter of the lumen of the distal end. The loading device defines a lumen that extends through a proximal end and a distal end thereof. A perimeter of the lumen of the loading device is substantially similar to the perimeter of the lumen at the distal end of the compression device. The proximal end of the loading device is coupleable to the compression device and the distal end of the loading device includes a first gate that is movable between an open state and a closed state in which the first gate at least partially occludes the lumen of the loading device. The delivery device has a handle and a delivery catheter extending distally from the handle. The handle and the delivery catheter collectively define a lumen that extends through the delivery device. A perimeter of the lumen of the delivery device is substantially similar to the perimeter of the lumen of the loading device. A proximal end of the handle is coupleable to the distal end of the loading device and includes a second gate that is movable between an open state and a closed state in which the second gate at least partially occludes the lumen of the delivery device.

BRIEF DESCRIPTION OF THE DRAWINGS

FIG. 29 is a perspective view of a control device included in the delivery system of FIG. 24.

FIG. 30 is a cross-sectional view of a multi-lumen control catheter included in the control device of FIG. 29 and taken along the line 30-30.

FIGS. 48A-48D are cross-sectional views of a portion of a delivery system illustrating a process of using a compression device of the delivery system to compress a prosthetic valve, having a guidewire device and a control device attached to a proximal portion thereof, for insertion into a loading device of the delivery system, according to an embodiment.

FIG. 48E is a side view of the portion of the delivery system of FIG. 48A illustrating the compression device being laterally separated from around the guidewire device and the control device to allow the compression device to be removed from the loading device.

FIG. 48F is a side view of a portion of the delivery system of FIG. 48A illustrating a portion of the loading device, with the compressed prosthetic valve disposed therein, disposed in a lumen of a delivery catheter included in the delivery system.

FIG. 48G is a side view of a portion of the delivery system of FIG. 48A illustrating a process of using a pushing device of the delivery system to push the compressed process from the loading device into the lumen of a delivery catheter.

FIG. 67 is a flowchart illustrating a method of preparing a prosthetic valve for side-delivery to a patient through a lumen of a delivery catheter included in a delivery device, according to an embodiment.

FIG. 68 is a flowchart illustrating a method of using a control device to selectively control a side-deliverable transcatheter prosthetic valve during at least one of delivery and deployment, according to an embodiment.

DETAILED DESCRIPTION

Figure 1A:
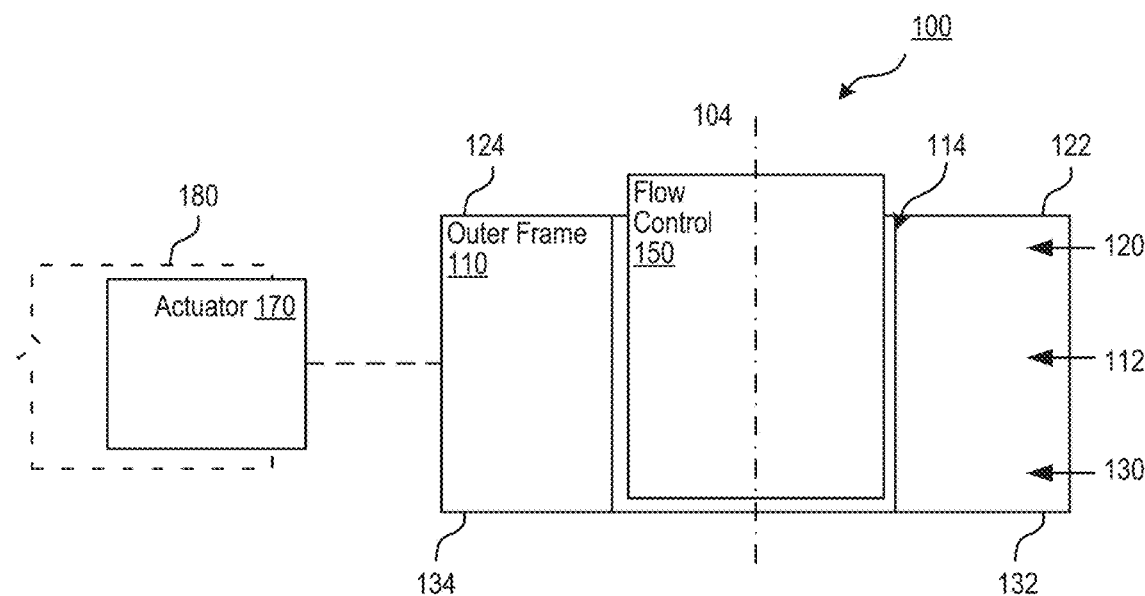
FIGS. 1A and 1B are front view schematic illustrations of a side-delivered transcatheter prosthetic heart valve (also referred to herein as "prosthetic valve"), according to an embodiment, and shown in an expanded configuration and a compressed configuration, respectively.

Disclosed embodiments are directed to side-deliverable transcatheter prosthetic valves (and/or components thereof) and methods of loading, delivering, deploying, and/or retrieving the prosthetic valves (and/or components thereof). In some embodiments, a side-deliverable prosthetic heart valve can include an outer frame and a flow control component. The outer frame can have a supra-annular region, a subannular region, and a transannular region coupled therebetween. The subannular region can form a distal anchoring element and a proximal anchoring element. The flow control component can be mounted to the supra-annular region of the outer frame such that at least a portion of the flow control component is disposed in the transannular region. The prosthetic valve can be placed in a delivery configuration for side-delivery of the prosthetic valve to a heart of a patient via a delivery catheter of a delivery system. The prosthetic valve can be allowed to transition to an expanded or released configuration when released from the delivery catheter. In some implementations, the subannular region of the outer frame can be in a first configuration as the prosthetic valve is seated in an annulus of a native heart valve and can be transitioned to a second configuration after the prosthetic valve is seated in the annulus of the native heart valve.

In some embodiments, a delivery and/or retrieval system 180 can facilitate the compression, loading, advancing, delivering, and/or deploying of a prosthetic valve through a delivery catheter of the delivery system and to a desired position relative to a native valve annulus. In some implementations, the delivery and/or retrieval system 180 can include a self-expanding capture element that can extend from an end of a delivery catheter and/or other member of the delivery system to funnel, wrap, and/or at least partially capture the prosthetic valve during or after deployment to facilitate a compression of the valve and an at least partial retrieval thereof.

In some embodiments, a delivery system for side-delivery of a transcatheter prosthetic valve can include a compression device, a loading device, and a delivery device. The compression device defines a lumen extending through a proximal end and a distal end. The perimeter of the lumen at the proximal end being larger than a perimeter of the lumen at the distal end. The loading device defines a lumen extending through a proximal end and a distal end of the loading device. A perimeter of the lumen of the loading device is substantially similar to the perimeter of the lumen at the distal end of the compression device. The proximal end of the loading device is removably coupleable to the compression device. The distal end of the loading device includes a first gate that is movable between an open state and a closed state in which the first gate at least partially occludes the lumen of the loading device. The delivery device has a handle and a delivery catheter extending distally from the handle. The handle and the delivery catheter collectively define a lumen extending through the delivery device. A perimeter of the lumen of the delivery device is substantially similar to the perimeter of the lumen of the loading device. A proximal end of the handle is coupleable to the distal end of the loading device and includes a second gate movable between an open state and a closed state in which the second gate at least partially occludes the lumen of the delivery device.

In some implementations, a method for compressing a prosthetic valve into a delivery configuration for side-delivery to a patient by a delivery catheter can include compressing the prosthetic valve along a lateral axis of the prosthetic valve perpendicular to a central axis of the prosthetic valve, which in turn, is parallel to a fluid flow direction through the prosthetic valve. After compressing, the prosthetic valve is inserted into a proximal end of a compression device. The compression device defines a lumen extending through the proximal end and a distal end. A perimeter of the lumen at the proximal end is larger than a perimeter of the lumen at the distal end. The prosthetic valve is advanced through the lumen of the compression device to compress the prosthetic valve along the central axis. The prosthetic valve in the delivery configuration is transferred from the distal end of the compression device into a loading device coupled to the distal end of the compression device. The loading device defines a lumen having a perimeter that is substantially similar to (i) the perimeter of the lumen at the distal end of the compression device and (ii) a perimeter of a lumen of the delivery catheter.

In some implementations, a method for preparing a side-deliverable prosthetic valve for side-delivery to a patient via a delivery catheter can include compressing the prosthetic valve along a lateral axis of the prosthetic valve perpendicular to a central axis of the prosthetic valve, which in turn, is parallel to a fluid flow direction through the prosthetic valve. After compressing, the prosthetic valve is inserted into a lumen of a compression device. The prosthetic valve is pulled through the lumen of the compression device and into a lumen of a loading device coupled to the compression device via a tether attached to a distal end portion of the prosthetic valve. The prosthetic valve is compressed along the central axis such that the prosthetic valve is in a delivery configuration when in the lumen of the loading device. The tether is removed from the distal end portion of the prosthetic valve and a distal end and a distal end of the loading device is coupled to a delivery device including the delivery catheter.

In some implementations, A method for preparing a side-deliverable prosthetic valve for side-delivery to a patient through a lumen of a delivery catheter included in a delivery device can include compressing the prosthetic valve along a central axis parallel to a fluid flow direction through the prosthetic valve and a lateral axis perpendicular to the central axis to transition the prosthetic valve from an expanded configuration to a delivery configuration. The prosthetic valve in the delivery configuration is advanced into a lumen of a loading device while a first gate at a distal end of the loading device is in a closed state to at least partially occlude the lumen of the loading device. A distal end of the loading device is coupled to a handle of the delivery device while (i) the first gate is in the closed state and (ii) while a second gate at a proximal end of the handle is in a closed state to at least partially occlude a lumen of the handle. The lumen of the delivery catheter is in fluid communication with the lumen of the handle distal to the second gate. After coupling, each of the first gate and the second gate is transitioned from the closed state to an open state.

In some embodiments, an apparatus for selectively engaging a side-deliverable transcatheter prosthetic valve can include a multi-lumen catheter having a distal end and a proximal end. A control portion is coupled to the proximal end of the multi-lumen catheter and a yoke coupled to the distal end of the multi-lumen catheter. A first tether is extendable through a first control arm of the control portion and a first lumen of the multi-lumen catheter, and a portion of the first tether is configured to be looped through a first side of the yoke. A second tether is extendable through a second control arm of the control portion and a second lumen of the multi-lumen catheter, and a portion of the second tether is configured to be looped through a second side of the yoke. A tension member is extendable through a third control arm of the control portion and a third lumen of the multi-lumen catheter, and a portion of the tension member is configured to be removably coupled to a proximal subannular anchoring element of the prosthetic valve.

In some embodiments, a control device can include at least a control catheter having a first tether, a second tether, and a tension member extending therethrough, and a yoke coupled to a distal end of the control catheter. In some implementations, a method of using the control device to selectively control a side-deliverable transcatheter prosthetic valve during at least one of delivery and deployment can include increasing a tension along the first tether and the second tether to secure the yoke against a surface of the prosthetic valve. The prosthetic valve is advanced through a lumen of a delivery catheter while the yoke is secured against the surface of the prosthetic valve. The prosthetic valve is released from a distal end of the delivery catheter. After releasing, a tension along the tension member is increased to transition a proximal subannular anchoring element from a first configuration to a second configuration. The prosthetic valve is seated in an annulus of a native valve in response to a force exerted by the yoke on the surface of the prosthetic valve. After seating the prosthetic valve, the tension along the tension member is released to allow the proximal subannular anchoring element to transition from the second configuration toward the first configuration. The control device is then decoupled from the prosthetic valve.

In some embodiments, a delivery and retrieval system for a side-deliverable prosthetic valve can include a catheter, a capture element, and a control device. The catheter has a distal end and defines a lumen. The prosthetic valve has a delivery configuration for side delivery through the lumen of the catheter and a deployment configuration when released from the distal end of the catheter. The capture element is disposable in the lumen of the catheter in a substantially closed configuration and can be transitioned to an open configuration when advanced beyond the distal end of the catheter. The control device can be at least partially disposed in the lumen of the catheter and can be attached to the prosthetic valve. The control device is operable to (i) exert a distally directed force to advance the prosthetic valve in the delivery configuration through the lumen of the catheter and (ii) exert a proximally directed force to pull the prosthetic valve in the deployment configuration into the distal end of the catheter. The capture element can be extended around at least a portion of the prosthetic valve to transition the prosthetic valve from the deployment configuration to the delivery configuration as the control device pulls the prosthetic valve into the distal end of the catheter.

In some embodiments, a retrieval system for a side-deliverable prosthetic valve can include a control device and a self-expanding capture element. The control device is removably coupleable to the prosthetic valve during delivery and deployment of the prosthetic valve in an annulus of a native heart valve. The self-expanding capture element is extendable from a distal end of a delivery catheter to funnel or wrap at least a portion of the prosthetic valve at least partially deployed in the annulus to facilitate a compression of the prosthetic valve in response to a force exerted by the control device moving the prosthetic valve in a proximal direction toward the delivery catheter.

In some implementations, a method of retrieving a side-deliverable prosthetic heart valve can include extending a self-expanding capture element from a distal end of a catheter disposed in a native atrium of a heart. The capture element is configured to have and/or define a cavity shape when in an extended position. The prosthetic heart valve is pulled into the cavity of the extended capture element to facilitate a compressing of the prosthetic heart valve. The pulling of the prosthetic heart valve into the capture element is operable to transition the capture element from the extended position to or toward a retracted position, in which the prosthetic heart valve is wrapped by the capture element. After wrapping, the prosthetic heart valve that is wrapped (at least partially) by the capture element is pulled into the catheter using a cable.

Any of the prosthetic heart valves described herein can be a relatively low profile, side-deliverable implantable prosthetic heart valve (also referred to herein as "prosthetic valve" or simply, "valve"). Any of the prosthetic valves can be transcatheter prosthetic valves configured to be delivered into a heart via a delivery catheter. The prosthetic valves can have at least an annular outer valve frame and an inner flow control component (e.g., a 2-leaflet or 3-leaflet valve, sleeve, and/or the like) mounted within and/or extending through a central lumen or aperture of the valve frame. The flow control component can be configured to permit blood flow in a first direction through an inflow end of the valve and block blood flow in a second direction, opposite the first direction, through an outflow end of the valve. In addition, the prosthetic valves can include a single anchoring element or multiple anchoring elements configured to anchor the valve in the annulus of a native valve.

Any of the prosthetic valves described herein can be configured to transition between a compressed or delivery configuration for introduction into the body using the delivery catheter, and an expanded or deployed configuration for implanting at a desired location in the body. For example, any of the embodiments described herein can be a balloon-inflated prosthetic valve, a self-expanding prosthetic valve, and/or the like.

Any of the prosthetic valves described herein can be compressible—into the compressed or delivery configuration—in a lengthwise or orthogonal direction relative to the central axis of the flow control component (e.g., along a longitudinal axis) that can allow a large diameter valve (e.g., having a height of about 5-60 mm and a diameter of about 20-80 mm) to be delivered and deployed from the inferior vena cava directly into the annulus of a native mitral or tricuspid valve using, for example, a 24-36 Fr delivery catheter. The longitudinal axis can be substantially parallel to a lengthwise cylindrical axis of the delivery catheter, which can allow deployment of the prosthetic valves without an acute angle of approach common in traditional transcatheter delivery.

Any of the prosthetic valves described herein can have a central axis that is co-axial or at least substantially parallel with blood flow direction through the valve. In some embodiments, the compressed or delivery configuration of the valve is orthogonal to the blood flow direction. In some embodiments, the compressed or delivery configuration of the valve is parallel to or aligned with the blood flow direction. In some embodiment, the valve can be compressed to the compressed or delivery configuration in two directions—orthogonal to the blood flow direction (e.g., laterally) and parallel to the blood flow (e.g., axially). In some embodiments, a long-axis or longitudinal axis is oriented at an intersecting angle of between 45-135 degrees to the first direction when in the compressed or delivery configuration and/or the expanded or deployed configuration.

Any of the prosthetic valves described herein can include an outer support frame that includes a set of compressible wire cells having an orientation and cell geometry substantially orthogonal to the central axis to minimize wire cell strain when the outer support frame is in a delivery configuration (e.g., a compressed configuration, a rolled and compressed configuration, or a folded and compressed configuration).

Any of the outer support frames described herein can have a supra-annular region, a subannular region, and a transannular region coupled therebetween. The supra-annular region can form, for example, an upper collar portion of the outer support frame and can include any number of features configured to engage native tissue, an inner flow control component of the prosthetic valve, and/or a delivery, actuator, and/or retrieval mechanism. The subannular region can form, for example, a distal anchoring element and a proximal anchoring element configured to engage subannular (ventricle) tissue when the prosthetic valve is seated in the native annulus. The transannular region can be coupled between the supra-annular region and the subannular region. The transannular region can form a shape such as a funnel, cylinder, flat cone, or circular hyperboloid when the outer support frame is in an expanded configuration. In some embodiments, the outer support frame is formed from a wire, a braided wire, or a laser-cut wire frame, and is covered with a biocompatible material. The biocompatible material can cover the outer support frame such that an inner surface is covered with pericardial tissue, an outer surface is covered with a woven synthetic polyester material, and/or both the inner surface is covered with pericardial tissue and the outer surface is covered with a woven synthetic polyester material.

Any of the outer support frames described herein can have a side profile of a flat cone shape having an outer diameter R of 40-80 mm, an inner diameter r of 20-60 mm, and a height of 5-60 mm. In some embodiments, an annular support frame has a side profile of an hourglass shape having a top diameter R1 of 40-80 mm, a bottom diameter R2 of 50-70 mm, an internal diameter r of 20-60 mm, and a height of 5-60 mm.

Any of the prosthetic valves described herein can include one or more anchoring element extending from, coupled to, and/or otherwise integral with a portion of a valve frame. For example, any of the prosthetic valves can include a distal anchoring element, which can be used, for example, as a Right Ventricular Outflow Tract ("RVOT") tab or a Left Ventricular Outflow Tract ("LVOT") tab. Any of the valves described herein can also include an anchoring element extending from a proximal sided of the valve frame, which can be used, for example, to anchor the valve to proximal subannular tissue of the ventricle. The anchoring elements can include and/or can be formed from a wire loop or wire frame, an integrated frame section, and/or a stent, extending from about 10-40 mm away from the tubular frame. For example, any of the prosthetic valves described herein can include a valve frame having a wire or laser cut subannular region or member that forms a distal and proximal anchoring element.

Any of the prosthetic valves described herein can also include (i) a distal upper (supra-annular) anchoring element extending from, attached to, and/or otherwise integral with a distal upper edge of the valve frame and (ii) a proximal upper (supra-annular) anchoring element extending from, attached to, and/or otherwise integral with a proximal upper edge of the valve frame. The distal and proximal upper anchoring elements can include or be formed from a wire loop or wire frame extending from about 2-20 mm away from the valve frame. In some embodiments, the prosthetic valves described herein can include a wire or laser cut supra-annular region or member that forms the distal and proximal upper anchoring elements. The distal and proximal upper anchoring elements are configured to be positioned into a supra-annular position in contact with and/or adjacent to supra-annular tissue of the atrium. In some implementations, the prosthetic valves described herein can be cinched or at least partially compressed after being seated in a native annulus such that the proximal and distal upper anchoring elements exert a force on supra-annular tissue and the proximal and distal lower anchoring elements exert a force in an opposite direction on subannular tissue, thereby securing the prosthetic valve in the native annulus. Any of the valves described herein can also include an anterior or posterior anchoring element extending from and/or attached to an anterior or posterior side of the valve frame, respectively.

Any of the prosthetic valves described herein can include an inner flow control component that has a leaflet frame with 2-4 flexible leaflets mounted thereon. The 2-4 leaflets are configured to permit blood flow in a first direction through an inflow end of the flow control component and block blood flow in a second direction, opposite the first direction, through an outflow end of the flow control component. The leaflet frame can include two or more panels of diamond-shaped or eye-shaped wire cells made from heat-set shape memory alloy material such as, for example, Nitinol. The leaflet frame can be configured to be foldable along a z-axis (e.g., a longitudinal axis) from a rounded or cylindrical configuration to a flattened cylinder configuration, and compressible along a vertical y-axis (e.g., a central axis) to a compressed configuration. In some implementations, the leaflet frame can include a pair of hinge areas, fold areas, connection points, etc. that can allow the leaflet frame to be folded flat along the z-axis prior to the leaflet frame being compressed along the vertical y-axis. The leaflet frame can be, for example, a single-piece structure with two or more living hinges (e.g., stress concentration riser and/or any suitable structure configured to allow for elastic/nonpermanent deformation of the leaflet frame) or a two-piece structure where the hinge areas are formed using a secondary attachment method (e.g. sutures, fabrics, molded polymer components, etc.)

In some embodiments, the inner flow control component in an expanded configuration forms a shape such as a funnel, cylinder, flat cone, or circular hyperboloid. In some embodiments, the inner flow control component has a leaflet frame with a side profile of a flat cone shape having an outer diameter R of 20-60 mm, an inner diameter r of 10-50 mm, where diameter R is great than diameter r, and a height of 5-60 mm. In some embodiments, the leaflet frame is comprised of a wire, a braided wire, or a laser-cut wire frame. In some embodiments, the leaflet frame can have one or more longitudinal supports integrated into or mounted thereon and selected from rigid or semi-rigid posts, rigid or semi-rigid ribs, rigid or semi-rigid batons, rigid or semi-rigid panels, and combinations thereof.

Any of the prosthetic valves and/or components thereof may be fabricated from any suitable biocompatible material or combination of materials. For example, an outer valve frame, an inner valve frame (e.g., of an inner flow control component), and/or components thereof may be fabricated from biocompatible metals, metal alloys, polymer coated metals, and/or the like. Suitable biocompatible metals and/or metal alloys can include stainless steel (e.g., 316 L stainless steel), cobalt chromium (Co—Cr) alloys, nickel-titanium alloys (e.g., Nitinol®), and/or the like. Moreover, any of the outer or inner frames described herein can be formed from superelastic or shape-memory alloys such as nickel-titanium alloys (e.g., Nitinol®). Suitable polymer coatings can include polyethylene vinyl acetate (PEVA), poly-butyl methacrylate (PBMA), translute Styrene Isoprene Butadiene (SIBS) copolymer, polylactic acid, polyester, polylactide, D-lactic polylactic acid (DLPLA), polylactic-co-glycolic acid (PLGA), and/or the like. Some such polymer coatings may form a suitable carrier matrix for drugs such as, for example, Sirolimus, Zotarolimus, Biolimus, Novolimus, Tacrolimus, Paclitaxel, Probucol, and/or the like.

Some biocompatible synthetic material(s) can include, for example, polyesters, polyurethanes, polytetrafluoroethylene (PTFE) (e.g., Teflon), and/or the like. Where a thin, durable synthetic material is contemplated (e.g., for a covering), synthetic polymer materials such expanded PTFE or polyester may optionally be used. Other suitable materials may optionally include elastomers, thermoplastics, polyurethanes, thermoplastic polycarbonate urethane, polyether urethane, segmented polyether urethane, silicone polyether urethane, polyetheretherketone (PEEK), silicone-polycarbonate urethane, polypropylene, polyethylene, low-density polyethylene (LDPE), high-density polyethylene (HDPE), ultra-high density polyethylene (UHDPE), polyolefins, polyethylene-glycols, polyethersulphones, polysulphones, polyvinylpyrrolidones, polyvinylchlorides, other fluoropolymers, polyesters, polyethylene-terephthalate (PET) (e.g., Dacron), Poly-L-lactic acids (PLLA), polyglycolic acid (PGA), poly(D, L-lactide/glycolide) copolymer (PDLA), silicone polyesters, polyamides (Nylon), PTFE, elongated PTFE, expanded PTFE, siloxane polymers and/or oligomers, and/or polylactones, and block co-polymers using the same.

Any of the outer valve frames, inner valve frames (e.g., of the flow control components), and/or portions or components thereof can be internally or externally covered, partially or completely, with a biocompatible material such as pericardium. A valve frame may also be optionally externally covered, partially or completely, with a second biocompatible material such as polyester or Dacron®. Disclosed embodiments may use tissue, such as a biological tissue that is a chemically stabilized pericardial tissue of an animal, such as a cow (bovine pericardium), sheep (ovine pericardium), pig (porcine pericardium), or horse (equine pericardium). Preferably, the tissue is bovine pericardial tissue. Examples of suitable tissue include that used in the products Duraguard®, Peri-Guard®, and Vascu-Guard®, all products currently used in surgical procedures, and which are marketed as being harvested generally from cattle less than 30 months old.

Any method for manufacturing prosthetic valves described herein can include using additive or subtractive metal or metal-alloy manufacturing to produce, for example, a compressible/expandable outer support frame and/or a compressible/expandable inner leaflet frame. Additive metal or metal-alloy manufacturing can include but is not limited to 3D printing, direct metal laser sintering (powder melt), and/or the like. Subtractive metal or metal-alloy manufacturing can include but is not limited to photolithography, laser sintering/cutting, CNC machining, electrical discharge machining, and/or the like. Moreover, any of the manufacturing processes described herein can include forming and/or setting (e.g., heat setting) a cut or machined workpiece into any suitable shape, size, and/or configuration. For example, any of the outer support frames and/or inner leaflet frames described herein can be laser cut from one or more workpieces and heat set into a desired shape, size, and/or configuration. Moreover, any of the frames described herein can include multiple independent components that are formed into desired shapes and coupled together to form the frames.

In some embodiments, a process of manufacturing can further include mounting 2-4 flexible leaflets to the inner leaflet frame to collectively form a flow control component, mounting the flow control component within the outer support frame, and/or covering at least a portion of the outer support frame with a pericardium material or similar biocompatible material.

Any of the delivery systems described herein can be configured to deliver a side-deliverable transcatheter prosthetic valve to a target location within a patient (e.g., to or into an annulus of a native heart valve). Such delivery systems can include one or more of the following components: (i) a dilator for dilating at least a portion of an arterial pathway to the heart such as the femoral artery, the IVC, and/or the SVC, (ii) a compression device such as a funnel or the like for compressing the prosthetic valve to a delivery configuration, (iii) a loader, capsule, chamber, etc., for receiving the prosthetic valve in the delivery configuration, (iv) a delivery device including a handle and a delivery catheter extending therefrom for delivering the prosthetic valve in the delivery configuration to a space within the heart such as an atrium, (v) a control device, controller, and/or actuator such as a multi-lumen control catheter or the like for engaging and/or actuating one or more portions of the prosthetic valve, and (vi) a guidewire catheter for coupling to the prosthetic valve and for receiving a guidewire allowing the prosthetic valve to be advanced along the guidewire during delivery and/or deployment.

Any of the delivery systems described herein can include a delivery catheter for side-delivery of a side-deliverable prosthetic valve. The delivery catheter can include an outer shaft having an outer proximal end, an outer distal end, and an outer shaft lumen, wherein the outer distal end is closed with an atraumatic ball mounted thereon. The outer shaft lumen has an inner diameter of 8-10 mm sized for passage of a side delivered transcatheter prosthetic valve (e.g., a prosthetic tricuspid valve and/or a prosthetic mitral valve) therethrough.

Any of the delivery systems described herein can include a delivery catheter, a control catheter, and/or other suitable portion that includes one or more members, components, features, and/or the like configured to facilitate at least partial retrieval of the valve from an annulus of a native heart valve. For example, such a delivery system can include, for example, a self-expanding capture element that can be placed in an extended position to at least partially surround and/or capture a portion of the prosthetic valve. In some implementations, the prosthetic valve can be pulled and/or drawn into the self-expanding capture element by virtue of a control catheter and/or other component attached to the prosthetic valve during delivery and/or deployment. As such, the self-expanding capture element can surround and/or capture at least a portion of the prosthetic valve, which in turn, can facilitate a transitioning of the prosthetic valve from an at least partially expanded configuration to an at least partially compressed configuration, allowing the prosthetic valve to be at least partially retracted into the delivery catheter used to deliver the prosthetic valve.

Any method for delivering and deploying a prosthetic valve in an annulus of a native heart valve can include removably coupling a prosthetic valve or an outer frame thereof to a portion of a delivery system. The prosthetic valve is placed into a delivery configuration, loaded into a delivery device including a delivery catheter, and advanced through a lumen of a delivery catheter. The prosthetic valve can then be released from a distal end of the delivery catheter, which is disposed in an atrium of the heart. In some implementations, after releasing the prosthetic valve, a proximal anchoring element of a subannular member of the prosthetic valve can be placed in a first configuration and the prosthetic valve is seated in the annulus of the native heart valve while the proximal anchoring element is in the first configuration. The proximal anchoring element can then be transitioned from the first configuration to a second configuration after seating the prosthetic valve in the annulus. In some implementations, the method for delivering and/or deploying the prosthetic valve can optionally include retrieving at least a portion of the prosthetic valve from the annulus to allow for a repositioning and/or reseating of at least a portion of the prosthetic valve.

Any method for delivering and/or deploying prosthetic heart valves described herein can include orthogonal delivery of the prosthetic heart valve to a native annulus of a human heart that includes at least one of (i) advancing a delivery catheter to the tricuspid valve or pulmonary artery of the heart through the inferior vena cava (IVC) via the femoral vein, (ii) advancing to the tricuspid valve or pulmonary artery of the heart through the superior vena cava (SVC) via the jugular vein, or (iii) advancing to the mitral valve of the heart through a trans-atrial approach (e.g., fossa ovalis or lower), via the IVC-femoral or the SVC jugular approach; and (iv) delivering and/or deploying the prosthetic heart valve to the native annulus by releasing the valve from the delivery catheter.

Any method for delivering prosthetic valves described herein can include placing the prosthetic valves in a delivery configuration. The delivery configuration can include at least one of (i) compressing the valve along a central vertical axis to reduce a vertical dimension of the valve from top to bottom to place the valve in the delivery configuration, (ii) flattening the valve into two parallel panels that are substantially parallel to the long-axis to place the valve in the delivery configuration, or (iii) flattening the valve into two parallel panels that are substantially parallel to the long-axis and then compressing the valve along a central vertical axis to reduce a vertical dimension of the valve from top to bottom to place the valve in the delivery configuration.

Any method for delivering prosthetic valves described herein can include orthogonal delivery of the prosthetic valve to a desired location in the body that includes advancing a delivery catheter to the desired location in the body and delivering the prosthetic valve to the desired location in the body by releasing the valve from the delivery catheter. The valve is in a compressed or delivery configuration when in the delivery catheter and transitions to an expanded or released configuration when released from the delivery catheter.

Any method for delivering prosthetic valves described herein can include releasing the valve from the delivery catheter by (i) pulling the valve out of the delivery catheter using a pulling member (e.g., a wire or rod) that is releasably connected to a sidewall, a drum or collar, and/or an anchoring element (e.g., a distal anchoring element), wherein advancing the pulling member away from the delivery catheter pulls the valve out of the delivery catheter, or (ii) pushing the valve out of the delivery catheter using a pushing member (e.g., a wire, rod, catheter, delivery member, yoke, etc.) that is releasably connected to a sidewall, a drum or collar, and/or an anchoring element (e.g., a proximal and/or distal anchoring element), wherein advancing the pushing member out of a distal end of the delivery catheter pushes the valve out of the delivery catheter. Moreover, releasing the valve from the delivery catheter allows the valve to transition and/or expand from its delivery configuration to an expanded and/or deployment configuration.

Any method for delivering and/or deploying prosthetic valves described herein can include releasing the valve from a delivery catheter while increasing blood flow during deployment of the valve by (i) partially releasing the valve from the delivery catheter to establish blood flow around the partially released valve and blood flow through the flow control component; (ii) completely releasing the valve from the delivery catheter while maintaining attachment to the valve to transition to a state with increased blood flow through the flow control component and decreased blood flow around the valve; (iii) deploying the valve into a final mounted or seated position in a native annulus to transition to a state with complete blood flow through the flow control component and minimal or no blood flow around the valve; and (iv) disconnecting and withdrawing a positioning catheter, pulling or pushing wire or rod, delivery catheter, actuator, and/or other suitable portion of a delivery system.

In some implementations, prior to the disconnecting and withdrawing, the method optionally can include transitioning the valve to a secured or cinched state via an actuator or portion of a delivery system such that the valve contacts annular tissue to secure the valve in the native annulus. In some implementations, prior to the disconnecting and withdrawing, the method optionally can include retrieving, at least in part, the valve from the annulus and repositioning at least a portion of the valve in the annulus. In some implementations, the retrieving can include retrieving and/or retracting at least a portion of the valve into the delivery catheter.

Any method for delivering and/or deploying prosthetic valves described herein can include positioning the valve or a portion thereof in a desired position relative to the native tissue. For example, the method can include positioning a distal anchoring tab of the heart valve prosthesis into a ventricular outflow tract of the left or right ventricle. In some embodiments, the method can further include positioning an upper distal anchoring tab into a supra-annular position, where the upper distal anchoring tab provides a supra-annular downward force in the direction of the ventricle and the distal anchoring tab (e.g., the lower distal anchoring tab) provides a subannular upward force in the direction of the atrium. In some implementations, the method can include partially inserting the prosthetic valve into the annulus such that a distal portion thereof contact native annular tissue while a proximal portion of the prosthetic valve is at least partially compressed and disposed in the delivery catheter. In some embodiments, the method can include rotating the heart valve prosthesis, using a steerable catheter, a yoke, a set of tethers, an actuator, and/or any other portion of a delivery system (or combinations thereof), along an axis parallel to the plane of the valve annulus. In some embodiments, the method can include transitioning one or more anchoring elements into a desired position and/or state to engage native tissue surrounding at least a portion of the annulus. In some implementations, one or more tissue anchors may be attached to the valve and to native tissue to secure the valve in a desired position.

Any method for at least partially retrieving prosthetic valves described herein can include (i) extending a self-expanding capture element from a distal end of a delivery catheter that is disposed in an atrium of a heart, wherein the capture element is configured to have a cavity shape when in an extended position, and (ii) pulling the heart valve into the cavity of the extended capture element to facilitate compression of the heart valve to or toward its delivery (compressed) configuration, wherein pulling the heart valve into the capture element transitions the capture element from the extended position to a retracted position, wherein the heart valve is encompassed by the capture element in the retracted position, and wherein the heart valve-capture element combination is pulled into the delivery and/or retrieval catheter (e.g., using a cable, control catheter, actuator, and/or any other suitable portion of a delivery and retrieval system. In some implementations, the method optionally can include pre-compressing the valve by (a) suturing a proximal sub-annular anchoring element against an underside of an atrial or supra-annular collar or member, or (b) pinching proximal sidewall hips of the prosthetic valve, or (c) both, prior to pulling the heart valve into the cavity of the capture element, and subsequently into the delivery and/or retrieval catheter.

Any of the prosthetic valves (or components, features, and/or aspects thereof), delivery systems, methods of manufacturing, methods of delivery, methods of deployment, and/or methods of retrieval described herein can be similar to and/or substantially the same as any of those described in International Patent Application No. PCT/US2019/051087, filed Sep. 19, 2019, entitled "Transcatheter Deliverable Prosthetic Heart Valves and Method of Delivery" (referred to herein as "the '957 PCT"); International Patent Application No. PCT/US2019/067010, filed Dec. 18, 2019, entitled "Transcatheter Deliverable Prosthetic Heart Valves and Methods of Delivery" (referred to herein as "the '010 PCT"); International Patent Application No. PCT/US2020/015231, filed Jan. 27, 2020, entitled "Collapsible Inner Flow Control Component for Side-Deliverable Transcatheter Heart Valve Prosthesis" (referred to herein as "the '231 PCT"); International Patent Application No. PCT/US2020/031390, filed May 4, 2020, entitled "Cinch Device and Method for Deployment of a Side-Delivered Prosthetic Heart Valve in a Native Annulus," (referred to herein as "the '390 PCT"); and/or International Patent Application No. PCT/US2020/045108, filed Aug. 6, 2020, entitled "Side-Deliverable Transcatheter Prosthetic Valves and Methods for Delivering and Anchoring the Same" (referred to herein as "the '108 PCT"), the disclosures of which are incorporated herein by reference in their entireties.

Likewise, any of the prosthetic valves (or components, features, and/or aspects thereof), delivery systems, methods of manufacturing, methods of delivery, methods of deployment, and/or methods of retrieval described herein can be similar to and/or substantially the same as any of those described in U.S. Provisional Patent Application No. 62/889,327 (referred to herein as "the '327' Provisional"); U.S. Provisional Patent Application No. 62/891,964 (referred to herein as "the '964 Provisional"); U.S. Provisional Patent Application No. 63/027,345 (referred to herein as "the '345 Provisional"); and/or U.S. Provisional Patent Application No. 63/038,807 (referred to herein as "the '807 Provisional"); to which this application claims priority to and the benefit of and the disclosures of which have been incorporated above by reference in their entireties.

The terminology used herein is for the purpose of describing particular embodiments only and is not intended to limit the full scope of the claims. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention.

As used herein, the singular forms "a," "an," and "the" are intended to include the plural forms as well, unless the context clearly indicates otherwise. With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

In general, terms used herein, and especially in the appended claims (e.g., bodies of the appended claims) are generally intended as "open" terms (e.g., the term "including" should be interpreted as "including but not limited to," the term "having" should be interpreted as "having at least," etc.). Similarly, the terms "comprises" and/or "comprising," when used in this specification, specify the presence of stated features, integers (or fractions thereof), steps, operations, elements, and/or components, but do not preclude the presence or addition of one or more other features, integers (or fractions thereof), steps, operations, elements, components, and/or groups thereof. As used in this document, the term "comprising" means "including, but not limited to."

As used herein the term "and/or" includes any and all combinations of one or more of the associated listed items. It should be understood that any suitable disjunctive word and/or phrase presenting two or more alternative terms, whether in the description, claims, or drawings, contemplate the possibilities of including one of the terms, either of the terms, or both terms. For example, the phrase "A or B" will be understood to include the possibilities of "A" or "B" or "A and B."

All ranges disclosed herein also encompass any and all possible subranges and combinations of subranges thereof unless expressly stated otherwise. Any listed range should be recognized as sufficiently describing and enabling the same range being broken down into at least equal subparts unless expressly stated otherwise. As will be understood by one skilled in the art, a range includes each individual member.

The term "valve prosthesis," "prosthetic heart valve," and/or "prosthetic valve" can refer to a combination of a frame and a leaflet or flow control structure or component, and can encompass both complete replacement of an anatomical part (e.g., a new mechanical valve replaces a native valve), as well as medical devices that take the place of and/or assist, repair, or improve existing anatomical parts (e.g., the native valve is left in place).

Prosthetic valves disclosed herein can include a member (e.g., a frame) that can be seated within a native valve annulus and can be used as a mounting element for a leaflet structure, a flow control component, or a flexible reciprocating sleeve or sleeve-valve. It may or may not include such a leaflet structure or flow control component, depending on the embodiment. Such members can be referred to herein as an "annular support frame," "tubular frame," "wire frame," "valve frame," "flange," "collar," and/or any other similar terms.

The term "flow control component" can refer in a non-limiting sense to a leaflet structure having 2-, 3-, 4-leaflets of flexible biocompatible material such a treated or untreated pericardium that is sewn or joined to an annular support frame, to function as a prosthetic heart valve. Such a valve can be a heart valve, such as a tricuspid, mitral, aortic, or pulmonary, that is open to blood flowing during diastole from atrium to ventricle, and that closes from systolic ventricular pressure applied to the outer surface. Repeated opening and closing in sequence can be described as "reciprocating." The flow control component is contemplated to include a wide variety of (bio)prosthetic artificial heart valves. Bioprosthetic pericardial valves can include bioprosthetic aortic valves, bioprosthetic mitral valves, bioprosthetic tricuspid valves, and bioprosthetic pulmonary valves.

Any of the disclosed valve embodiments may be delivered by a transcatheter approach. The term "transcatheter" is used to define the process of accessing, controlling, and/or delivering a medical device or instrument within the lumen of a catheter that is deployed into a heart chamber (or other desired location in the body), as well as an item that has been delivered or controlled by such as process. Transcatheter access is known to include cardiac access via the lumen of the femoral artery and/or vein, via the lumen of the brachial artery and/or vein, via lumen of the carotid artery, via the lumen of the jugular vein, via the intercostal (rib) and/or sub-xiphoid space, and/or the like. Moreover, transcatheter cardiac access can be via the inferior vena cava (IVC), superior vena cava (SVC), and/or via a trans-atrial (e.g., fossa ovalis or lower). Transcatheter can be synonymous with transluminal and is functionally related to the term "percutaneous" as it relates to delivery of heart valves. As used herein, the term "lumen" can refer to the inside of a cylinder or tube. The term "bore" can refer to the inner diameter of the lumen.

The mode of cardiac access can be based at least in part on a "body channel," used to define a blood conduit or vessel within the body, and the particular application of the disclosed embodiments of prosthetic valves can determine the body channel at issue. An aortic valve replacement, for example, would be implanted in, or adjacent to, the aortic annulus. Likewise, a tricuspid or mitral valve replacement would be implanted at the tricuspid or mitral annulus, respectively. While certain features described herein may be particularly advantageous for a given implantation site, unless the combination of features is structurally impossible or excluded by claim language, any of the valve embodiments described herein could be implanted in any body channel.

The term "expandable" as used herein may refer to a prosthetic heart valve or a component of the prosthetic heart valve capable of expanding from a first, delivery size or configuration to a second, implantation size or configuration. An expandable structure, therefore, is not intended to refer to a structure that might undergo slight expansion, for example, from a rise in temperature or other such incidental cause, unless the context clearly indicates otherwise. Conversely, "non-expandable" should not be interpreted to mean completely rigid or a dimensionally stable, as some slight expansion of conventional "non-expandable" heart valves, for example, may be observed.

The prosthetic valves disclosed herein and/or components thereof are generally capable of transitioning between two or more configurations, states, shapes, and/or arrangements. For example, prosthetic valves described herein can be "compressible" and/or "expandable" between any suitable number of configurations. Various terms can be used to describe or refer to these configurations and are not intended to be limiting unless the context clearly states otherwise. For example, a prosthetic valve can be described as being placed in a "delivery configuration," which may be any suitable configuration that allows or enables delivery of the prosthetic valve. Examples of delivery configurations can include a compressed configuration, a folded configuration, a rolled configuration, and/or similar configuration or any suitable combinations thereof. Similarly, a prosthetic valve can be described as being placed in an "expanded configuration," which may be any suitable configuration that is not expressly intended for delivery of the prosthetic valve. Examples of expanded configuration can include a released configuration, a relaxed configuration, a deployed configuration, a non-delivery configuration, and/or similar configurations or any suitable combinations thereof. Some prosthetic valves described herein and/or components or features thereof can have a number of additional configurations that can be associated with various modes, levels, states, and/or portions of actuation, deployment, engagement, etc. Examples of such configurations can include an actuated configuration, a seated configuration, a secured configuration, an engaged configuration, and/or similar configurations or any suitable combinations thereof. While specific examples are provided above, it should be understood that they are not intended to be an exhaustive list of configurations. Other configurations may be possible. Moreover, various terms can be used to describe the same or substantially similar configurations and thus, the use of particular terms are not intended to be limiting and/or to the exclusion of other terms unless the terms and/or configurations are mutually exclusive, or the context clearly states otherwise.

In general, traditional delivery of prosthetic valves can be such that a central cylinder axis of the valve is substantially parallel to a lengthwise axis of a delivery catheter used to deliver the valve. Typically, the valves are compressed in a radial direction relative to the central cylinder axis and advanced through the lumen of the delivery catheter. The valves are deployed from the end of the delivery catheter and expanded outwardly in a radial direction from the central cylinder axis. The delivery orientation of the valve generally means that the valve is completely released from the delivery catheter while in the atrium of the heart and reoriented relative to the annulus, which in some instances, can limit a size of the valve.

The prosthetic valves described herein are configured to be delivered via side or orthogonal delivery techniques, unless clearly stated otherwise. As used herein the terms "side-delivered," "side-delivery," "orthogonal delivery," "orthogonally delivered," and/or so forth can be used interchangeably to describe such a delivery method and/or a valve delivered using such a method. Orthogonal delivery of prosthetic valves can be such that the central cylinder axis of the valve is substantially orthogonal to the lengthwise axis of the delivery catheter. With orthogonal delivery, the valves are compressed (or otherwise reduced in size) in a direction substantially parallel to the central cylinder axis and/or in a lateral direction relative to the central cylinder axis. As such, a lengthwise axis (e.g., a longitudinal axis) of an orthogonally delivered valve is substantially parallel to the lengthwise axis of the delivery catheter. In other words, an orthogonally delivered prosthetic valve is compressed and/or delivered at a roughly 90-degree angle compared to traditional processes of compressing and delivering transcatheter prosthetic valves. Moreover, in some instances, the orientation of orthogonally delivered valves relative to the annulus can allow a distal portion of the valve to be at least partially inserted into the annulus of the native heart valve while the proximal portion of the valve, at least in part, remains in the delivery catheter, thereby avoiding at least some of the size constraints faced with some know traditional delivery techniques. Examples of prosthetic valves configured to be orthogonally delivered and processes of delivering such valves are described in detail in the '957 PCT and/or the '010 PCT incorporated by reference hereinabove.

Mathematically, the term "orthogonal" refers to an intersecting angle of 90 degrees between two lines or planes. As used herein, the term "substantially orthogonal" refers to an intersecting angle of 90 degrees plus or minus a suitable tolerance. For example, "substantially orthogonal" can refer to an intersecting angle ranging from 75 to 105 degrees.

The embodiments herein, and/or the various features or advantageous details thereof, are explained more fully with reference to the non-limiting embodiments that are illustrated in the accompanying drawings and detailed in the following description. Descriptions of well-known components and processing techniques are omitted so as to not unnecessarily obscure the embodiments herein. Like numbers refer to like elements throughout.

A discussion of various embodiments, components, and/or features of a prosthetic valve is followed by a discussion of delivery and/or retrieval system 180s used to delivery, deploy, and/or at least partially retrieve such prosthetic valves. The examples and/or embodiments described herein are intended to facilitate an understanding of structures, functions, and/or aspects of the embodiments, ways in which the embodiments may be practiced, and/or to further enable those skilled in the art to practice the embodiments herein. Similarly, methods and/or ways of using the embodiments described herein are provided by way of example only and not limitation. Specific uses described herein are not provided to the exclusion of other uses unless the context expressly states otherwise. For example, any of the prosthetic valves described herein can be used to replace a native valve of a human heart including, for example, a mitral valve, a tricuspid valve, an aortic valve, and/or a pulmonary valve. While some prosthetic valves are described herein in the context of replacing a native mitral valve or a native tricuspid valve, it should be understood that such a prosthetic valve can be used to replace any native valve unless expressly stated otherwise or unless one skilled in the art would clearly recognize that one or more components and/or features would otherwise make the prosthetic valve incompatible for such use. Accordingly, specific examples, embodiments, methods, and/or uses described herein should not be construed as limiting the scope of the inventions or inventive concepts herein. Rather, examples and embodiments are provided so that this disclosure will be thorough and complete, and will fully convey the scope of the inventive concepts to those skilled in the art.

FIGS. 1A-1E are various schematic illustrations of a transcatheter prosthetic valve 100 according to an embodiment. The transcatheter prosthetic valve 100 is configured to be deployed in a desired location within a body (e.g., of a human patient) and to permit blood flow in a first direction through an inflow end of the transcatheter prosthetic valve 100 and to block blood flow in a second direction, opposite the first direction, through an outflow end of the transcatheter prosthetic valve 100. For example, the transcatheter prosthetic valve 100 can be a transcatheter prosthetic heart valve configured to be deployed within the annulus of a native tricuspid valve or native mitral valve of a human heart to supplement and/or replace the functioning of the native valve.

The transcatheter prosthetic valve 100 (also referred to herein as "prosthetic valve" or simply "valve") is compressible and expandable in at least one direction relative to a long-axis 102 of the valve 100 (also referred to herein as "horizontal axis," "longitudinal axis," or "lengthwise axis"). The valve 100 is compressible and expandable between an expanded configuration (FIGS. 1A, 1C, and 1E) for implanting at a desired location in a body (e.g., a human heart) and a compressed or delivery configuration (FIGS. 1B and 1D) for introduction into the body using a delivery catheter.

In some embodiments, the valve 100 (and/or at least a portion thereof) may start in a roughly tubular configuration and may be heat-shaped and/or otherwise formed into any desired shape. In some embodiments, the valve 100 can include an upper atrial cuff or flange for atrial sealing, a lower ventricle cuff or flange for ventricular sealing, and a transannular section or region (e.g., a body section, a tubular section, a cylindrical section, etc.) disposed therebetween. The transannular region can have an hourglass cross-section for about 60-80% of the circumference to conform to the native annulus along the posterior and anterior annular segments while remaining substantially vertically flat along 20-40% of the annular circumference to conform to the septal annular segment. While the valve 100 is shown in FIGS. 1A-1E as having a given shape, it should be understood that the size and/or shape of the valve 100 (and/or at least a portion thereof) can be based on a size and/or shape of the anatomical structures of the native tissue.

For example, the valve 100 can be centric (e.g., radially symmetrical relative to a central y-axis 104), or can be eccentric (e.g., radially asymmetrical relative to the central y-axis axis 104). In some eccentric embodiments, the valve 100, or an outer frame thereof, may have a complex shape determined by the anatomical structures where the valve 100 is being mounted. For example, in some instances, the valve 100 may be deployed in the tricuspid annulus having a circumference in the shape of a rounded ellipse with a substantially vertical septal wall, and which is known to enlarge in disease states along an anterior-posterior line. In some instances, the valve 100 may be deployed in the mitral annulus (e.g., near the anterior leaflet) having a circumference in the shape of a rounded ellipse with a substantially vertical septal wall, and which is known to enlarge in disease states. As such, the valve 100 can have a complex shape that determined, at least in part, by the native annulus and/or a disease state of the native valve. For example, in some such embodiments, the valve 100 or the outer frame thereof may have a D-shape (viewed from the top) so the flat portion can be matched to the anatomy in which the valve 100 will be deployed.

As shown, the valve 100 generally includes an annular support frame 110 and a flow control component 150. In addition, the valve 100 and/or at least the annular support frame 110 of the valve 100 can include and/or can couple to an actuator 170 and/or a delivery system interface 180. In some implementations, the valve 100 and/or aspects or portions thereof can be similar to and/or substantially the same as the valves (and/or the corresponding aspects or portions thereof) described in detail in the '957 PCT, the '010 PCT, the '231 PCT, the '390 PCT, the '108 PCT, the '327 Provisional, the '964 Provisional, the '345 Provisional, and/or the '807 Provisional incorporated by reference hereinabove. Accordingly, certain aspects, portions, and/or details of the valve 100 may not be described in further detail herein.

The annular support frame 110 (also referred to herein as "tubular frame," "valve frame," "wire frame," "outer frame," or "frame") can have a supra-annular region 120, a subannular region 130, and a transannular region 112, disposed and/or coupled therebetween. In some embodiments, the supra-annular region 120, the subannular region 130, and the transannular region 112 can be separate, independent, and/or modular components that are coupled to collectively form the frame 110. In some implementations, such a modular configuration can allow the frame 110 to be adapted to a given size and/or shape of the anatomical structures where the valve 100 is being mounted. For example, one or more of the supra-annular region(s) 120, the subannular region 130, and/or the transannular region 112 can be designed and/or adapted so that that the support frame has any desirable height, outer diameter, and/or inner diameter such as any of those described above. Moreover, such a modular configuration can allow the frame 110 to bend, flex, compress, fold, roll, and/or otherwise reconfigure without plastic or permanent deformation thereof. For example, the frame 110 is compressible to a compressed configuration for delivery and when released it is configured to return to its original shape (uncompressed or expanded configuration).

The support frame 110 and/or the supra-annular region 120, subannular region 130, and/or transannular region 112 can be formed from or of any suitable material. In some embodiments, the supra-annular region 120, the subannular region 130, and the transannular region 112 can be formed from or of a shape-memory or superelastic metal, metal alloy, plastic, and/or the like. For example, the supra-annular region 120, the subannular region 130, and the transannular region 112 can be formed from or of Nitinol or the like. Moreover, the supra-annular region 120, the subannular region 130, and the transannular region 112 can be coupled to from a wire frame portion of the support frame 110, which in turn, is covered by a biocompatible material such as, for example, pericardium tissue (e.g., Duraguard®, PeriGuard®, Vascu-Guard®, etc.), polymers (e.g., polyester, Dacron®, etc.), and/or the like, as described above.

The supra-annular region 120 of the frame 110 can be and/or can form, for example, a cuff or collar that can be attached or coupled to an upper edge or upper portion of the transannular region 112, as described in further detail herein. When the valve 100 is deployed within a human heart, the supra-annular region 120 can be an atrial collar that is shaped to conform to the native deployment location. In a tricuspid and/or mitral valve replacement, for example, the supra-annular region 120 collar can have various portions configured to conform to the native valve and/or a portion of the atrial floor surrounding the tricuspid and/or mitral valve, respectively. In some implementations, the supra-annular region 120 can be deployed on the atrial floor to direct blood from the atrium into the flow control component 150 of the valve 100 and to seal against blood leakage (perivalvular leakage) around the frame 110.

In some embodiments, the supra-annular region 120 can be a wire frame that is laser cut out of any suitable material. In some embodiments, the supra-annular region 120 can be formed from a shape-memory or superelastic material such as, for example, Nitinol. In some embodiments, the supra-annular region 120 can be laser cut from a sheet of a shape-memory metal alloy such as Nitinol and, for example, heat-set into a desired shape and/or configuration. In some embodiments, forming the supra-annular region 120 in such a manner can allow the supra-annular region 120 to bend, flex, fold, compress, and/or otherwise reconfigure substantially without plastically deforming and/or without fatigue that may result in failure or breaking of one or more portions thereof. Moreover, the wire frame of the supra-annular region 120 can be covered by any suitable biocompatible material such as any of those described above.

As shown in FIG. 1A, the supra-annular region 120 includes a distal portion 122 and a proximal portion 124. In some embodiments, the distal portion 122 can be and/or can include a distal supra-annular anchoring element and/or the like that can engage native tissue on a distal side of the annulus as the prosthetic valve 100 is seated into the annulus. In some embodiments, the proximal portion 124 can be and/or can include a proximal supra-annular anchoring element and/or the like that can engage native tissue on a proximal side of the annulus as the prosthetic valve 100 is seated in the annulus. In some embodiments, the distal portion 122 and/or the distal supra-annular anchoring element can be sized and/or shaped to correspond to a size and/or shape of the distal portion of the atrial floor of the heart in which the prosthetic valve 100 is disposed. Similarly, the proximal portion 124 and/or the proximal supra-annular anchoring element can be sized and/or shaped to correspond to a size and/or shape of a proximal portion of the atrial floor of the heart.

Although not shown in FIGS. 1A-1E, the supra-annular region 120 can be shaped and/or formed to include any number of features configured to engage native tissue and/or one or more other portions of the valve 100, the actuator 170, and/or the delivery system interface 180. For example, in some embodiments, the supra-annular region 120 can include and/or can form an outer portion, an inner portion, and one or more splines disposed between the outer portion and the inner portion. In some implementations, the outer portion can be sized and/or shaped to engage native tissue, the inner portion can provide structure for mounting the flow control component 150 to the support frame 110, and the one or more splines can receive, couple to, and/or otherwise engage the actuator 170 and/or the delivery system interface 180, as described in further detail herein with reference to specific embodiments.

The subannular region 130 of the frame 110 can be and/or can form, for example, a cuff or collar that can be attached or coupled to a lower edge or upper portion of the transannular region 112, as described in further detail herein. When the valve 100 is deployed within a human heart, the subannular region 130 can be a ventricular collar that is shaped to conform to the native deployment location. In a tricuspid and/or mitral valve replacement, for example, the subannular region 130 collar can have various portions configured to conform to the native valve and/or a portion of the ventricular ceiling surrounding the tricuspid and/or mitral valve, respectively. In some implementations, the subannular region 130 or at least a portion thereof can engage the ventricular ceiling surrounding the native annulus to secure the valve 100 in the native annulus, to prevent dislodging of the valve 100, to sandwich or compress the native annulus or adjacent tissue between the supra-annular region 120 and the subannular region 130, and/or to seal against blood leakage (perivalvular leakage and/or regurgitation during systole) around the frame 110.

In some embodiments, the subannular region 130 can be a wire frame that is laser cut out of any suitable material. In some embodiments, the subannular region 130 can be formed from a shape-memory or superelastic material such as, for example, Nitinol. In some embodiments, the subannular region 130 can be laser cut from a sheet of a shape-memory metal alloy such as Nitinol and, for example, heat-set into a desired shape and/or configuration. In some embodiments, forming the subannular region 130 in such a manner can allow the subannular region 130 to bend, flex, fold, compress, and/or otherwise reconfigure substantially without plastically deforming and/or without fatigue that may result in failure or breaking of one or more portions thereof. Moreover, the wire frame of the subannular region 130 can be covered by any suitable biocompatible material such as any of those described above.

The subannular region 130 can be shaped and/or formed to include any number of features configured to engage native tissue, one or more other portions of the valve 100, and/or the actuator 170. For example, in some embodiments, the subannular region 130 can include and/or can form a distal portion having a distal anchoring element 132 and a proximal portion having a proximal anchoring element 134. In some embodiments, the subannular region 130 can include and/or can form any other suitable anchoring element (not shown in FIGS. 1A-1E). In some embodiments, the anchoring elements 132 and 134 are integrally and/or monolithically formed with the subannular region 130. The distal anchoring element 132 and the proximal anchoring element 134 of the subannular region 130 can be any suitable shape, size, and/or configuration such as any of those described in detail in the '957 PCT, the '010 PCT, the '231 PCT, the '390 PCT, the '108 PCT, the '327 Provisional, the '964 Provisional, the '345 Provisional, and/or the '807 Provisional, and/or any of those described herein with respect to specific embodiments. For example, the anchoring elements 132 and 134 can extend from a portion of the subannular region 130 by about 10-40 mm.

In some embodiments, the distal anchoring element 132 can optionally include a guidewire coupler configured to selectively engage and/or receive a portion of a guidewire or a portion of a guidewire assembly. The guidewire coupler is configured to allow a portion of the guidewire to extend through an aperture of the guidewire coupler, thereby allowing the valve 100 to be advanced over or along the guidewire during delivery and deployment. In some embodiments, the guidewire coupler can selectively allow the guidewire to be advanced therethrough while blocking or preventing other elements and/or components such as a pusher or the like.

The anchoring elements 132 and/or 134 of the subannular region 130 can be configured to engage a desired portion of the native tissue to mount the valve 100 and/or the support frame 110 to the annulus of the native valve in which it is deployed. For example, in some implementations, the distal anchoring element 132 can be a projection or protrusion extending from the subannular region 130 and into a RVOT or a LVOT. In such implementations, the distal anchoring element 132 can be shaped and/or biased such that the distal anchoring element 132 exerts a force on the subannular tissue operable to at least partially secure the distal end portion of the valve 100 in the native annulus. In some implementations, the proximal anchoring element 134 can be configured to engage subannular tissue on a proximal side of the native annulus to aid in the securement of the valve 100 in the annulus.

In some implementations, at least the proximal anchoring element 134 can be configured to transition, move, and/or otherwise reconfigure between a first configuration in which the proximal anchoring element 134 extends from the subannular region 130 a first amount or distance and a second configuration in which the proximal anchoring element 134 extends from the subannular region 130 a second amount or distance. For example, in some embodiments, the proximal anchoring element 134 can have a first configuration in which the proximal anchoring element 134 is in a compressed, contracted, retracted, undeployed, folded, and/or restrained state (e.g., a position that is near, adjacent to, and/or in contact with the transannular region 112 and/or the supra-annular region 120 of the support frame 110), and a second configuration in which the proximal anchoring element 134 is in an expanded, extended, deployed, unfolded, and/or unrestrained state (e.g., extending away from the transannular region 112). Moreover, in some implementations, the proximal anchoring element 134 can be transitioned in response to actuation of the actuator 170, as described in further detail herein.

In some implementations, the proximal anchoring element 134 can be transitioned from the first configuration to the second configuration during deployment to selectively engage native tissue, chordae, trabeculae, annular tissue, leaflet tissue, and/or any other anatomic structures to aid in the securement of the valve 100 in the native annulus. The proximal anchoring element 134 (and/or the distal anchoring element 132) can include any suitable feature, surface, member, etc. configured to facilitate the engagement between the proximal anchoring element 134 (and/or the distal anchoring element 132) and the native tissue. For example, in some embodiments, the proximal anchoring element 134 can include one or more features configured to engage and/or become entangled in the native tissue, chordae, trabeculae, annular tissue, leaflet tissue, and/or any other anatomic structures when in the second configuration, as described in further detail herein with reference to specific embodiments.

The transannular region 112 of the support frame 110 is disposed between the supra-annular region 120 and the subannular region 130. In some embodiments, the transannular region 112 can be coupled to each of the supra-annular region 120 and the subannular region 130 such that a desired amount of movement and/or flex is allowed therebetween (e.g., welded, bonded, sewn, bound, and/or the like). For example, in some implementations, the transannular region 112 and/or portions thereof can be sewn to each of the supra-annular region 120 and the subannular region 130 (and/or portions thereof).

The transannular region 112 can be shaped and/or formed into a ring, a cylindrical tube, a conical tube, D-shaped tube, and/or any other suitable annular shape. In some embodiments, the transannular region 112 may have a side profile of a flat-cone shape, an inverted flat-cone shape (narrower at top, wider at bottom), a concave cylinder (walls bent in), a convex cylinder (walls bulging out), an angular hourglass, a curved, graduated hourglass, a ring or cylinder having a flared top, flared bottom, or both. Moreover, the transannular region 112 can form and/or define an aperture or central channel 114 that extends along the central axis 104 (e.g., the y-axis). The central channel 114 (e.g., a central axial lumen or channel) can be sized and configured to receive the flow control component 150 across a portion of a diameter of the central channel 114. In some embodiments, the transannular region 112 can have a shape and/or size that is at least partially based on a size, shape, and/or configuration of the supra-annular region 120 and/or subannular region 130 of the support frame 110, and/or the native annulus in which it is configured to be deployed. For example, the transannular region 112 can have an outer circumference surface for engaging native annular tissue that may be tensioned against an inner aspect of the native annulus to provide structural patency to a weakened native annular ring.

In some embodiments, the transannular region 112 can be a wire frame that is laser cut out of any suitable material. In some embodiments, the transannular region 112 can be formed from a shape-memory or superelastic material such as, for example, Nitinol. In some embodiments, the transannular region 112 can be laser cut from a sheet of a shape-memory metal alloy such as Nitinol and, for example, heat-set into a desired shape and/or configuration. Although not shown in FIGS. 1A-1E, in some embodiments, the transannular region 112 can include and/or can be formed with two laser cut halves that can be formed into a desired shape and/or configuration and coupled together to form the transannular region 112. The transannular region 112 can be formed to include a set of compressible wire cells having an orientation and/or cell geometry substantially orthogonal to the central axis 104 (FIG. 1A) to minimize wire cell strain when the transannular region 112 is in a vertical compressed configuration, a rolled and compressed configuration, or a folded and compressed configuration. In some embodiments, forming the transannular region 112 in such a manner can allow the transannular region 112 to bend, flex, fold, deform, and/or otherwise reconfigure (substantially without plastic deformation and/or undue fatigue) in response to lateral folding along or in a direction of a lateral axis 106 (FIG. 1C) and/or vertical compression along or in a direction of the central axis 104 (FIG. 1D), as described in further detail herein.

As described above with reference to the supra-annular region 120 and the subannular region 130, the wire frame of the transannular region 112 can be covered by any suitable biocompatible material such as any of those described above. In some implementations, the wire frames of the supra-annular region 120, transannular region 112, and subannular region 130 can be flexibly coupled (e.g., sewn) to form a wire frame portion of the support frame 110, which in turn, is covered in the biocompatible material. Said another way, the supra-annular region 120, the transannular region 112, and the subannular region 130 can be covered with the biocompatible material prior to being coupled or after being coupled. In embodiments in which the wire frames are covered after being coupled, the biocompatible material can facilitate and/or support the coupling therebetween.

Although not shown in FIGS. 1A-1E, the frame 110 may also have and/or form additional functional elements (e.g., loops, anchors, etc.) for attaching accessory components such as biocompatible covers, tissue anchors, releasable deployment and retrieval controls (e.g., the actuator 170, the delivery system interface 180, and/or other suitable guides, knobs, attachments, rigging, etc.) and so forth. In some implementations, the frame 110 (or aspects and/or portions thereof) can be structurally and/or functionally similar to the frames (or corresponding aspects and/or portions thereof) described in detail in the '957 PCT, the '010 PCT, the '231 PCT, the '390 PCT, the '108 PCT, the '327 Provisional, the '964 Provisional, the '345 Provisional, and/or the '807 Provisional.

The flow control component 150 can refer in a non-limiting sense to a device for controlling fluid flow therethrough. In some embodiments, the flow control component 150 can be a leaflet structure having 2-leaflets, 3-leaflets, 4-leaflets, or more, made of flexible biocompatible material such a treated or untreated pericardium. The leaflets can be sewn or joined to a support structure such as an inner frame, which in turn, can be sewn or joined to the outer frame 110. The leaflets can be configured to move between an open and a closed or substantially sealed state to allow blood to flow through the flow control component 150 in a first direction through an inflow end of the valve 100 and block blood flow in a second direction, opposite to the first direction, through an outflow end of the valve 100. For example, the flow control component 150 can be configured such that the valve 100 functions, for example, as a heart valve, such as a tricuspid valve, mitral valve, aortic valve, or pulmonary valve, that can open to blood flowing during diastole from atrium to ventricle, and that can close from systolic ventricular pressure applied to the outer surface. Repeated opening and closing in sequence can be described as "reciprocating."

The inner frame and/or portions or aspects thereof can be similar in at least form and/or function to the outer frame 110 and/or portions or aspects thereof. For example, the inner frame can be a laser cut wire frame formed from or of a shape-memory material such as Nitinol. Moreover, the inner frame can be compressible for delivery and configured to return to its original (uncompressed) shape when released (e.g., after delivery). In some embodiments, the inner frame can include and/or can form any suitable number of compressible, elastically deformable diamond-shaped or eye-shaped wire cells, and/or the like. The wire cells can have an orientation and cell geometry substantially orthogonal to an axis of the flow control component 150 to minimize wire cell strain when the inner frame is in a compressed configuration.

Figure 1B:
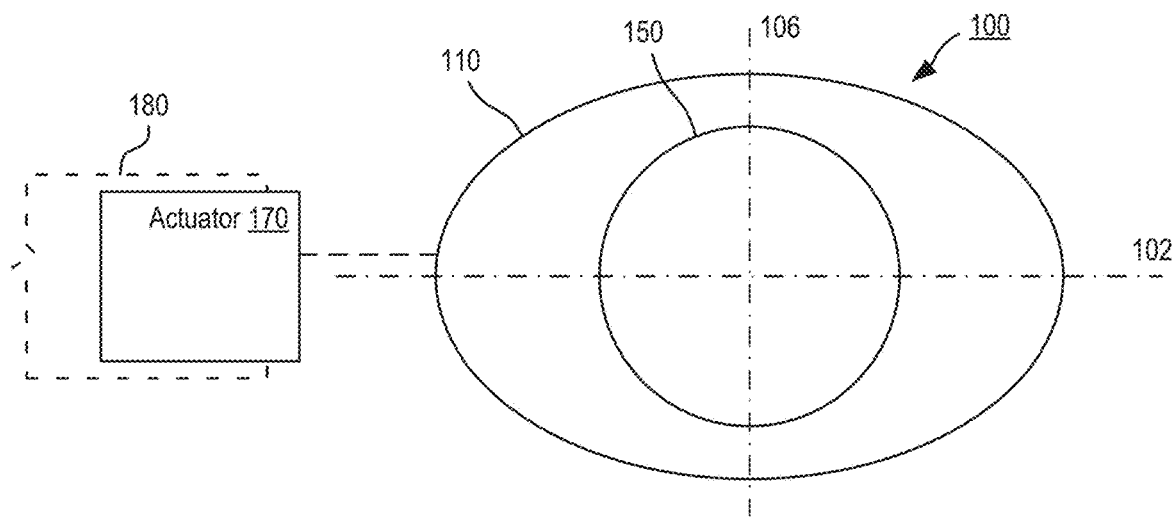
Figure 1C:
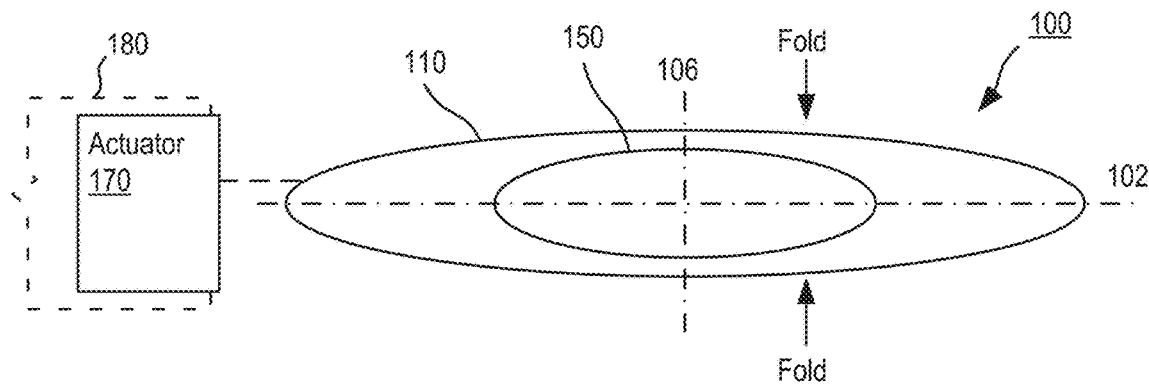
FIGS. 1C and 1D are top view schematic illustrations of the prosthetic valve of FIGS. 1A and 1B and shown in the expanded configuration and the compressed configuration, respectively.
Figure 1D:
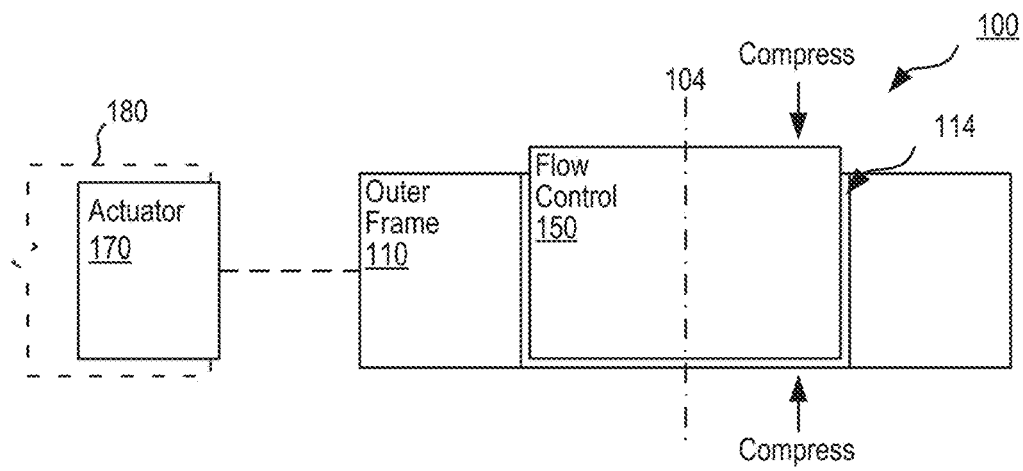

In some embodiments, the flow control component 150 and/or the inner frame thereof can have a substantially cylindrical or tubular shape when the valve 100 is in the expanded configuration (see e.g., FIG. 1C) and can be configured to elastically deform when the valve 100 is placed in the compressed configuration (see e.g., FIGS. 1B and 1D). Although not shown in FIGS. 1A-1E, in some embodiments, the inner frame of the flow control component 150 can include and/or can be formed with two halves that can be coupled together to allow the inner frame to elastically deform in response to lateral compression or folding along or in a direction of the lateral axis 106 (FIG. 1C), as described in further detail herein.

As shown in FIGS. 1A-1D, the flow control component 150 is mounted within the central channel 114 of the frame 110. More specifically, the flow control component 150 is mounted and/or coupled to the supra-annular region 120 (e.g., an inner portion thereof) and is configured to extended into and/or through the central channel 114 formed and/or defined by the transannular region 112. In some embodiments, the flow control component 150 can be coupled to the supra-annular region 120 via tissue, a biocompatible mesh, one or more woven or knitted fabrics, one or more superelastic or shape-memory alloy structures, which is sewn, sutured, and/or otherwise secured to a portion supra-annular region 120. In some embodiments, the flow control component 150 can be coupled to the supra-annular region 120 such that a portion of the flow control component 150 is disposed above and/or otherwise extends beyond the supra-annular region 120 (e.g., extends away from the annulus in the direction of the atrium). In some embodiments, the portion of the flow control component 150 extending above and/or beyond the supra-annular region 120 can form a ridge, ledge, wall, step-up, and/or the like. In some implementations, such an arrangement can facilitate ingrowth of native tissue over the supra-annular region 120 without occluding the flow control component 150.

The flow control component 150 can be at least partially disposed in the central channel 114 such that the axis of the flow control component 150 that extends in the direction of blood flow through the flow control component 150 is substantially parallel to the central axis 104 of the frame 110. In some embodiments, the arrangement of the support frame 110 can be such that the flow control component 150 is centered within the central channel 114. In other embodiments, the arrangement of the support frame 110 can be such that the flow control component 150 is off centered within the central channel 114. In some embodiments, the central channel 114 can have a diameter and/or perimeter that is larger than a diameter and/or perimeter of the flow control component 150. Although not shown in FIGS. 1A-1E, in some embodiments, the valve 100 can include a spacer or the like that can be disposed within the central channel 114 adjacent to the flow control component 150. In other embodiments, a spacer can be a cover, or the like coupled to a portion of the frame 110 and configured to cover a portion of the central channel 114. In some instances, the spacer can be used to facilitate the coupling of the flow control component 150 to the frame 110.

In some embodiments, the flow control component 150 (or portions and/or aspects thereof) can be similar to, for example, any of the flow control components described in the '231 PCT. Thus, the flow control component 150 and/or aspects or portions thereof are not described in further detail herein.

Referring back to FIG. 1A, the valve 100 includes and/or is coupled to the actuator 170 and the delivery interface 180. The actuator 170 can be any suitable member, mechanism, and/or device configured to actuate at least a portion of the valve 100. For example, in some embodiments, the actuator 170 and/or a portion of the actuator 170 can be configured to at least temporarily couple to the supra-annular region 120 of the support frame 110 (e.g., a spline and/or other portion thereof) and can be configured to actuate one or more portions of the valve 100. More specifically, the actuator 170 can be configured to actuate at least the proximal anchoring element 134 of the subannular region 120 of the support frame 110 to transition the proximal anchoring element 134 between its first and second configurations. In some implementations, the actuator 170 can include one or more cables, tethers, linkages, joints, connections etc., that can exert a force (or can remove an exerted force) on a portion of the proximal anchoring element 134 operable to transition the proximal anchoring element 134 between the first and second configuration. For example, the subannular region 130 of the support frame 110 can be formed with the proximal anchoring element 134 biased in the uncompressed and/or expanded configuration and the actuator 170 can be actuated to exert a force, via the one or more cables, tethers, etc., operable to transition the proximal anchoring element 134 to the compressed and/or retracted configuration.

In some implementations, the actuator 170 can be secured and/or locked when the proximal anchoring element 134 is compressed and/or retracted (e.g., a first configuration) to at least temporarily maintain the proximal anchoring element 134 in the first configuration. As described above, in some implementations, the proximal anchoring element 134 can be in the first configuration for delivery and deployment prior to seating the valve 100 in the native annulus. Once the valve 100 is seated in the native annulus, a user can manipulate a portion of the delivery system to actuate the actuator 170. In this example, actuating the actuator 170 can cause the actuator 170 to release and/or remove the force exerted on the proximal anchoring element 134 (e.g., via the cable(s), tether(s), etc.), thereby allowing the proximal anchoring element 134 to return to its original or biased configuration (e.g., a second configuration), as described above.

The delivery system interface 180, shown in FIG. 1A, can include any number of components having any suitable shape, size, and/or configuration. In some implementations, the delivery system interface 180 can be and/or can include, for example, a distal end portion of the delivery system used to deliver the valve 100 to a desired location in the body of a patient (e.g., the annulus of a native heart valve). In some embodiments, the delivery system interface can include a delivery catheter such as, for example, a 12-34 Fr delivery catheter with any suitable corresponding internal lumen diameter sufficient to receive the prosthetic valve 100 in the compressed configuration, as described, for example, in the '957 PCT. Moreover, the delivery system can include a secondary catheter that can be, for example, a multi-lumen catheter configured to engage the valve 100 to advance the valve 100 through the delivery catheter. In some embodiments, each lumen of the multi-lumen secondary catheter can include, for example, a cable, tether, and/or any other suitable component associated with and/or included in the actuator 170. Each cable, tether, and/or component can, in turn, be coupled to a portion of the valve 100 or support frame 110 and configured to actuate a portion thereof, as described in further detail herein with reference to specific embodiments.

Furthermore, a lumen of the multi-lumen secondary catheter (e.g., a central lumen) can include and/or can receive a torque cable and a guidewire. The guidewire extends though the secondary catheter and into a desired position relative to the native tissue (e.g., the RVOT or the LVOT) to provide a path along which the valve 100 travels during delivery and/or deployment, as described in the '957 PCT. The torque cable can be any suitable cable, or the like configured to removably couple to the supra-annular region 120 of the frame 110 (e.g., a waypoint coupled to and/or formed by the supra-annular region 120). The torque cable can be a relatively stiff cable that can be configured to facilitate delivery and/or deployment of the valve 100 as well as retraction of the valve 100 if desirable. In this manner, the delivery system interface 180 shown in FIG. 1A, can be a distal end portion of the delivery system including any of the components described above. Thus, the delivery system interface 180 can be used in and/or otherwise can facilitate delivery of the valve 100, deployment and/or actuation of the valve 100 or a portion thereof (e.g., the proximal anchoring element 134), and/or retraction of the valve 100.

Moreover, the delivery system interface 180 can be configured to decouple, disengage, and/or otherwise release the valve 100 after the valve 100 is deployed in a native annulus, as described in further detail herein with reference to specific embodiments.

As described above, the valve 100 is compressible and expandable between the expanded configuration and the compressed configuration. The valve 100 can have a first height or size along the central axis 104 when in the expanded configuration and can have a second height or size, less than the first height or size, along the central axis 104 when in the compressed configuration. The valve 100 can also be compressed in additional directions. For example, the valve 100 can be compressed along the lateral axis 106 that is perpendicular to both the longitudinal axis 102 and the central axis 104 (see e.g., FIGS. 1B and 1C).

The valve 100 is compressed during delivery of the valve 100 and is configured to expand once released from the delivery catheter. More specifically, the valve 100 is configured for transcatheter orthogonal delivery to the desired location in the body (e.g., the annulus of a native valve), in which the valve 100 is compressed in an orthogonal or lateral direction relative to the dimensions of the valve 100 in the expanded configuration (e.g., along the central axis 104 and/or the lateral axis 106). During delivery, the longitudinal axis 102 of the valve 100 is substantially parallel to a longitudinal axis of the delivery catheter, as described in the '957 PCT.

The valve 100 is in the expanded configuration prior to being loaded into the delivery system and after being released from the delivery catheter and deployed or implanted (or ready to be deployed or implanted) at the desired location in the body. When in the expanded configuration shown in FIGS. 1A, 1B, and 1E, the valve 100 has an extent in any direction orthogonal or lateral to the longitudinal axis 102 (e.g., along the central axis 104 and/or the lateral axis 106) that is larger than a diameter of the lumen of the delivery catheter used to deliver the valve 100. For example, in some embodiments, the valve 100 can have an expanded height (e.g., along the central axis 104) of 5-60 mm. In some embodiments, the valve 100 can have an expanded diameter length (e.g., along the longitudinal axis 102) and width (e.g., along the lateral axis 106) of about 20-80 mm, or about 40-80 mm.

When in the compressed configuration shown in FIGS. 1C and 1D, the valve 100 has an extent in any direction orthogonal or lateral to the longitudinal axis 102 (e.g., along the central axis 104 and/or the lateral axis 106) that is smaller than the diameter of the lumen of the delivery catheter, allowing the valve 100 to be delivered therethrough. For example, in some embodiments, the valve 100 can have a compressed height (e.g., along the central axis 104) and a compressed width (e.g., along the lateral axis 106) of about 6-15 mm, about 8-12 mm, or about 9-10 mm. The valve 100 can be compressed by compressing, rolling, folding, and/or any other suitable manner, or combinations thereof, as described in detail in the '957 PCT, the '010 PCT, the '231 PCT, the '390 PCT, the '108 PCT, the '327 Provisional, the '964 Provisional, the '345 Provisional, and/or the '807 Provisional. It is contemplated in some embodiments that the length of the valve 100 (e.g., along the longitudinal axis 102) is not compressed for delivery. Rather, in some embodiments, the length of the valve 100 can be increased in response to compression of the valve 100 along the central axis 104 and/or the lateral axis 106.

Figure 1E:
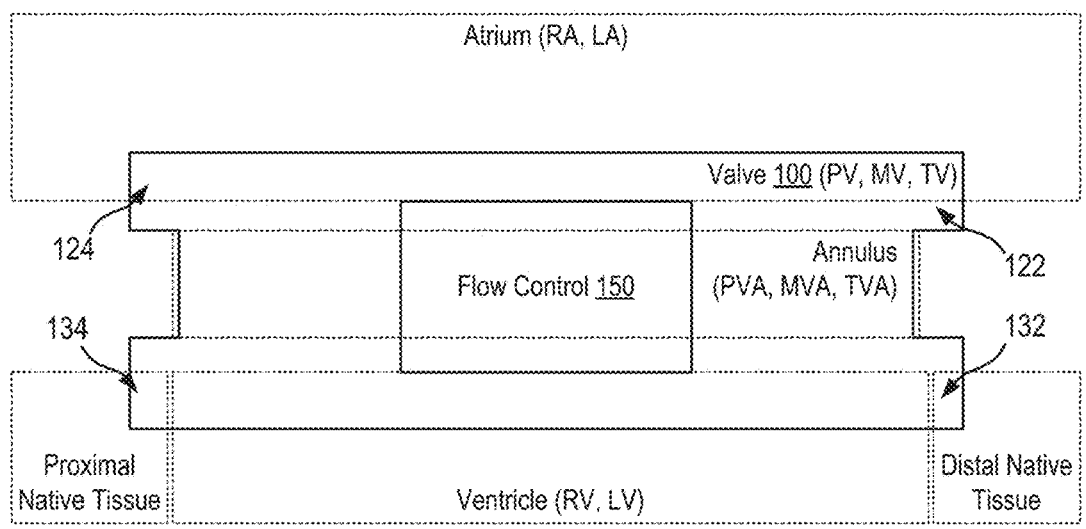
FIG. 1E is a schematic illustration of the prosthetic valve of FIGS. 1A-1D deployed within an annulus of a native heart valve.

As shown in FIG. 1E, the valve 100 can be delivered, for example, to an atrium of the human heart and disposed within an annulus of a native valve such as, for example, the pulmonary valve (PV), the mitral valve (MV), the aortic valve (AV), and/or the tricuspid valve (TV). As described above, the valve 100 can be in the compressed configuration and delivered to the annulus via the delivery system and can be released from the delivery system and allowed to expand to the expanded configuration. For example, the valve 100 can be delivered to the atrium of the human heart and released from the delivery catheter (not shown) via any of the delivery systems, devices, and/or methods described in detail in the '957 PCT, the '010 PCT, the '231 PCT, the '390 PCT, the '108 PCT, the '327 Provisional, the '964 Provisional, the '345 Provisional, and/or the '807 Provisional.

In some implementations, the delivery of the valve 100 can include advancing a guidewire into the atrium of the human heart, through the native valve, and to a desired position within the ventricle (e.g., the RVOT or the LVOT). After positioning the guidewire, the delivery catheter can be advanced along and/or over the guidewire and into the atrium (e.g., via the IVC, the SVC, and/or a trans-septal access). In some embodiments, a guidewire coupler of the valve 100 (e.g., included in or on the distal anchoring element 132) can be coupled to a proximal end portion of the guidewire and the valve 100 can be placed in the compressed configuration, allowing the valve 100 to be advanced along the guidewire and through a lumen of the delivery catheter, and into the atrium.

The deployment of the valve 100 can include placing the distal anchoring element 132 of the subannular region 130 in the ventricle (RV, LV) below the annulus while the remaining portions of the valve 100 are in the atrium (RA, LA). In some instances, the distal anchoring element 132 can be advanced over and/or along the guidewire to a desired position within the ventricle such as, for example, an outflow tract of the ventricle. For example, in some implementations, the valve 100 can be delivered to the annulus of the native tricuspid valve (TV) and at least a portion of the distal anchoring element 132 can be positioned in the RVOT. In other implementations, the valve 100 can be delivered to the annulus of the native mitral valve (MV) and at least a portion of the distal anchoring element 132 can be positioned in the LVOT.

In some implementations, the prosthetic valve 100 can be temporarily maintained in a partially deployed state. For example, the valve 100 can be partially inserted into the annulus and held at an angle relative to the annulus to allow blood to flow from the atrium to the ventricle partially through the native valve annulus around the valve 100, and partially through the valve 100, which can allow for assessment of the valve function.

The valve 100 can be placed or seated in the annulus (PVA, MVA, AVA, and/or TVA) of the native valve (PV, MV, AV, and/or TV) such that the subannular region 130 (e.g., a ventricular collar) is disposed in a subannular position, the transannular region 112 of the valve frame 110 extends through the annulus, and the supra-annular region 120 (e.g., a atrial collar) remains in a supra-annular position. For example, in some embodiments, the delivery system, the delivery system interface 180, the actuator 170, and/or any other suitable member, tool, etc. can be used to push at least the proximal end portion of the valve 100 into the annulus. In some implementations, the proximal anchoring element 134 can be maintained in its first configuration as the valve 100 is seated in the annulus. For example, as described above, the proximal anchoring element 134 can be in a compressed, contracted, and/or retracted configuration in which the proximal anchoring element 134 is in contact with, adjacent to, and/or near the transannular region 112 and/or the supra-annular region 120 of the frame 110, which in turn, can limit an overall circumference of the subannular region 130 of the frame 110, thereby allowing the subannular region 130 and the transannular region 112 of the frame 110 to be inserted into and/or through the annulus.

Once seated, the proximal anchoring element 134 can be transitioned from its first configuration to its second configuration, as described in detail in the '010 PCT, the '108 PCT, and/or the '345 Provisional. For example, in some implementations, a user can manipulate a portion of the delivery system to actuate the actuator 170. In some implementations, actuating the actuator 170 can release and/or reduce an amount of tension within or more tethers, cables, connections, and/or portions of the actuator 170, thereby allowing the proximal anchoring element 134 to transition Accordingly, once the valve 100 is seated in the annulus, the proximal anchoring element 134 can be placed in its second configuration in which the proximal anchoring element 134 contacts, engages, and/or is otherwise disposed adjacent to subannular tissue. In some implementations, the proximal anchoring element 134 can be configured to engage and/or capture native tissue, chordae, trabeculae, annular tissue, leaflet tissue, and/or the like when the proximal anchoring element 134 is disposed in the ventricle. For example, in some implementations, after seating the valve 100 in the annulus, the proximal anchoring element 134 can be transitioned from the first (compressed) configuration to the second (extended) configuration such that the proximal anchoring element 134 extends around and/or through one or more portions of native tissue, chordae, etc. The proximal anchoring element 134 can then be returned to the first configuration to capture and/or secure the one or more portions of native tissue, chordae, trabeculae, annular tissue, leaflet tissue, etc. between the proximal anchoring element 134 and, for example, the transannular section of the outer frame 110. In other implementations, the proximal anchoring element 134 can be maintained in the second (extended) configuration after the valve 100 is seated in the native annulus. In such implementations, the proximal anchoring element 134, for example, can contact and/or engage subannular tissue on a proximal side of the annulus such that the proximal anchoring element and a proximal portion of the atrial collar exert a compressive force on a proximal portion of the annular tissue.

In this manner, the distal anchoring element 132 can be configured to engage native tissue on a distal side of the annulus and the proximal anchoring element 134 can be configured to engage native tissue on a proximal side of the annulus (e.g., when in the second or expanded configuration), thereby securely seating the valve 100 in the native annulus, as shown in FIG. 1E. In some implementations, any other or additional portions of the valve can similarly engage native tissue to securely seat the valve 100 in the native annulus and/or to form a seal between the support frame 110 and the tissue forming the native annulus (e.g., the distal portion 122 and/or the proximal portion 124 of the supra-annular region 120, the transannular region 112, and/or one or more other or additional anchoring elements (not shown in FIGS. 1A-1E).

While not shown in FIGS. 1A-1E, in some implementations, the valve 100 and/or the delivery system can include one or more tissue anchors that can be used to anchor one or more portions of the valve 100 to the annular tissue, as described in detail in the '957 PCT. In some embodiments, the tissue anchors can be configured to puncture, pierce, and/or otherwise secure the anchoring elements 132 and/or 134, and/or the atrial collar to the annular tissue. In other embodiments, the tissue anchors can be, for example, atraumatic anchors configured to secure the anchoring elements 132 and/or 134, and/or the atrial collar to the annular tissue without puncturing, piercing, and/or otherwise causing trauma to the native tissue.

FIGS. 2A-2D are schematic illustrations of an annular support frame 210 according to an embodiment. The annular support frame 210 (also referred to herein as "tubular frame," "valve frame," "wire frame," "outer frame," "support frame," or "frame") can include and/or can be coupled to an actuator 270 configured to actuate one or more portions of the support frame 210. In some embodiments, the support frame 210 and/or the actuator 270 can be substantially similar in at least form and/or function to the support frame 110 and/or the actuator 170, respectively, described above with reference to FIGS. 1A-1E. Thus, portions and/or aspects of the support frame 210 and/or the actuator 270 are not described in further detail herein.

As shown, the annular support frame 210 has a supra-annular member and/or region 220, a subannular member and/or region 230, and a transannular member and/or region 212, disposed and/or coupled therebetween. In the embodiment shown in FIGS. 2A-2D, the supra-annular member and/or region 220, the subannular member and/or region 230, and the transannular member and/or region 212 are separate, independent, and/or modular components that are coupled to collectively form the frame 210. Each of the supra-annular member and/or region 220, the subannular member and/or region 230, and the transannular member and/or region 212 (referred to herein as the supra-annular, subannular, and transannular "member") are a wire frame that is laser cut out of any suitable material such as a shape-memory or superelastic material like Nitinol. In some implementations, each of the supra-annular member 220, the subannular member 230, and the transannular member 212 can be laser cut from a sheet of Nitinol and, for example, heat-set into a desired shape and/or configuration. As described above, forming the supra-annular member 220, the subannular member 230, and the transannular member 212 in such a manner can provide a desired amount of flexibility and/or resistance to plastic or permanent deformation that can allow the frame 210 to be folded and/or compressed for delivery. Moreover, the wire frame portions of the supra-annular member 220, the subannular member 230, and the transannular member 212 can be covered by any suitable biocompatible material such as any of those described above.

In some embodiments, the supra-annular member 220 of the frame 210 can be similar in at least form and/or function to the supra-annular member 120 described above with reference to FIGS. 1A-1E. For example, the supra-annular member 220 can be and/or can form, for example, a cuff or collar that can be attached or coupled to an upper edge or upper portion of the transannular member 212, as described in further detail herein. In some implementations, the supra-annular member 220 can be deployed on the atrial floor to direct blood from the atrium into a flow control component mounted to the frame 210, as described in detail above. The supra-annular member 220 can be shaped and/or formed to include any number of features configured to engage native tissue and/or one or more other portions of the frame 210 and/or the actuator 270. For example, in some embodiments, the supra-annular member 220 can include and/or can form an outer portion or loop, an inner portion or loop, and one or more splines disposed between the outer and inner portions or loops.

In some embodiments, the outer portion or loop (referred to herein as "outer loop") can be shaped and/or sized to engage native tissue. More specifically, the supra-annular member 220 (or an outer loop thereof) can have a distal portion 222 configured to engage distal supra-annular tissue and a proximal portion 224 configured to engage proximal supra-annular tissue. In some embodiments, the distal and proximal portions 222 and 224 can have a rounded and/or curved shape, wherein a radius of curvature of the proximal portion 224 is larger than a radius of curvature of the distal portion 222. In some implementations, the distal portion 222 can form, for example, a distal upper anchoring element that can engage distal supra-annular tissue to at least partially stabilize and/or secure the frame 210 in the native annulus. Similarly, the proximal portion 224 can form, for example, a proximal upper anchoring element that can engage proximal supra-annular tissue to at least partially stabilize and/or secure the frame 210 in the native annulus.

The inner portion or loop (referred to herein as "inner loop") of the supra-annular member 220 can be substantially circular and can be coupled to and/or suspended from the outer loop by the one or more splines. As described in further detail herein with reference to specific embodiments, the inner loop can be coupled to an inner frame of the flow control component to at least partially mount the flow control component to the support frame 210. In some implementations, suspending the inner loop from the outer loop (via the one or more splines) can, for example, at least partially isolate the inner loop from at least a portion of the force associated with transitioning the frame 210 between the expanded configuration and the compressed configuration, as described in further detail herein. Moreover, mounting the flow control component to the inner loop of the supra-annular member 220 similarly at least partially isolates and/or reduces an amount of force transferred to the flow control component when the frame 210 is transitioned between its expanded configuration and its compressed configuration.

The one or more splines of the supra-annular member 220 can be any suitable shape, size, and/or configuration. For example, in some embodiments, the supra-annular member 220 can include a distal spline and a proximal spline. As described above, the splines can be configured to support the inner loop and/or otherwise couple the inner loop to the outer loop. In some embodiments, the supra-annular member 220 can include a spline (e.g., a proximal spline) configured to receive, couple to, and/or otherwise engage the actuator 270 and/or delivery system interface. For example, in some embodiments, a proximal spline can form a connection point, attachment point, waypoint, and/or any other suitable feature that can temporarily and/or removably couple to the actuator 270, as described in further detail herein with reference to specific embodiments.

In some embodiments, the subannular member 230 of the frame 210 can be similar in at least form and/or function to the subannular region 130 described above with reference to FIGS. 1A-1E. For example, the subannular member 230 of the frame 210 can be and/or can form, for example, a cuff or collar that can be attached or coupled to a lower edge or upper portion of the transannular member 212, as described in further detail herein. When the frame 210 is deployed within a human heart, the subannular member 230 can be a ventricular collar that is shaped to conform to the native deployment location. In a tricuspid and/or mitral valve replacement, for example, the subannular member 230 collar can have various portions configured to conform to the native valve and/or a portion of the ventricular ceiling surrounding the tricuspid and/or mitral valve, respectively. In some implementations, the subannular member 230 or at least a portion thereof can engage the ventricular ceiling surrounding the native annulus to secure the frame 210 in the native annulus, to prevent dislodging of the frame 210, to sandwich or compress the native annulus or adjacent tissue between the supra-annular member 220 and the subannular member 230, and/or to seal against blood leakage (perivalvular leakage and/or regurgitation during systole) around the frame 210.

The subannular member 230 can be shaped and/or formed to include any number of features configured to engage native tissue, one or more other portions of the frame 210, and/or the actuator 270. For example, in some embodiments, the subannular member 230 can include and/or can form a distal portion having a distal anchoring element 232 and a proximal portion having a proximal anchoring element 234. In some embodiments, the subannular member 230 can include and/or can form any other suitable anchoring element (not shown in FIGS. 2A-2D). In some embodiments, the anchoring elements 232 and 234 are integrally and/or monolithically formed with the subannular member 230. The distal anchoring element 232 and the proximal anchoring element 234 of the subannular member 230 can be any suitable shape, size, and/or configuration such as any of those described in detail in the '957 PCT, the '010 PCT, the '231 PCT, the '390 PCT, the '108 PCT, the '327 Provisional, the '964 Provisional, the '345 Provisional, the '807 Provisional, any of those described above with reference to the valve 100, and/or any of those described herein with respect to specific embodiments.

In some embodiments, the distal anchoring element 232 can optionally include a guidewire coupler configured to selectively engage and/or receive a portion of a guidewire or a portion of a guidewire assembly. The guidewire coupler is configured to allow a portion of the guidewire to extend through an aperture of the guidewire coupler, thereby allowing the frame 210 to be advanced over or along the guidewire during delivery and deployment. In some embodiments, the guidewire coupler can selectively allow the guidewire to be advanced therethrough while blocking or preventing other elements and/or components such as a pusher or the like.

The anchoring elements 232 and/or 234 of the subannular member 230 can be configured to engage a desired portion of the native tissue to mount the frame 210 to the annulus of the native valve in which it is deployed. For example, in some implementations, the distal anchoring element 232 can be a projection or protrusion extending from the subannular member 230 and into a RVOT or a LVOT. In such implementations, the distal anchoring element 232 can be shaped and/or biased such that the distal anchoring element 232 exerts a force on the subannular tissue operable to at least partially secure the distal end portion of the frame 210 in the native annulus. In some implementations, the proximal anchoring element 234 can be configured to engage subannular tissue on a proximal side of the native annulus to aid in the securement of the frame 210 in the annulus.

In some implementations, at least the proximal anchoring element 234 can be configured to transition, move, and/or otherwise reconfigure between a first configuration in which the proximal anchoring element 234 extends from the subannular member 230 a first amount or distance and a second configuration in which the proximal anchoring element 234 extends from the subannular member 230 a second amount or distance. As described above, the subannular member 230 of the frame 210 can be and/or can include, for example, a laser cut wire frame formed of a shape-memory material such as Nitinol, which is heat-set into a desired shape. In some embodiments, heat-setting the subannular member 230 can include forming one or more twists in a portion of the laser cut wire, which in turn, can allow one or more portions of the subannular member 230 to be biased in different directions and/or orientations. For example, in general, the subannular member 230 of the frame 210 can be formed to provide a high amount of flexibility in a direction that allows the subannular member 230 to be folded and/or compressed (e.g., relative to a longitudinal axis of the subannular member 230). In some embodiments, however, a portion of the subannular member 230 can be twisted and/or otherwise oriented to provide a high amount of flexibility in a direction that allows the proximal anchoring element 234 to be actuated and/or to otherwise transition between its first and second configurations (e.g., in a direction orthogonal to the longitudinal axis of the subannular member 230 and orthogonal to a fold and/or compression direction.

In some embodiments, the proximal anchoring element 234 can be in a compressed, contracted, retracted, undeployed, folded, and/or restrained state (e.g., a position that is near, adjacent to, and/or in contact with the transannular member 212 and/or the supra-annular member 220 of the support frame 210) when in the first configuration, and can be in an expanded, extended, deployed, unfolded, and/or unrestrained state (e.g., extending away from the transannular member 212) when in the second state. In some embodiments, the proximal anchoring element 234 can be biased and/or heat-set in the second configuration. Moreover, in some implementations, the proximal anchoring element 234 can be transitioned in response to actuation of the actuator 270, as described in further detail herein.

In some implementations, the proximal anchoring element 234 can be transitioned from the first configuration to the second configuration during deployment to selectively engage native tissue, chordae, trabeculae, annular tissue, leaflet tissue, and/or any other anatomic structures to aid in the securement of the frame 210 in the native annulus. The proximal anchoring element 234 (and/or the distal anchoring element 232) can include any suitable feature, surface, member, etc. configured to facilitate the engagement between the proximal anchoring element 234 (and/or the distal anchoring element 232) and the native tissue. For example, in some embodiments, the proximal anchoring element 234 can include one or more features configured to engage and/or become entangled in the native tissue, chordae, trabeculae, annular tissue, leaflet tissue, and/or any other anatomic structures when in the second configuration, as described in further detail herein with reference to specific embodiments.

In some embodiments, the transannular member 212 of the frame 210 can be similar in at least form and/or function to the transannular region 112 described above with reference to FIGS. 1A-1E. For example, the transannular member 212 is disposed between the supra-annular member 220 and the subannular member 230. In some embodiments, the transannular member 212 can be coupled to each of the supra-annular member 220 and the subannular member 230 such that a desired amount of movement and/or flex is allowed therebetween (e.g., welded, bonded, sewn, bound, and/or the like). For example, in some implementations, the transannular member 212 and/or portions thereof can be sewn to each of the supra-annular member 220 and the subannular member 230 (and/or portions thereof). The transannular member 212 can be shaped and/or formed into a ring, a cylindrical tube, a conical tube, D-shaped tube, and/or any other suitable annular shape, as described above with reference to the transannular member 112. In some embodiments, the transannular member 212 can have a shape and/or size that is at least partially based on a size, shape, and/or configuration of the supra-annular member 220 and/or subannular member 230 of the support frame 210, the flow control component configured to be coupled to the support frame 210, and/or the native annulus in which it is configured to be deployed. For example, the transannular member 212 can have an outer circumference surface for engaging native annular tissue that may be tensioned against an inner aspect of the native annulus to provide structural patency to a weakened native annular ring.

As described above, the supra-annular member 220, the subannular member 230, and the transannular member 212 can be independent and/or modular components that are coupled to collectively form the frame 210. In some embodiments, the supra-annular member 220 is configured to engage supra-annular tissue of the native valve and can be shaped and/or biased to form a substantially fluid tight seal with the atrial floor to limit and/or substantially prevent leakage around the frame (e.g., perivalvular leaks). Similarly, the subannular member 220 is configured to engage subannular tissue of the native valve and can be shaped and/or biased to form a substantially fluid tight seal with the ventricular ceiling to limit and/or substantially prevent leakage around the frame. Moreover, in some implementations, the transannular member 212 can have a slightly oversized circumference relative to the native annular tissue and can, for example, form at least a partial seal between the transannular member 212 of the frame 210 and the native tissue forming the walls of the annulus. In such implementations, forming a seal against the atrial floor, the ventricular ceiling, and the walls of the annulus can provide redundancy in the event of an imperfect or partial seal formed by one or more of the supra-annular member(s) 220, the subannular member 230, and/or the transannular member 212.

In other implementations, the distal and proximal anchoring elements 232 and 234 can exert a force on the subannular tissue that is operable in pulling the supra-annular member 220 of the frame 210 toward the atrial floor, thereby facilitating the formation of a seal. In such implementations, for example, the subannular member 230 and/or the transannular member 212 need not form a seal or can form a partially seal with the native tissue because of the seal formed by the supra-annular member 220.

In some implementations, the arrangement of the frame 210 can be such that structural support and/or stiffness is provided by the supra-annular member 220 and the subannular member 230, while the transannular member 212 need not provide substantial support and/or stiffness. In some such implementations, the transannular member 212 can be configured to couple the supra-annular member 220 to the subannular member 230 and to easily deform (elastically) for delivery rather than provide substantial support and/or stiffness. Moreover, while the transannular member 212 is described above as being formed by a laser cut wire frame that is covered by biocompatible material, in other embodiments, the transannular member 212 can be formed from any suitable flexible material such as pericardial tissue, fabric, polyester, and/or the like. In some such embodiments, forming the flexible material without the laser cut wire frame can, for example, reduce a size of the frame 210 when in the compressed configuration, thereby allowing a valve to be delivered using a smaller delivery catheter. In some embodiments, the frame 210 need not include a separate transannular member 212. For example, in such embodiments, a flow control component can be coupled between the supra-annular member 220 and the subannular member 230, thereby allowing a further reduction in a size of a valve in the compressed configuration.

As shown in FIGS. 2A-2D, the actuator 270 can be at least temporarily coupled to the supra-annular member 220 and the subannular member 230. In some embodiments, the actuator 270 or a portion thereof can also at least temporarily couple to a portion of the transannular member 212. The actuator 270 can be any suitable member, mechanism, and/or device configured to actuate at least a portion of the frame 210. Moreover, a portion of the actuator 270 can extend through a portion of a delivery system used to deliver the frame 210 and/or a valve including the frame 210. In this manner, a user can manipulate a proximal end portion of the actuator 270 to actuate the actuator 270.

In some embodiments, the actuator 270 and/or a portion of the actuator 270 can be configured to at least temporarily couple to the spline of the supra-annular member 220 (e.g., an attachment point, waypoint, connector, threaded coupler, etc.) and can be configured to actuate one or more portions of the frame 210. The actuator 270 can be configured to actuate at least the proximal anchoring element 234 of the subannular member 220 of the support frame 210 to transition the proximal anchoring element 234 between its first and second configurations (described above).

In some implementations, the actuator 270 can include one or more cables, tethers, linkages, joints, connections etc., that can exert a force (or can remove an exerted force) on a portion of the proximal anchoring element 234 operable to transition the proximal anchoring element 234 between the first and second configuration. For example, the actuator 270 can couple to a waypoint or the like of the supra-annular member 220 and can include one or more tethers, cables, and/or members that extend through the waypoint and/or one or more openings or apertures and couple to the proximal anchoring element 234. In some implementations, the one or more tethers, cables, and/or members can be removably and/or temporarily coupled to the proximal anchoring element 234, as described, for example, in the '010 PCT, the '108 PCT, and/or the '345 Provisional.

Figure 2A:
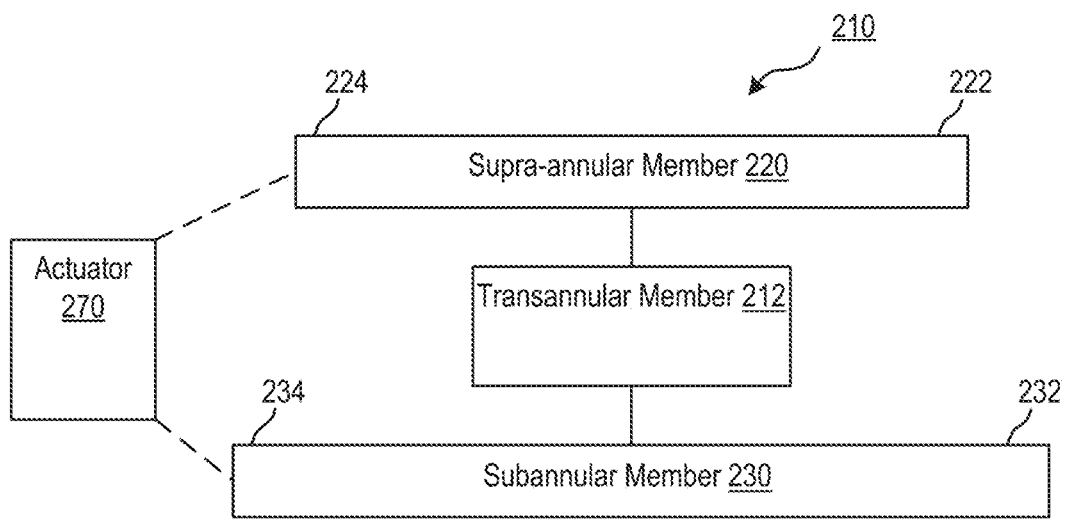
FIGS. 2A and 2B are side-view schematic illustrations of a prosthetic valve in a first configuration and a second configuration, respectively, according to an embodiment.
Figure 2B:
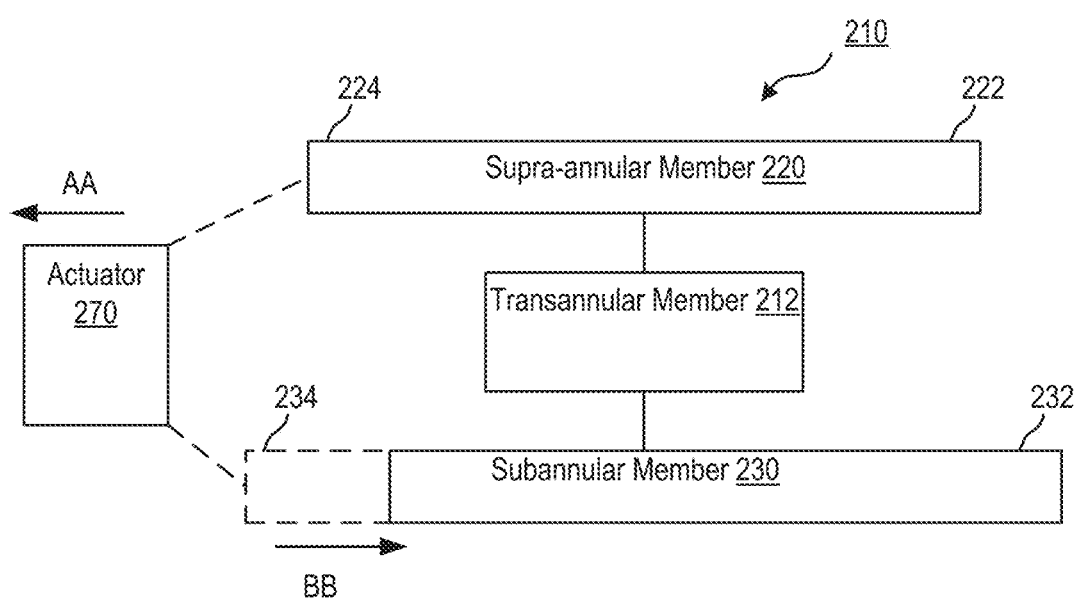

As described above, the subannular member 230 can be formed with the proximal anchoring element 234 biased in the uncompressed and/or expanded configuration. In this manner, the actuator 270 can be actuated to exert a force, via the one or more cables, tethers, etc., operable to transition the proximal anchoring element 234 to the compressed and/or retracted configuration. More specifically, the user can manipulate the proximal end portion of the actuator 270 to actuate a distal end portion of the actuator 270 that is coupled to the frame 210. For example, actuating the actuator 270 can be such that the one or more cables, tethers, and/or members are pulled in a proximal direction (e.g., away from the frame 210 and/or in a manner that increases a tension therein), as indicated by the arrow AA in FIG. 2B. The coupling of the distal end portion of the actuator 270 to the frame 210 can be such that the proximal movement of the cables, tethers, etc., pull the proximal anchoring element 234 toward a central axis of the frame 210, as indicated by the arrow BB in FIG. 2B. As such, actuating the actuator 270 can exert a force on the proximal anchoring element 234 operable to place the proximal anchoring element 234 in a compressed, retracted, restrained, and/or actuated configuration, as shown in FIG. 2B.

Figure 2C:
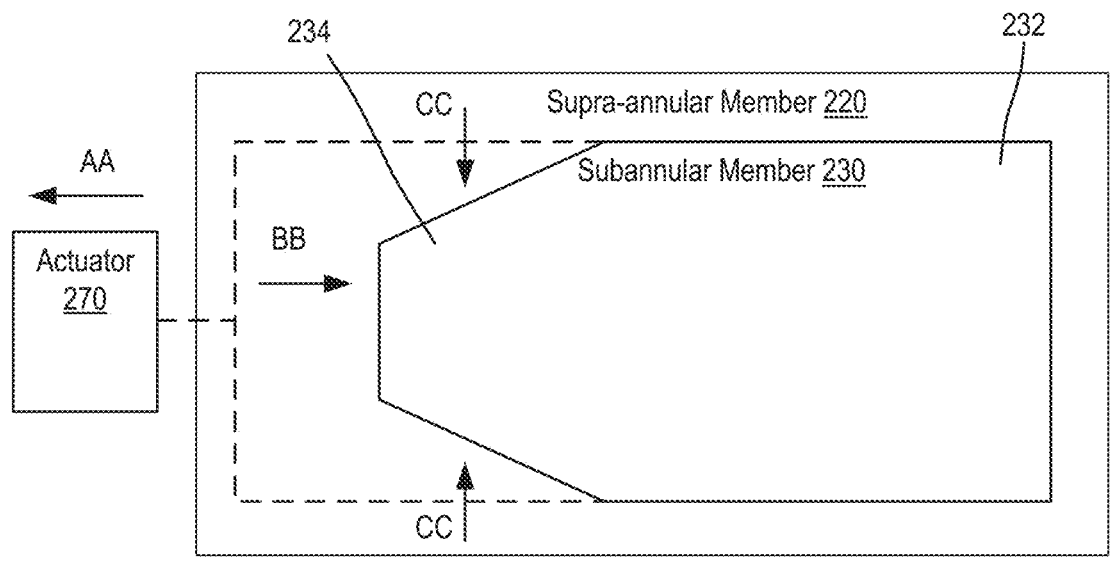
FIGS. 2C and 2D are a bottom-view schematic illustration and a side-view schematic illustration of the prosthetic valve of FIGS. 2A-2B and shown in the second configuration and a third configuration, respectively.

In some implementations, actuating the actuator 270 also can be operable to pull a proximal-anterior portion of the subannular member and/or transannular wall and a proximal-posterior portion of the subannular member and/or transannular wall to or toward the longitudinal axis of the valve 200. For example, FIG. 2C shows that the actuation of the actuator 270 (e.g., moving the actuator 270 or tethers in the AA direction) compresses and/or moves the proximal anchoring element 234 toward a central portion of the valve frame 210, as indicated by the arrow BB, and compresses the posterior and anterior sidewalls toward a central portion of the valve frame 210, as indicated by the arrows CC. As such, actuating the actuator 270 can reduce a perimeter of at least the subannular member 230 allowing a desired portion of the valve frame 210 to be inserted into the annulus of the native valve.

In some implementations, the actuator 270 can be secured and/or locked when the proximal anchoring element 234 is compressed and/or retracted (e.g., a first configuration) to at least temporarily maintain the proximal anchoring element 234 in the first configuration. As described above, in some implementations, the proximal anchoring element 234 can be in the first configuration for delivery and deployment prior to seating the frame 210 (or valve) in the native annulus. Once the frame 210 is seated in the native annulus, a user can manipulate the proximal portion of the actuator 270 to actuate and/or release the actuator 270. In this example, the actuation can cause the actuator 270 to release and/or remove at least a portion of the force exerted on the proximal anchoring element 234 (e.g., via the cable(s), tether(s), etc.), thereby allowing the proximal anchoring element 234 (and/or one or more portions of the anterior and/or posterior walls) to return to its biased configuration or a second configuration (see e.g., FIG. 2A), as described above.

In some implementations, the actuator 270 can be configured to further actuate the frame 210 after the frame 210 (or valve) is seated in the native annulus. For example, in some implementations, the user can manipulate the proximal end portion of the actuator 270 (e.g., in the same way as just described or in a different manner) to move one or more cables, tethers, and/or members of the actuator 270 in the proximal direction (e.g., away from the frame 210 and/or in a manner that increases a tension therein), as indicated by the arrow DD in FIG. 2D. In this example, the proximal anchoring element 234 is in its uncompressed or unactuated state after seating the frame 210 in the native annulus. The actuator 270 can be coupled to the supra-annular member 220, the subannular member 230, and/or the proximal anchoring element 234 such that the actuation of the actuator 270 results in a force operable to pull the proximal anchoring element 234 toward the proximal portion 224 of the supra-annular member 220, as indicated by the arrow EE in FIG. 2D. For example, the actuator 270 can exert a compressive force or the like that is operable in cinching at least portion of the frame 210.

Figure 2D:
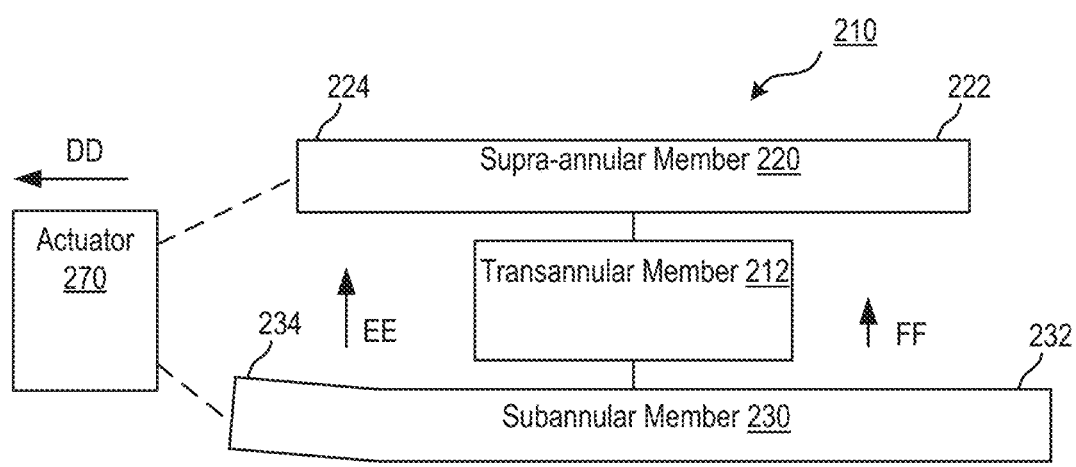

As shown in FIG. 2D, in some instances, the proximal anchoring element 234 can flex in the direction of the native annulus (e.g., beyond its biased position), which can facilitate an engagement between the proximal anchoring element 234 and the native tissue and/or chordae on the proximal side of the native annulus. In some implementations, the force resulting from the actuation of the actuator 270 can be operable to pull, move, compress, and/or cinch other portions of the subannular member 230 toward the supra-annular member 220, as indicated by the arrow FF in FIG. 2D. In some such implementations, an amount of cinching can be varied across the frame 210. For example, an amount of cinching at or near a proximal portion of the frame 210 can be greater than an amount of cinching at or near a distal portion of the frame 210. In other implementations, the amount of cinching can be substantially consistent across the frame 210. Moreover, at least some tissue surrounding the native annulus can be disposed between the supra-annular member 220 and the subannular member 230 when the frame 210 is seated in the native annulus and thus, the cinching of the supra-annular member 220 and the subannular member 230 can be operable to squeeze and/or sandwich the native tissue between the members 220 and 230. In this manner, the cinching can enhance a securement of the frame 210 in the native annulus.

Although not shown in FIGS. 2A-2D, in some embodiments, the proximal anchoring element 234 can be sized and/or shaped to engage native tissue, chordae, trabeculae, annular tissue, leaflet tissue, and/or the like when the frame 210 is cinched against or relative to the native annulus. In some embodiments, the proximal anchoring element 234 can include one or more protrusions, features, ridges, ribs, knobs, knots, beads, loops, etc. that can engage and/or that can facilitate the engagement of the native tissue when the frame 210 is cinched against or relative to the native annulus.

While the frame 210 and/or one or more portions of the subannular member 230 are described above as being compressed to move inward toward a central axis of the frame 210 in response to actuation of the actuator 270, in other embodiments, the actuator 270 can be removably coupled to one or more portions of the frame 210 and configured to move such portions in any suitable manner. For example, in some implementations, the actuator 270 (e.g., one or more tethers or the like, as described above) can be coupled to the proximal anchoring element 234 such that actuation of the actuator 270 results in the proximal anchoring element 234 folding or wrapping around the transannular member 212 of the frame 210 in either an anterior direction or a posterior direction, or both directions depending on the mode of actuation. As described above, the folding and/or wrapping of the proximal anchoring element 234 around the transannular member 212 can reduce a circumference or diameter of at least the subannular member 230 allowing the frame 210 to be inserted into and/or at least partially through the annulus of the native heart valve.

Figure 3A:
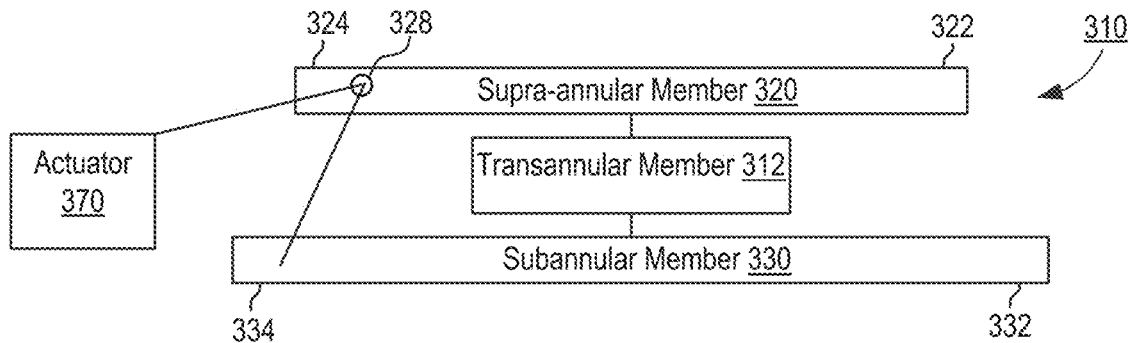
FIGS. 3A-3C are schematic illustrations of an outer frame of a side-delivered transcatheter prosthetic heart valve, according to an embodiment, and shown in a delivery configuration, a seating configuration, and a deployed configuration, respectively.
Figure 3B:
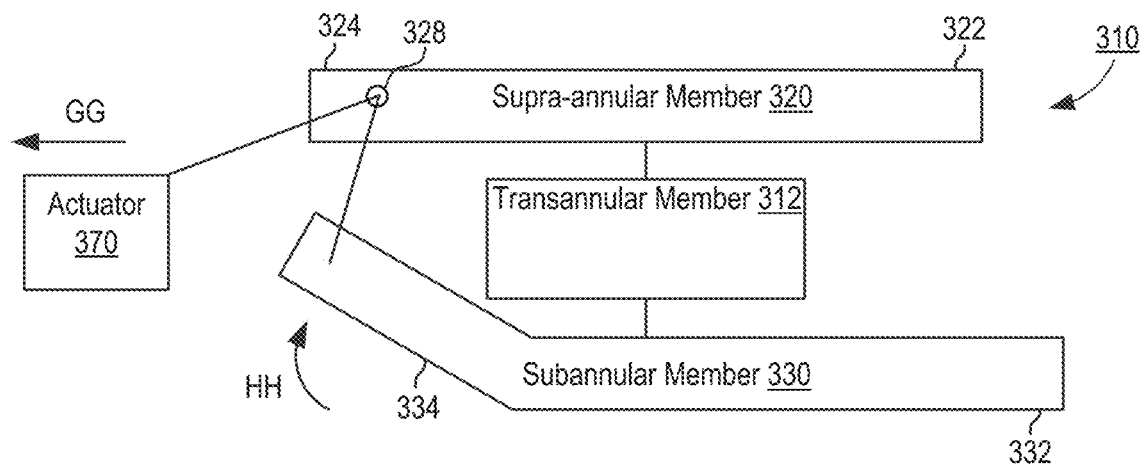
Figure 3C:
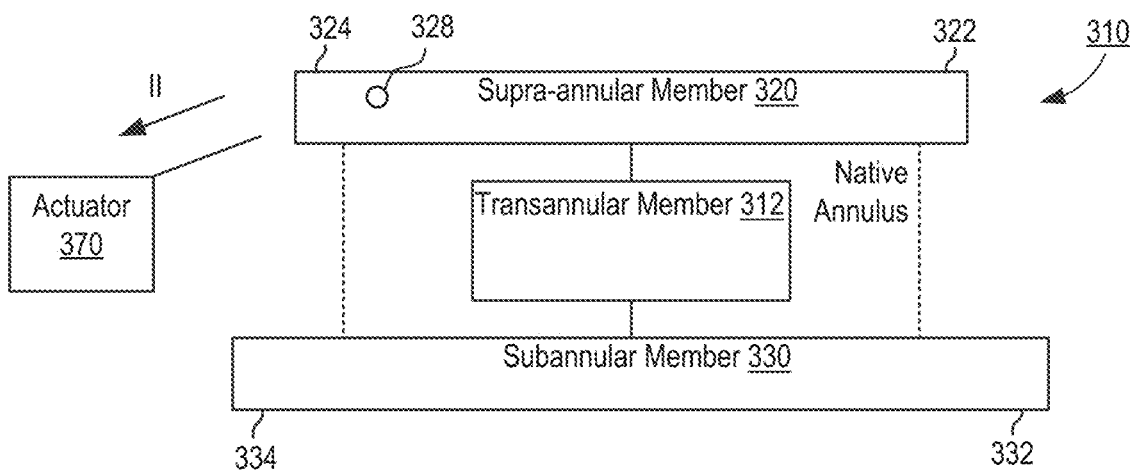

FIGS. 3A-3C are schematic illustrations of an annular support frame 310 according to an embodiment. The annular support frame 310 (also referred to herein as "tubular frame," "valve frame," "wire frame," "outer frame," "support frame," or "frame") can include and/or can be coupled to an actuator 370 configured to actuate one or more portions of the support frame 310. In some embodiments, the support frame 310 and/or the actuator 370 can be substantially similar in at least form and/or function to the support frames 110, 210 and/or the actuators 170, 270, respectively. Thus, portions and/or aspects of the support frame 310 and/or the actuator 370 are not described in further detail herein.

As shown, the annular support frame 310 has a supra-annular member and/or region 320, a subannular member and/or region 330, and a transannular member and/or region 312, disposed and/or coupled therebetween. In the embodiment shown in FIGS. 3A-3C, the supra-annular member and/or region 320, the subannular member and/or region 330, and the transannular member and/or region 312 are separate, independent, and/or modular components that are coupled to collectively form the frame 310. Each of the supra-annular member and/or region 320, the subannular member and/or region 330, and the transannular member and/or region 312 (referred to herein as the supra-annular, subannular, and transannular "member") are a wire frame that is laser cut out of any suitable material such as a shape-memory or superelastic material like Nitinol. In some implementations, each of the supra-annular member 320, the subannular member 330, and the transannular member 312 can be laser cut from a sheet of Nitinol and, for example, heat-set into a desired shape and/or configuration. As described above, forming the supra-annular member 320, the subannular member 330, and the transannular member 312 in such a manner can provide a desired amount of flexibility and/or resistance to plastic or permanent deformation that can allow the frame 310 to be folded and/or compressed for delivery. Moreover, the wire frame portions of the supra-annular member 320, the subannular member 330, and the transannular member 312 can be covered by any suitable biocompatible material such as any of those described above.

In some embodiments, the supra-annular member 320 of the frame 310 can be similar in at least form and/or function to the supra-annular members 120, 220 described above. For example, the supra-annular member 320 can be and/or can form, for example, a cuff or collar that can be attached or coupled to an upper edge or upper portion of the transannular member 312. The supra-annular member 320 can be shaped and/or formed to include any number of features configured to engage native tissue and/or one or more other portions of the frame 310 and/or the actuator 370. For example, the supra-annular member 320 (or an outer loop thereof) can have a distal portion 322 configured to engage distal supra-annular tissue and a proximal portion 324 configured to engage proximal supra-annular tissue.

As described above, the supra-annular member 320 can include and/or can form an outer portion or loop, an inner portion or loop, and one or more splines disposed between the outer and inner portions or loops. The outer portion or loop (referred to herein as "outer loop") can be shaped and/or sized to engage native tissue. In some implementations, the outer loop can form, for example, one or more upper or supra-annular anchoring elements that can engage supra-annular tissue to at least partially stabilize and/or secure the frame 310 in the native annulus. The inner portion or loop (referred to herein as "inner loop") of the supra-annular member 320 is coupled to and/or suspended from the outer loop by the one or more splines and is coupleable to an inner frame of the flow control component to at least partially mount the flow control component to the support frame 310, as described above with reference to the supra-annular member 220. The one or more splines of the supra-annular member 320 can be any suitable shape, size, and/or configuration. For example, in some embodiments, the supra-annular member 320 can include a distal spline and a proximal spline. In some embodiments, the supra-annular member 320 can include a spline (e.g., a proximal spline) configured to receive, couple to, and/or otherwise engage the actuator 370 and/or delivery system interface. For example, in the embodiment shown in FIGS. 3A-3C, the supra-annular member 330 (e.g., a spline thereof) can form a waypoint and/or the like that can temporarily and/or removably couple to and/or receive the actuator 370 and any other suitable portion of the delivery system, as described in further detail herein with reference to specific embodiments.

The subannular member 330 of the frame 310 can be similar in at least form and/or function to the subannular regions and/or members 130, 230 described above. For example, the subannular member 330 of the frame 310 can be and/or can form, for example, a cuff or collar that can be attached or coupled to a lower edge or upper portion of the transannular member 312. When the frame 310 is deployed within a human heart, the subannular member 330 can be a ventricular collar that is shaped to conform to the native deployment location. In some implementations, the subannular member 330 or at least a portion thereof can engage the ventricular ceiling surrounding the native annulus to secure the frame 310 in the native annulus, to prevent dislodging of the frame 310 and/or to seal against blood leakage (perivalvular leakage and/or regurgitation during systole) around the frame 310.

The subannular member 330 included in the frame 310 shown in FIGS. 3A-3C can include and/or can form a distal portion having a distal anchoring element 332 and a proximal portion having a proximal anchoring element 334. In some embodiments, the subannular member 330 can include and/or can form any other suitable anchoring element (not shown in FIGS. 3A-3C). The anchoring elements 332 and 334 can be integrally and/or monolithically formed with the subannular member 330. The distal anchoring element 332 and the proximal anchoring element 334 of the subannular member 330 can be any suitable shape, size, and/or configuration such as any of those described in detail in the '957 PCT, the '010 PCT, the '231 PCT, the '390 PCT, the '108 PCT, the '327 Provisional, the '964 Provisional, the '345 Provisional, the '807 Provisional, any of those described above with reference to the valve 100, and/or any of those described herein with respect to specific embodiments. The distal anchoring element 332 can be substantially similar to the distal anchoring elements 132, 232 and therefore, is not described in further detail herein.

The proximal anchoring element 334 can be configured to transition, move, and/or otherwise reconfigure between a first configuration in which the proximal anchoring element 334 extends from the subannular member 330 a first amount, distance, and/or direction and a second configuration in which the proximal anchoring element 334 extends from the subannular member 330 a second amount, distance, and/or direction. In some embodiments, the proximal anchoring element 334 can be substantially similar in at least form and/or function to the proximal anchoring element 234 described above with reference to FIGS. 2A-2D. Accordingly, such similarities are not described in further detail herein.

In some embodiments, the proximal anchoring element 334 can be in a compressed, contracted, retracted, undeployed, folded, and/or restrained state (e.g., a position that is near, adjacent to, and/or in contact with the transannular member 312 and/or the supra-annular member 320 of the support frame 310) when in the first configuration, and can be in an expanded, extended, deployed, unfolded, and/or unrestrained state (e.g., extending away from the transannular member 312) when in the second state. In some embodiments, the proximal anchoring element 334 can be biased and/or heat-set in the second configuration. Moreover, in some implementations, the proximal anchoring element 334 can be transitioned in response to actuation of the actuator 370, as described in further detail herein.

The transannular member 312 is disposed between the supra-annular member 320 and the sub annular member 330. In some embodiments, the transannular member 312 can be coupled to each of the supra-annular member 320 and the subannular member 330 such that a desired amount of movement and/or flex is allowed therebetween (e.g., welded, bonded, sewn, bound, and/or the like). In some embodiments, the transannular member 312 of the frame 310 can be similar in at least form and/or function to the transannular regions 112, 212 described above and thus, is not described in further detail herein.

While the frame 310 is described above as being substantially similar to the frame 210 described above with reference to FIGS. 2A-2D, the frame 310 can differ from the frame 210 in the engagement with the actuator and the movement of the proximal anchoring element 334. As shown in FIGS. 3A-3C, the actuator 370 can at least temporarily engage with the supra-annular member 320 and the subannular member 330. The actuator 370 can be any suitable member, mechanism, and/or device configured to actuate at least a portion of the frame 310. Moreover, a portion of the actuator 370 can extend through a portion of a delivery system used to deliver the frame 310 and/or a valve including the frame 310. In this manner, a user can manipulate a proximal end portion of the actuator 370 to actuate the actuator 370.

FIG. 3A shows the actuator 370 engaged with the frame 310 while the frame 310 is in a compressed or delivery configuration. As described above with reference to the valve 100, the frame 310 can be compressed, folded, and/or otherwise placed into a delivery configuration for side-delivery via a delivery catheter. Prior to placing the frame 310 in the delivery system, the actuator 370 can be removably coupled to the frame 310 such that the frame 310 (or valve) and the actuator 370 are advanced through the delivery catheter together. In this embodiment, the actuator 370 can be a tether that extends through the waypoint 328 defined by the supra-annular member 320, looped through one or more attachment points of the subannular member 330 (e.g., one or more attachment points on or near the proximal anchoring element 334, and then looped back through the waypoint 328. As such, both ends of the tether are proximal to the frame 310 and can be maintained proximal to and/or at a proximal end of the delivery system, allowing an operator to manipulate the actuator 370 (tether) to actuate the proximal anchoring element 334. FIG. 3A shows that the proximal anchoring element 334 is in an extended or unactuated configuration when the frame 310 is in the delivery configuration for side-delivery through the delivery catheter.

FIG. 3B shows the actuator 370 being actuated to move the proximal anchoring element 334 from the first position or configuration to the second position or configuration. More specifically, the frame 310 (and/or valve) can advanced through the delivery catheter and allowed to at least partially expand as the frame 310 is released from the delivery catheter. In some implementations, the frame 310 is at least partially inserted into the annulus while the proximal end portion of the frame 310 remains in the delivery catheter. After fully releasing the frame 310 from the delivery catheter, the operator can manipulate the proximal end portion of the actuator 370 to actuate a distal end portion of the actuator 370 that is coupled to the proximal anchoring element 334.

For example, actuating the actuator 370 can be such that the one or more tethers are pulled in a proximal direction (e.g., away from the frame 310 and/or in a manner that increases a tension therein), as indicated by the arrow GG in FIG. 3B. With the actuator 370 passing through the waypoint 328 of the supra-annular member 320, which in this embodiment is not actuated by the actuator 370), the proximal movement of the cables, tethers, etc., pull the proximal anchoring element 334 toward the waypoint 328, as indicated by the arrow HH in FIG. 3B. As such, actuating the actuator 370 can exert a force on the proximal anchoring element 334 operable to place the proximal anchoring element 334 in a compressed, retracted, restrained, and/or actuated configuration, as shown in FIG. 3B. As described above, placing the proximal anchoring element 334 in the compressed and/or actuated configuration reduces a perimeter of at least the subannular member 330 allowing the subannular member 330 to be passed through the annulus of the native valve.

After the frame 310 (or valve) is seated in the annulus, the actuator 370 can be actuated again and/or otherwise returned to an unactuated state or configuration. As such, the proximal anchoring element 334 is allowed to return to the extended and/or unactuated configuration. In the embodiment shown in FIGS. 3A-3C, the proximal anchoring element 334 can be biased such that in the extended and/or unactuated configuration, the proximal anchoring element 334 engages native subannular tissue to at least partially secure the frame 310 in the annulus. FIG. 3C shows that once the frame 310 is seated in the annulus, the operator can manipulate the actuator 370 to remove the actuator 370 from the frame 310. For example, the operator can pull on one end of the tether (e.g., actuator 370) such that the tether is withdrawn from the attachment points of the subannular member 330 and the waypoint 328 of the supra-annular member 320. As such, the actuator 370 and/or a delivery system of which the actuator 370 is a part can be withdrawn from a patient while the frame 310 remains in the annulus of the native heart valve.

Provided below is a discussion of certain aspects or embodiments of side deliverable transcatheter prosthetic valves (e.g., prosthetic valves). The transcatheter prosthetic valves (or aspects or portions thereof) described below with respect to specific embodiments can be substantially similar in at least form and/or function to the valves 100 and/or 200 (or corresponding aspects or portions thereof). Similarly, the valves described below (or aspects or portions thereof) can be similar in at least form and/or function to the valves described in detail in the '957 PCT, the '010 PCT, the '231 PCT, the '390 PCT, the '108 PCT, the '327 Provisional, the '964 Provisional, the '345 Provisional, and/or the '807 Provisional. Thus, certain aspects and/or portions of the specific embodiments may not be described in further detail herein.

Figure 4:
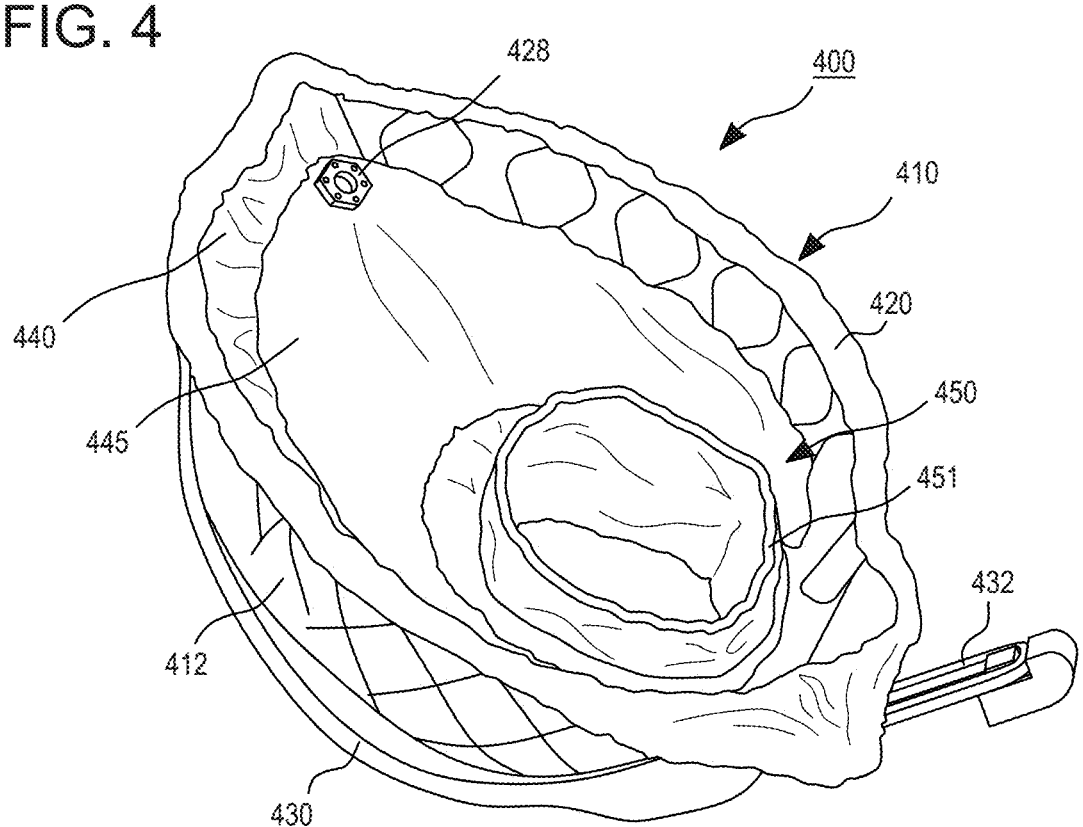
FIG. 4 is a perspective view of a prosthetic valve according to an embodiment.

FIGS. 4-10 illustrate a side-deliverable (orthogonally deliverable) transcatheter prosthetic heart valve 400 (also referred to herein as "prosthetic valve" or "valve"), according to an embodiment. FIG. 4 is an illustration of a top perspective view of the valve 400. In some implementations, the valve 400 can be deployed in, for example, an annulus of a native tricuspid and/or mitral valve. The valve 400 is configured to permit blood flow in a first direction through an inflow end of the valve 400 and to block blood flow in a second direction, opposite the first direction, through an outflow end of the valve 400. For example, the prosthetic valve 400 can be a side deliverable transcatheter prosthetic heart valve configured to be deployed within the annulus of a native tricuspid valve or native mitral valve of a human heart to supplement and/or replace the functioning of the native valve.

The valve 400 is compressible and expandable in at least one direction relative to an x-axis of the valve 400 (also referred to herein as "horizontal axis," "longitudinal axis," "long axis," and/or "lengthwise axis"). The valve 400 is compressible and expandable between an expanded configuration for implanting at a desired location in a body (e.g., a human heart) and a compressed configuration for introduction into the body using a delivery catheter (not shown in FIG. 4). In some embodiments, the horizontal x-axis of the valve 400 is orthogonal to (90 degrees), or substantially orthogonal to (75-105 degrees), or substantially oblique to (45-135 degrees) to a central (vertical) y-axis when in the expanded and/or compressed configuration. Moreover, the horizontal x-axis of the valve 400 in the compressed configuration is substantially parallel to a lengthwise cylindrical axis of the delivery catheter in which the valve 400 is disposed.

In some embodiments, the valve 400 has an expanded or deployed height of about 5-60 mm, about 5-30 mm, about 5-20 mm, about 8-12 mm, or about 8-10 mm, and an expanded or deployed diameter (e.g., length and/or width) of about 25-80 mm, or about 40-80 mm. In some embodiments, the valve 400 has a compressed height (y-axis) and width (z-axis) of about 6-15 mm, about 8-12 mm, or about 9-10 mm. It is contemplated in some implementations that the length of the valve 400 (e.g., along the x-axis) is not compressed or otherwise reduced since it can extend along the length of the central cylindrical axis of the delivery catheter.

In certain embodiments, the valve 400 is centric, or radially symmetrical. In other embodiments, the valve 400 is eccentric, or radially asymmetrical (e.g., along or relative to the y-axis). In some eccentric embodiments, the frame 410 may have a D-shape in cross-section, with a flat portion or surface configured to substantially match an annulus of a native mitral valve at or near the anterior leaflet. In the example shown in FIGS. 4-10, the valve 400 is eccentric with one or more components being offset or asymmetrical region to the y-axis.

The valve 400 includes an annular outer support frame 410 and a collapsible flow control component 450 mounted within the annular outer support frame 410. The annular outer support frame 410 (also referred to herein as "outer frame") is made from a shape-memory material such as Nickel-Titanium alloy (Nitinol) and is therefore a self-expanding structure from a compressed configuration to an expanded configuration. As shown in FIG. 4, at least the outer support frame 410 of the valve 400 is covered, wrapped, and/or surrounded by a biocompatible cover 440. The biocompatible cover 440 can be a mesh material, a pericardial tissue, a woven synthetic polyester material, and/or any other suitable biocompatible material such as those described above.

The outer frame 410 has a transannular member 412 and/or body that circumscribes, forms, and/or defines a central (interior) channel about and/or along the vertical or central axis (y-axis). The outer frame 410 has a supra-annular member 420 attached circumferentially at a top edge of the transannular member 412 and a subannular member 410 attached circumferentially at a bottom edge of the transannular member 412. The supra-annular member 420 is shaped to conform to the native deployment location. In a tricuspid replacement, for example, the supra-annular member 420 or atrial collar can have a tall back wall portion to conform to the septal area of the native valve and can have a distal and proximal portion. The distal portion can be larger than the proximal portion to account for the larger flat space above (atrial) the ventricular outflow tract (VOT) subannular area. In a mitral replacement, for example, the supra-annular member 420 of the outer frame 410 may be D-shaped or shaped like a hyperbolic paraboloid to mimic the native structure.

The collapsible (inner) flow control component 450 is mounted within the outer frame 410. The flow control component 450 has a foldable and compressible inner wire frame 35 (also referred to as "inner leaflet frame" or "inner frame") with two (or more) fold areas, hinge areas, coupling areas, elastically deformable regions, etc. A set of 2-4 flexible leaflets 456 are mounted in or on the inner frame 451 (not shown in FIG. 4). In some embodiments, the flow control component 450 has three leaflets 456 cusps or pockets mounted within the inner frame 451, as described in further detail herein.

The inner flow control component 450, like the outer frame 410, is foldable and compressible. For example, the inner frame 451 is foldable along or in the direction of a z-axis (e.g., foldable at the fold areas or the like) from a cylindrical configuration to a flattened cylinder configuration (or a two-layer band), where the fold areas are located on a distal side and on a proximal side of the inner frame 451. The flow control component 450, like the outer frame 410, is also vertically (y-axis) compressible to a shortened or compressed configuration. By folding (compressing) in the direction of the z-axis and vertically compressing in the y-axis, the valve 400 is permitted to maintain a relatively large dimension along the horizontal (x-axis). In some implementations, the outer frame 410 and the flow control component 450 are reduced along z-axis until the side walls are in contact or nearly so. This also allows the outer frame 410 and the flow control component 450 to maintain the radius along the horizontal axis (x-axis), to minimize the number of wire cells, which make up the outer and the inner frames, that can be damaged by forces applied during folding and/or compression necessary for loading into the delivery catheter.

The flow control component 450 has a diameter and/or perimeter that is smaller than a diameter and/or perimeter of the central channel of the outer frame 410. The flow control component 450 is mounted to or within the outer frame 410 such that a central or vertical axis (y-axis) of the inner frame 451 is parallel to the central or vertical axis (y-axis) of the outer frame 410. In some embodiments, the y-axis defined by the inner frame 451 is parallel to but offset from the y-axis defined by the outer frame 410 (FIG. 4). In some implementations, a spacer element 445 is disposed within and/or across the central channel and can facilitate the mounting of a portion of the flow control component 450 (e.g., an otherwise unsupported portion) to the outer support frame 410 and/or an ingrowth of native tissue over at least a portion of the supra-annular member 420 of the valve 400, in some embodiments, the spacer element 445 can be similar to any of those described in the '231 PCT.

In certain embodiments, the inner frame 451 can have a diameter of about 25-30 mm, the outer frame 410 (or the transannular member 412 thereof) can have a diameter of about 50-80 mm, and the supra-annular member 420 (or atrial collar) extend beyond the top edge of the transannular member 412 by about 20-30 mm to provide a seal on the atrial floor against perivalvular leaks (PVLs). The flow control component 450 and the outer frame 410 can be foldable (e.g., in the direction of the z-axis) and/or compressible (e.g., in the direction of the y-axis) to reduce a size of the entire valve 400 to fit within the inner diameter of a 24-36 Fr (8-12 mm inner diameter) delivery catheter (not shown in this FIG. 4).

Figure 5:
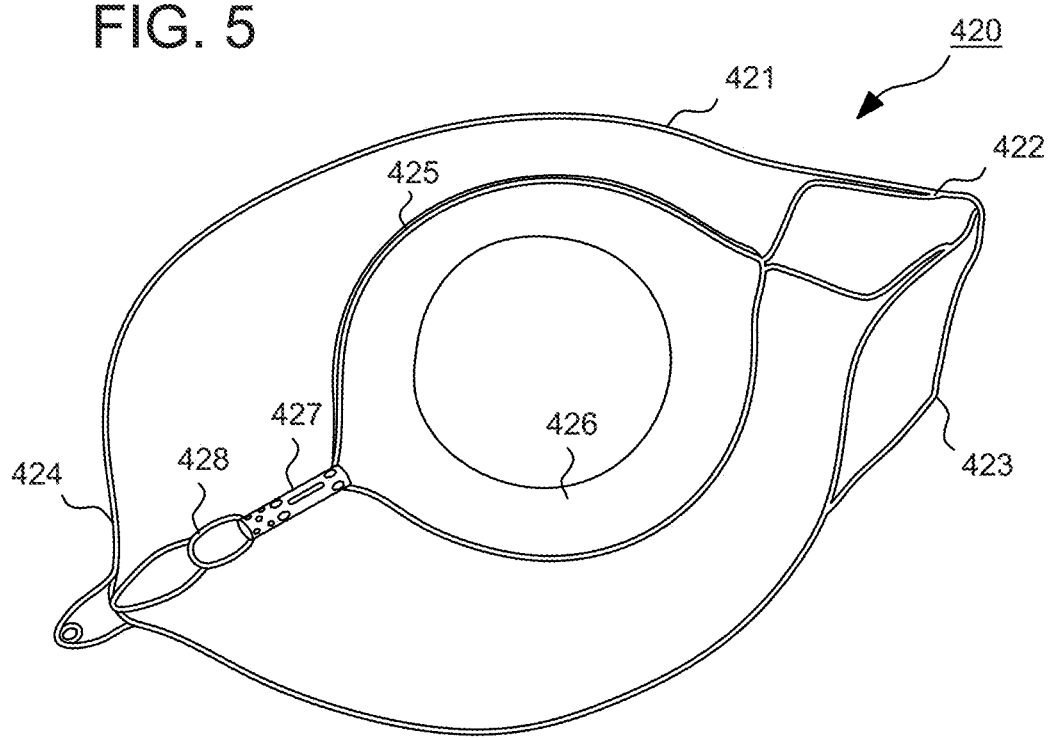
FIG. 5 is a top perspective view a supra-annular region of an outer support frame of the prosthetic valve shown in FIG. 4.

FIG. 5 is a top perspective view illustrating the supra-annular member 420 of the outer support frame 410 of the valve 400 shown in FIG. 4. FIG. 5 shows a laser cut wire frame of the supra-annular member 420 with a biocompatible material 426 coupled thereto to facilitate the mounting of the inner flow control component 450 to the outer frame 410. In some embodiments, the supra-annular member 420 of the outer frame 410 can be substantially similar in at least form and/or function to the supra-annular members 120 and/or 220 described above. Thus, portions and/or aspects of the supra-annular member 420 may not be described in further detail herein.

As shown, the supra-annular member 420 includes a distal portion 422, a proximal portion 424, an outer loop 421, an inner loop 425, and at least one spline 427. In some embodiments, the outer loop 421 can be shaped and/or sized to engage native tissue. For example, the distal portion 422 of the supra-annular member 420 (formed at least in part by the outer loop 421) is configured to engage distal supra-annular tissue and the proximal portion 424 (formed at least in part by the outer loop 421) is configured to engage proximal supra-annular tissue. The distal and proximal portions 422 and 424 can have a rounded and/or curved shape, wherein a radius of curvature of the proximal portion 424 is larger than a radius of curvature of the distal portion 422. The distal portion 422 can form, for example, a distal anchoring loop 423 that can engage distal supra-annular tissue to at least partially stabilize and/or secure the frame 410 in the native annulus. Although not shown in FIG. 5, the proximal portion 424 similarly can form a proximal upper anchoring element that can engage proximal supra-annular tissue to at least partially stabilize and/or secure the frame 410 in the native annulus.

The inner loop 425 of the supra-annular member 420 can be substantially circular and can be coupled to and/or suspended from the outer loop by the one or more splines 427. As shown in FIG. 5, the inner loop 425 can be coupled to biocompatible material 426, which can be used to couple the inner frame 451 of the flow control component 450 to the inner loop 425 of the support frame 410. In some implementations, suspending the inner loop 425 from the outer loop 421 can, for example, at least partially isolate the inner loop 425 (and the flow control component 450 coupled to the inner loop 425) from at least a portion of the force associated with transitioning the frame 410 between the expanded configuration and the compressed configuration, as described above with reference to the frame 210.

The one or more splines 427 of the supra-annular member 420 can be any suitable shape, size, and/or configuration. For example, in some embodiments, the supra-annular member 420 can include a proximal spline 427 and one or more distal splines 427. The distal splines 427 can couple a distal portion of the inner loop 425 to a distal portion of the outer loop 421. Similarly, the proximal spline 427 can couple a proximal portion of the inner loop 425 to a proximal portion of the outer loop 421. In some embodiments, the proximal spline 427 can be configured to receive, couple to, and/or otherwise engage an actuator and/or a portion of a delivery system. For example, the proximal spline 427 includes, forms, and/or can be coupled to a waypoint 428 that can be used to couple to one or more portions of the actuator and/or delivery system, as described above with reference to the frames 110 and 210.

Figure 6:
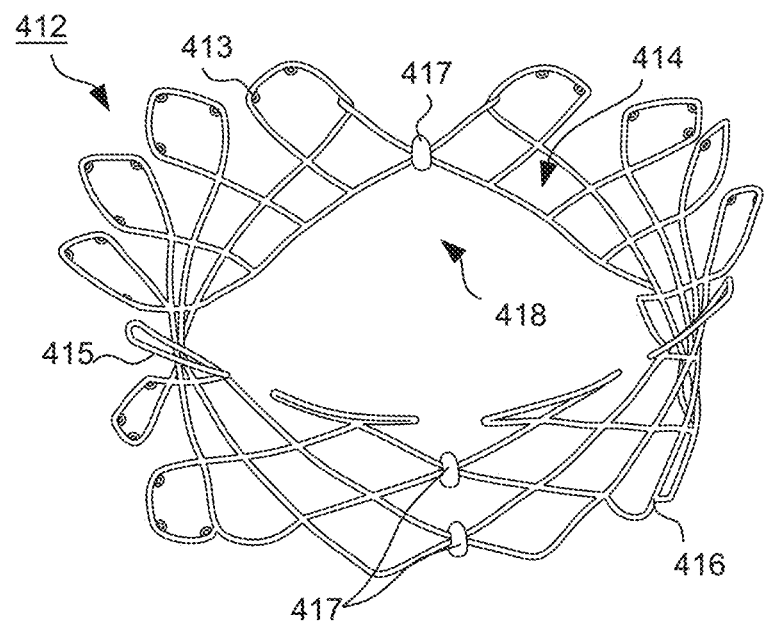
FIG. 6 is a distal perspective view a transannular region of the outer support frame of the prosthetic valve shown in FIG. 4.

FIG. 6 is a distal perspective view illustrating the transannular member 412 of the outer frame 410 of the valve 400 shown in FIG. 4. In some embodiments, the transannular member 420 of the outer frame 410 can be substantially similar in at least form and/or function to the transannular regions and/or members 112 and/or 212 described above. Thus, portions and/or aspects of the transannular member 412 may not be described in further detail herein.

The transannular member 412 can be shaped and/or formed into a ring, a cylindrical tube, a conical tube, and/or any other suitable annular shape. In some embodiments, the transannular member 412 may have a side profile of a concave cylinder (walls bent in), an angular hourglass, a curved, graduated hourglass, a ring or cylinder having a flared top, flared bottom, or both. Moreover, the transannular member 412 can form and/or define an aperture or central channel 414 that extends along the central axis 404 (e.g., the y-axis). The central channel 414 (e.g., a central axial lumen or channel) can be sized and configured to receive the flow control component 450 across a portion of a diameter of the central channel 414. In some embodiments, the transannular member 412 can have a shape and/or size that is at least partially based on a size, shape, and/or configuration of the supra-annular member 420 and/or subannular member 430 of the support frame 410, and/or the native annulus in which it is configured to be deployed, as described above.

The transannular member 412 can be and/or can include a wire frame that is laser cut out of Nitinol or the like and, for example, heat-set into a desired shape and/or configuration. The transannular member 412 can be formed to include a set of compressible wire cells 413 having an orientation and/or cell geometry substantially orthogonal to the central axis extending through the central channel 414 to minimize wire cell strain when the transannular member 412 is in a vertical compressed configuration, a rolled and compressed configuration, or a folded and compressed configuration. As shown in FIG. 6, the transannular member 412 includes a first laser cut half 415 (e.g., an anterior side) and a second laser cut half 416 (e.g., a posterior side) that can be formed into a desired shape and coupled together to form the transannular member 412. The anterior side 415 and the posterior side 416 can be coupled at one or more hinge points 417 along a distal portion and a proximal portion of the transannular member 412. More specifically, the anterior side 415 and the posterior side 416 can be coupled along the distal side of the transannular member 412 via two sutures forming two hinge or coupling points 417 and can be coupled along the proximal side of the transannular member 412 via one suture forming a single hinge or coupling point 417.

In some embodiments, forming the transannular member 412 in such a manner can allow the transannular member 412 to bend, flex, fold, deform, and/or otherwise reconfigure (substantially without plastic deformation and/or undue fatigue) in response to lateral folding along or in a direction of a lateral or z-axis and/or vertical compression along or in a direction of the central or y-axis. Moreover, coupling at the hinge points 417 using sutures can allow for a desired amount of slippage between the sutures and the anterior/posterior sides 415/416, which in turn, can limit and/or substantially prevent binding, sticking, and/or failure in response to folding along the lateral or z-axis.

As shown in FIG. 6, the proximal portion of the transannular member 412 includes a single hinge or coupling point 417. In some embodiments, the transannular member 412 can define a gap or space 418 below the proximal hinge or coupling point 417 that can provide space to allow a proximal anchoring element of the subannular member 430 to transition between a first configuration and a second configuration, as described in further detail herein.

Figure 7:
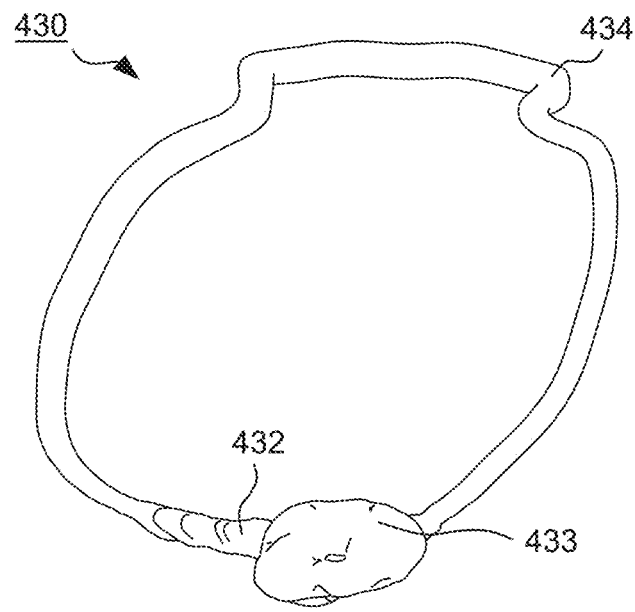
FIG. 7 is a distal perspective view a subannular region of the outer support frame of the prosthetic valve shown in FIG. 4.

FIG. 7 is a distal perspective view illustrating the subannular member 430 of the outer frame 410 of the valve 400 shown in FIG. 4. In some embodiments, the subannular member 430 of the frame 410 can be similar in at least form and/or function to the subannular regions and/or members 130 and/or 230 described above. Thus, portions and/or aspects of the transannular member 412 may not be described in further detail herein.

As shown, the subannular member 430 of the frame 410 includes and/or forms a distal portion having a distal anchoring element 432 and a proximal portion having a proximal anchoring element 434. The anchoring elements 432 and 434 are integrally and/or monolithically formed with the subannular member 430. The distal anchoring element 432 and the proximal anchoring element 434 of the subannular member 430 can be any suitable shape, size, and/or configuration such as any of those described in detail in the '957 PCT, the '010 PCT, the '231 PCT, the '390 PCT, the '108 PCT, the '327 Provisional, the '964 Provisional, the '345 Provisional, the '807 Provisional, any of those described above with reference to the frames 110 and/or 210, and/or any of those described herein with respect to specific embodiments.

The distal anchoring element 432 is shown as including an atraumatic end that forms a guidewire coupler 433 configured to selectively engage and/or receive a portion of a guidewire or a portion of a guidewire assembly. The guidewire coupler 433, for example, is configured to allow a portion of the guidewire to extend through an opening and/or aperture of the guidewire coupler 433, thereby allowing the frame 410 to be advanced over or along the guidewire during delivery and deployment. In some embodiments, the guidewire coupler 433 can selectively allow the guidewire to be advanced therethrough while blocking or preventing other elements and/or components such as a pusher or the like.

The anchoring elements 432 and/or 434 are configured to engage a desired portion of the native tissue to mount the frame 410 to the annulus of the native valve in which it is deployed. For example, the distal anchoring element 432 can extend (e.g., about 10-40 mm) from the subannular member 430 and into a RVOT or a LVOT. The distal anchoring element 432 can be shaped and/or biased such that the distal anchoring element 432 exerts a force on the subannular tissue operable to at least partially secure the distal end portion of the frame 410 in the native annulus.

The proximal anchoring element 434 can be configured to engage subannular tissue on a proximal side of the native annulus to aid in the securement of the frame 410 in the annulus. More specifically, the proximal anchoring element 434 is configured to transition, move, and/or otherwise reconfigure between a first configuration in which the proximal anchoring element 434 extends from the subannular member 430 a first amount or distance and a second configuration in which the proximal anchoring element 434 extends from the subannular member 430 a second amount or distance. As described above, the subannular member 430 of the frame 410 can be and/or can include, for example, a laser cut wire frame formed of a shape-memory material such as Nitinol, which is heat-set into a desired shape and wrapped in a biocompatible material (e.g., a fabric as shown in FIG. 7).

As described above, the proximal anchoring element 434 can be in a compressed, contracted, retracted, undeployed, folded, and/or restrained state (e.g., a position that is near, adjacent to, and/or in contact with the transannular member 412 and/or the supra-annular member 420 of the support frame 410) when in the first configuration, and can be in an expanded, extended, deployed, unfolded, and/or unrestrained state (e.g., extending away from the transannular member 412) when in the second state. In some embodiments, the proximal anchoring element 434 can be biased and/or heat-set in the second configuration. Moreover, in some implementations, the space 418 defined by the transannular member 412 of the outer frame 410 is configured to provide sufficient room to allow the proximal anchoring element 434 to transition between the first and second configurations.

Figure 8:
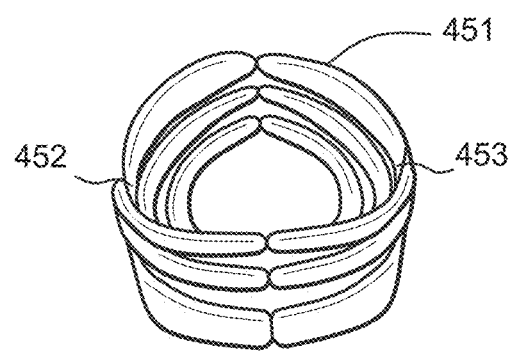
FIG. 8 is a top perspective view an inner frame of a flow control component included in the prosthetic valve shown in FIG. 4.
Figure 9:
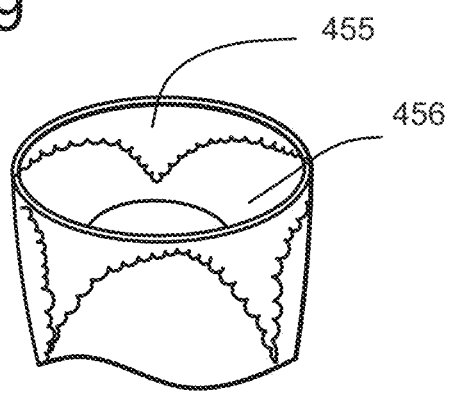
FIG. 9 is a side perspective view of a leaflet band of the inner flow control component having leaflet pockets sewn into a structural band and shown in a cylindrical configuration suitable for coupling to the inner frame of FIG. 8.
Figure 10:
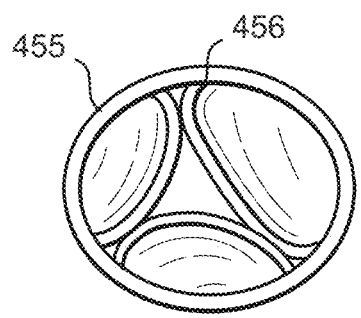
FIG. 10 is a bottom view of the leaflet band of FIG. 9 in the cylindrical configuration and showing partial coaptation of the leaflets to form a partially closed fluid-seal.

FIGS. 8-10 illustrate at least a portion of the flow control component 450 included in the valve 400 shown in FIG. 4. For example, FIG. 8 is an illustration of a top perspective view of the inner leaflet frame 451. In some embodiments, the inner leaflet frame 451 is formed of two separate wireframe sheets or members that are coupled at lateral connection points 451 and 453 (e.g., fold areas, elastically deformable regions, coupled edged portions, etc.). The inner leaflet frame 451 is shown in an expanded or cylindrical configuration (e.g., prior to being folded and/or compressed).

Although not shown, the inner leaflet frame 451 can be transitioned from the expanded or cylindrical configuration to an at least partially folded configuration. The inner leaflet frame 451 can have wireframe sidewalls that allow for rotating or hinging at least at the lateral connection points 451 and 453. The inner leaflet frame 451 can be configured to fold in response to the valve 400 being folded and/or compressed for delivery. When transitioned, for example, to a completely folded configuration, the wireframe sidewalls can be rotated, hinged, and/or folded at their lateral connection points 451 and 453. In addition, the inner leaflet frame 451 can be vertically compressed into a compressed configuration. The wireframe sidewalls can form cells (e.g., diamond-shaped cells or the like) that can be oriented in a direction of compression to allow for elastic compression of the inner frame 451. In some embodiments, the inner frame 451 can be vertically compressed into a pleated or accordion (compressed) configuration.

In some embodiments, the inner leaflet frame 451 of the flow control component 450 can be formed from a linear wireframe or laser cut sheet prior to being further assembled into a cylinder structure (e.g., as shown in FIG. 8). The inner leaflet frame 451 can be formed into the cylinder structure or configuration (or a conical structure or configuration) with edge portions of the linear wireframe sheet being connected or coupled at the lateral connection points 451 and 453 (e.g., hinge areas, fold areas, etc.). Moreover, the inner leaflet frame 451 can be expanded (e.g., driven, formed, bent, etc.) from the linear sheet configuration into the cylinder structure or configuration.

FIGS. 9 and 10 illustrate a structural band 455 of pericardial tissue with leaflet pockets 456 sewn into the structural band 455. FIGS. 9 and 10 are a side perspective view and a bottom view, respectively, illustrating the structural band 455 and leaflet pockets 456 before assembly and/or mounting on and/or into the inner frame 451 to form the collapsible (foldable, compressible) flow control component 450. FIG. 9 shows the structural band 455 formed of pericardial tissue with the leaflet pockets 456 sewn into the structural band 455, after assembly into the cylindrical leaflet configuration, the leaflet pockets 456 being disposed on an inner surface of the structural band 455. The leaflet pocket 456 can be sewn into the structural band 455 such that an open edge extends outward and a sewn edge forms a closed top parabolic edge providing attachment. FIG. 10 is an illustration of a bottom view of the flow control component 450. The cylindrical structural band 455 and leaflet components 456 are shown with partial coaptation towards forming a closed fluid-seal. Although not show, the cylindrical structural band 455 can be mounted to or in the inner leaflet frame 451 (FIG. 8) to collective form the flow control component. The flow control component 450, in turn, is mounted to the outer support frame 410, as described in detail above with reference to FIG. 4.

FIGS. 11-14 are sequence illustrations showing a bottom view of a prosthetic valve 500 removably coupled to an actuator 570 used to actuator one or more portions of the valve 500 according to an embodiment. The valve 500 has a subannular member 530 that can have and/or can form a laser-cut or wire loop (and attached to sidewalls), which is/are drawn inward to reduce the perimeter or circumference of the at least the subannular member 530 to facilitate deployment of the valve 500 in the native annulus. In this embodiment, the actuator 570 can be and/or can include a set of tethers, tensile members, sutures, cables, and/or any other suitable connectors that can be attached to one or more attachment points along the subannular member 530 (e.g., a proximal anchoring element of the subannular member 530). The actuator 570 can also include and/or can be at least partially disposed in a catheter that can be inserted through a dynamic waypoint, opening, attachment point, through hole, etc. formed by a supra-annular member of the valve frame. In some implementations, the actuator 570 can be and/or can include separate tethers used to actuate (e.g., fold) the proximal anchoring element), to actuate (e.g., fold) the septal wall sidewall, and/or to actuate (e.g., fold) the freewall sidewall.

FIGS. 11-14 show a set of tethers of the actuator 570 extending from a catheter that extends through and/or is at least partially disposed below a supra-annular member of the valve frame. For example, the tethers can be run through a relatively small dynamic waypoint catheter and can be actuated outside of the patient to manipulate a shape of the proximal anchoring element, the subannular member 530, and/or the valve 500 to facilitate seating a proximal side of the valve 500 into the native annulus. In some implementations, during delivery, the dynamic waypoint catheter can be proximal to the compressed valve 500 in a delivery catheter to avoid having the dynamic waypoint catheter stacked on top of the compressed valve 500 within the delivery catheter. An actuator with a single tether or multiple tethers is contemplated within the scope of the invention (e.g., one tether, two tethers, three tethers, four tethers, five tethers, six tethers, seven tethers, eight tethers, nine tethers, ten tethers, or more, each of which can be removably coupled to one or more attachment points on the valve 500). The actuator 570 and/or the tethers may be equipped with disconnection elements to allow the actuator 570 and/or tethers to be withdrawn after the valve 500 is deployed and secured in the native annulus. The dynamic waypoint catheter may also be included in and/or housed within a portion of a delivery system such as, for example, a pusher catheter, a multi-lumen control catheter, and/or the like, whereby the dynamic waypoint catheter can drop through the waypoint, a through hole, an opening, etc. of the valve 500 to a subannular position, while the pusher catheter, multi-lumen control catheter, and/or other portion(s) of the delivery system is too large to pass through the waypoint. As such, the pusher catheter, control catheter, and/or other portion(s) of the delivery system can be used to control a placement of at least a portion of the valve 500. For example, the pusher catheter, control catheter, and/or other portion of the delivery system can be used to push down onto a surface of the supra-annular member to seat the proximal side of the valve 500 in the native annulus while the subannular member 530 is in an actuated configuration.

Figure 11:
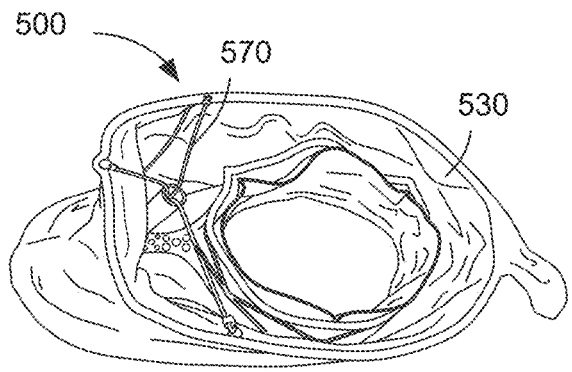
FIGS. 11-14 are bottom perspective views is a bottom-side perspective view of a side-delivered transcatheter prosthetic heart valve, according to an embodiment, and showing a sequence of actuating one or more portions of the prosthetic valve to reduce a perimeter and/or circumference of a subannular member to facilitate deployment of the valve in the native annulus.

FIG. 11 is a bottom perspective view of the valve 500 and the actuator 570 and shows the subannular member 530 in an at least partially extended or unactuated configuration.

Figure 12:
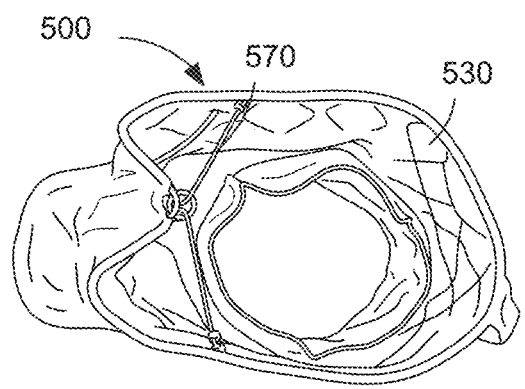
Figure 13:
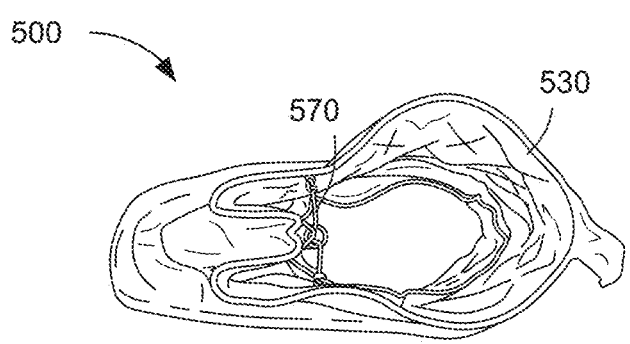
Figure 14:
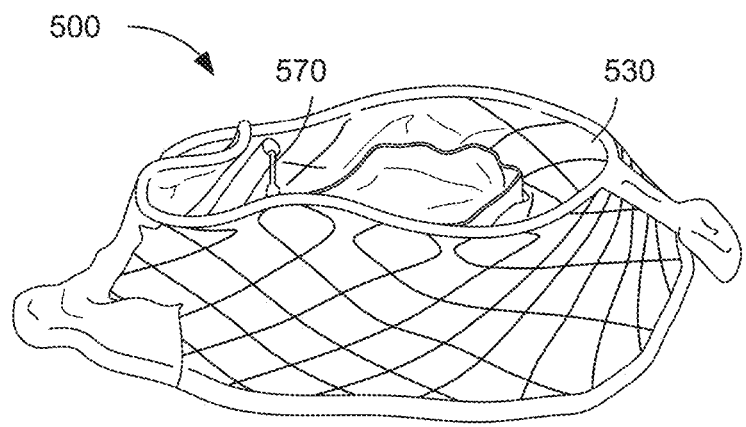

FIG. 12 is a bottom perspective view of the valve 500 and the actuator 570 and shows the subannular member 530 partially actuated such that, for example, the proximal anchoring element of the subannular member 530 is drawn toward the dynamic waypoint catheter and/or the inner flow control component of the valve 500. FIG. 13 is a bottom perspective view of the valve 500 and the actuator 570 and shows the subannular member 530 in a compressed, folded, and/or actuated configuration such that the proximal anchoring element and, for example, a proximal portion of a septal wall sidewall and a freewall sidewall of the valve 500 are drawn toward the dynamic waypoint catheter and/or the inner flow control component of the valve 500. FIG. 14 is a side perspective upside down view of the valve 500 and the actuator 570 and shows the subannular member 530 in the actuated configuration, the dynamic waypoint catheter extending below the supra-annular member of the valve frame, and the tethers retracted or pulled toward and/or into the dynamic waypoint catheter. FIG. 14 shows that the dynamic waypoint catheter can also be used to pull the valve down into the ventricle (e.g., via the retracted tethers), avoiding the need to push a compressible valve into the native annulus.

While the actuator 570 is shown in FIGS. 11-14 and described above as including the waypoint catheter that extends through the dynamic waypoint of the valve 500, in other implementations, the actuator 570 need not include a waypoint catheter. For example, any number of tethers, cables, tension members, sutures, etc., can be routed through one or more lumens of a multi-lumen control catheter and can extend through the waypoint, a through-hole, an opening, and/or the like defined by the valve 500 to removably couple to the proximal subannular anchoring element.

Figure 15:
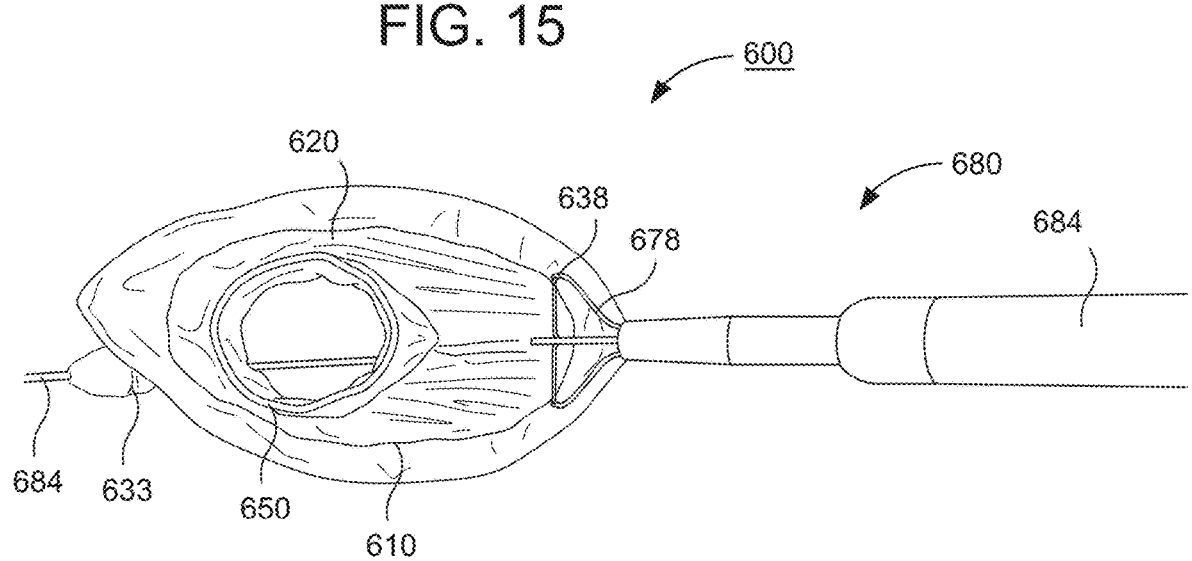
FIGS. 15 and 16 are a top view and a bottom perspective view, respectively, of a prosthetic valve removably coupled to at least a portion of a delivery and/or actuating system, according to an embodiment.
Figure 16:
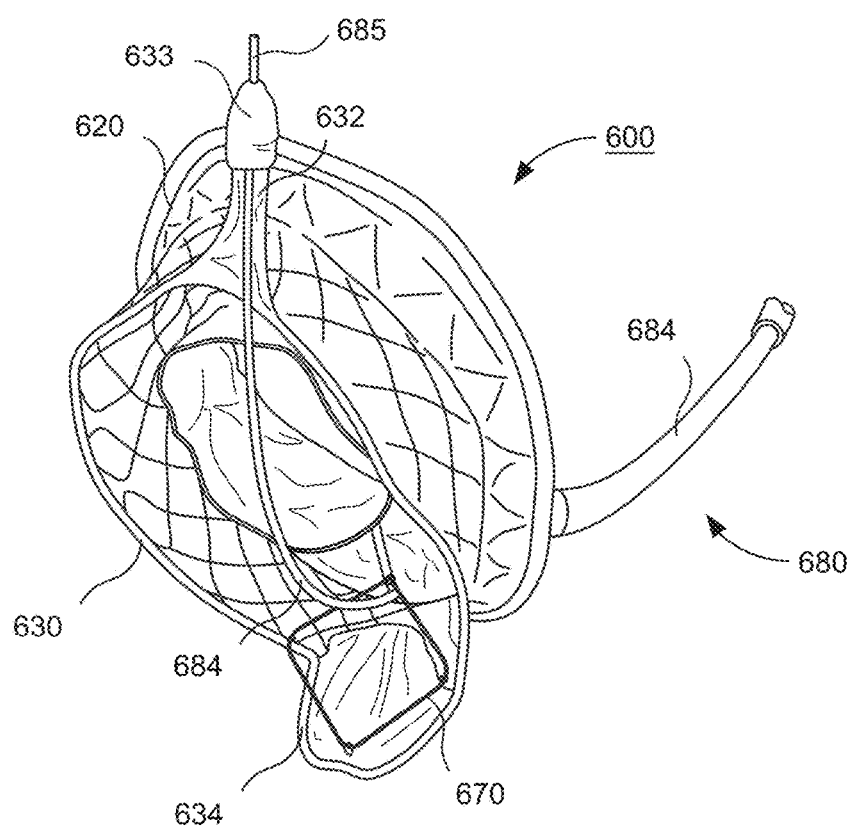

FIGS. 15 and 16 are a top view and a bottom perspective view, respectively, of a side-deliverable transcatheter prosthetic valve 600 removably coupled to a delivery system 680 according to an embodiment. The valve 600 includes a valve frame 610 and a flow control component 650 mounted therein. The valve frame 610 includes a supra-annular member 620, a subannular member 630, and a transannular member 612 coupling the supra-annular member 620 to the subannular member 630. The delivery system 680 and/or at least a portion of the delivery system 680 includes a delivery catheter 682 through which the valve 600 is delivered into an atrium of a heart. The delivery system 680 further includes a connection member 678 that is removably couple-able to the valve 600. FIGS. 15 and 16 show the connection member 678 having a wishbone or yoke configuration, though other configurations are possible. The connection member 678 can be coupled to and/or included in a distal end portion of a multi-lumen steerable catheter, which can be used to deliver one or more components of the valve 600 and/or the delivery system 680.

FIG. 15 shows the connection member 678 (e.g., a yoke) in contact with the supra-annular member 620 of the valve frame 610. In some embodiments, the connection member 678 can be in contact with and/or removably coupled to a drum or the transannular member 612 of the frame 610. In other embodiments, the connection member 678 can be in contact with and/or coupled to any suitable portion of the valve 600. The connection member 678 can removably couple to the valve 600 via sutures, tethers, cables, clips, couplers, and/or any other removable coupling. For example, FIG. 15 shows an attachment member 638 of the valve 600 coupled to and/or extending from the supra-annular member 620. In some embodiments, the attachment member 638 of the valve 600 can be a tether, suture, cable, frame structure, and/or the like that can be coupled to and/or extend from a wire frame portion of the supra-annular member 620 or, for example, a drum or biocompatible covering. In such embodiments, the connection member 678 of the delivery system 680 can be removably coupled (e.g., via a suture, tether, and/or any other removable coupling) to the attachment member 638 of the valve 600.

FIGS. 15 and 16 further show a guidewire catheter 684 of the delivery system 680 extending through, for example, a waypoint or opening in the supra-annular member 630 and/or drum thereof and extending through a guidewire coupler 633 of a distal anchoring element 632 of the subannular member 630. FIG. 16 shows the guidewire catheter 684 extending below the flow control component 650 of the valve 600. Prior to and/or as a part of delivery, the guidewire catheter 684 can be advanced and/or inserted through the valve 600 (as shown in FIG. 53) and advanced over a guidewire already placed in a desired position within the heart. As such, delivering the valve 600 in a compressed configuration through the delivery catheter 682 includes advancing the guidewire catheter 684 along the guidewire. The guidewire catheter 684 can extend through the guidewire coupler 633 of the distal anchoring element 632 (e.g., a distal end of the guidewire catheter 684 can be distal to the guidewire coupler by about 0.1 cm to about 1.0 cm, or more).

The guidewire catheter 684 can be sufficiently stiff to, for example, limit and/or define (at least in part) a range of motion of the valve 600 during delivery. For example, the guidewire catheter 684 can define an axis about which the valve 600 can rotate during delivery but can substantially limit or oppose movement of the valve 600 in other directions. In some implementations, the arrangement of the connection member 678 (e.g., yoke) and the guidewire catheter 684 can allow for greater control of a position of the valve 600 during delivery. The guidewire catheter 684 and/or one or more portions of the valve 600 (e.g., the subannular member 630) can also include radiopaque markers allowing for enhanced visualization during image guided delivery. For example, in some instances, a radiopaque marker or wire can be placed relative to an annular plane of the native valve and can define a landmark during image guided delivery. In such instances, the radiopaque markers on the guidewire catheter 684 and/or other portion(s) of the valve 600 (e.g., the subannular member 630) can be used to align, orient, locate, index, etc. the valve 600 relative to the landmark, which in turn, corresponds to the annular plane of the native valve. Thus, image guided delivery can allow a user to visualize the valve 600 during delivery and/or deployment and can allow the user to visualize when the valve 600 has been seated in the annulus (e.g., the radiopaque marker bands of the valve 600 are below or in a subannular direction relative to the radiopaque landmark.

FIG. 16 further shows an actuator 670 (or at least a portion of the actuator 670) included in the portion of the delivery system 680. The actuator 670 can be and/or can include, for example, one or more tethers, sutures, cables, tensile members, ties, etc. removably coupled to one or more attachment points on the valve 600. For example, the tether(s) are shown removably coupled to a proximal anchoring element 634 of the subannular member 630. The actuator 670 (e.g., tether(s)) can be used to actuate the proximal anchoring element 634 between two or more configurations, positions, states, etc. FIG. 16 shows the proximal anchoring element 634 in an expanded or unactuated configuration. During deployment, an operator can actuate a proximal end portion of the actuator 670 (e.g., disposed outside of the body) to, for example, pull the tether(s) in a proximal direction, thereby folding or compressing the proximal anchoring element 634 toward the flow control component 650. The actuation of the actuator 670 can also fold, compress, and/or draw a proximal portion of a posterior and anterior wall of the transannular member 612 inward toward the flow control component 650 (e.g., as described above with reference to FIGS. 11-14). After deploying the valve 600 in the annulus of the native valve, the actuator 670 can be removed or decoupled from the valve 600, the guidewire catheter 684 (and the guidewire extending therethrough) can be retracted through the waypoint or opening in the supra-annular member 620, and the portion of the delivery system 680 can be decoupled from the valve 600 and withdrawn from the patient, leaving the deployed prosthetic valve 600 in place in the annulus of the native heart valve.

While the valves 500 and/or 600 are described above as actuating and/or transitioning the corresponding proximal anchoring element in a particular manner, it should be understood that a proximal anchoring element of a valve can be actuated, moved, swung, rotated, and/or otherwise transitioned in any suitable manner. For example, FIGS. 17-20 are bottom perspective views of a prosthetic valve 700 and illustrate a process of transitioning a proximal anchoring element 734 of the prosthetic valve 700 between a first configuration and a second configuration, according to an embodiment. The valve 700 is shown as including an outer support frame 710 and a flow control component 750 mounted within a central region of the outer support frame 710. The frame 710 is shown having at least a supra-annular member 720 and a subannular member 730. The supra-annular member 720 and the subannular member 730 can be similar to any of those described above. Accordingly, certain aspects and/or features may not be described in further detail herein.

Figure 17:
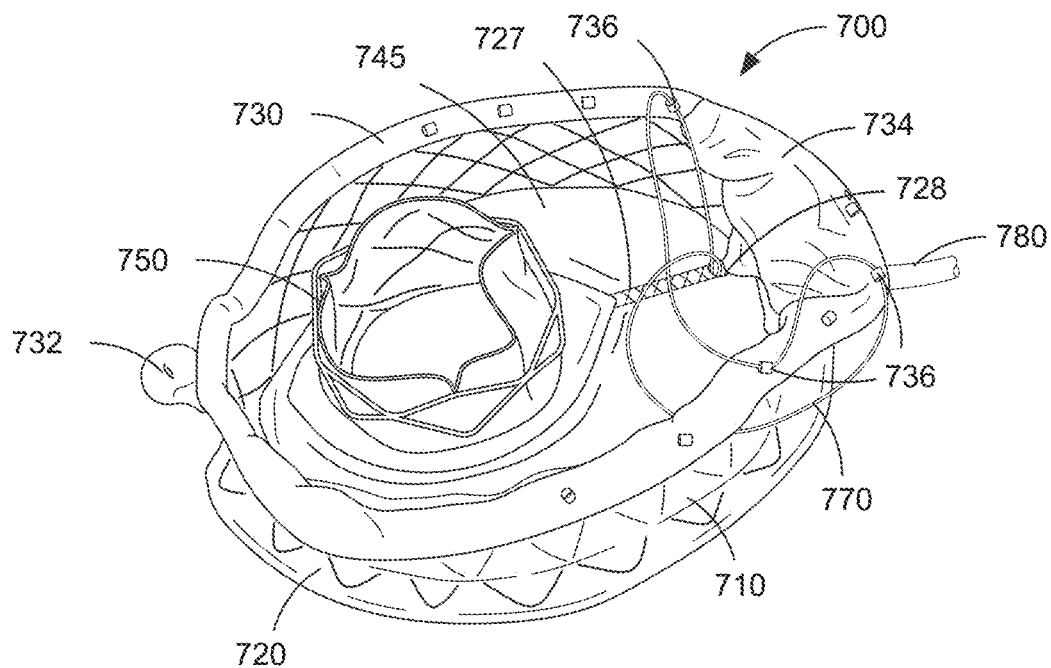
FIGS. 17-20 are bottom perspective views of a prosthetic valve and illustrating a process of transitioning a proximal anchoring element of the prosthetic valve between a first configuration and a second configuration, according to an embodiment.

FIG. 17 shows the subannular member 730 having and/or forming a distal anchoring element 732 and the proximal anchoring element 734. The supra-annular member 720 is shown including a spline 727 (e.g., extending between an outer loop and an inner loop of the supra-annular member 720 (not shown)) that defines a waypoint 728 at or near a proximal end portion of the supra-annular member 720. The supra-annular member 720 is further shown as including a drum 3445 that extends between and/or is coupled to the inner and outer loops of the supra-annular member 720 and covers a space not otherwise occupied by the flow control component 750. The supra-annular member 720 (or an inner loop thereof) is shown coupled to the flow control component 750, which is distally offset relative to the valve 700.

The valve 700 is configured to engage or to be engaged by at least a portion of a delivery system 780, or the like. The delivery system 780 can include any suitable component for delivering, retrieving, deploying, moving, manipulating, actuating, and/or otherwise interacting with one or more portions of the valve 700. In this embodiment, the delivery system 780 can include, for example, one or more catheters. For example, the delivery system 780 can include a delivery catheter through which the valve 700 is delivered to an annulus of a native heart valve. The delivery system 780 can also include one or more steerable catheters, control catheters, multi-lumen catheters, and/or the like, or combinations thereof. In some embodiments, the delivery system 780 can include a multi-lumen control catheter that has a distal end portion configured to removably engage and/or couple to one or more portions of the valve 700 to facilitate delivery, deployment, and/or retrieval of the valve 700. Although not shown in FIGS. 17-20, the delivery system 780 can also include a guidewire catheter that can be advanced over a guidewire during delivery and/or deployment. In such implementations, the guidewire catheter can pass through the waypoint 728, below the flow control component 750, and through a guidewire coupler of the distal anchoring element, as described above with reference to the valve 700 shown in FIGS. 15 and 16.

FIG. 17 further shows the delivery system 780 including an actuator 770. The actuator 770 can be similar to those described above with reference to, for example, 170, 270, and/or 370. For example, the actuator 770 can be and/or can include a tether that extends through the waypoint 728 of the spline 727 and is threaded through one or more attachment point(s) 736 coupled to and/or formed along the subannular member 730. The tether loops through the attachment(s) 736 and extends in a proximal direction back through the waypoint 728. As such, both ends of the tether can be maintained outside of the body, allowing a user to manipulate the tether (actuator 770). In this embodiment, the tether is shown threaded through multiple attachment points 736 at or along the proximal anchoring element 734 of the subannular member 730 such that actuation of the actuator 770 (e.g., tether(s)) transitions and/or moves at least the proximal anchoring element 734 between the first configuration and the second configuration. The tether can be threaded through the attachment points 736 in any suitable manner, which in turn, can control and/or determine a way that the proximal anchoring element 734 is transitioned or moved. Moreover, the attachment points 736 can be formed from any suitable material that can facilitate the passage or threading of the tether therethrough. For example, the attachment points 736 can be included in and/or integrally formed with a laser-cut wire frame of the subannular member 720 (e.g., like eyelets and/or the like). In other embodiments, the attachment points 736 can be sutured loops and/or loops formed in or by a biocompatible fabric at least partially wrapping around the subannular member 720. In still other embodiments, the attachment points 736 can be formed from a biocompatible polymer such as, for example, polyethylene, and/or the like. In some such embodiments, the biocompatible material can be, for example, a self-lubricating polymer composite and/or the like that can facilitate the movement of the tether through the attachment point 736.

Figure 18:
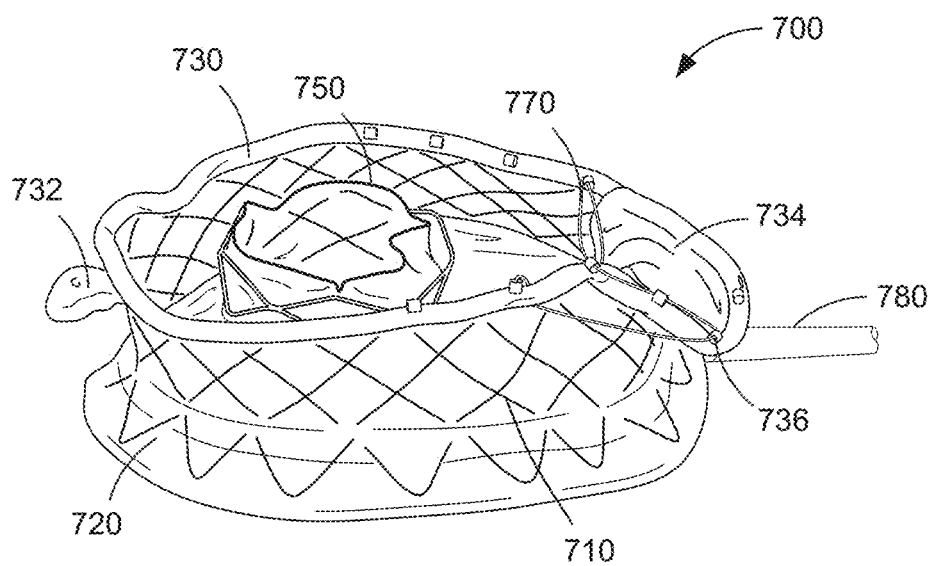
Figure 19:
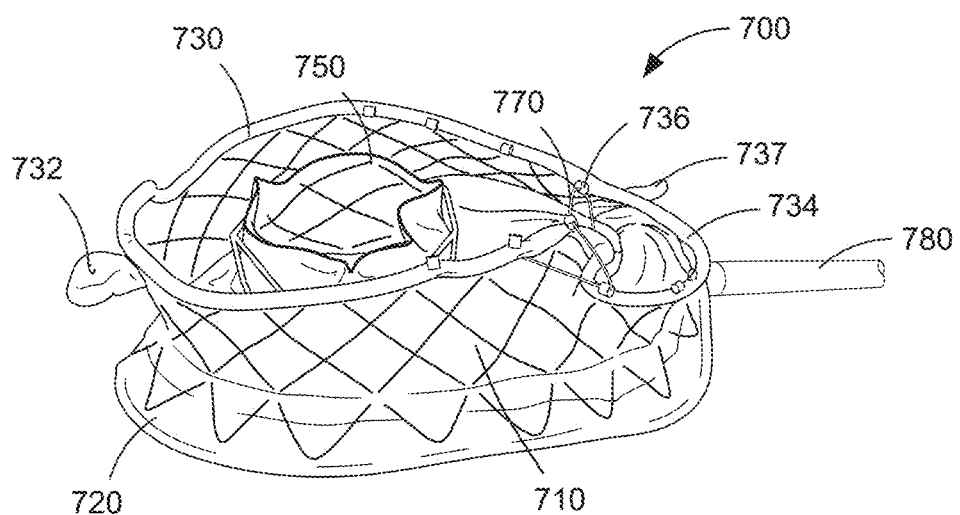
Figure 20:
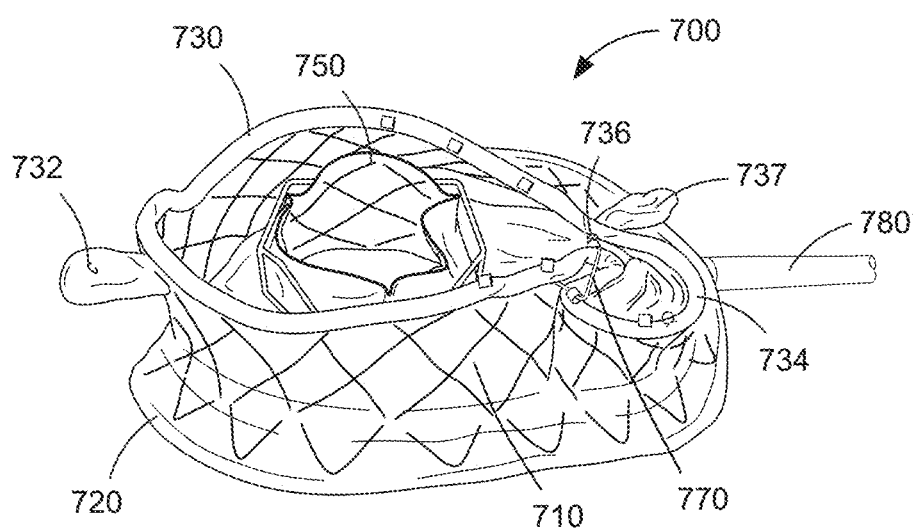

FIG. 17 shows the proximal anchoring element 734 in a first or unactuated configuration with the tether (actuator 770) looped through the attachment points 736 in a serpentine manner. FIGS. 18 and 19 show the proximal anchoring element 734 as it is transitioned from the first, unactuated configuration toward a second, actuated configuration in response to an actuation of the actuator 770 (e.g., pulling on the tether in a proximal direction and/or in a direction that otherwise results in tension along a length of the tether). FIG. 20 shows the proximal anchoring element 734 in the second, actuated configuration.

In the embodiment shown in FIGS. 17-20, the actuator 770 engages the proximal anchoring element 734 such that one of the attachment points 736 on an anterior or freewall side of the subannular member 730 acts as a pivot point about which the proximal anchoring element 734 is at least partially rotated, folded, rolled, etc. In other embodiments, the actuator 770 can engage the proximal anchoring element 734 such that an attachment point 736 on a posterior or septal side of the subannular member 730 acts as the pivot point. In other words, the proximal anchoring element 734 can be rotated, folded, rolled, pivoted, swung, and/or otherwise moved toward an anterior side of the valve 700 or a posterior side of the valve 700 depending on how the actuator 770 engages the attachment points 736 of the proximal anchoring element 734.

FIGS. 19 and 20 also show a tab 737 included on and/or formed by the proximal anchoring element 734. In some implementations, the tab 737 can contact native subannular tissue to facilitate securement of a proximal side of the valve 700 in the annulus of the native valve. More specifically, the tab 737 can be positioned along and/or adjacent to the proximal anchoring element 734 and can rotate, swing, pivot, and/or otherwise move with the proximal anchoring element 734 in response to actuation of the actuator 770. In some implementations, the placement of the tab 737 can be such that as the proximal anchoring element 734 is moved (e.g., from the compressed configuration to the expanded configuration, after the valve 700 is deployed and/or seated in the annulus), the tab 737 moves or slides behind, for example, a commissure, posterior or septal leaflets, chordae, trabeculae, and/or any other desirable portion of native tissue. While one tab 737 is shown in FIGS. 19 and 20, in other embodiments, the proximal anchoring element 734 can include two or more tabs 737 that can be arranged and/or otherwise act as hooks or the like to hook onto or behind native tissue, thereby securing the proximal anchoring element 734 to native subannular tissue.

Figure 21:
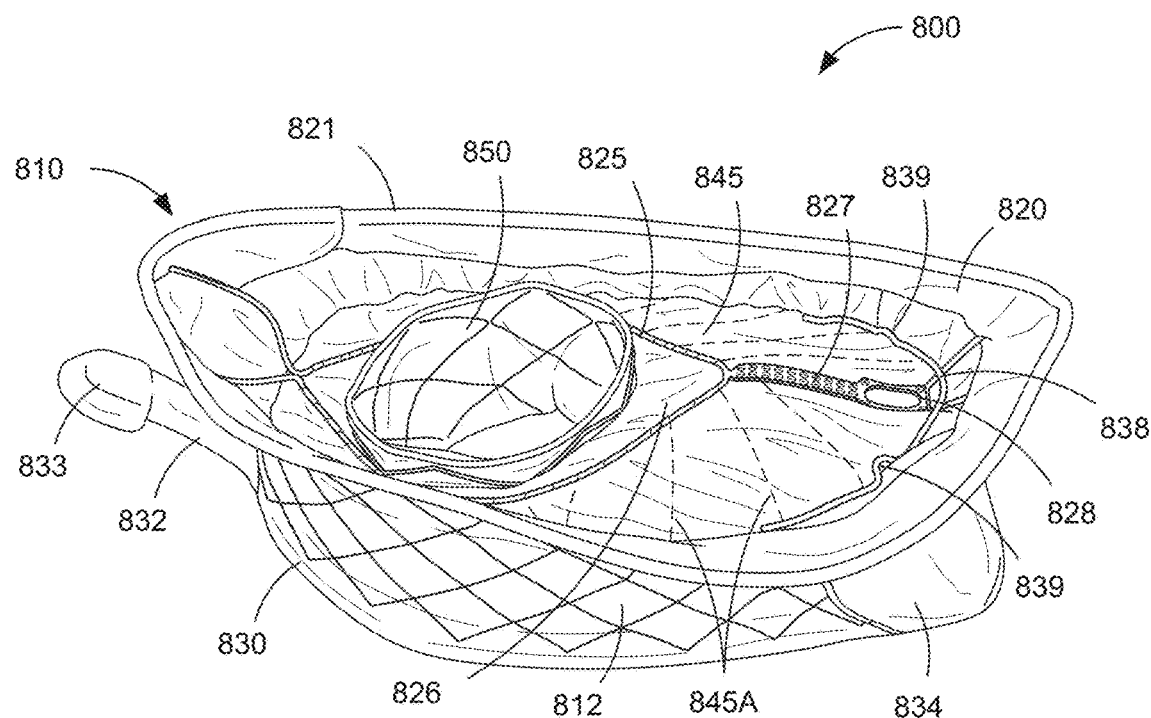
FIGS. 21 and 22 are a side perspective view and a bottom view, respectively, of a prosthetic valve and illustrating a supra-annular member having a bowed configuration, according to an embodiment.
Figure 22:
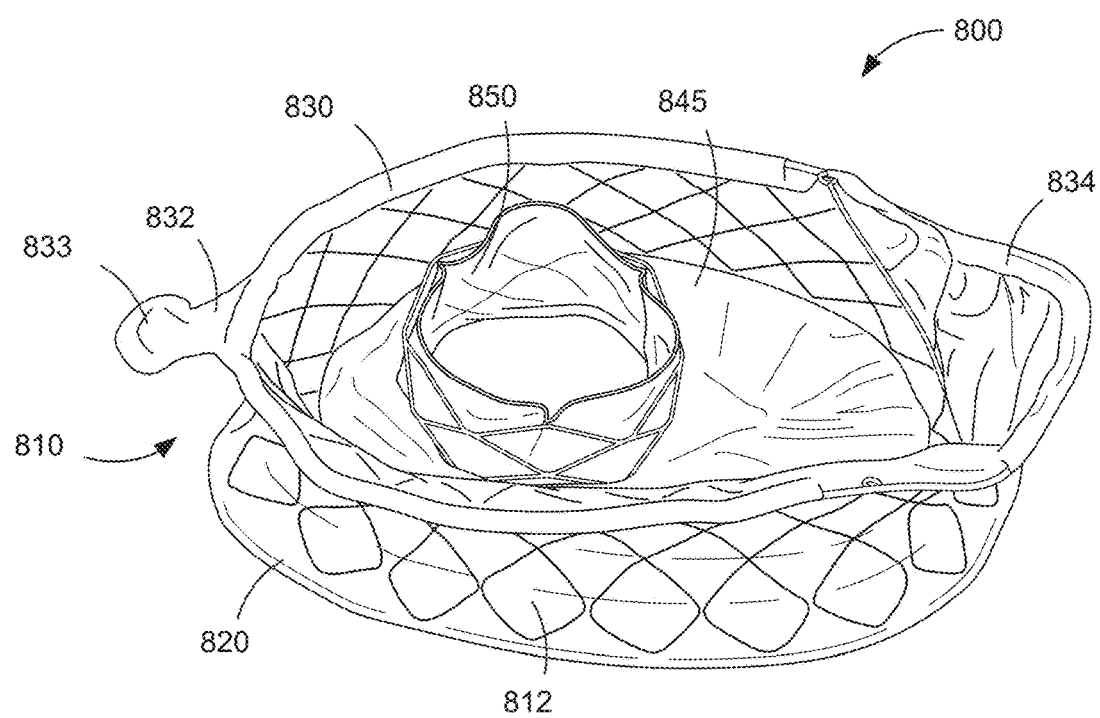

FIGS. 21 and 22 are various views of a side-deliverable prosthetic valve 800 and illustrating a portion of a supra-annular member 820 having a bowed configuration, according to an embodiment. The valve 800 is shown as including an outer support frame 810 and a flow control component 850 mounted within a central region of the outer support frame 810. The frame 810 is shown having at least a supra-annular member 820, a subannular member 830, and a transannular member 812 coupled therebetween. The frame 810 and/or aspects thereof can be similar to any of those described above. Accordingly, certain aspects and/or features may not be described in further detail herein.

The valve 800 is shown with the subannular member 830 having and/or forming a distal anchoring element 832 and a proximal anchoring element 834. The distal anchoring element 832 includes a guidewire coupler 833 that can receive a guidewire and/or a guidewire catheter through an opening, hole, aperture, port, etc., defined by the guidewire coupler 833. In some implementations, a guidewire catheter can extend beyond the distal anchoring element 832 and can have and/or can provide sufficient stiffness to allow the valve 800 be advanced along a guidewire that is threaded through a lumen of the guidewire catheter. The proximal anchoring element 834 can be, for example, a movable anchoring element configured to be moved and/or otherwise transitioned (e.g., by an actuator) between a first configuration and a second configuration to reduce a perimeter of the subannular member 820 during delivery and/or deployment.

The proximal anchoring element 834 can be configured to move in any suitable direction from the first, extended configuration (FIG. 21) to the second, compressed configuration based at least in part on how the proximal anchoring element 834 is coupled to an actuator. For example, the proximal anchoring element 834 can be moved inward toward the inner flow control component 850, moved upward toward the supra-annular member 820 and/or portion thereof, and/or moved toward an anterior side or a posterior side of the valve 800. Moreover, with the transannular member 812 of the frame 810 coupled to the subannular member 830, actuation of an actuator can, in some implementations, move one or more portions of the transannular member 812.

The supra-annular member 820 is shown having laser cut wire frame that is wrapped or covered in a biocompatible material. The supra-annular member 820 includes a distal portion 822, a proximal portion 824, an outer loop 821, an inner loop 825, and at least one spline 827. In some embodiments, the outer loop 821 can be shaped and/or sized to engage native tissue. For example, the distal portion 822 of the supra-annular member 820 (formed at least in part by the outer loop 821) is configured to engage distal supra-annular tissue and the proximal portion 824 (formed at least in part by the outer loop 821) is configured to engage proximal supra-annular tissue. The distal and proximal portions 822 and 824 can have a rounded and/or curved shape, wherein a radius of curvature of the proximal portion 824 is larger than a radius of curvature of the distal portion 822. The distal portion 822 and/or the proximal portion 824 can form, for example, a distal supra-annular anchoring element and/or a proximal supra-annular anchoring element, respectively, each of which can engage supra-annular tissue to at least partially stabilize and/or secure the frame 810 in the native annulus.

The inner loop 825 of the supra-annular member 820 can have an oblong or teardrop-shape can be coupled to and/or suspended from the outer loop 821 by the one or more splines 827. The inner loop 825 can be coupled to the flow control component 850 via, for example, biocompatible material 826. The inner loop 825 is shown as being coupled to the flow control component 850 such that the flow control component 850 is distally offset relative to the valve 800. In some implementations, suspending the inner loop 825 from the outer loop 821 can, for example, at least partially isolate the inner loop 825 (and the flow control component 850 coupled to the inner loop 825) from at least a portion of the force associated with transitioning the frame 810 between the expanded configuration and the compressed configuration (e.g., during delivery and/or deployment).

The one or more splines 827 of the supra-annular member 820 can be any suitable shape, size, and/or configuration. For example, in some embodiments, the supra-annular member 820 can include a proximal spline 827 that defines a waypoint 828. The waypoint 828 can be, for example, an opening, a hole, an aperture, a port, a coupler, a sealable/resealable access point, and/or the like configured to at least temporarily couple to and/or receive a portion of a delivery system. For example, in some implementations, the portion of the delivery system can include at least an actuator and a guidewire catheter.

The supra-annular member 820 is further shown as including a drum 845 that extends between and/or is coupled to the outer loop 821 and the inner loop 825 and covers a space not otherwise occupied by the flow control component 850. FIG. 21 shows the drum 845 having and/or forming a set of spokes 845A that can be used to increase a stiffness of the drum 845. The spokes 845A can be, for example, sutures that are sewn into the drum 845 to increase the stiffness of the drum 845 and/or to otherwise modify a deformation mode of the drum 845 during, for example, systole, which in turn, can enhance performance of the valve 800 and/or reduce fatigue in or along the drum 845. While particularly shown in FIG. 21, the spokes 845A can be arranged in any suitable manner that results in an increase in drum stiffness. For example, the spokes 845A can be arranged longitudinally, laterally, and/or at angles relative to a longitudinal or lateral direction. In other embodiments, the spokes 845A can be arranged in a crosshatch pattern and/or any other suitable pattern.

FIG. 21 further shows the drum 845 including an attachment member 838 that can facilitate a temporary attachment to a portion of the delivery system. The attachment member 838 can be, for example, a braided thread, a suture, a tether, a cable, and/or the like. As described above, in some implementations, a delivery system can include a control or steerable catheter that can include an integrated yoke or other suitable removable coupler. More particularly, the attachment member 838 can include a set of loops 839 through which a set of tethers can be threaded to removably couple the yoke of the delivery system to the valve 800. The tethers can be passed through the loops 839 such that each end of the tethers is maintained outside the patient allowing an operator to manipulate the tethers to control a contact between the yoke and the drum 845.

While the attachment member 838 is shown coupled to the drum 845 at or near a proximal edge of the drum 845, in other embodiments, the attachment member 838 can be coupled to the drum 845 in any suitable location (e.g., a proximal position adjacent to the flow control component 850, a distal position as shown in FIG. 21, or any suitable position therebetween). Although the attachment member 838 is described above as being coupled to the drum 845, in other embodiments, any portion of the valve 800 can include an attachment member 838. In some embodiments, for example, the supra-annular member 820 can include a laser cut portion of the wire frame that extends across a portion of the outer loop 825 (e.g., perpendicular to the spline 827).

FIGS. 21 and 22 further show the spline 827 of the supra-annular member 820 having a bowed shape and/or configuration, in which the spline 827 protrudes away from the subannular member 820. For example, in some embodiments, a laser cut frame of the supra-annular member 820 can be formed with the spline 827 having the bowed configuration. In some implementations, bowed spline 827 can exert a force on the drum 845 that bows the drum 845 and increases a tension across the area of the drum 845. The increase in tension, in turn, increases a relative stiffness of the drum 845, which can reduce and/or limit an amount of drum deformation during, for example, diastole or systole, thereby enhancing performance of the valve 800 and/or reduce fatigue in or along the drum 845. Said another way, the pressure produced on the atrial side of the drum 845 during contraction of the atrium (diastole) is not sufficient to invert the bowed configuration of the drum 845 (i.e., will not produce an oil-can like deflection) due to the bowed spline 827. The bowed configuration of the drum 845 can also withstand the greater pressure produced on the ventricle side of the drum 845 during contraction of the ventricle (systole) without substantial deflection. Moreover, the bow in the spline 827 can be such that the waypoint 828 is positioned at a desired angle and/or orientation to facilitate the insertion or retrieval of one or more portions of the delivery system through the waypoint 828.

The valves described herein are configured to be delivered to a desired target location within a patient via side or orthogonal delivery techniques, methods, and/or systems. A delivery system for side-delivering a transcatheter prosthetic valve can be any shape, size, and/or configuration, and can include any suitable feature, component, member, mechanism, assembly, subsystem, and/or the like. In some implementations, a delivery system can be similar to and/or can include any suitable combination of components from the delivery systems described in any of the '957 PCT, the '010 PCT, the '231 PCT, the '390 PCT, the '108 PCT, the '327 Provisional, the '964 Provisional, the '345 Provisional, and/or the '807 Provisional.

Figure 23A:
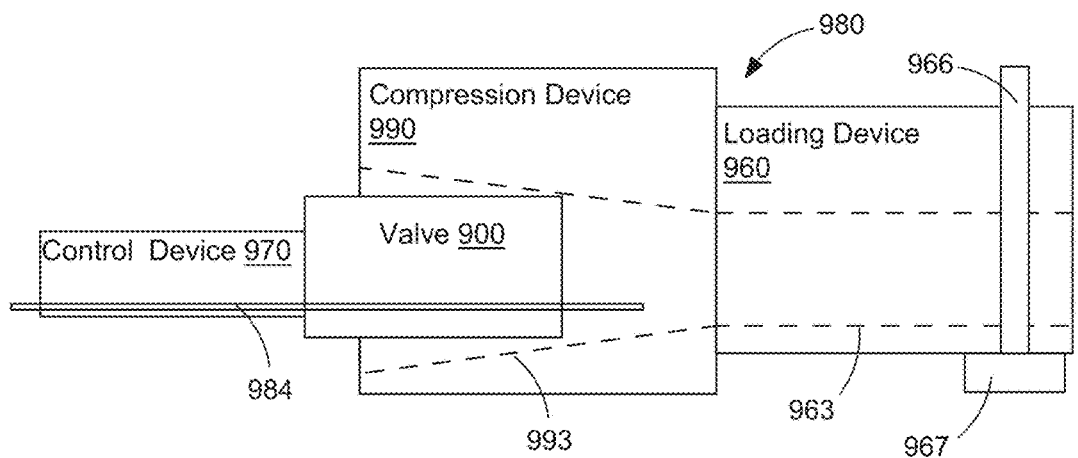
FIGS. 23A-23C are schematic illustrations of a side-deliverable prosthetic valve and at least a portion of a delivery system for delivering the prosthetic valve, according to an embodiment.
Figure 23B:
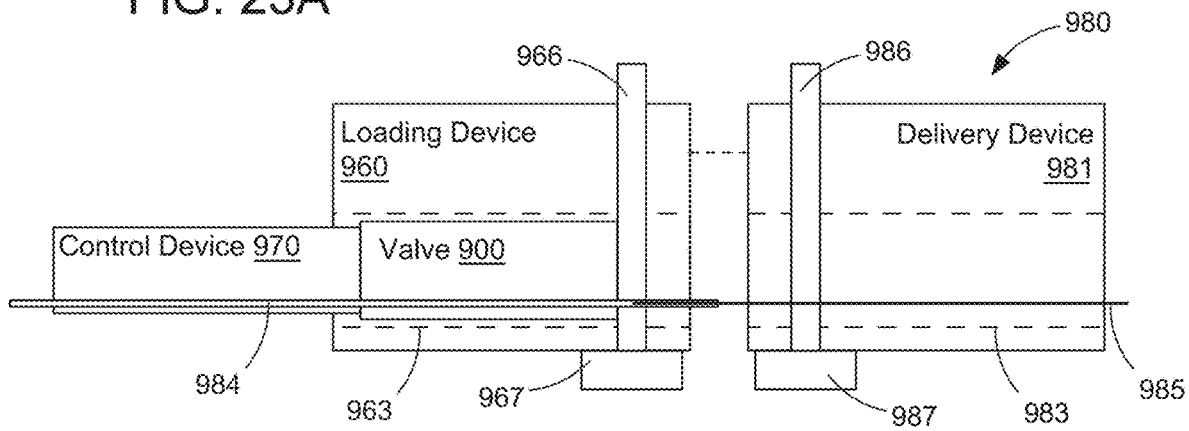
Figure 23C:
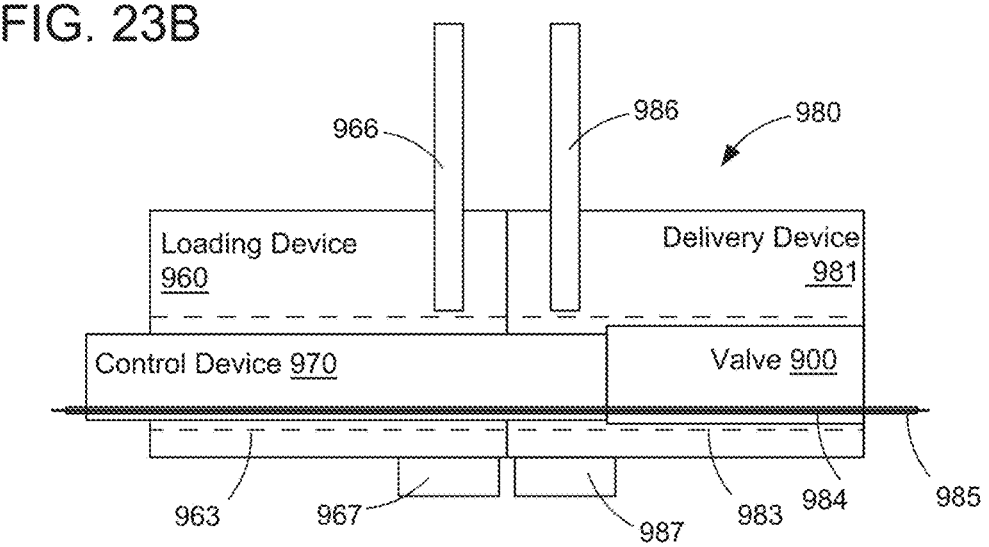

For example, FIGS. 23A-23C are schematic illustrations of a side-deliverable prosthetic valve 900 and at least a portion of a delivery system 980 for side-delivering the prosthetic valve to an annulus of a native heart valve, according to an embodiment. The side-deliverable prosthetic valve 900 ("valve") can be, for example, substantially similar to the valves 100, 400, 500, 600, 700, and/or 800. For example, the valve 900 can have an outer frame with an inner flow control component mounted therein. The valve 900 is compressible and expandable in at least one direction relative to a longitudinal axis, as described in further detail herein.

The delivery system 980 can include any suitable component(s) configured to place the valve 900 in a delivery configuration, load the valve 900 into a portion of the delivery system 980, deliver the valve 900 in the delivery configuration through a portion of the delivery system 980, control and/or facilitate a deployment of the valve 900 in the annulus of the native valve, and in some instances, at least partially retrieve the valve 900 from the annulus to allow for adjustment and/or reseating of the valve 900 or removal of the valve 900 from the heart (e.g., in the case of failure or patient distress).

In the embodiment shown in FIGS. 23A-23C, the delivery system 980 includes at least a control device 970, a compression device 990, a loading device 960, and a delivery device 981. The control device 970 can be and/or can include any number of components that can be at least temporarily coupled to and/or in contact with one or more portions of the valve 900 and configured to control and/or facilitate, for example, a delivery, deployment, and/or retrieval of the valve 900. For example, in some embodiments, the control device 970 can include a control catheter that includes a connection member disposed at a distal end of the control catheter. In some embodiments, the connection member can have a wishbone or yoke configuration, though other configurations are possible.

The connection member is removably coupleable to the valve 900. More specifically, the connection member can be removably coupled to and placed in contact with a supra-annular member or region of the valve frame. In some embodiments, the connection member can be in contact with and/or removably coupled to a drum extending across the supra-annulus member or region, a transannular member or region of the frame, and/or any other suitable portion of the valve 900. The connection member can removably couple to the valve 900 via sutures, tethers, cables, clips, couplers, and/or any other removable coupling. For example, in some embodiments, the valve 900 can include one or more attachment members such as a tether, suture, cable, frame structure, drum structure, and/or the like to which the connection member of the control device 970 can be removably coupled (e.g., via a suture, tether, and/or any other removable coupling).

The control device 970 can include a control catheter that is coupled to and/or that otherwise includes the connection member at a distal end thereof. In some embodiments, the control catheter can be a steerable, multi-lumen catheter. The multiple lumens can be configured to provide one or more paths through which one or more components can extend to selectively engage the valve 900. For example, as shown in FIG. 23A, the delivery system 980 can include a guidewire catheter 984 that extends through a lumen of the control catheter and through one or more portions of the valve 900. More particularly, the guidewire catheter 984 can extend through a waypoint or opening defined in or by the supra-annular member or region of the valve 900, can traverse a distance below the inner flow control component of the valve 900, and can extend through, for example, a guidewire coupler included in distal subannular anchoring element, as described in detail above with reference to the valve 600 shown in FIGS. 15 and 16.

In addition, one or more of the lumens of the multi-lumen control catheter can receive a tether, suture, wire, etc., configured to loop through a portion or side of the connection member (e.g., a yoke), around an attachment point of the valve 900, through the portion or side of the connection member again, back through the same lumen of the control catheter, thereby coupling the connection member to the valve 900. Moreover, such an arrangement can allow an operator to pull on one end of the tether, suture, wire, etc., ("tether") to remove the tether from the control device 970, which in turn, can at least partially decouple the connection member from the valve 900 (e.g., after a successful deployment of the valve). Similarly, one or more of the lumens of the control catheter can receive an actuator, tension member, tether, cable, wire, etc., that can be routed through a lumen of the control catheter to engage a proximal anchoring element of the valve 900. Accordingly, the tension member or the like can be actuated (e.g., placed under tension) to transition the proximal anchoring element between two or more configurations, as described in detail above with reference to the valves 500, 600, and/or 700.

FIG. 23A shows the compression device 990 removably coupled to the loading device 960 and shows the valve 900 at least partially disposed in a lumen 995 of the compression device 990. In some implementations, it is desirable to couple the control device 970 to the valve 900 prior to inserting the valve 900 into the compression device 990. As such, the compression device 990 can be, for example, a multi-component device that can be separated to allow the compression device 990 to be decoupled from the loading device 960 and from around at least a portion of the control device after the valve 900 has been advanced therethrough, as described in further detail herein.

FIG. 23A shows the lumen 995 of the compression device 990 being tapered in at least one direction as the lumen extends from a proximal end of the compression device 990 to a distal end of the compression device 990. In some embodiments, for example, the lumen 995 can be tapered in one direction such as an axial direction (e.g., a direction parallel to a flow of fluid through the valve) that is orthogonal to a longitudinal direction (e.g., a proximal-distal direction). In such embodiments, a size and/or perimeter of the lumen 995 at the proximal end of the compression device 990 can be such that an operator or user compresses and/or folds the valve 900 in a lateral direction orthogonal to both the axial and longitudinal directions prior to inserting the valve 900 into the proximal end of the compression device. In other embodiments, the lumen 995 can be tapered in two directions—namely, the axial direction and the lateral direction. In either embodiment, a size and/or perimeter of the lumen 995 at the proximal end of the compression device 990 is larger than a size and/or perimeter of the lumen 995 at a distal end of the compression device 990. Moreover, in some embodiments, a shape of the lumen 995 at the proximal end of the compression device 990 can be different from a shape of the lumen at the distal end of the compression device 990. For example, in some embodiments, the lumen 995 at the proximal end of the compression device 990 can have a substantially rectangular perimeter while the lumen 995 at the distal end of the compression device 990 can have a substantially circular perimeter. In other embodiments, the lumen 995 can have substantially the same shape at the proximal end and the distal end or can have any suitable combination of shapes at the proximal and distal ends.

In some implementations, after initially inserting the valve 900 into the proximal end of the compression device 990 a user or operator can, for example, exert a force on the control device 970 such that the connection member (e.g., a yoke) pushes the valve 900 through the compression device 990. In other implementations, the control device 970 can include a pusher and/or the guidewire catheter 984 can include a pusher that can selectively engage a portion of the distal subannular anchoring element to pull the valve 900 through the compression device 990 in response to a distally directed force exerted on the control device 970. In some implementations, the delivery system 980 can include a pulling device and/or the like (not shown) that can be removably coupled to a distal portion of the loading device 960 and a distal end of the valve 900 (e.g., via a tether or the like) and can be manipulated to pull the valve 900 through the compression device 990. In some implementations, the pulling device can be used to pull the valve 900 and the control device 970 can be used to push and/or pull the valve 900 to collectively advance the valve 900 through the compression device 990.

The valve 900 is shown in FIG. 23A as being advanced through the lumen 995 of the compression device 990 from the proximal end to the distal end and the compression device 990 compresses the valve 900 in at least the axial direction as the valve 900 is advanced therethrough. In some instance, the valve 900 can be in a substantially uncompressed or a laterally compressed configuration when inserted into the proximal end of the compression device 990 and can be compressed to a compressed or delivery configuration when advanced to and/or through the distal end of the compression device 990. Although not shown, in some instances, the valve 900 can be loaded into the compression device 990 and advanced through the lumen 995 while at least the compression device 990 is disposed in a saline bath or the like, which can facilitate the advancement of the valve 900 through the compression device 990 and can maintain a substantial sterility of the valve 900.

FIG. 23A shows a proximal end of the loading device 960 being removably coupled to the distal end of the compression device 990. The loading device 960 can be any suitable shape, size, and/or configuration. FIG. 23A shows the loading device 960 as defining a lumen 963 that extends through the loading device 960 and having a gate 966 at a distal end of the loading device 960. The gate 966 is movable between a closed state (FIGS. 23A and 23B) and an open state (FIG. 23C). The gate 966 in the closed state can selectively occlude a portion of the lumen 963, as described in further detail herein.

The distal end of the loading device 960 is further shown as including at least one port 967. The at least one port 967 is in fluid communication with the lumen 963 and is configured to provide selective flushing of at least a portion the lumen 963. In some embodiments, for example, the loading device 960 can include a first port that is disposed proximal to the gate 966 and in fluid communication with at least a portion of the lumen 963 proximal to the gate 966, and a second port that is disposed distal to the gate 966 and in fluid communication with at least a portion of the lumen 963 distal to the gate 966. In some implementations, the port 967 (e.g., via a first portion of the port 967 or a first port) can be used to provide suction to at least a portion of the lumen 963 as well as a flow of fluid for flushing at least a portion of the lumen 963 (e.g., via a second portion of the port 967 or a second port). In some instances, the port 967 can provide flushing (e.g., a flow of sterile fluid such as saline with or without simultaneous suctioning) of at least a portion of the lumen 963 while the gate 966 is in the closed state and/or after the gate 966 is transitioned to the open state.

The lumen 963 of the loading device 960 has a diameter and/or perimeter that is substantially similar to a diameter and/or perimeter of the lumen 995 at the distal end of the compression device 990. As such, the valve 900 can be compressed to the delivery configuration and advanced from the compression device 990 into the lumen 963 of the loading device 960. FIG. 23B shows the valve 900 in the delivery configuration disposed in the lumen 963 of the loading device 900. FIG. 23B further shows that the compression device 990 is removed and/or decoupled from the proximal end of the loading device 960 after the valve 900 is advanced into the lumen 963. In some implementations, for example, the compression device 990 can be laterally separated and removed from around the control device 970 and withdrawn from the loading device 960, as described above. Although not shown in FIGS. 23A-23B, after removing the compression device 990 from the loading device 960, a hemostasis valve and/or the like can be advanced over a portion of the control device 970 and coupled to the proximal end of the loading device 960. The hemostasis valve and/or the like can form a substantially fluid tight seal at the proximal end of the loading device 960 (e.g., and around the control device 970 and/or a control catheter thereof). Moreover, in implementations in which a pulling device or the like is coupled to the distal end of the loading device 960 to pull the valve 900 into the loading device, the pulling device can be decoupled from the loading device 960 and any tether, cable, and/or connection attached to the distal end of the valve 900 can be removed therefrom.

FIG. 23B shows that the valve 900 is loaded into the loading device 960 while the gate 966 is in the closed state. In some implementations, the valve 900 can be advanced through the lumen 963 until, for example, the distal anchoring element (or a distal most portion) of the valve 900 contacts and/or is adjacent to a proximal surface of the gate 966 in the closed state. FIG. 23B further shows that the guidewire catheter 984 extends distally from the valve 900, through the gate 966 in the closed state, and beyond the distal end of the loading device 960. In some embodiments, for example, the gate 966 can have a shape and/or size such that a space is defined between an edge of the gate 966 and an inner surface of the loading device 960 allowing the guidewire catheter 984 to extend therethrough. In some embodiments, the gate 966 can define an opening, a hole, a notch, a recess, and/or the like through which the guidewire catheter 984 can extend.

FIGS. 23B and 23C show that the distal end of the loading device 960 can be coupled to a proximal end of the delivery device 981. In some implementations, the delivery device 981 and/or at least a delivery catheter thereof can be inserted into the patient and advanced through the patient such that a distal end of the delivery device 981 (delivery catheter) is disposed in a space or volume of a heart. Moreover, the delivery device 981 and/or at least the delivery catheter thereof can be tracked and/or advanced over a guidewire 985 that is previously inserted through the patient and placed in a desired position relative to an annulus of the native heart valve. FIG. 23B shows that a proximal end of the guidewire 985 extends from the proximal end of the delivery device 981. As described above, in some instances, the valve 900 is loaded into the loading device 960 while the compression device 990 and the loading device 960 are disposed in a fluid (e.g., saline) bath. In such instances, the loading device 960 with the valve 900 in the delivery configuration disposed in the lumen 963, the hemostasis valve or the like coupled to the proximal end, and the gate 966 in the closed state can be removed from the bath and brought to, for example, an operating table or the like to be coupled to the proximal end of the delivery device 981 that is already inserted into the patient.

FIG. 23B shows that prior to coupling the distal end of the loading device 960 to the delivery device 981 the guidewire 985 extending through the proximal end of the delivery device 981 is inserted into the guidewire catheter 984. The delivery device 981 is shown as defining a lumen 983 that has a perimeter and/or diameter that is substantially similar to the perimeter and/or diameter of the lumen 963 of the loading device 960. FIG. 23B shows that the proximal end of the delivery device 981 includes a gate 966 that is movable between a closed state (FIG. 23B) and an open state (FIG. 23C). The proximal end of the delivery device 981 is further shown as including at least one port 987. The at least one port 987 is in fluid communication with the lumen 983 and is configured to provide selective flushing of at least a portion the lumen 983. In some embodiments, for example, the delivery device 981 can include a first port that is disposed proximal to the gate 986 and in fluid communication with at least a portion of the lumen 983 proximal to the gate 986, and a second port that is disposed distal to the gate 986 and in fluid communication with at least a portion of the lumen 983 distal to the gate 986. In some implementations, the port 987 (e.g., via a first portion of the port 987 or a first port) can be used to provide suction to at least a portion of the lumen 983 as well as a flow of fluid for flushing at least a portion of the lumen 983 (e.g., via a second portion of the port 987 or a second port), as described above with reference to the loading device 960.

FIG. 23B shows that the distal end of the loading device 960 is coupled to the proximal end of the delivery device 981 while each of the gates 966 and 986 are in the closed state. In some implementations, after coupling the loading device 960 to the delivery device 981, a volume collectively defined by the lumens 963 and 983 disposed between the gates 966 and 986 in the closed state can be flushed via the ports 967 and 987. For example, in some implementations, the port 987 can provide a flow of saline and/or other sterile fluid into the volume while the port 967 can provide a suction to and/or through at least the volume (or vice versa).

FIG. 23C shows that after coupling the loading device 960 to the delivery device 981 and after flushing the volume defined between the gates 966 and 986, the gates 966 and 986 can be transitioned from the closed state to the open state. As such, the lumens 963 and 983 are substantially open or otherwise not occluded. Thus, a user and/or operator can exert a distal force on a portion of the control device 970 to advance the valve 900 in the delivery configuration from the loading device 960 and into the lumen 983 of the delivery device 981. Moreover, the distal force can be operable to advance the valve 900 through a delivery catheter of the delivery device (not shown) and to release the valve 900 from a distal end thereof. Once released (or at least partially released), the control device 970 can control and/or manipulate the valve 900 to seat the valve in the annulus of the native heart valve.

In some instances, it may be desirable to at least partially retrieve the valve 900 from the annulus during deployment (e.g., to adjust a position, orientation, and/or seating of the valve 900 in the annulus). In such instances, the control device 970 further can be used to at least partially retrieve the valve 900 into the distal end of the delivery catheter (included in the delivery device). For example, with the connection member (e.g., a yoke) coupled to a portion of the valve 900, the user and/or operator can exert a proximally directed force on the control device 970 that can pull that valve 900 proximally toward and/or into the delivery catheter. Moreover, the delivery system 980 can include any suitable capture element, feature, member, mechanism, etc. configured to facilitate a compression of the valve 900 as the valve 900 is pulled in a proximal direction toward and/or into the delivery catheter. In some instances, after partially retrieving the valve 900, the control device 970 can be manipulated to reseat the valve 900 in the annulus in a desired orientation and/or configuration.

FIG. 24-39 illustrate various portions of a delivery and/or retrieval system 1080 for delivering, deploying, and/or at least partially retrieving a prosthetic valve 1000, according to an embodiment. The delivery and/or retrieval system 1080 ("delivery system") can be any suitable shape, size, and/or configuration and can include any suitable component or combination of components. In some embodiments, for example, the delivery system 1080 and/or at least portions or aspects thereof can be similar to and/or substantially the same as the delivery system 980 described above with reference to FIGS. 23A-23C. Accordingly, portions and/or aspects of the delivery system 1080 may not be described in further detail herein. Moreover, the delivery system 1080 can be used to delivery, deploy, and/or at least partially retrieve any suitable valve such as, for example, any of the valves 100, 400, 500, 600, 700, 800, and/or 900. For example, the valve 1000 can have an outer frame with an inner flow control component mounted therein. The valve 1000 is compressible and expandable in an axial direction and a lateral direction relative to a longitudinal axis of the valve 1000, as described in further detail herein.

The delivery system 1080 can include any suitable component(s) configured to place the valve 1000 in a delivery configuration, load the valve 1000 into a portion of the delivery system 1080, deliver the valve 1000 in the delivery configuration through a portion of the delivery system 1080, control and/or facilitate a deployment of the valve 1000 in the annulus of the native valve, and in some instances, at least partially retrieve the valve 1000 from the annulus to allow for adjustment and/or reseating of the valve 1000 or removal of the valve 1000 from the heart (e.g., in the case of failure or patient distress).

Figure 24:
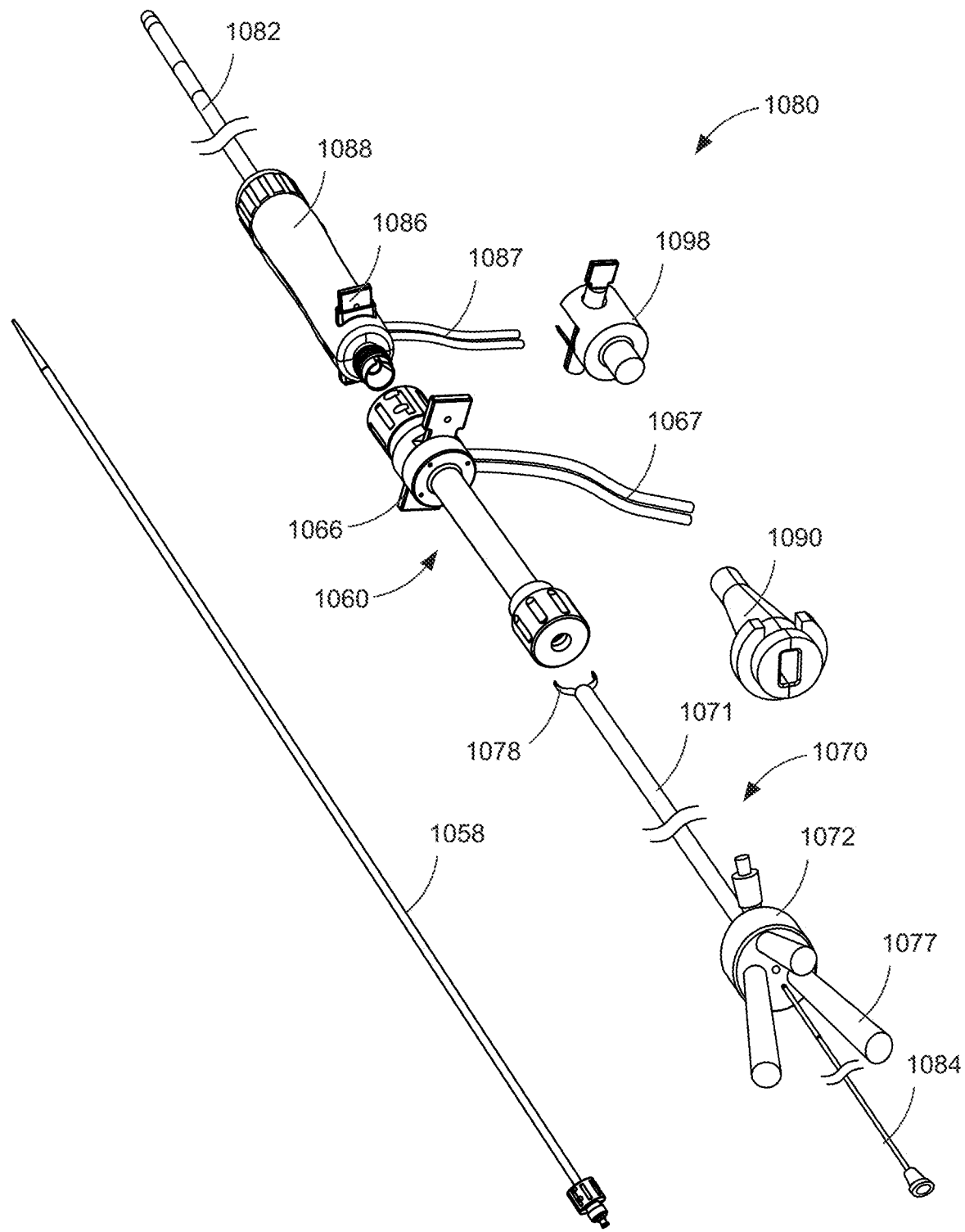
FIG. 24 is a partially exploded perspective view of a delivery system for side-delivery of a prosthetic valve according to an embodiment.

FIG. 24 is a partially exploded perspective view of the delivery system 1080. As shown, the delivery system 1080 includes a dilator 1058, a loading device 1060, a control device 1070, a delivery device 1081, a compression device 1090, a guidewire catheter 1084, and a pulling device 1098. The dilator 1058 can be any suitable dilator configured to dilate at least a portion of a pathway within the body to allow, for example, a delivery catheter and/or other relatively large gauge catheter to be advanced through the pathway. In this embodiment, the dilator 1058 can be configured to dilate a pathway through, for example, the femoral vein and the IVC to allow a delivery catheter 1082 of the delivery device 1081 to be advanced into a heart of the patient.

The pulling device 1098 can be any suitable device configured to removably couple to the valve 1000 to facilitate advancement (e.g., a pulling) of the valve 1000 through one or more portions of the delivery system 1080. For example, in some embodiments, the pulling device 1098 can include a tether (e.g., a suture, tension member, cable, wire, etc.) that can be coupled to a distal end of the valve 1000 at a first end. An opposite end of the tether can be coupled to the pulling device 1098, which can be and/or can include a spool mechanism or the like about which at least a portion of the tether can be spooled or wound. As described in further detail herein, the spooling and/or winding of the tether can be operable to pull the valve 1000 through the one or more portions of the delivery system 1080.

Figure 25A:
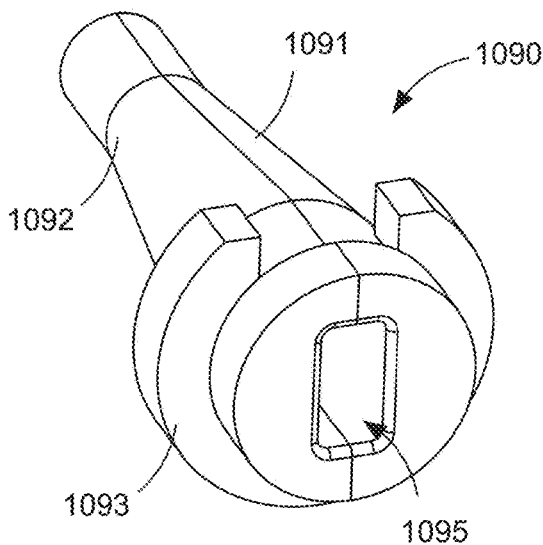
FIGS. 25A-25E are various views of a compression device included in the delivery system of FIG. 24.
Figure 25B:
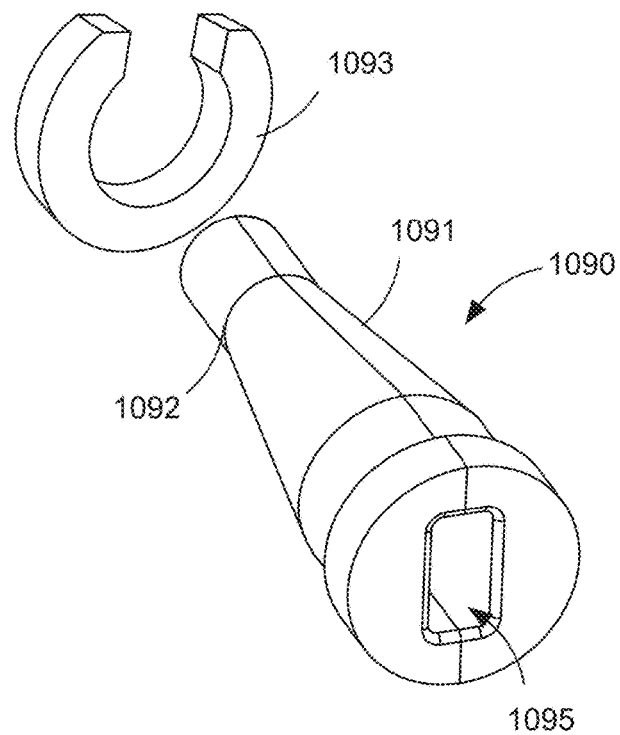
Figure 25C:
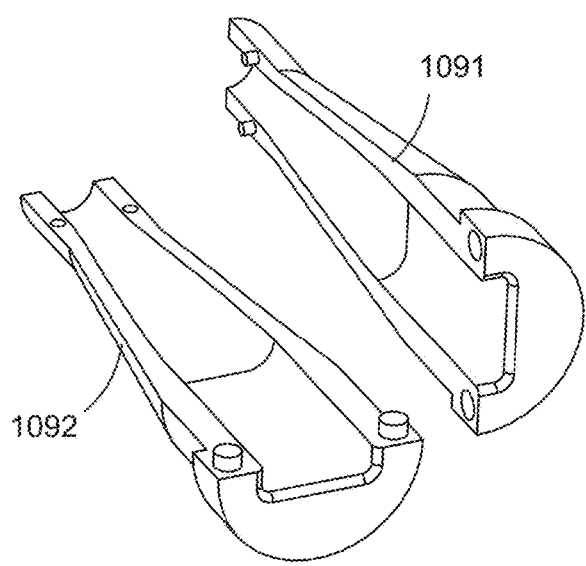

FIGS. 25A-25E and 26A-26G show various views and/or aspects of the compression device 1090. As described above, the valve 1000 can be inserted into the compression device 1090 to transition the valve 1000 from an uncompressed or a partially compressed (e.g., laterally compressed) configuration to a compressed or delivery configuration. The compression device 1090 is shown including a first member 1091, a second member 1091, and a coupler 1092. The compression device 1090 can have a funnel-like shape and defines a lumen 1095 that extends through a proximal end and a distal end of the compression device. FIGS. 25A-25C show that the coupler 1092 can be removably disposed about at least a portion the first member 1091 and the second member 1092 to couple the members 1091 and 1092 together. FIG. 25A shows that the funnel-like shape of the compression device 1090 allows the coupler 1092 to be slid over a portion of the first member 1091 and the second member 1092 and advanced to a position in which an outer surface of the compression device 1090 collectively formed by the first and second members 1091 and 1092 forms a friction fit with an inner surface of the coupler 1092, thereby forming the compression device 1090. FIG. 25B shows that the coupler 1092 can be removed from the first member 1091 and the second member 1092 in, for example, a distal direction.

FIG. 25C shows that the first member 1091 and the second member 1092 are laterally separable. That is to say, the first member 1091 and the second member 1092 are separable about a plane that extends in a longitudinal direction (e.g., proximal-distal direction) and an axial direction, and orthogonal to a lateral axis and/or direction. The first member 1091 and the second member 1092 are shown as having a substantially mirrored arrangement. Moreover, an inner surface of the first member 1091 and an inner surface of the second member 1092 collectively define the lumen 1095.

Figure 25D:
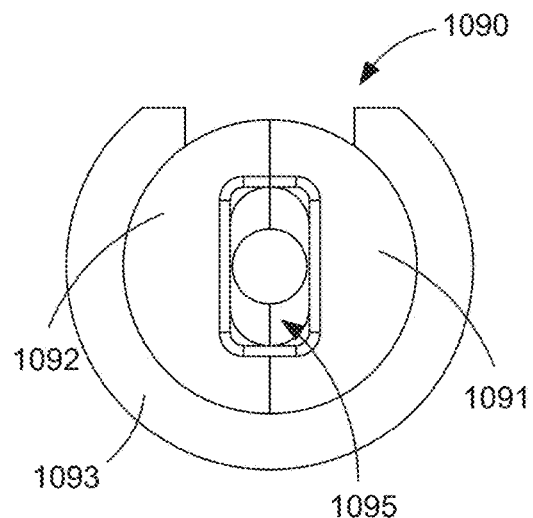

FIG. 25D is a proximal view of the compression device 1090 and shows the lumen 1095 extending through the proximal end of the compression device 1090. The lumen 1095 at the proximal end has a substantially rectangular shape. Specifically, the lumen 1095 and/or the perimeter of the lumen 1095 has an axial dimension that substantially corresponds to an axial height of the valve 1000 configured to be inserted therein. In some embodiments, the axial dimension can be slightly larger than the axial height of the valve 1000 allowing the valve 1000 to be substantially uncompressed in the axial direction when inserted into the proximal end of the compression device 1090. In other embodiments, the axial dimension can be slightly smaller than the axial height of the valve 1000 such that inserting the valve 1000 into the proximal end of the compression device 1090 includes at least slightly compressing the valve 1000 in the axial direction.

The lumen 1095 and/or the perimeter of the lumen 1095 at the proximal end has a lateral dimension that substantially corresponds to a lateral width of the valve 1000 configured to be inserted therein. More specifically, the lateral dimension substantially corresponds to a width of the valve 1000 in a laterally compressed configuration. As described in detail above, the valve 1000 can be compressed and/or folded in the lateral direction. In this embodiment, the lateral dimension of the lumen 1095 at the proximal end is such that the valve 1000 is manually compressed and/or folded prior to being inserted into the proximal end of the compression device 1090.

Figure 25E:
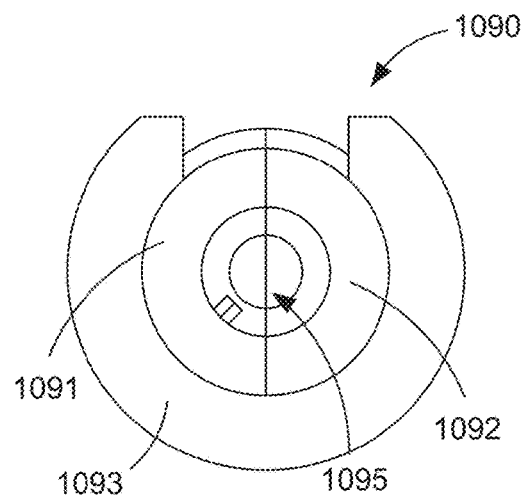

FIG. 25E is a distal view of the compression device 1090 and shows the lumen 1095 extending through the distal end of the compression device 1090. The lumen 1095 at the distal end has a substantially circular shape. Specifically, the lumen 1095 and/or the perimeter of the lumen 1095 has a size and/or diameter that substantially corresponds to a perimeter and/or axial-lateral extent of the valve 1000 in the delivery configuration. In some embodiments, a lateral dimension of the lumen 1095 at the distal end of the compression device 1090 (e.g., the diameter of the lumen 1095 at the distal end) can be substantially the same as the lateral dimension of the lumen 1095 at the proximal end of the compression device 1090. Accordingly, in such embodiments, the compression device 1090 is configured to compress the valve 1000 in the axial direction. In other embodiments, the diameter of the lumen 1095 at the distal end can be smaller than the axial dimension and the lateral dimension of the lumen 1095 at the proximal end. The decreasing size and/or perimeter of the lumen 1095 of the compression device 1090 is configured to transition the valve 1000 to a compressed or delivery configuration as the valve 1000 is advanced therethrough.

Figure 26A:
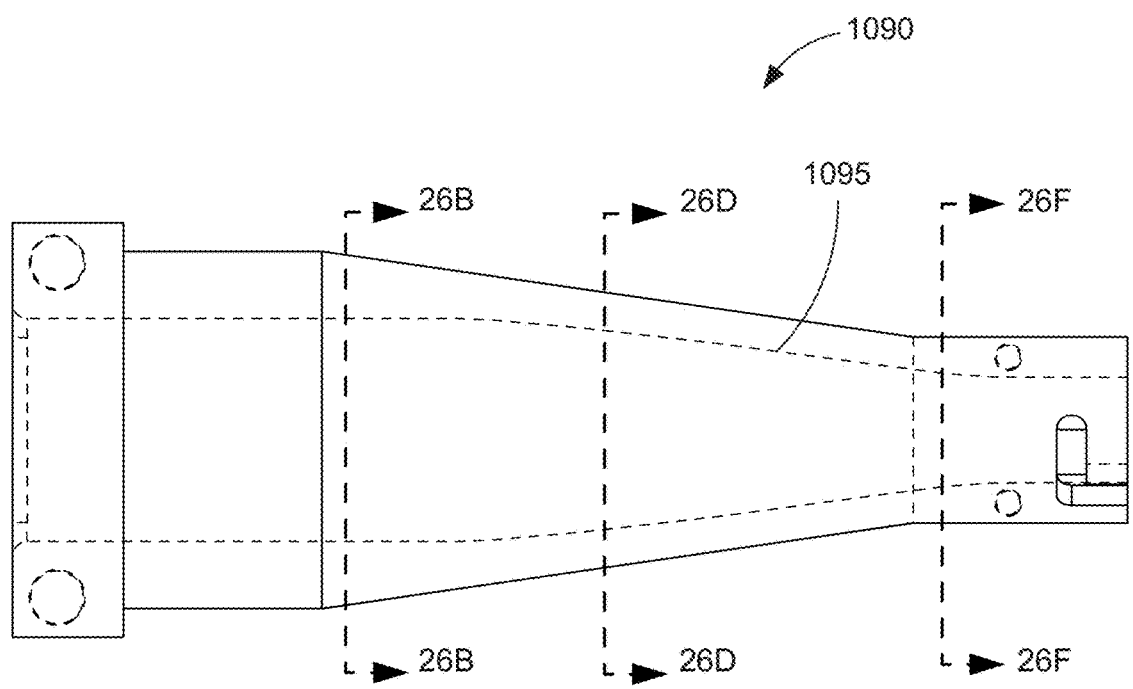
FIG. 26A is a side view of the compression device of FIGS. 25A-25E and shown without a coupling member.
Figure 26B:
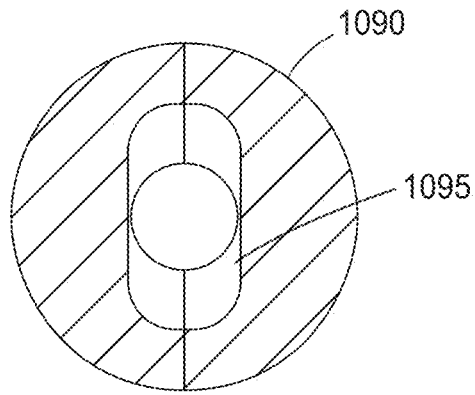
FIG. 26B is a cross-sectional view of the compression device taken along the line 26B-26B in FIG. 26A.
Figure 26C:
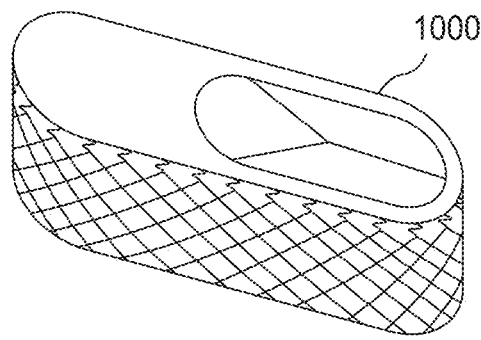
FIG. 26C is a side perspective view of a semi-compressed prosthetic valve corresponding to a size of a lumen of the compression device at the cross-sectional plane shown in FIG. 26B.

FIG. 26A is a side view of the compression device 1090 and shows three planes 26B-26B, 26D-26D, and 26F-26F along a length of the compression device 1090 corresponding to cross-sectional views that show a size and/or shape of the lumen 1095 at the location of the planes. For example, FIG. 26B is a cross-sectional view of the compression device 1090 taken along the plan 26B-26B in FIG. 26A. The lumen 1095 of the compression device 1090 is shown as being substantially rectangular with corners that are more rounded than the corresponding corners of the lumen 1095 at the proximal end of the compression device 1090 (see e.g., FIG. 25D). The lumen 1095 is further shown as having a perimeter with an axial dimension (e.g., a maximum axial dimension) and a lateral dimension (e.g., a maximum lateral dimension) that are substantially similar to the perimeter of the lumen 1095 at the proximal end. FIG. 26C shows the valve 1000 in a partially compressed configuration corresponding to the perimeter of the lumen 1095 shown in FIG. 26B. For example, the valve 1000 can be laterally compressed with little to no axial compression.

Figure 26D:
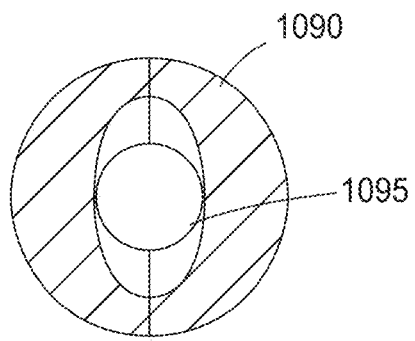
FIG. 26D is a cross-sectional view of the compression device taken along the line 26D-26D in FIG. 26A.
Figure 26E:
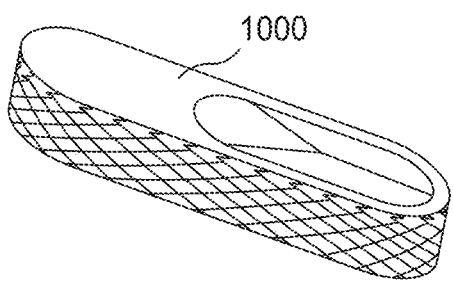
FIG. 26E is a side perspective view of a semi-compressed prosthetic valve corresponding to a size of a lumen of the compression device at the cross-sectional plane shown in FIG. 26D.

FIG. 26D is a cross-sectional view of the compression device 1090 taken along the plan 26D-26D in FIG. 26A. The lumen 1095 of the compression device 1090 is shown as being substantially elliptical or oval-shaped with corners that are more rounded than the corresponding corners of the lumen 1095 at the position shown in FIG. 26B. The lumen 1095 is further shown as having a perimeter with a lateral dimension (e.g., a maximum lateral dimension) that is substantially similar to the lateral dimension of the perimeter of the lumen 1095 at the proximal end. FIG. 26D shows that the perimeter of the lumen 1095 has an axial dimension (e.g., a maximum axial dimension) that is smaller than the axial dimension of the perimeter of the lumen 1095 at the position shown in FIG. 26B. FIG. 26E shows the valve 1000 in a partially compressed configuration corresponding to the perimeter of the lumen 1095 shown in FIG. 26D. For example, the valve 1000 can be compressed in the lateral direction and partially compressed in the axial dimension.

Figure 26F:
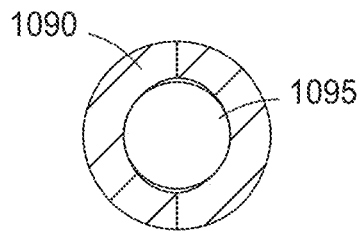
FIG. 26F is a cross-sectional view of the compression device taken along the line 26F-26F in FIG. 26A.
Figure 26G:
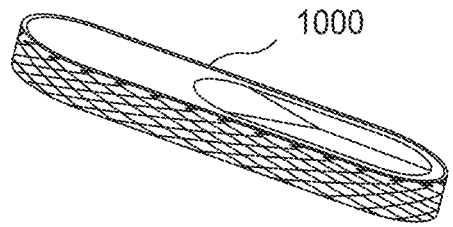
FIG. 26G is a side perspective view of a semi-compressed prosthetic valve corresponding to a size of a lumen of the compression device at the cross-sectional plane shown in FIG. 26F.

FIG. 26F is a cross-sectional view of the compression device 1090 taken along the plane 26F-26F in FIG. 26A. The lumen 1095 of the compression device 1090 is shown as being substantially circular with a perimeter and/or diameter that is substantially similar to the perimeter and/or diameter of the lumen 1095 at the distal end of the compression device 1090 (see e.g., FIG. 25E). FIG. 26G shows the valve 1000 substantially in a compressed and/or delivery configuration corresponding to the perimeter of the lumen 1095 shown in FIG. 26G. Thus, the compression device 1090 is configured to compress the valve 1000 to the delivery configuration as the valve 1000 is advanced therethrough. As described in further detail herein, the control device 1070 and/or the pulling device 1098 can be used to push, pull, and/or otherwise advance the valve 1000 through the compression device 1090.

Figure 27:
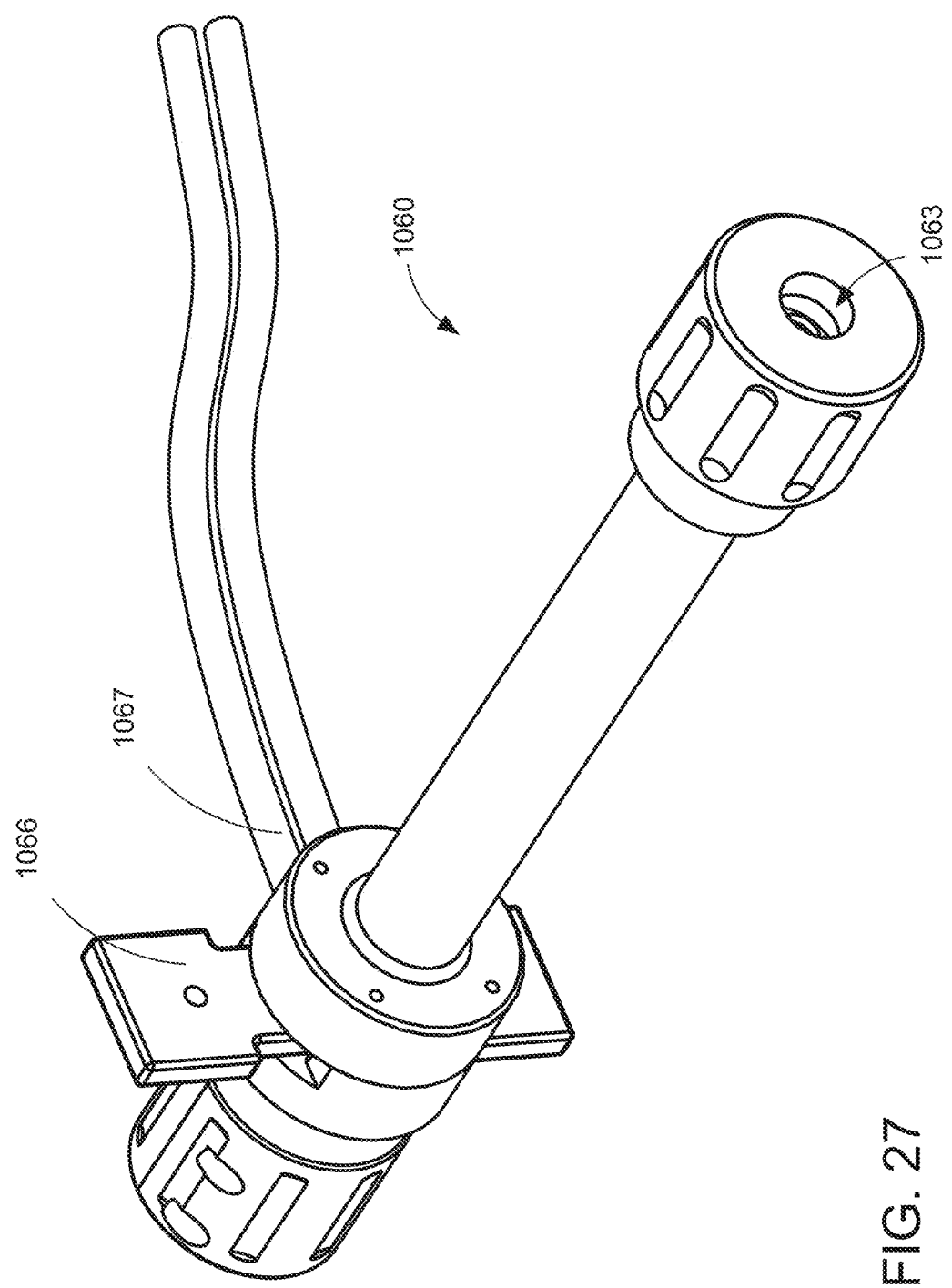
FIG. 27 is a perspective view of a loading device included in the delivery system of FIG. 24.

FIG. 27 is a perspective view of the loading device 1060 included in the delivery system 1080. The loading device 1060 has a distal end and a proximal end and defines a lumen 1063 that extends through the loading device 1060. The lumen 1063 has a substantially circular perimeter with a diameter that is similar to and/or substantially the same as the diameter of the lumen 1095 at the distal end of the compression device 1090. The proximal end of the loading device 1060 is configured to be removably coupled to the distal end of the compression device 1090 and the distal end of the loading device is configured to be removably coupled to each of the pulling device 1098 and the delivery device 1081 (e.g., one at a time), as described in further detail herein. FIG. 27 further shows the proximal end of the loading device 1060 including a gate 1066 that is movable between an open state and a closed state to at least partially occlude the lumen 1063 of the loading device 1060, as described in further detail herein. The proximal end of the loading device 1060 is also shown as including a set of ports 1067, to which sterile flexible tubing is coupled, that can be used to flush and/or suction at least a portion of the lumen 1063, as described in further detail herein.

Figure 28:
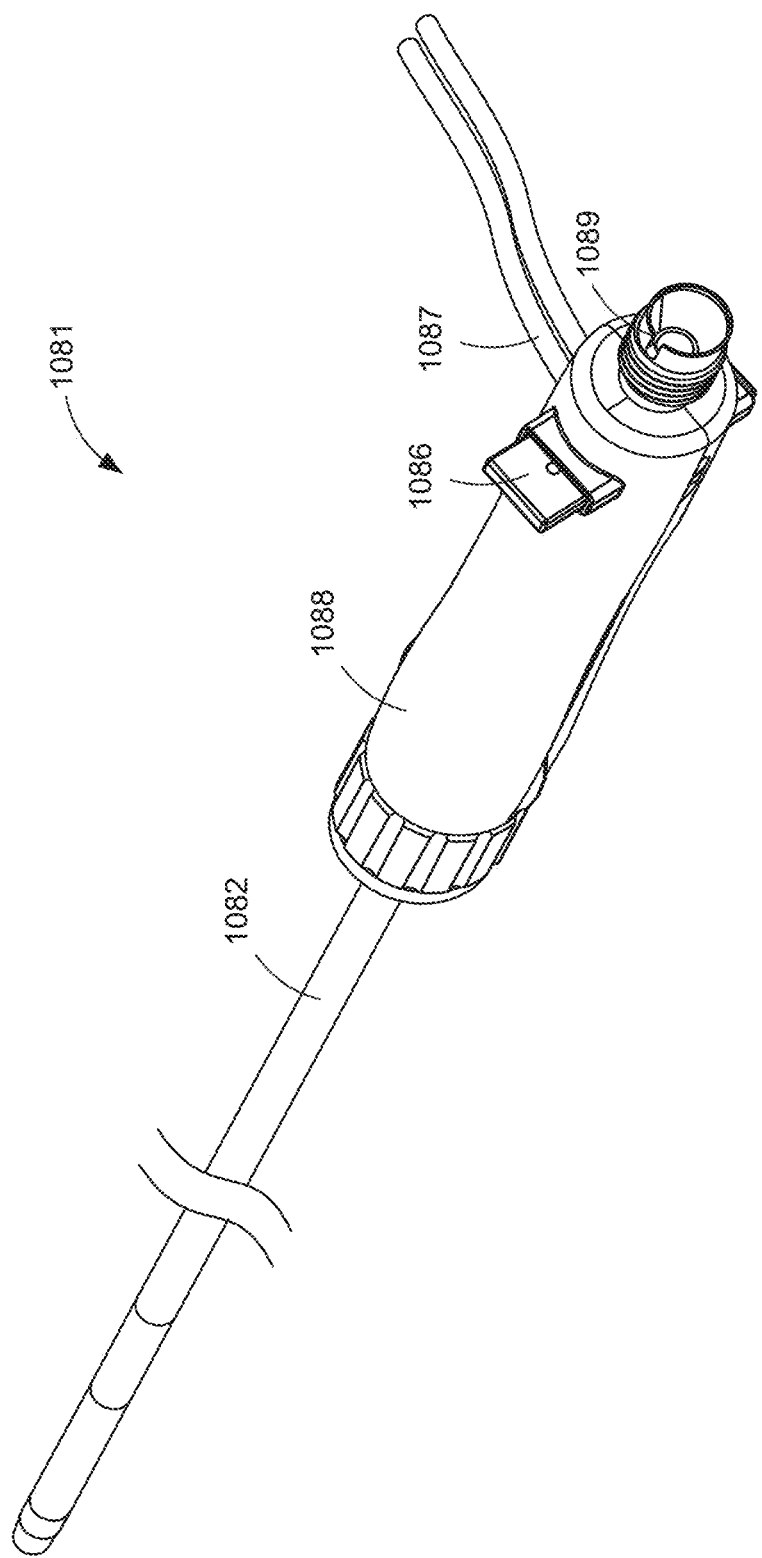
FIG. 28 is a perspective view of a delivery device included in the delivery system of FIG. 24.

FIG. 28 is a perspective view of the delivery device 1081 included in the delivery system 1080. The delivery device 1081 includes a handle 1088 and a delivery catheter 1082 extending from a distal end of the handle 1081. The handle 1088 and the delivery catheter 1082 collectively define a lumen 1083 that extends through the delivery device 1081. The lumen 1083 has a substantially circular perimeter with a diameter that is similar to and/or substantially the same as the diameter of the lumen 1063 of the loading device 1060. The proximal end of the handle 1088 is configured to be removably coupled to the distal end of the loading device 1060, as described in further detail herein. FIG. 28 further shows the proximal end of the handle 1088 including a gate 1086 that is movable between an open state and a closed state to at least partially occlude the lumen 1083 of the delivery device 1081, as described in further detail herein. The proximal end of the handle 1088 is also shown as including a set of ports 1087, to which sterile flexible tubing is coupled, that can be used to flush and/or suction at least a portion of the lumen 1083, as described in further detail herein. The proximal end of the handle 1088 is also shown including a coupler with an indexing feature 1089 configured to align the delivery handle 1088 when coupled to the loading device 1060. The indexing feature 1089 is shown as a slot that can receive a corresponding indexing feature (e.g., a protrusion) included in the distal end of the loading device 1060. In this manner, the delivery device 1081 and the loading device 1060 can be in a predetermined and/or desired orientation when coupled.

FIGS. 29-34B illustrate various portions of the control device 1070 included in the delivery system 1080. The control device 1070 can be and/or can include any number of components that can be at least temporarily coupled to and/or in contact with one or more portions of the valve 1000 and configured to control and/or facilitate, for example, a delivery, deployment, and/or retrieval of the valve 1000. For example, in some embodiments, the control device 1070 can include a control catheter 1071 that has a connection member 1078 disposed at a distal end of the control catheter 1071 and a control portion 1072 at a proximal end of the control catheter 1071.

The control portion 1072 can be any suitable shape, size, and/or configuration and can provide a way for a user and/or operator to engage one or more portions of the control device 1072. The control portion 1072 is shown having a number of control arms 1077, each of which can receive and provide a way of controlling a portion of the control device 1070 such as, for example, one or more tethers, tension members, cables, wires, sutures, etc.

The control catheter 1071 can be a steerable, multi-lumen catheter. For example, FIG. 30 is a cross-sectional view of the control catheter 1071 taken along the line 30-30 in FIG. 29. The control catheter 1071 is shown as including a set of tether or tension member lumens 1073 and a guidewire catheter lumen 1074. Each tether or tension member lumen 1073 is in communication with a different and/or corresponding control arm 1077 of the control portion 1072, which provides proximal access to the corresponding lumen 1073. The tether or tension member lumens 1073 are shown as having a smaller diameter than the guidewire catheter lumen 1074 and extending through a sidewall portion of the control catheter 1071 between an outer surface and an inner surface defining the guidewire catheter lumen 1074. The tether or tension member lumens 1073 provide one or more paths through which one or more tethers, tension members, cables, wires, sutures, etc. can extend to selectively engage portions of the valve 1000, as described in further detail herein. The guidewire catheter lumen 1074 extends through the control portion 1072 of the control device 1070 and provides a path through which the guidewire catheter 1084 can extend to allow a distal end of the guidewire catheter 1084 to engage and/or extend through one or more portions of the valve 1000, as described in further detail herein.

Figure 31A:
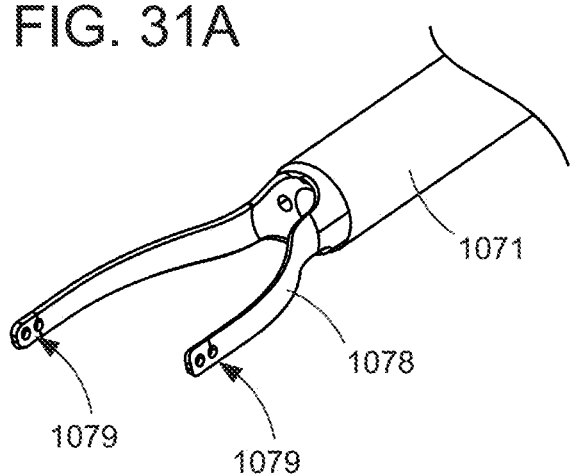
FIG. 31A is perspective views of a distal end portion of the control device of FIG. 29 illustrating a yoke included in the distal end portion.
Figure 31B:
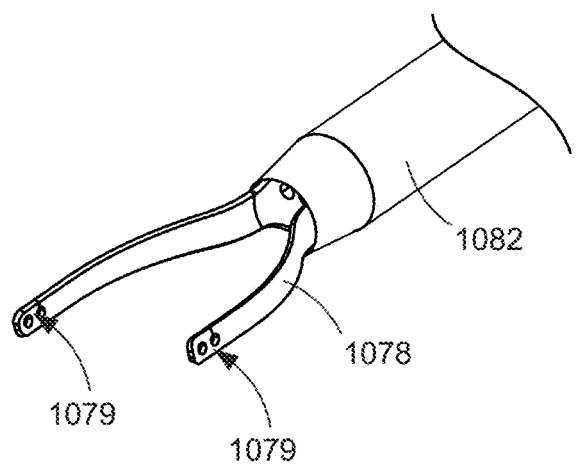
FIGS. 31B and 31C are perspective views of the distal end portion of the control delivery of FIG. 29 at least partially disposed in a delivery catheter of the delivery system and shown in a first configuration and a second configuration, respectively.
Figure 31C:
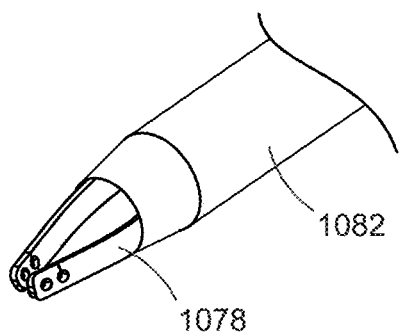

FIGS. 31A-31C are perspective views of the distal end of the control device 1070 and illustrate the connection member 1078 transitioning between an expanded configuration and a compressed configuration. The connection member 1078 can be formed from any suitable material such as a shape-memory allow like nitinol or the like. FIG. 31A shows the connection member 1078 having a wishbone or yoke design as described above, for example, with reference to the connection member 1078 shown in FIG. 15. As such, the connection member 1078 can have a first portion, side, and/or arm and a second portion, size, and/or arm opposite the first portion, side, and/or arm. FIG. 31A shows the connection member 1078 in the expanded configuration. FIG. 31B shows the connection member 1078 beginning to be transitioned from the expanded configuration to the compressed configuration in response to the delivery catheter 1082 being disposed at or near the distal end of the control device 1070. FIG. 31C shows the connection member 1078 in the compressed configuration when the connection member 1078 is at least partially disposed in the lumen of the delivery catheter 1082. A diameter of the lumen of the delivery catheter 1082 is smaller than a width of the connection member 1078 in the expanded configuration and thus, the delivery catheter 1082 is shown squeezing the connection member 1078 into the compressed configuration when the connection member 1078 is at least partially disposed in the delivery catheter 1082. The connection member 1078 in the compressed configuration allows the control catheter 1071 to be advanced through the delivery catheter 1082 and the connection member 1078 can automatically transition from the compressed configuration to the expanded configuration when released from and/or otherwise moved to a distal position relative to the delivery catheter 1082.

Figure 32:
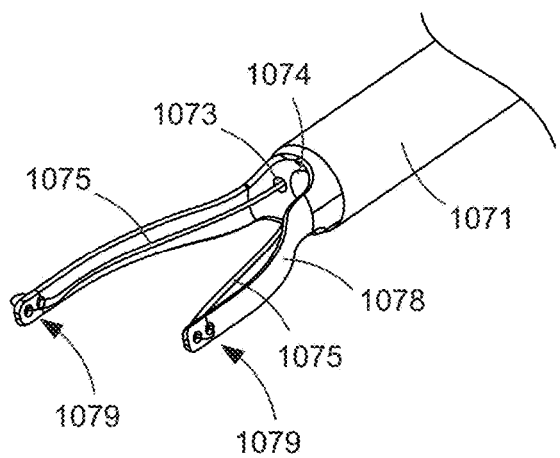
FIG. 32 is a perspective view of the distal end portion of the control device of FIG. 29 illustrating the yoke removably coupled to a pair of tethers.

FIG. 32 is a perspective view of the distal end of the control device 1070 and illustrates the connection member 1078 and a set of tethers 1075 extending from corresponding tether and/or tension member lumens 1073 of the control catheter 1071. The tethers 1075 are shown extending from the control catheter 1071, looping through a set of openings 1079 defined along or by each side or arm of the connection member 1078 (yoke), and extending back into the corresponding tether and/or tension member lumen 1073. The tethers 1075 can be used to removably connect the connection member 1078 to the valve 1000.

Figure 33:
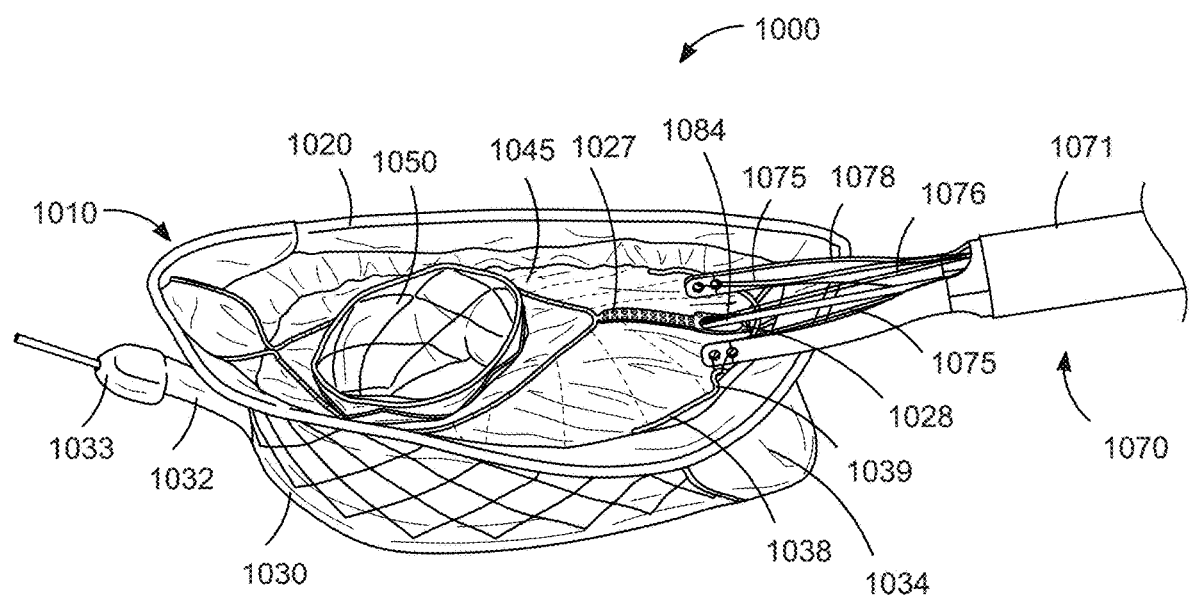
FIG. 33 is a side perspective view of the distal end portion of the control device of FIG. 29 illustrating the yoke and the pair of tethers removably coupling the yoke to a prosthetic valve.

FIG. 33 is a side perspective view of the distal end of the control device 1070 showing the connection member 1078 removably coupled to the valve 1000. The valve 1000 is shown having an outer frame 1010 with a flow control component 1050 mounted therein, as described above with reference to the valves 400, 500, 600, 700, and/or 1000. The frame 1010 has a supra-annular region 1020 and a subannular region 1030 with a transannular region coupled therebetween.

The supra-annular region 1020 is shown having a laser cut frame that is wrapped or covered in a biocompatible material. The supra-annular region 1020 includes a proximal spline 1027 that extends between an outer loop and an inner loop of the supra-annular region 1020, as described above with reference to the valve 800. The flow control component 1050 is shown mounted to the inner loop of the supra-annular region 1020. The spline 1027 is shown having a bowed configuration and defining a waypoint 1028. The waypoint 1028 can be, for example, an opening, a hole, an aperture, a port, a coupler, a sealable/resealable access point, and/or the like configured to at least temporarily couple to and/or receive a portion of the delivery system 1080.

The supra-annular region 1020 is further shown as including a drum 1045 that extends between and/or is coupled to the outer loop and the inner loop and covers a space not otherwise occupied by the flow control component 1050. The drum 1045 can have and/or can form a set of spokes that can be used to increase a stiffness of the drum 1045, as described above with reference to the valve 800. The bowed spline 1027 can exert a force on the drum 1045 that bows the drum 1045 and increases a tension across the area of the drum 1045. The increase in tension in the drum 105 and the increase in stiffness of the drum 1045 due to the spokes can, in turn, reduce and/or limit an amount of drum deformation during, for example, diastole or systole, thereby enhancing performance of the valve 1000 and/or reduce fatigue in or along the drum 1045, as described in detail above with reference to the valve 800. The supra-annular region 1020 and/or the drum 1045 is further shown having an attachment member 1038 that can extend along or across a portion of the drum 1045. The attachment member 1038 facilitates a temporary and/or removable attachment to a portion of the control device 1070. The attachment member 1038 can be, for example, a braided thread, a suture, a tether, a cable, and/or the like that can include and/or form a set of loops 1039 or the like allowing for selective engagement of the attachment member 1038.

FIG. 33 shows the distal end of the control device 1078 being removably connected to the valve 1000. Specifically, the connection member 1078 (yoke) is shown in contact with the drum 1045. The tethers 1075 are shown extending from the control catheter 1071 and looping through or around each side or arm of the connection member 1078 and a corresponding loop 1039 of the attachment member 1038. The looped arrangement of the tethers 1075 through and/or around the connection member 1078 and the attachment member 1038 of the valve 1000 is such that each of the proximal end and the distal end of the tether 1075 extends through and outside of (e.g., proximal to) a single control arm 1077 of the control portion 1072. As such, a proximally directed force can be exerted on each of the proximal end and the distal end of the tether(s) 1075 to increase a tension along the tether 1075, which pulls the connection member 1038 toward the drum 1045, thereby securing the connection member 1078 to the valve. Conversely, a proximally directed force exerted on only one of the proximal end or the distal end of the tether(s) 1075 can disengage the tether(s) 1075 from the connection member 1078 and can withdraw the tether(s) 1075 from the control device 1070, which in turn, can allow the connection member 1078 to be decoupled or removed from the valve 1000.

FIG. 33 further shows a tension member 1076 extending from the control catheter 1071 (e.g., through one of the tether or tension member lumens 1073) and through the waypoint 1028. The tension member 1076 can be, for example, an actuator or the like that can selectively engage a proximal anchoring element 1034 formed by the subannular region 1030 of the valve 1000. The tension member 1076 can be routed through one of the control arms 1077 of the control portion 1072, one of the lumens 1073 corresponding to that control arm 1077, around and/or through one or more portions of the proximal anchoring element 1034, and back through the corresponding lumen 1073. As such, the tension member 1076 can be actuated (or placed in tension) and/or release in a manner similar to that described above with reference to the tethers 1075. Moreover, increasing an amount of tension along the tension member 1076 can be operable to transition the proximal anchoring element 1034 between a first configuration and a second configuration, as described in detail above with reference to the valves 600 and/or 700.

FIG. 33 further shows the guidewire catheter 1084 extending from the control catheter 1071 (e.g., through the guidewire catheter lumen 1074) and through the waypoint 1028. The valve 1000 is shown with the subannular member 1030 having and/or forming a distal anchoring element 1032 having a guidewire coupler 1033 that can receive the guidewire catheter 1084 through an opening, hole, aperture, port, etc., defined by the guidewire coupler 1033. Thus, the guidewire catheter 1084 is shown extending from the control catheter 1071 (in a supra-annular position relative to the valve 1000), through the waypoint 1028 of the valve 1000, below the flow control component 1050, and through the distal subannular anchoring element 1032. Moreover, the guidewire catheter 1084 is shown extending beyond the distal anchoring element 1032 and can have and/or can provide sufficient stiffness to allow the valve 1000 be advanced along a guidewire 1085 over which the guidewire catheter 1084 is disposed. The arrangement of the control device 1072 just described allows the control device 1072, including the connection member 1078, the tethers 1075, the tension member 1076, and the guidewire catheter 1084, to be decoupled from the valve 1000 and withdrawn through the delivery catheter 1082 after successful deployment of the valve 1000.

Figure 34A:
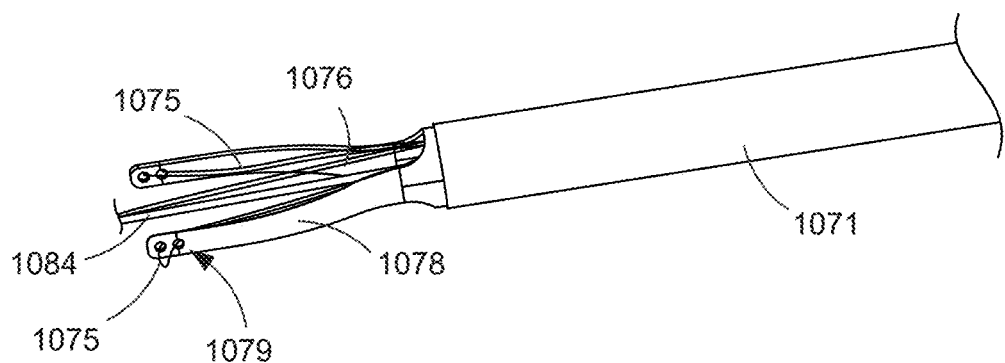
FIGS. 34A and 34B are side perspective views of the distal end portion of the control device of FIG. 29 illustrating the yoke, the pair of tethers, a tension member, and a guidewire catheter extending from the multi-lumen control catheter, with the multi-lumen control catheter being shown in a first configuration and a second configuration, respectively.
Figure 34B:
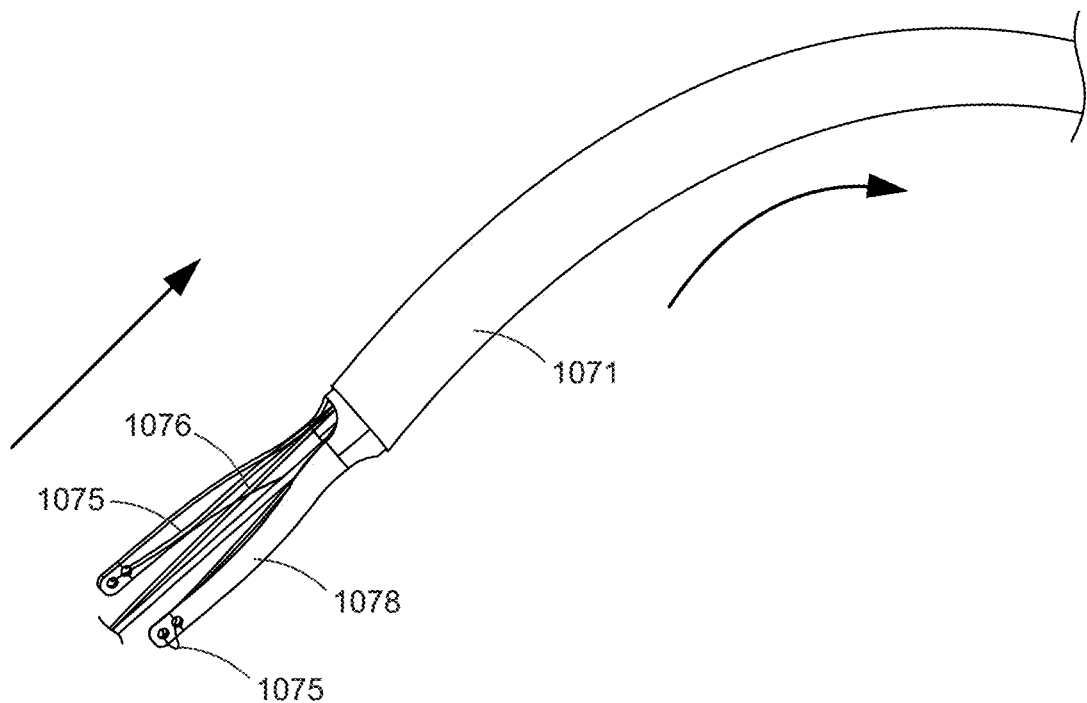

FIGS. 34A and 34B show the distal end of the control device 1070 in a first configuration and a second configuration, respectively. The distal end of the control device 1070 is removably coupled to the valve 1000 as described above. FIG. 34A shows the distal end of the control catheter 1071 having a substantially straight or undeformed shape when in the first configuration. FIG. 34B shows the distal end of the control catheter 1071 in a second configuration in which the distal end is bent, flexed, steered, curved, deflected, deformed, and/or the like. For example, as described above, the tethers 1075 can be looped through the attachment member 1038 to removably couple the connection member 1078 to the supra-annular region 1020 of the valve 1000 while the tension member 1076 can be looped around and/or through one or more portions of the proximal subannular anchoring element 1034. In some instances, a tension along the tension member 1076 can be increased to transition the proximal anchoring element 1034 between the first configuration and the second configuration. In some instances, the tension along the tethers 1075 and the tension along the tension member 1076 can be at least partially opposing forces exerted on a relative small portion of the valve 1000 and while the valve 1000 has a somewhat limited range of motion (e.g., due to the guidewire catheter 1084, as described above). As such, a tension along the tension member 1076 that exceeds a threshold amount of tension can be operable to bend, flex, steer, curve, deflect, and/or otherwise deform the distal end of the control catheter 1071. In other words, increasing a tension along the tension member 1076 can, in some instances, allow for a steering and/or otherwise desired deflection of the control catheter 1071. In some instances, for example, the control catheter 1071 can be deflected and/or bent in a supra-annular direction relative to the valve 1000 such that a distally directed force along the control catheter 1071 results in the connection member 1078 exerting a force on the valve 1000 that is at least partially in a subannular direction, thereby facilitating a deployment and/or seating of the valve 1000 in the native annulus.

FIGS. 35-39 are cross-sectional views of the delivery system 1080 showing a process of placing the valve 1000 in the delivery configuration and loading the valve 1000 into the delivery device 1081 for side-delivery into the heart. Prior to loading the valve 1000 (or in an at least partially concurrent process), a user, operator, surgeon, etc., can manipulate the delivery device 1081 to advance the guidewire 1085 along a pathway through the patient and into a desired position with the heart. In some instances, the dilator 1058 can be advanced along the guidewire 1085 and manipulated to dilate at least a portion of the pathway through the patient. The delivery catheter 1082 can then be advanced through the pathway to place the distal end of the delivery catheter 1082 in a volume of the heart (e.g., an atrium). Moreover, the arrangement of the delivery device 1081 is such that a proximal end of the guidewire 1085 extends from a proximal end of the handle 1088 of the delivery device 1081, as described in further detail herein.

Figure 35:
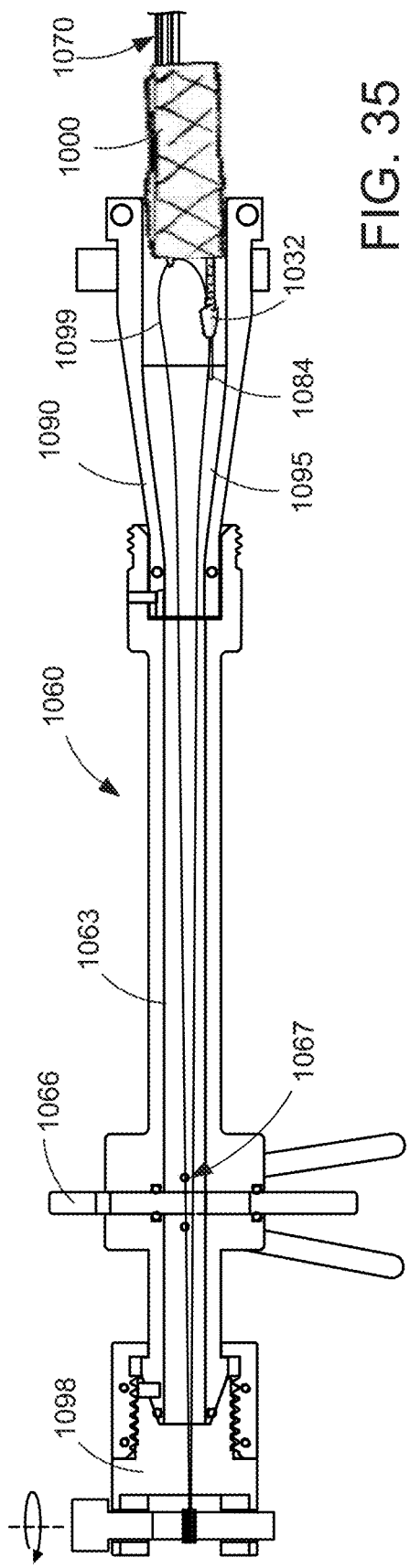
FIGS. 35-38 are cross-sectional views of portions of the delivery system of FIG. 24 illustrating a process of compressing a prosthetic valve and loading the prosthetic valve into the delivery device for side-delivery to a target location in a patient.

FIG. 35 shows the compression device 1090 removably coupled to the proximal end of the loading device 1060 and the distal end of the loading device 1060 removably coupled to the pulling device 1098. More specifically, the tether 1099 of the pulling device 1098 can extend through the lumen 1063 of the loading device 1060 and the lumen 1095 of the compression device and can be removably coupled to the distal end of the valve 1000 (e.g., looped around or through one or more portions of the distal end of the valve 1000). The ends of the tether 1099 are shown disposed about and/or at least partially wrapped around a spool or the like of the pulling device 1098. In this embodiment, rotation of the spool or portion of the pulling device 1098 increases a tension along the tether 1099, which is operable to pull the valve 1000 through the compression device 1090 and/or the loading device 1060. Moreover, during a loading of the valve 1000 into the loading device 1060, the gate 1066 is in the close state and thus, the tether 1099 can be configured to extend through a space defined between the gate 1066 and an inner surface of the loading device 1060 (as described above).

FIG. 35 shows the distal end of the valve 1000 removably coupled to the tether 1099 of the pulling device 1098 and the proximal end of the valve 1000 removably coupled to the control device 1070. The guidewire catheter 1084 is shown as extending through the valve 1000 and distal to the distal subannular anchoring element. FIG. 35 further shows the valve 1000 partially inserted into the lumen 1095 of the compression device 1090. As described above, the valve 1000 can be at least partially compressed in the later direction prior to inserting the valve 1000 into the compression device 1090. Thus, the valve 1000 is shown being laterally compressed but not yet axially compressed (substantially). As described above, in some instances, the valve 1000 can be loaded into the compression device 1090 and advanced through the lumen 1095 while at least the compression device 1090 is disposed in a saline bath or the like, which can facilitate the advancement of the valve 1000 through the compression device 1090 and can maintain a substantial sterility of the valve 1000.

Figure 36:
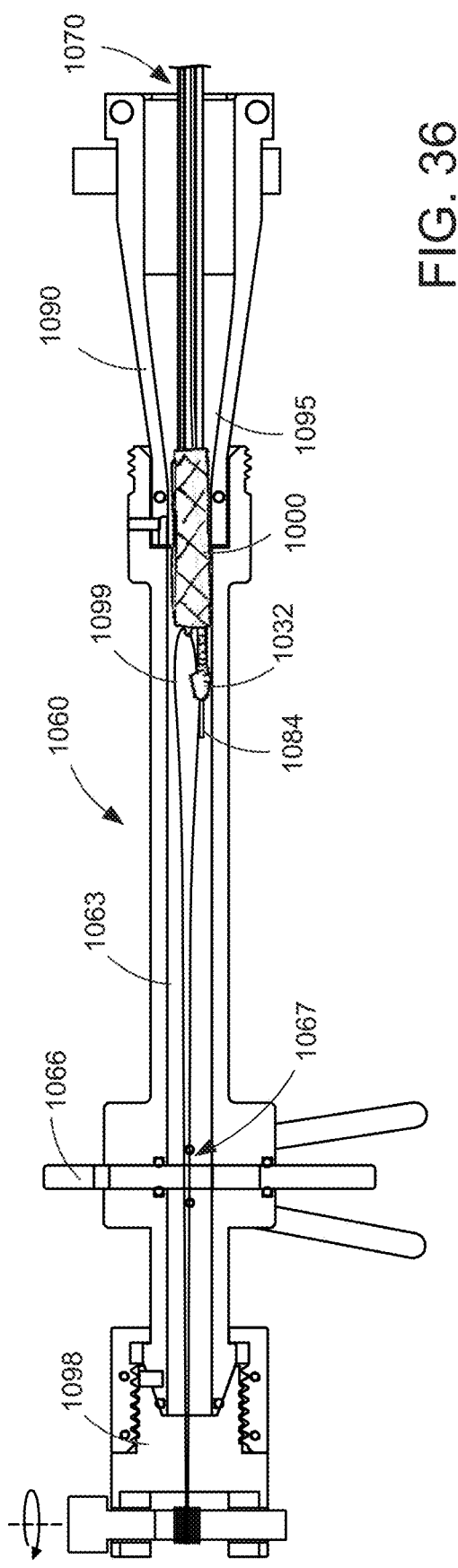

FIG. 36 shows the valve 1000 at least partially advanced through the compression device 1090 and into the lumen 1063 of the loading device 1060. For example, after initially inserting the valve 1000 into the proximal end of the compression device 1090 a user or operator can, for example, manipulate the pulling device 1098 to further spool and/or wrap the tether 1099. In some implementations, a user and/or operator can also exert a force on the control device 1070 such that the connection member (not shown) pushes the valve 1000 through the compression device 1090. The valve 1000 is shown as being advanced through the lumen 1095 of the compression device 1090 from the proximal end to the distal end and the compression device 1090 compresses the valve 1000 in at least the axial direction as the valve 1000 is advanced therethrough. In some instance, the valve 1000 can be in a substantially uncompressed or a laterally compressed configuration when inserted into the proximal end of the compression device 1090 and can be compressed to a compressed or delivery configuration when advanced to and/or through the distal end of the compression device 1090 and into the lumen 1063 of the loading device 1060 (FIG. 36).

Figure 37:
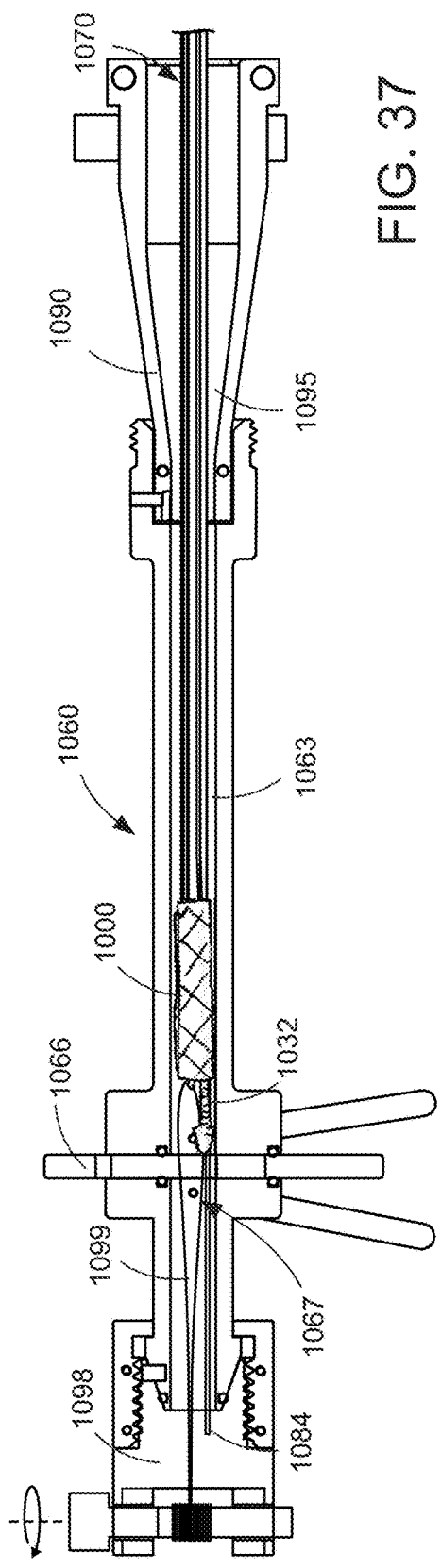

FIGS. 35-37 show that the valve 1000 is loaded into the loading device 1060 while the gate 1066 is in the closed state. FIG. 37 shows the valve 1000 advanced through the lumen 1063 until, for example, the distal anchoring element (or a distal most portion) of the valve 1000 contacts and/or is adjacent to a proximal surface of the gate 1066 in the closed state. The guidewire catheter 1084 extends distally from the valve 1000, through the gate 1066 in the closed state, and beyond the distal end of the loading device 1060. In some embodiments, for example, the gate 1066 can have a shape and/or size such that a space is defined between an edge of the gate 1066 and an inner surface of the loading device 1060 allowing the guidewire catheter 1084 and the tether 1099 of the pulling device 1098 to extend therethrough. In some embodiments, the gate 1066 can define an opening, a hole, a notch, a recess, and/or the like through which the guidewire catheter 1084 and the tether 1099 can extend.

After advancing the valve 1000 into the loading device 1060, the compression device 1090 can be removed from the proximal end of the loading device 1060. As described above, the first member 1091 and second member 1092 of the compression device 1090 are laterally separable when the coupler 1093 is removed. Thus, the coupler 1093 can be removed and the first member 1091 and the second member 1092 can be separated to decouple the compression device 1090 from the proximal end of the loading device 1060 without, for example, disconnecting, removing, and/or substantially changing the control device 1070 relative to the valve 1000. After removing the compression device 1090 from the loading device 1060, a hemostasis valve 1068 and/or the like can be advanced over a portion of the control device 1070 and coupled to the proximal end of the loading device 1060 (see e.g., FIG. 38). The hemostasis valve 1068 a form a substantially fluid tight seal at the proximal end of the loading device 1060 (e.g., and around the control device 1070 and/or a control catheter thereof). Moreover, the pulling device 1098 can also be decoupled and/or removed from the distal end of the loading device 1060 and the tether 1098 can be decoupled from the valve 1000 and withdrawn from the loading device 1060.

With the hemostasis valve 1068 coupled to the proximal end of the loading device 1060 and the distal end of the loading device 1060 decoupled from the loading device 1060, the loading device 1060 is ready for coupling to the delivery device 1081. Thus, with the valve 1000 being loaded into the loading device 1060 while in the fluid (e.g., saline) bath, the loading device 1060 with the valve 1000 in the delivery configuration disposed in the lumen 1063, the hemostasis valve 1068 coupled to the proximal end, and the gate 1066 in the closed state can be removed from the bath and brought to, for example, an operating table or the like to be coupled to the proximal end of the delivery device 1081 that is already inserted into the patient.

Figure 38:
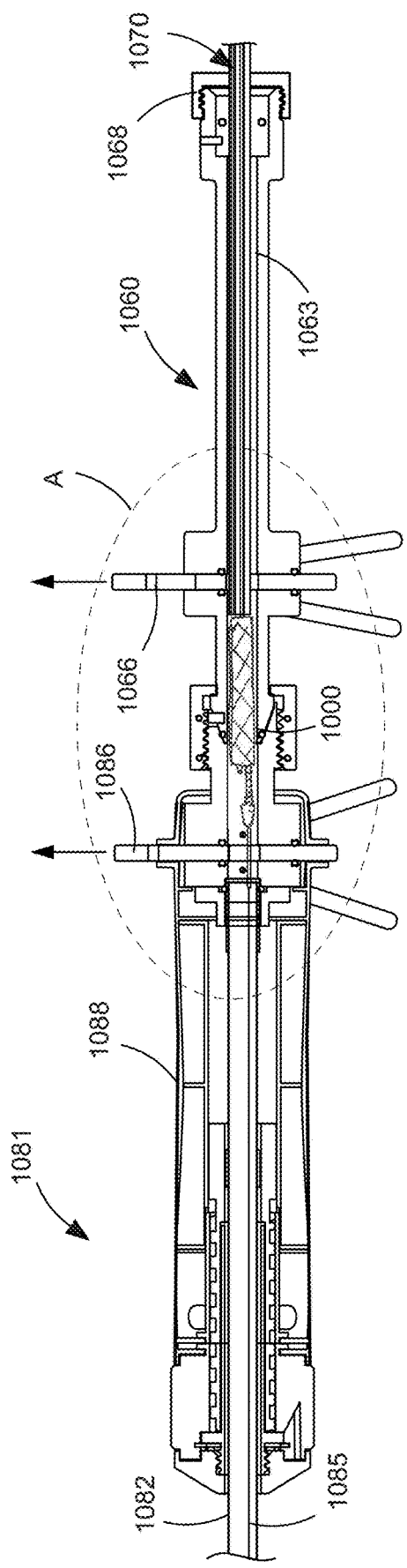
Figure 39:
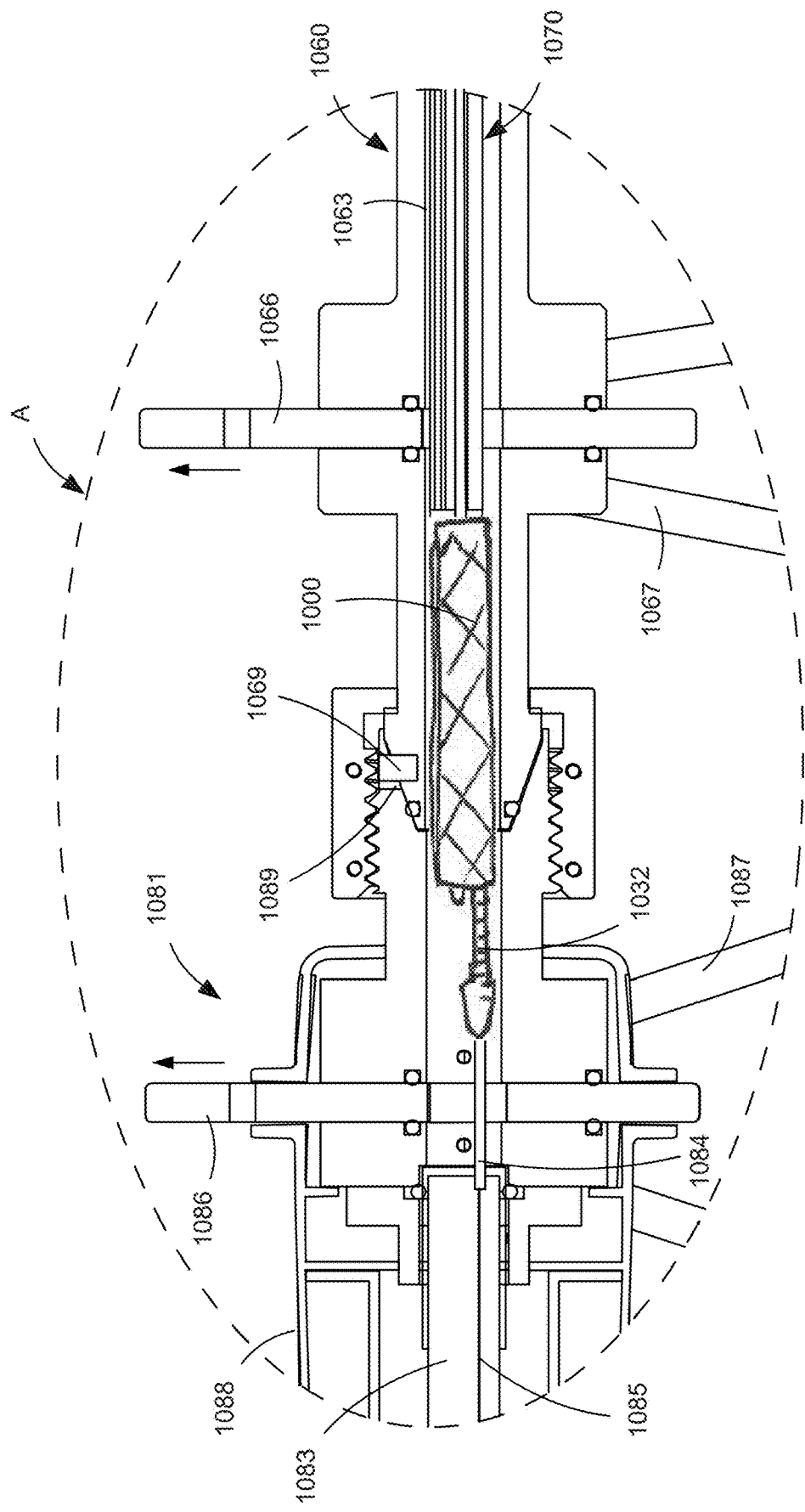
FIG. 39 is an enlarged cross-section view of a portion the delivery system identified by the region A in FIG. 32 and showing the side-deliverable valve being loaded into the delivery device.

FIG. 38 show the distal end of the loading device 1060 coupled to the proximal end of the delivery device 1081. FIG. 39 is an enlarged view of a portion of the delivery system 1080 and shows the indexing feature 1089 of the handle 1088 engaging an indexing feature 1069 included in the distal end portion of the loading device 1069. The indexing features 1089 and 1069 are show having a key-and-slot arrangement, though other modes of indexing are possible. The indexing features 1089 and 1069 ensure that the delivery device 1081 is in a predetermined and/or desired orientation relative to the loading device 1060, and as such, the valve 1000 can be transferred into the delivery device 1000 in a predetermined and/or desired orientation (e.g., set and/or defined, for example, by the way the valve 1000 is inserted into the lumen 1095 of the compression device 1090—according to the perimeter of the lumen 1095 at the proximal end of the compression member 1090).

As described above, the delivery catheter 1082 is previous inserted into the patient and the proximal end of the guidewire 1085 extends from the proximal end of the handle 1088 of the delivery device 1081. Accordingly, prior to coupling the distal end of the loading device 1060 to the proximal end of the handle 1088, the proximal end of the guidewire 1085 is inserted into the guidewire catheter 1084. As described above, the loading device 1060 is coupled to the the proximal end of the handle 1088 while the valve 1000 is proximal to the 1066 of the loading device 1060 and each of the gates 1066 and 1086 of the loading device 1060 and the delivery device 1081, respectively, is in a closed state. In some implementations, after coupling the loading device 1060 to the delivery device 1081 and before transitioning the gates 1066 and 1086 to the open state, the volume collectively defined by the lumens 1063 and 1083 disposed between the gates 1066 and 1086 can be flushed via the ports 1067 and 1087. For example, in some implementations, the port(s) 1087 can provide a flow of saline and/or other sterile fluid into the volume while the port(s) 1067 can provide a suction to and/or through at least the volume (or vice versa).

FIGS. 38 and 39 show that after coupling the loading device 1060 to the handle 1088 of the delivery device 1081 and after flushing the volume defined between the gates 1066 and 1086, the gates 1066 and 1086 can be transitioned from the closed state to the open state. As such, the lumens 1063 and 1083 are substantially open or otherwise not occluded. Thus, a user and/or operator can exert a distal force on, for example, the control portion 1072 of the control device 1070 to advance the valve 1000 in the delivery configuration from the loading device 1060 and into the lumen 1083 of the delivery device 1081 and through the delivery catheter 1082. The valve 1000 can then be at least partially released from distal end delivery catheter 1082 and once released (or at least partially released), the control device 1070 can control and/or manipulate the valve 1000 to seat the valve in the annulus of the native heart valve (e.g., as described above with reference to FIGS. 29-34B).

In some instances, it may be desirable to at least partially retrieve the valve 1000 from the annulus during deployment (e.g., to adjust a position, orientation, and/or seating of the valve 1000 in the annulus). In such instances, the control device 1070 further can be used to at least partially retrieve the valve 1000 into the distal end of the delivery catheter 1082. For example, with the connection member 1078 (yoke) removably coupled to the valve 1000, the user and/or operator can exert a proximally directed force on the control device 1070 that can pull that valve 1000 proximally toward and/or into the delivery catheter 1082. Moreover, the delivery system 1080 can include any suitable capture element, feature, member, mechanism, etc. (such as those described herein with reference to specific embodiments) configured to facilitate a compression of the valve 1000 as the valve 1000 is pulled in a proximal direction toward and/or into the delivery catheter 1082. In some instances, after partially retrieving the valve 1000, the control device 1070 can be manipulated to reseat the valve 1000 in the annulus in a desired orientation and/or configuration.

Figure 40:
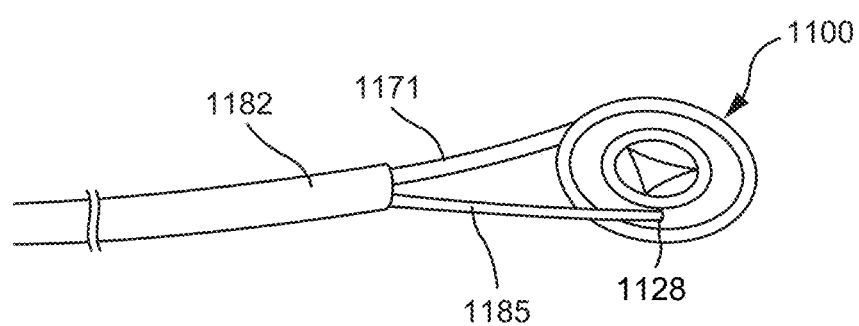
FIGS. 40-42 are various views of a prosthetic valve illustrating way of attaching at least one of a guidewire and/or a control catheter to one or more portions of the prosthetic valves, each according to a different embodiment.

FIG. 40 is an illustration of a top perspective view of a valve 1100 with a guidewire 1185 threaded through a waypoint 1128 and a positioning and/or control catheter 1171 attached on a proximal side of the valve 1100. A delivery catheter 1182 is shown having the guidewire 1185 and the positioning and/or control catheter 1171 disposed within a lumen of the delivery catheter 1182.

Figure 41:
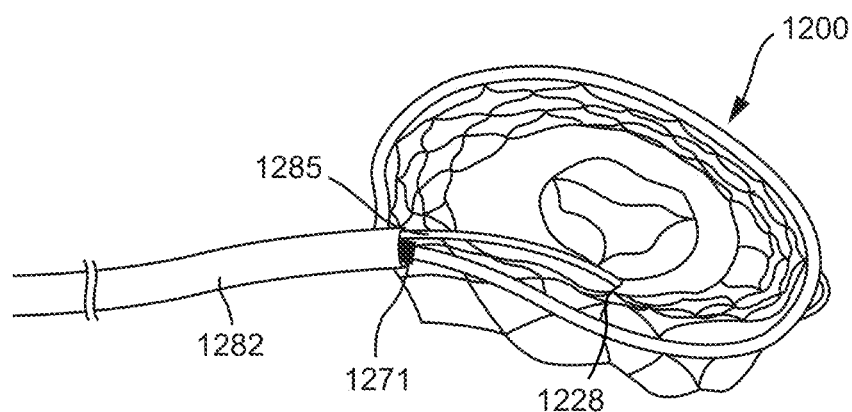

FIG. 41 is an illustration of a side perspective view of a valve 1200 with a guidewire 1285 threaded through a waypoint 1228 and a positioning and/or control catheter 1271 is attached on a proximal side of the valve 1200. A delivery catheter 1282 is shown having the guidewire 1285 and the positioning and/or control catheter 1271 disposed within a lumen of the delivery catheter 1282.

Figure 42:
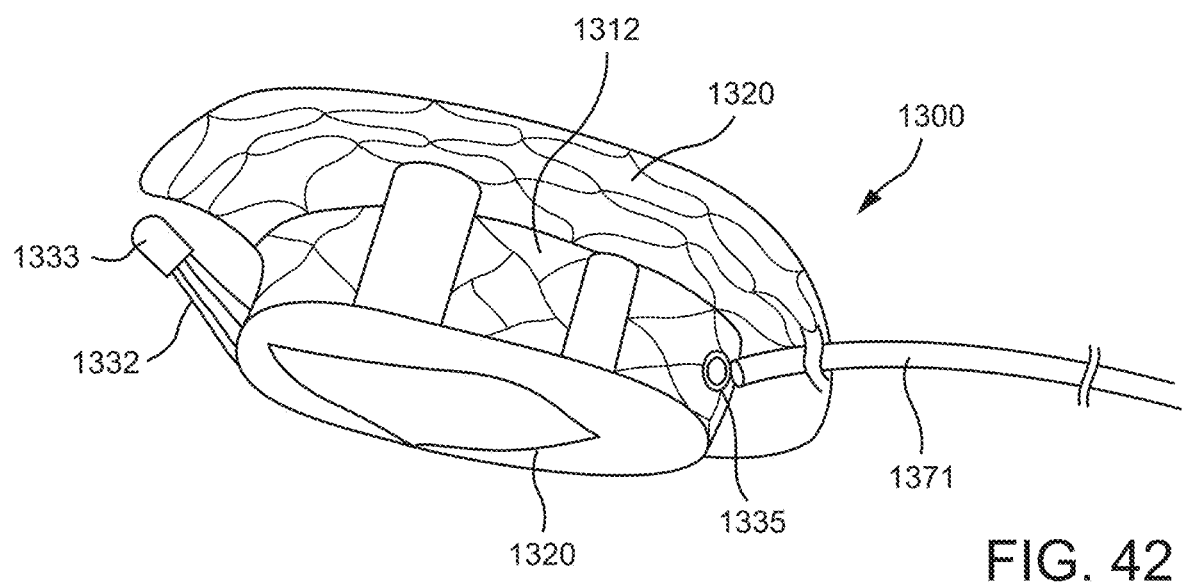

FIG. 42 is an illustration of a below perspective view of a valve 1300 being coupled to a positioning and/or control catheter 1371. A catheter guide and/or support can provide additional connection and support of the positioning and/or control catheter 1371 during attachment with the valve 1300. A mount 1335 is shown for attaching the positioning and/or control catheter 1371 to the valve 1300. In some embodiments, the positioning and/or control catheter 1371 has a threaded portion that engages a matching threaded component on the valve 1300, whereby the positioning and/or control catheter 1371 can be rotated to engage/disengage the positioning and/or control catheter 1371 from the valve 1300. A distal anchor channel and proximal anchor channel can be included and/or formed by an outside portion of a sidewall 1312 of the valve 1300 and provide, for example, subannular access from a collar portion 1320 through the channel, to the subannular space for deploying a tissue anchor (not shown). A distal anchoring element 1332 and a guidewire coupler or anchor head 1333 are shown extending distally from the lower portion or subannular region 1320 of the valve 1300.

Figure 43:
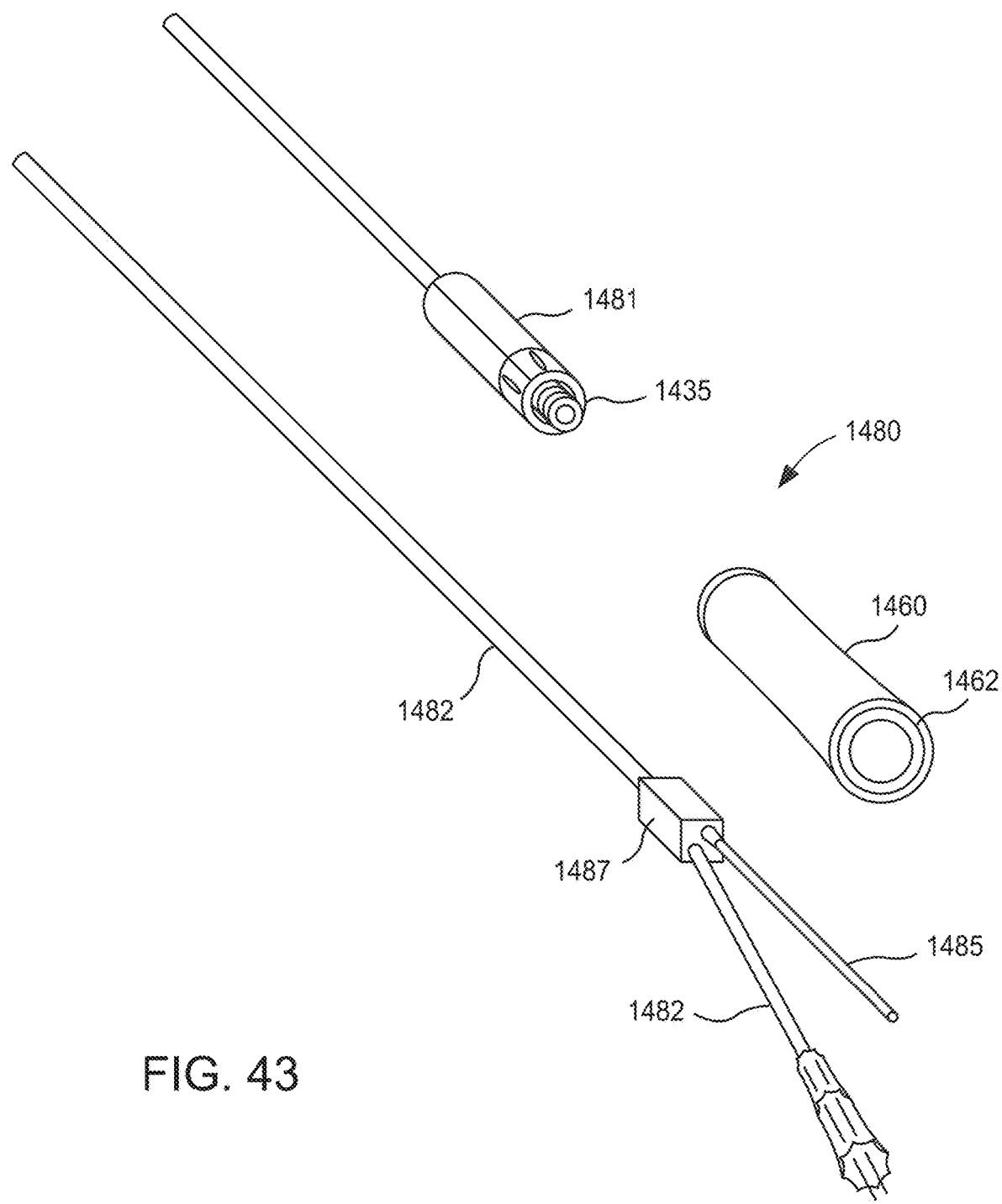
FIG. 43 is a partially exploded perspective view of at least a portion of a delivery system for side-delivery of a prosthetic valve according to an embodiment.

FIG. 43 is an illustration of a side perspective view of components of a delivery system 1480. A loading device 1460 with a loading compression cylinder 1462 are shown in one component. A delivery device 1481 and threaded mount 1435 are shown in a second component. A guidewire 1485 and a positioning and/or control catheter 1471 are shown threaded through a receiver at a proximal end of a delivery catheter 1482. The positioning and/or control catheter 1471 can be equipped with a luer lock and/or the like to provide a port 1487 for flushing liquid through the lumen of the positioning and/or control catheter 1471 and/or the deliver catheter 1482.

Figure 44:
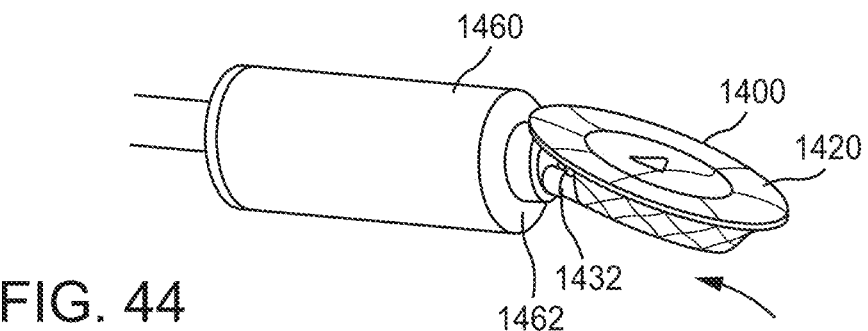
FIGS. 44 and 45 are side perspective views of a loading device included in the delivery system of FIG. 43 and illustrating a compression process associated with inserting the prosthetic valve into the loading device.

FIG. 44 is an illustration of a side perspective view of the valve 1400 starting a compression process associated with loading the valve 1400 into the loading device 1460. A distal anchoring element 1432 is shown leading the valve 1400 into the loading compression cylinder 1462. A collar or supra-annular region 1420 of the valve 1400 is shown with lateral portions starting to fold downward and/or inward to lay flat against the sidewall of the valve 1400.

Figure 45:
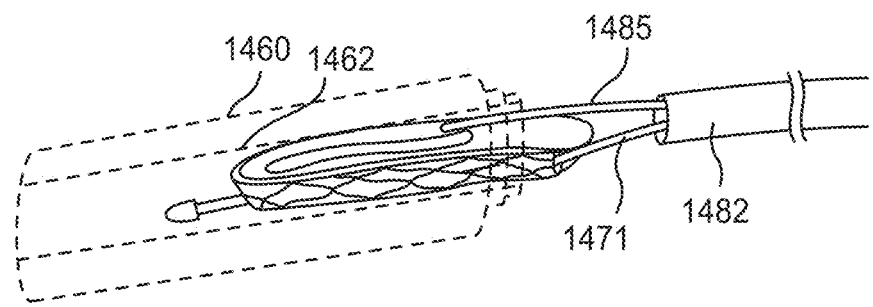

FIG. 45 is an illustration of a side perspective view of the valve 1400 partially inserted into the loading compression cylinder 1462. The valve 1400 is further compressed as the valve 1400 is inserted into the loading device 1460. FIG. 45 shows the valve 1400 nearly completely loaded into the loading compression cylinder 1462. The guidewire 1485 and the positioning and/or control catheter 1471 are shown attached to the valve 1400 as it is compressed.

Figure 46:
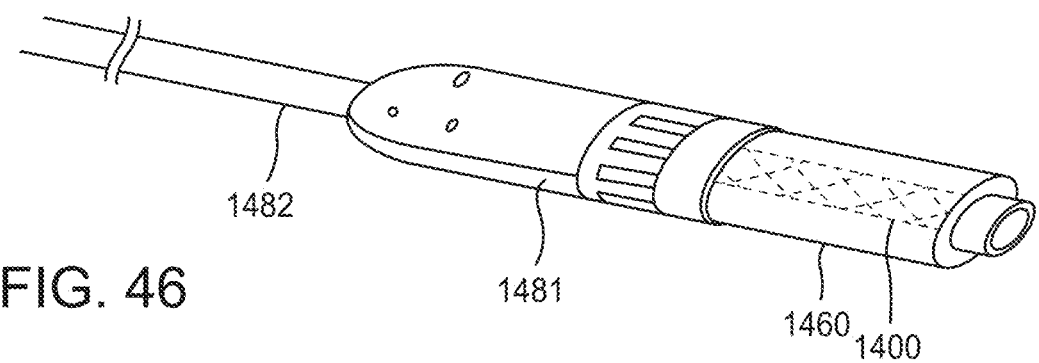
FIG. 46 is a side perspective view of the loading device, with the compressed prosthetic valve disposed therein, connected to a delivery device of the delivery system of FIG. 42.

FIG. 46 is an illustration of a side perspective view of the loading device 1460 connected to the delivery device 1481. The valve 1400 is shown fully compressed into a compressed or delivery configuration within the loading compression cylinder 1462. The connection of the loading device 1460 to the delivery device 1481 allows the valve 1400 to be advanced from the loading device 1460 and through the delivery catheter 1482 for deployment in the patient.

Figure 47A:
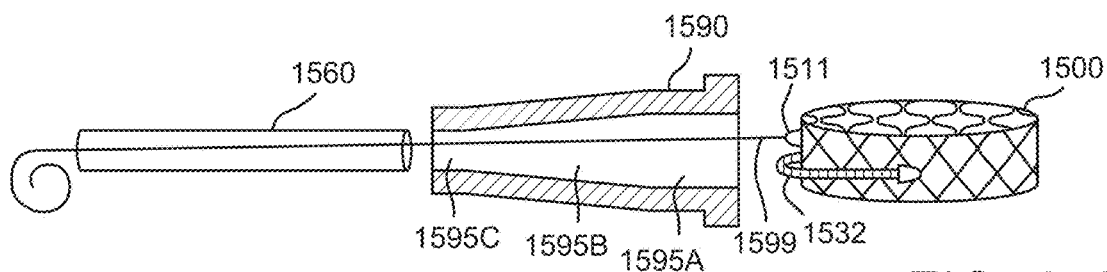
FIGS. 47A-47E are cross-sectional views of a portion of a delivery system illustrating a process of using a compression device of the delivery system to compress a prosthetic valve for insertion into a loading device of the delivery system, according to an embodiment.

FIG. 47A is an illustration of a side view of compression device 1590 with a loading device 1560 (e.g., a compression or receiver catheter) located at a distal end and a tether 1599 attached to a side-delivered valve 1500, according to an embodiment. FIG. 47A shows the valve 1500 having a distal tether ring 1511 that is adjacent a distal anchoring element 1532. The compression device 1590 defines a lumen, volume, space, and/or the like that has and/or forms a rectangular cavity 1595A (e.g., at a proximal end), which leads to transition cavity 1595B, which leads to circular cavity 1595C (e.g., at a distal end and adjacent the loading device 1560).

Figure 47B:
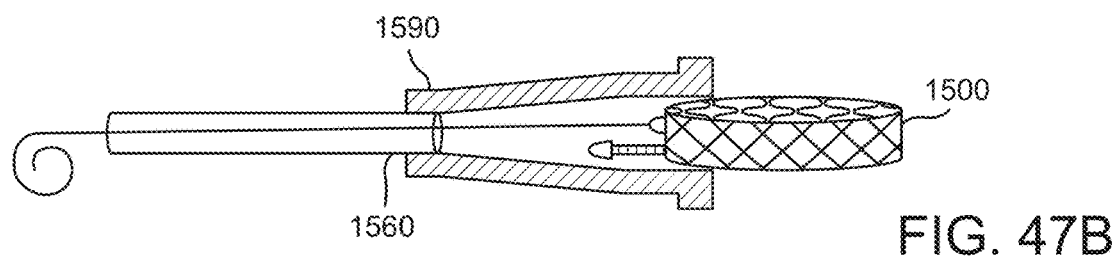
Figure 47C:
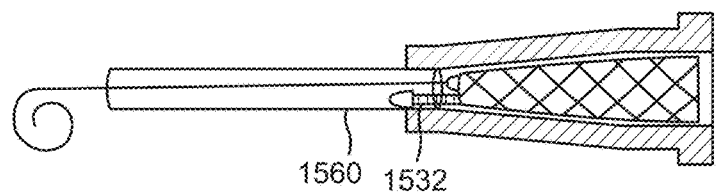

FIG. 47B is an illustration of a side view of the valve 1500 being pulled by the tether 1599 right to left into the rectangular cavity 1595A of the compression device 1590, towards the transition cavity 1595B. The loading device 1560 is connected to the compression device 1590 at a distal end (e.g., adjacent the circular cavity 1595C). This connection can be a threaded connection, a tension/form-fitting connection, or other type of connection such as bead-and-channel, or a clamp-on connection. FIG. 47C is an illustration of a side view of the valve 1500 being pulled further right to left from the rectangular cavity 1595A, through the transition cavity 1595B, and into the circular cavity 1595C of the compression device 1590. The distal anchoring element 1532 is shown as leading the valve 1500 into a lumen of the loading device 1560.

Figure 47D:
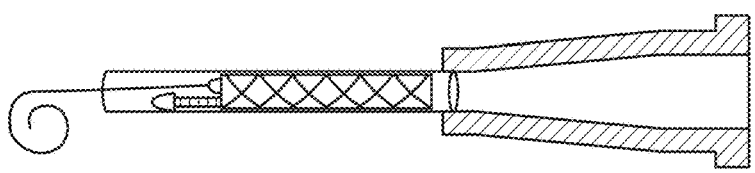
Figure 47E:
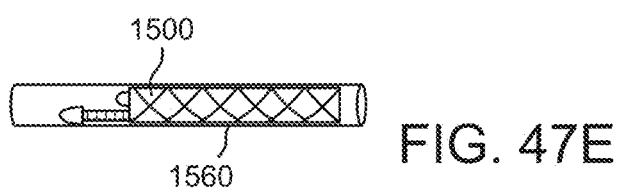

FIG. 47D is an illustration of a side view of the valve 1500 being pulled by the tether 1599 right to left out of the compression device 1590 and into the lumen of the loading device 1560 coupled to the compression device 1590 at the distal end (e.g., adjacent the circular cavity 1595C). FIG. 47E is an illustration of a side view of the valve 1500 in a compressed and/or delivery configuration entirely disposed within the loading device 1560. The loading device 1560 is shown decoupled and/or otherwise removed from the compression device 1590.

Figure 47F:
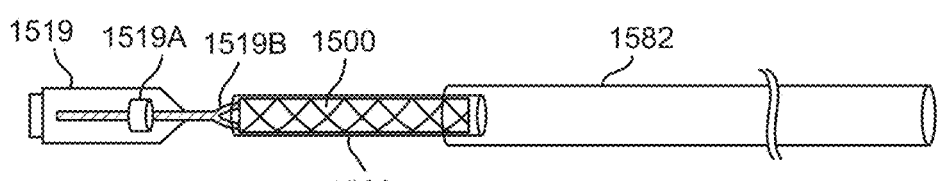
FIGS. 47F and 47G are cross-sectional views of a portion of the delivery system of FIG. 47A illustrating a process of using a pushing device of the delivery system to push the compressed prosthetic valve from the loading device into a lumen of a delivery catheter.
Figure 47G:
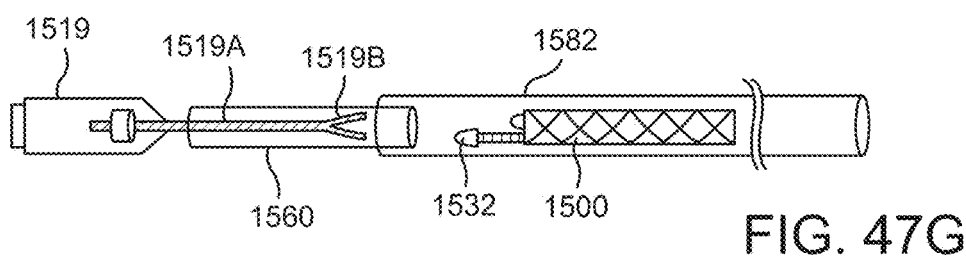

FIG. 47F is an illustration of a side view of a pushing device 1519 engaging the valve 1500 in the compressed configuration within the loading device 1560. Moreover, the loading device 1560 is shown connected to a delivery catheter 1582. The pushing device 1519 can include a screw mechanism or the like, which can be used to advance a push rod 1519A to push the compressed valve 1500. The push rod 1519A is shown with a distal end 1519B that engages a sidewall of the valve 1500 to advance and/or push the valve 1500 in the delivery configuration from the loading device 1560 to the delivery catheter 1582. Once the valve 1500 in the delivery configuration is disposed in the delivery catheter 1582, the distal anchoring element 1532 can be pointed toward a distal open end of the delivery catheter 1582 through which the valve 1500 was just advanced. FIG. 47G is an illustration of a side view of the valve 1500 in the delivery configuration disposed in a lumen of the delivery catheter 1582 via the pushing device 1519. The valve 1500 is shown successfully loaded into the delivery catheter 1582, and the loading device 1560 can be disengaged from the valve 1500 and withdrawn from the delivery catheter 1582. Thus, the valve 1500 is ready for side-delivery into a native annulus via the delivery catheter 1582.

FIG. 48A is an illustration of a side view of compression device 1690 with a loading device 1660 located at a distal end of the compression device 1690 and with a tether 1699 attached to a distal end of a side-deliverable valve 1600 having a guidewire 1685 and a torque and/or positioning cable 1647 attached to a proximal end of the valve 1600. FIG. 48A shows the valve 1600 having a distal tether ring 1611 that is adjacent a distal anchoring element 1632. The compression device 1690 defines a lumen, volume, space, and/or the like that has and/or forms a rectangular cavity 1695A (e.g., at a proximal end), which leads to transition cavity 1695B, which leads to circular cavity 1695C (e.g., at a distal end and adjacent the loading device 1660).

FIG. 48A shows an embodiment of the compression device 1690 that has a two-part or otherwise multi-part construction. For example, the compression device 1690 can include two, substantially mirrored parts that can be laterally separable or disassembled and removed without disconnecting wires, cables, tethers, catheters, etc. from the valve 1600. The valve 1600 includes a waypoint 1628 for running the guidewire 1685 through a supra-annular region 1620 (e.g., a collar, drum, etc.) and through the distal subannular anchoring element 1632. The torque and/or positioning cable 1647 is attached to the valve 1600 using a threaded receiver 1635 that can be remotely disconnected by axially rotating the torque and/or positioning cable 1647.

FIG. 48B is an illustration of a side view of the valve 1600 (and the guidewire 1685 and the torque and/or positioning catheter 1647 attached thereto) being pulled by the tether 1699 right to left into the rectangular cavity 1695A of the compression device 1690 and towards the transition cavity 1695B. The loading device 1660 is shown connected to a distal end of the compression device 1690. This connection can be a threaded connection, a tension/form-fitting connection, or other type of connection such as bead-and-channel, or a clamp-on connection. FIG. 48C is an illustration of a side view of the valve 1600, the guidewire 1685, and the cable 1647 being pulled further right to left through the transition cavity 1695B and into the circular cavity 1695C of the compression device 1690. The distal anchoring element 1632 is shown leading the valve 1600 into a lumen of the loading device 1660.

FIG. 48D is an illustration of a side view of the valve 1600, the guidewire 1685, and the cable 1647 pulled by the tether 1699 right to left out of the compression device 1690 and into the loading device 1660 coupled to the compression device 1690 at the distal end. FIG. 48E is an illustration of a side view of the valve 1600 in a compressed and/or delivery configuration entirely disposed within the loading device 1660 and having the guidewire 1685 and the cable 1647 coupled thereto. The compression device 1690 is shown as being laterally separated into first part 1691 and a second part 1692 allowing the compression device 1690 to be removed from the loading device 1660 while maintaining connection of the valve 1600 to the pre-attached guidewire 1685 and cable 1647.

FIG. 48F is an illustration of a side view of the valve 1600 in the delivery configuration, and with the guidewire 1685 and cable 1647 attached, disposed within the loading device 1660 and the loading device 1660 connected, coupled, and/or inserted into the delivery catheter 1682. FIG. 48G is an illustration of a side view of a pushing device 1619 after engaging the valve 1600 within the loading device 1660 to push the compressed valve 1600 from the loading device 1660 to a delivery catheter 1682, according to the invention. The pushing device 1619 can include a screw mechanism 1619B, which can be used to advance a push rod 1619 to push the compressed valve 1600. The push rod 1619 is shown with a distal end 1619A that engages a sidewall of the valve 1600 to advance and/or push the valve 1600 in the delivery configuration from the loading device 1660 to the delivery catheter 1682. The valve 1600 is advanced from the loading device 1660 (in which the valve 1600 is disposed with the distal anchoring element 1632 facing an opposite direction from that used during an anchor-first delivery to the atrioventricular valve) to the delivery catheter 1682 to correct the orientation of the valve 1600 and the distal anchoring element 1632. Once the valve 1600 in the delivery configuration is disposed in the delivery catheter 1682, the distal anchoring element 1632 can be pointed toward a distal open end of the delivery catheter 1682 through which the valve 1600 was just advanced. FIG. 48G shows the valve 1600 successfully loaded into the delivery catheter 1682, and the loading device 1660 is shown as being disengaged from the valve 1600 and withdrawn from the delivery catheter 1682. Thus, the valve 1600 is ready for side-delivery into a native annulus via the delivery catheter 1682.

Figure 49A:
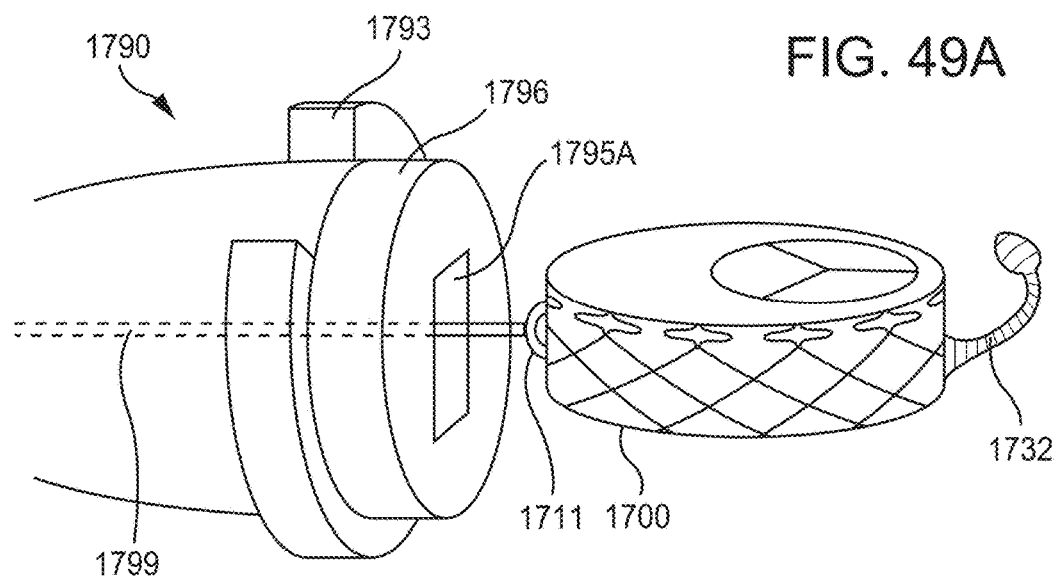
FIGS. 49A-49C are a side perspective view, and a partial cross-sectional views, respectively, of a compression device of a delivery system and a prosthetic valve and illustrating a process of using a pulling device coupled to a proximal side of the prosthetic valve to pull the prosthetic valve through the compression device and into a loading device, according to an embodiment.

FIG. 49A is an illustration of a perspective view of a compression device 1790 receiving a valve 1700, proximal side first, with a valve tether ring 1711 attached to a tether 1799. FIG. 49A shows a coupler 1793 holding two halves of the compression device 1790 together, with the coupler 1793 seated on a funnel neck element and abutting a shoulder element 1796. FIG. 49A shows a portion of a lumen extending through the compression device the defines and/or forms a rectangular cavity 1795A at a proximal end of the compression device 1790. In some embodiments, the rectangular cavity 1795A can be sized and/or shaped to receive the valve 1700 in an uncompressed configuration. In other embodiments, the rectangular cavity 1795A can be size and/or shaped to receive the valve 1700 at least partially in a laterally compressed or folded configuration and an axially uncompressed configuration. In still other embodiments, the rectangular cavity 1795A can be sized and/or shaped to receive the valve 1700 at least partially in a laterally compressed and at least partially in an axially compressed configuration.

Figure 49B:
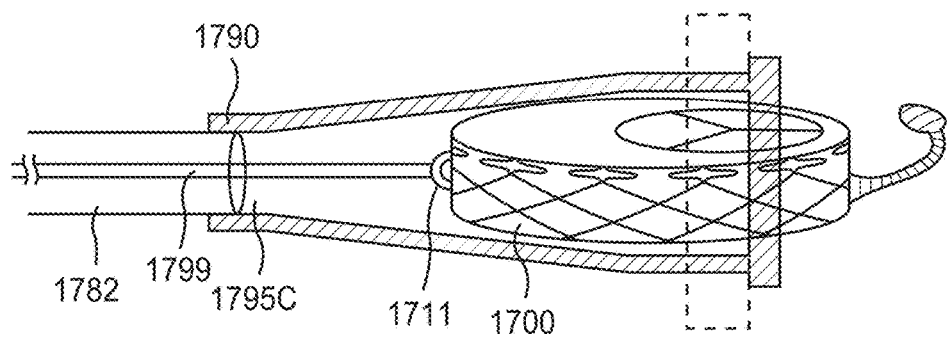

FIG. 49B is an illustration of a side cross-sectional view of the valve 1700 being pulled into the compression device 1790, proximal side first, with a distal anchoring element 1732 trailing the valve 1700 through the compression device 1790. A delivery catheter 1782 is shown connected to a distal end of the compression device 1790 (e.g., at or adjacent to a circular cavity 1795C portion of the lumen) and ready to receive the valve 1700 in a delivery configuration from the compression device 1790.

Figure 49C:
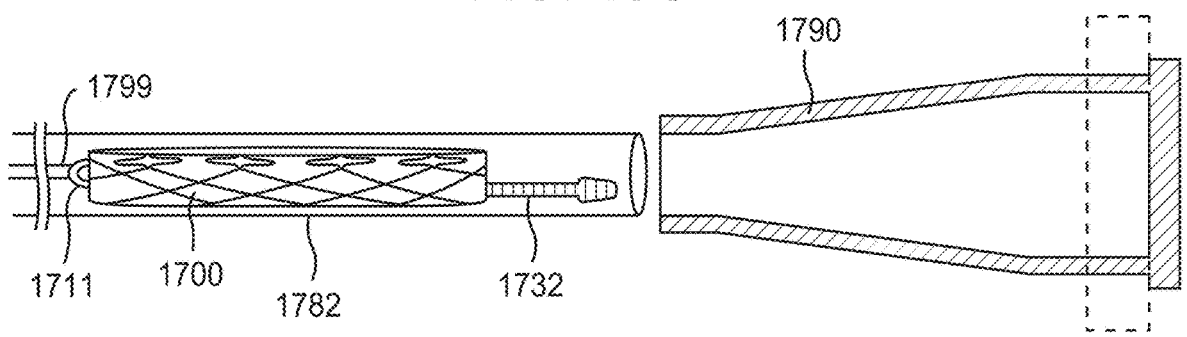

FIG. 49C is an illustration of a side cross-sectional view of the valve 1700 in the compressed or delivery configuration that has been pulled directly into the delivery catheter 1782 with the distal anchoring element 1732 in a desired position (e.g., a distal position and/or otherwise oriented towards a distal end of delivery catheter), without using a pushing device and/or the like otherwise associated with using the compression device 1790 to compress the valve 1700 to the delivery configuration via a distal-anchor-first approach. Although not shown, this process of compressing and loading the valve 1700 can be used with a guidewire and a torque and/or positioning catheter pre-attached to the valve 1700 (e.g., as described above with reference to FIGS. 48A-48G).

Figure 50A:
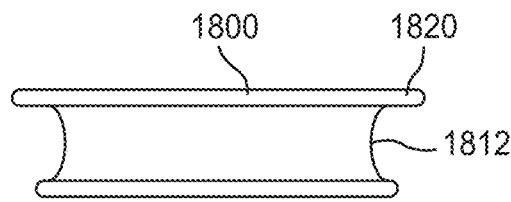
FIGS. 50A-50E are proximal views of a prosthetic valve showing a process of compressing the prosthetic valve in an axial direction and a lateral direction from an expanded or deployment configuration to a compressed or delivery configuration, according to an embodiment.
Figure 50B:
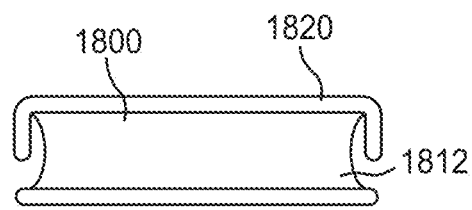
Figure 50C:
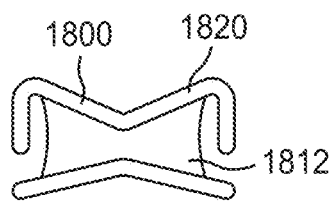
Figure 50D:
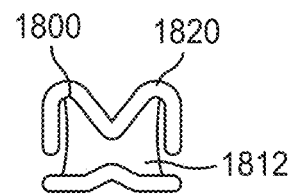
Figure 50E:
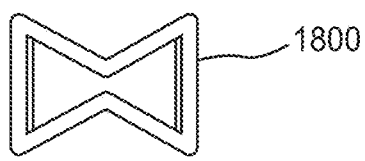
Figure 50F:
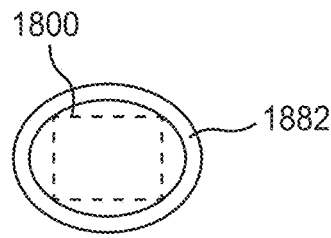
FIG. 50F is a cross-sectional view of a delivery catheter illustrating the prosthetic valve in the compressed or delivery configuration disposed in a lumen thereof.

FIGS. 50A-50E are proximal end views of a prosthetic valve 1800 and illustrate a process of compressing the valve 1800 from an expanded or uncompressed configuration to a compressed and/or delivery configuration, according to an embodiment. FIG. 50A shows the valve 1800 in an uncompressed configuration. As shown, the valve 1800 has a supra-annular region (or collar portion) 1820 and a sidewall portion 1812 (or transannular region). FIG. 50B shows the valve 1800 partially compressed with sides of the collar 1820 being folded down parallel with the sidewall portion 1812. FIG. 50C shows the valve 1800 further compressed with the sides of the collar 1820 folded down and the sidewall portion 1812 folding inward. FIG. 50D shows the valve 1800 further compressed with the sides of the collar 1820 folded down and the sidewall portion 1812 folding further inward. FIG. 50E shows the valve 1800 further compressed with the sides of the collar 1820 folded down, the sidewall portion 1812 folded completely inward, and an axial height of the valve 1800 compressed to place the valve 1800 in the delivery configuration. FIG. 50F is an illustration of a cross-section of a delivery catheter 1882 showing how the compressed valve 1800 can fit within an inner diameter of the delivery catheter 1882.

Figure 51A:
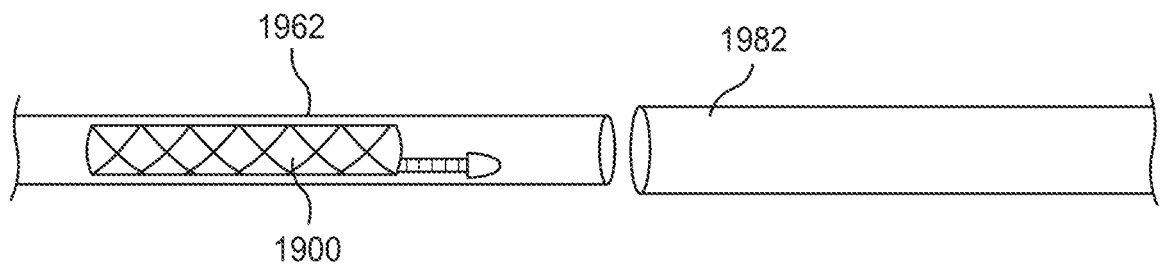
FIGS. 51A and 51B are side view illustrations of a prosthetic valve in a compressed or delivery configuration disposed in a loading (or control) catheter device, which can be used to advance the prosthetic valve in the compressed or delivery configuration through a delivery catheter and into a target location within a patient (e.g., a space within a human heart), accord to an embodiment.
Figure 51B:
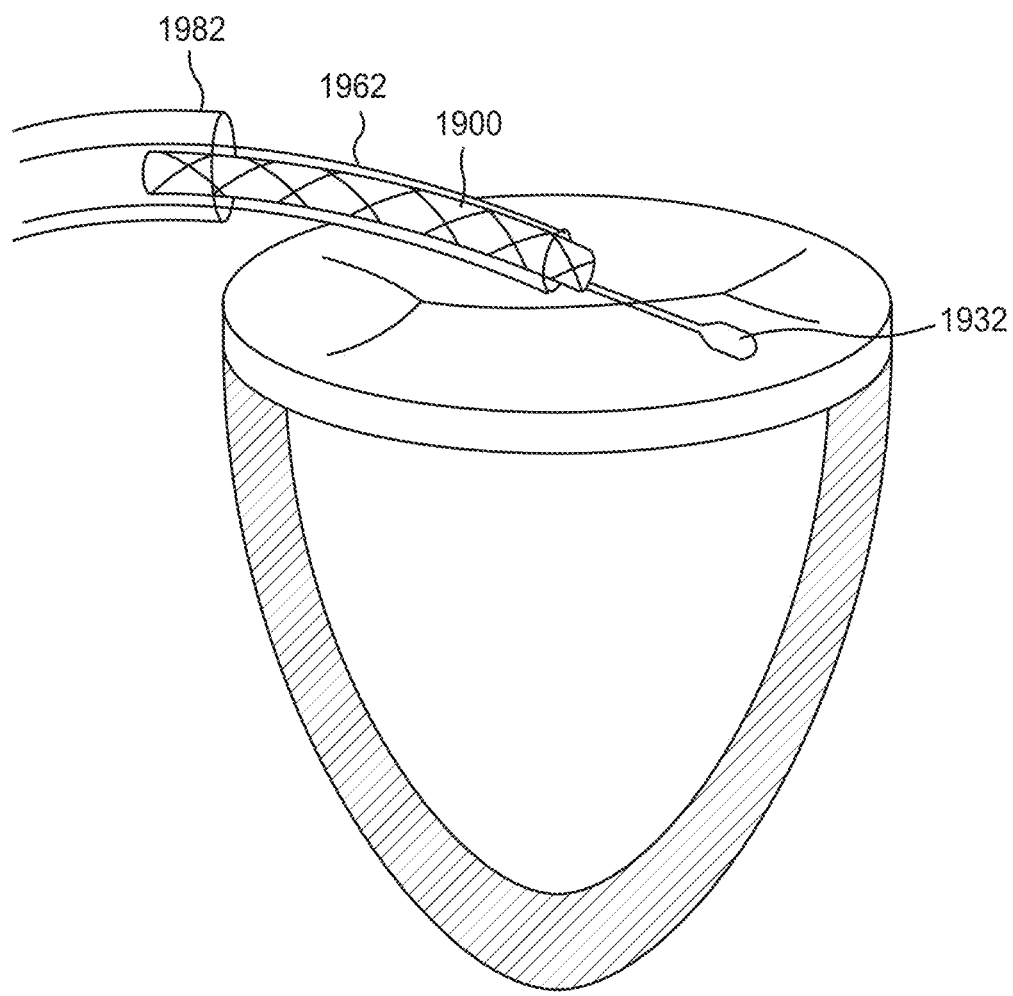

FIGS. 51A and 51B illustrate a compressed valve 1900 disposed within a shuttle, loading, and/or valve catheter 1962, which is used to shuttle the compressed valve 1900 within a larger outer delivery catheter 1982, in a tube-in-a-tube arrangement, according to an embodiment. FIG. 51A shows the compressed valve 1900 within the shuttle catheter 1962, which in turn, is being loaded and/or inserted into the delivery catheter 1982. FIG. 51B shows the compressed valve 1900 partially disposed within the shuttle catheter 1962, which is partially disposed within the delivery catheter 1982 during deployment of the valve 1900 into the native annulus. The valve 1900 is shown partially released from the shuttle catheter 1962 with a distal anchoring element 1932 extending to the native annulus while a remaining portion of the valve 1900 is disposed in the shuttle catheter 1962.

As described above, any of the prosthetic valves described herein can be delivered via a delivery system and can be configured to engage with the delivery system in any suitable manner. In some implementations, a prosthetic valve can be configured to engage a delivery system in a manner similar to those described in the '010 PCT, the '108 PCT, the '327 Provisional, the '964 Provisional, the '345 Provisional, and/or the '807 Provisional incorporated by reference hereinabove.

Figure 52A:
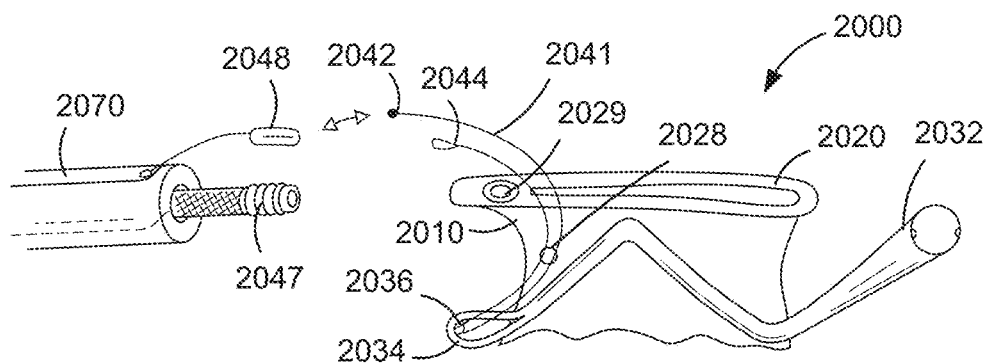
FIGS. 52A-52C are side perspective view illustrations of a portion of a proximal anchoring element of a prosthetic valve being coupled to and decoupled from an actuator or the like, according to an embodiment.
Figure 52B:
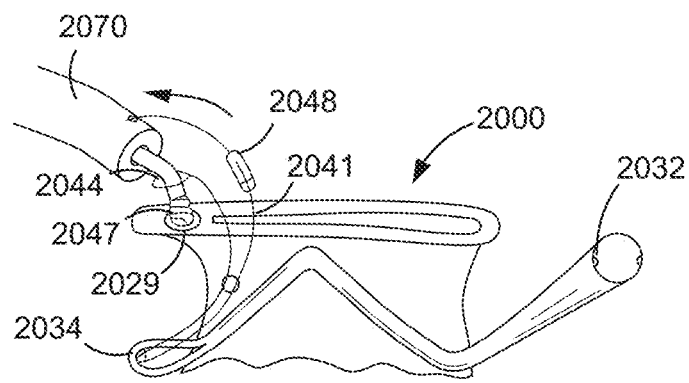
Figure 52C:
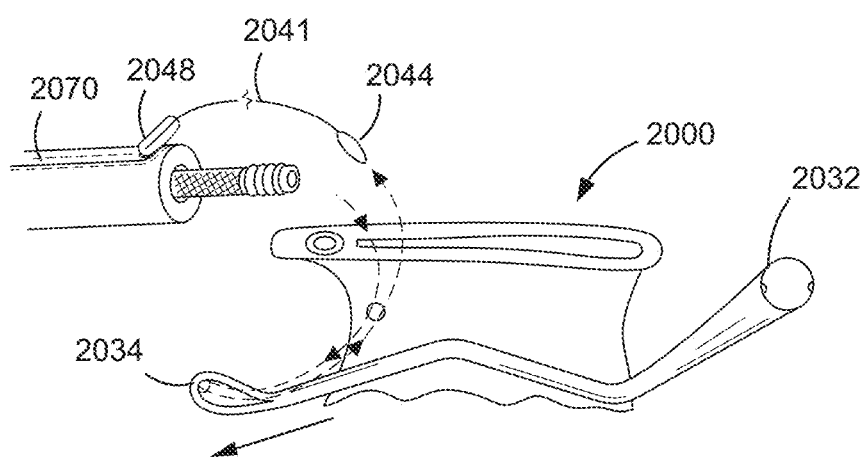

For example, FIGS. 52A-52C illustrate side perspective views of a side delivered transcatheter prosthetic heart valve 2000 and an actuator 2070 according to an embodiment. The valve 2000 has a frame 2010 with a collar 2020 (e.g., a supra-annular member), a distal anchoring element 2032, and a proximal anchoring element 2034 (e.g., wire loop anchoring elements and/or any other suitable type of anchoring element). The frame 2010 defines a waypoint 2028. The collar 2020 includes and/or forms an attachment point 2029. While the waypoint 2028 is shown along a body of the frame 2010, in other embodiments, the collar 2020 and/or any other suitable portion of the valve 2000 can form and/or define the waypoint 2028. Similarly, while the attachment point 2029 is shown along the collar 2020, in other embodiments, the body of the frame 2010 and/or any other suitable portion of the valve 2000 can include the attachment point 2029.

In the embodiment shown in FIGS. 52A-52C, the actuator 2070 is arranged as a tensile member and/or the like. The actuator 2070 includes a lead 2041 configured to be coupled to and/or threaded through an attachment point 2036 of the proximal anchoring element 2034. The lead 2041 includes a first end that has and/or forms a first coupling feature 2044 and a second end that has and/or forms a second coupling feature 2044. The coupling features can be any suitable configuration. For example, in this embodiment, the first coupling feature 2044 is and/or forms a loop, eyelet, opening, and/or the like, and the second coupling feature 2042 is and/or forms a ball, protrusion, knob, knot, and/or the like. The actuator 2070 can be and/or can include any suitable cable, tether, wire, catheter, conduit, etc. In some implementations, the actuator 2070 can be used, for example, as a pusher or the like configured to push and/or otherwise advance the valve 2000 through a delivery system.

In this embodiment, the actuator 2070 includes a first cable 2047 with an end portion that forms a threaded coupler configured to engage and/or couple to the attachment point 2029 formed by the collar (e.g., a threaded nut or the like). The actuator 2070 includes a second cable 2048 with an end portion that forms a receiving member configured to receive and/or removably couple to the second end of the lead 2041. For example, the receiving member of the second cable 2048 and the coupling feature 2042 formed by the second end of the lead 2041 can be a ball and cup coupling mechanism. Moreover, the actuator 2070 can include and/or can form an outer sheath or catheter configured to at least partially house the first cable 2047 and the second cable 2048.

FIG. 52A shows the actuator 2070 prior to coupling to the valve 2000 and/or the lead 2041. The lead 2041 is shown threaded through a portion of the valve 2000 and the waypoint 2028, looped around or through the attachment point 2036 of the proximal anchoring element 2034, and threaded back through the waypoint 2028 and portion of the valve 2000 such that the first end 2044 and the second end 2042 are each outside of the valve 2000 and/or above or proximal to the collar 2020.

FIG. 52B shows, the end portion of the first cable 2047 of the actuator 2070 coupled to the attachment point 2029 of the collar 2020, for example, via a threaded coupling. The first coupling feature 2044 of the lead 2041 is coupled to the first cable 2047 (e.g., the first coupling feature 2044 can be a loop that is disposed on or about the first cable 2047). In some implementations, the actuator 2070 can be used as a proximal pusher by virtue of the first cable 2047 being coupled to the attachment point 2029 formed by the collar 2020. For example, a substantially fixed portion of the first cable 2047 can extend from the actuator 2070 (e.g., the outer sheath) such that a distal or pushing force applied to the actuator 2070, via the first cable 2047, pushes the valve 2000. With the first coupling feature 2044 coupled to the first cable 2047, the first end of the lead 2041 is maintained in a relatively fixed position relative to the valve 2000. The second cable 2048 of the actuator 2070 is shown coupled to the second coupling feature 2042 of the lead 2041 (e.g., via a ball and cup coupling mechanism and/or the like). Thus, while the actuator 2070 and/or the first cable 2047 can be used to push the valve 2000, a tensile or pulling force can be applied to the second cable 2048, which can pull the second end of the lead 2041 in a proximal direction, thereby placing the lead in tension. Accordingly, the lead 2041 can maintain the proximal anchoring element 2034 in its first configuration during deployment.

FIG. 52C shows the first cable 2047 decoupled from the attachment point 2029 of the collar 2020 and the first coupling feature 2044 at the first end of the lead 2041. The second coupling feature 2042 at the second end of the lead 2041 can remain coupled to the second cable 2048. After the valve has been deployed, the actuator 2070 is pulled to remove the actuator 2070 and the lead 2041 from the valve 2000 and the delivery system. With the actuator 2070 removed, the proximal anchoring element 2034 is allowed to transition to its second configuration.

Figure 53A:
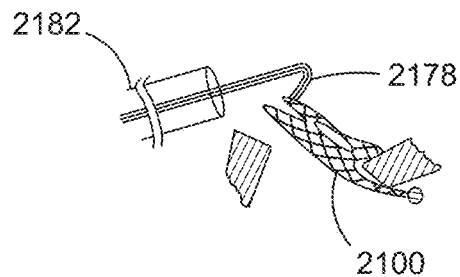
FIGS. 53A-53C are side view schematic illustrations of a prosthetic valve showing a sequence of retracting the valve into a portion of a delivery and/or retraction system according to an embodiment.
Figure 53B:
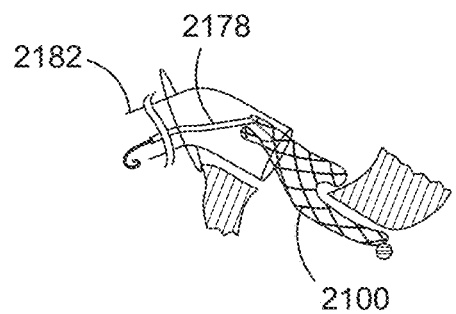
Figure 53C:
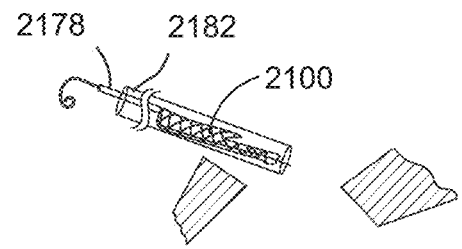

FIGS. 53A-53C are illustrations according to the invention of a series of three images showing a prosthetic valve 2100 being retrieved into a delivery/retrieval catheter 2182 where the longitudinal axis of the catheter 2182 is not parallel to the central blood flow axis through the valve 2100 like in traditional replacement valves, but instead approaches from the side (i.e., orthogonally) relative to the orientation of the blood flow through the valve 2100.

FIG. 53A shows a distal end portion of the delivery/retrieval catheter 2182 accessing an atrium of the heart (e.g., via the inferior vena cava using a transfemoral delivery and/or the like). FIG. 53B shows how an elongated connection member 2178 (e.g., a guidewire, a control push rod, a steerable catheter, a yoke, a tensile member, a suture, a tether, a retrieval tool, etc.) connects to a proximal side of the valve 2100 (e.g., to a delivery system-valve attachment point, waypoint, connector, and/or the like). In some implementations, the elongated connection member 2178 is already attached to the valve 2100 (e.g., for delivery of the valve 2100 to the annulus.

In some implementations, a retrieval process (or a portion thereof) may be performed during the initial valve deployment/delivery procedure and while the valve 2100 is still attached and/or connected to the elongated connection member 2178. For example, the retrieval process can be performed to at least partially withdraw the prosthetic valve 2100 due to a problem or medical issue identified by the interventionalist that calls for the valve 2100 that was being deployed, to be retrieved or at least partially retrieved. In other implementations, a retrieval process (or a portion thereof) may be performed after the valve 2100 has been deployed and disconnected from the elongated connection member 2178. In such implementations, the elongated connection member 2178 can be reconnected to the valve 2100 (or a new elongated connection member can be connected to the valve 2100). In some implementations, attachment and/or connection can be aided by the use of radio-markers on the elongated connection member 2178 and on a proximal portion of the valve 2100.

FIG. 53C shows the valve 2100 pulled into the delivery/retrieval catheter 2182. For example, the elongated connection member 2178 can be used to pull the proximal end of the valve 2100 into the distal end portion of the catheter 2182. In some implementations, the distal end portion of the catheter 2182 can be and/or can include a compression tip with one or more features to assist compression and retraction of the valve 2100, such as a surface coating, spiraled bead lines, spiraled channels, and/or the like on the inner surface of the distal end portion of the catheter 2182 to assist compression and retraction of the valve 2100 into the catheter 2100. As shown, the valve 2100 is folded and compressed into the catheter 2182 with the elongated connection member 2178 attached so that, in some instances, the delivery catheter 2182 can be withdrawn and the valve 2100 retrieved from the patient.

FIGS. 54A to 54I are illustrations according to the invention of a series of nine images showing a valve 2200 being retrieved from a native annulus model and into a delivery/retrieval catheter 2282 where the longitudinal axis of the catheter 2282 is orthogonal to the orientation of the frame and flow control (valve leaflets) component of the valve 2200.

Figure 54A:
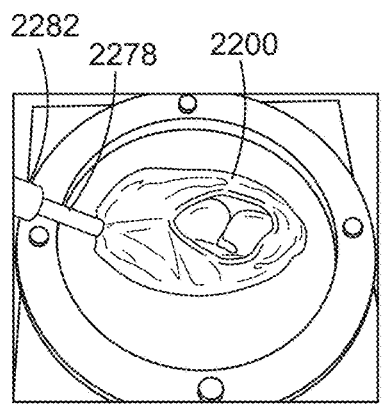
FIGS. 54A to 54I are top perspective views of a valve sequence illustrations showing a sequence of retracting a prosthetic valve into a portion of a delivery and/or retraction system according to an embodiment.

FIG. 54A shows a distal end portion of the delivery/retrieval catheter 2282 having an elongated connection member 2278 (e.g., a guidewire, a control push rod, a steerable catheter, a yoke, a tensile member, a suture, a tether, a retrieval tool, etc.) attached to a proximal portion of the prosthetic valve 2200. FIG. 54A shows a relatively large diameter valve (e.g., 65 mm×45 mm tubular frame (110 mm×72 mm including atrial collar), with a 29 mm flow control component mounted within the tubular frame of the valve 2200) at least partially disposed in an opening corresponding to and/or representing an annulus of a native heart valve.

Figure 54B:
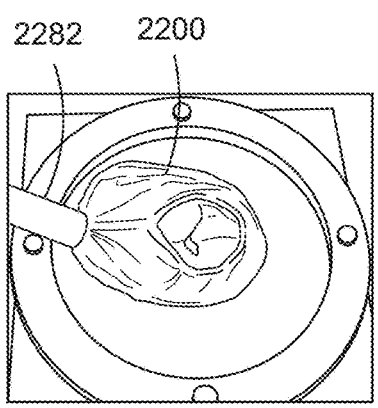

FIG. 54B shows the prosthetic valve 2200 being drawn into the delivery/retrieval catheter 2282 with about 10-20% of the valve 2200 compressed within a lumen of the catheter 2282. FIG. 54B illustrates how the prosthetic valve 2200 is designed to fold, front side approaching back side, and is designed to vertically compress, so that the large valve becomes compressed within a standard sized transfemoral catheter (e.g., 22-32 Fr, or about a 28 Fr catheter). For sake of definition, French sizing can be converted to millimeter by dividing by 3, so that a 22 Fr catheter has about an 8 mm inner diameter, a 30 Fr catheter has about a 10 mm inner diameter, and so forth.

Figure 54C:
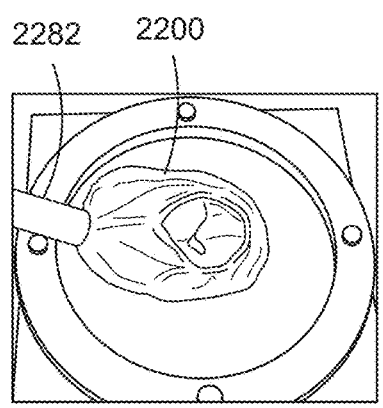

FIG. 54C shows the prosthetic valve 2200 being drawn into the delivery/retrieval catheter 2282 with about 20-30% of the valve 2200 compressed within the lumen of the catheter 2282. FIG. 54C shows, for example, a proximal anchoring location at least partially housed within the catheter 2282.

Figure 54D:
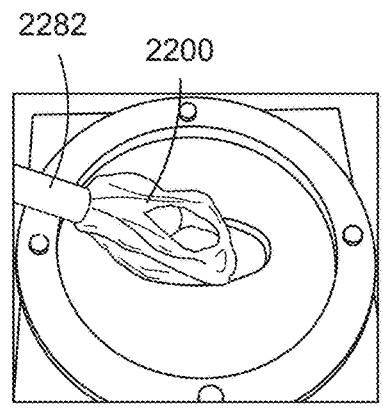

FIG. 54D shows the prosthetic valve 2200 being drawn into the delivery/retrieval catheter 2282 with about 30-40% of the valve 2200 compressed within the lumen of the catheter 2282. FIG. 54D shows, for example, an atrial collar and/or supra-annular member of the valve frame beginning to fold inward toward a longitudinal axis (not shown).

Figure 54E:
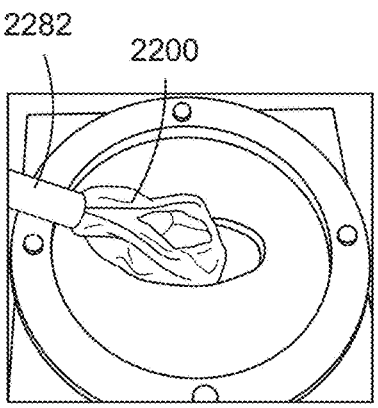
Figure 54F:
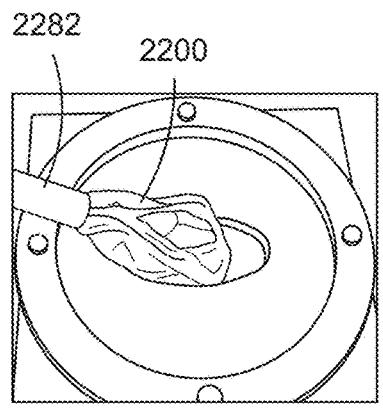

FIGS. 54E and 54F show the prosthetic valve 2200 being drawn into the delivery/retrieval catheter 2282 with about 50-60% of the valve 2200 compressed within the lumen of the catheter 2282. FIGS. 54E and 54F show how the valve 2200 has been at least partially withdrawn from the opening (annulus) and the valve 2200 has started to be vertically compressed.

Figure 54G:
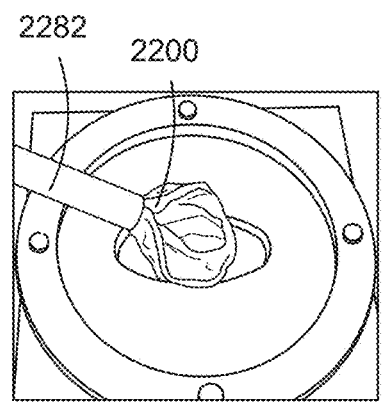
Figure 54H:
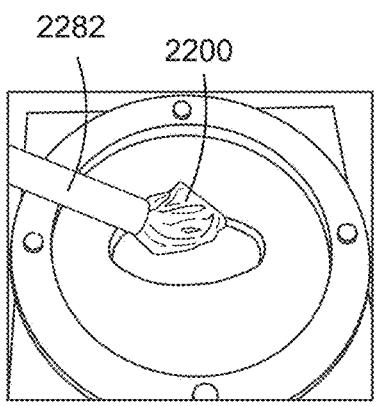
Figure 54I:
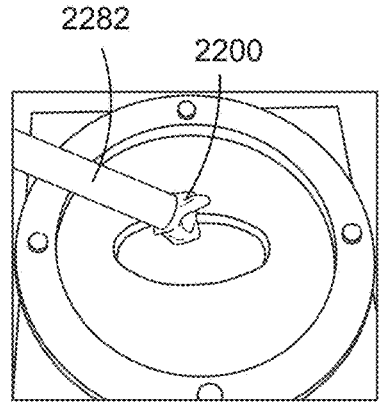

FIGS. 54G to 54I show the valve 2200 continuing to be drawn into the lumen of the delivery/retrieval catheter 2282 with about 70%, 80%, and over 90%, respectively, of the valve 2200 shown compressed within the lumen of the catheter 2282. FIGS. 54G to 54I show how the valve 2200 continues to fold and/or compress and retract into the delivery/retrieval catheter 2282.

Figure 55A:
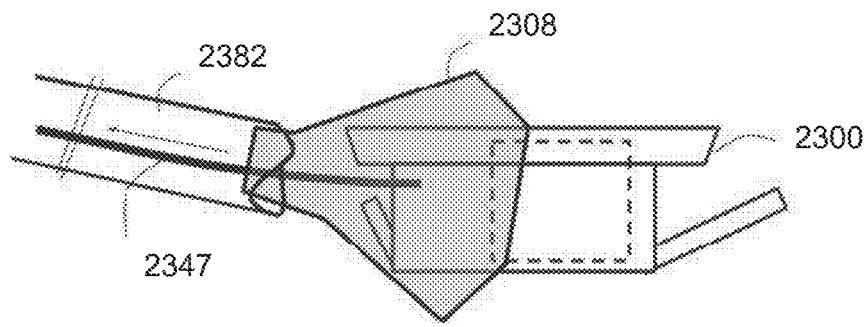
FIGS. 55A-55D are schematic illustrations of an anterior side view of a delivery catheter having an extendable capture element for capturing and/or encompassing at least a portion of a prosthetic valve to facilitate a compression and retrieval process thereof, according to an embodiment.
Figure 55B:
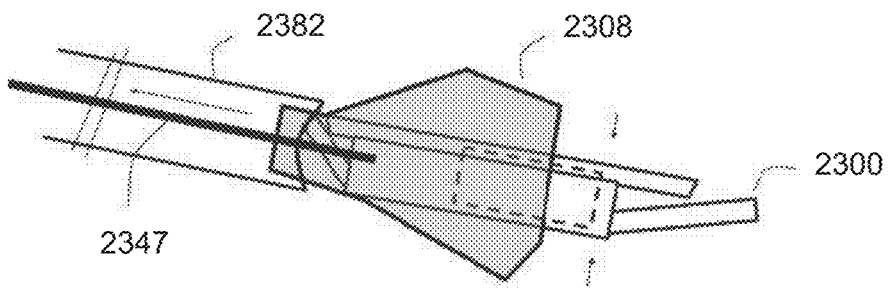
Figure 55C:
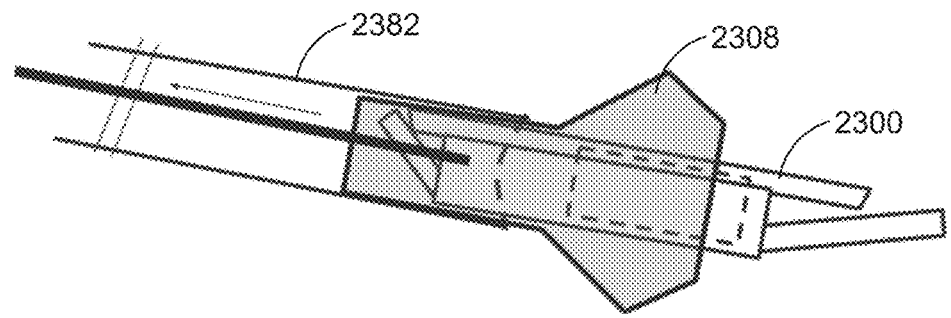
Figure 55D:
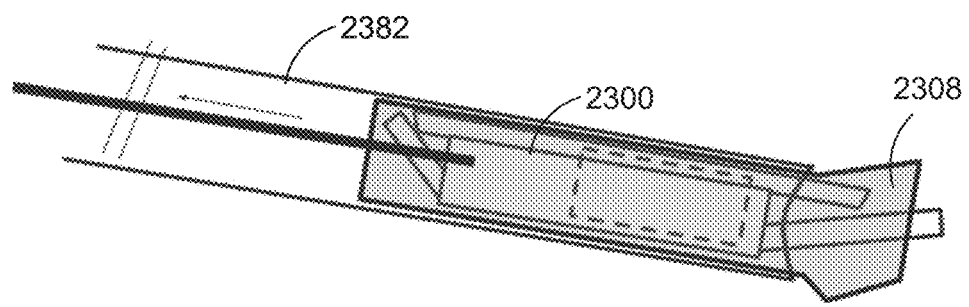

FIGS. 55A-55D are schematic illustrations of a prosthetic valve 2300 and show a process of retrieving the prosthetic valve into a delivery and/or retrieval catheter 2382, according to an embodiment. FIG. 55A is an anterior side view of the delivery and/or retrieval catheter 2382 having an extended capture element 2308 encompassing a proximal end of the valve 2300. A push/pull cable 2347 is shown extending through the delivery catheter 2382 and attaching to the valve 2300. FIG. 55B is an anterior side view of the delivery and/or retrieval catheter 2382 having the extended capture element 2308 encompassing the proximal end of the valve 2300, and the valve 2300 being compressed in height (y-axis) and depth (z-axis) but not length (x-axis). FIG. 55C is an anterior side view of the delivery and/or retrieval catheter 2382 having the extended capture element 2308 encompassing the proximal end of the valve 2300 and facilitating further compression of the valve 2300 and capture/retrieval of the valve 2300 into a lumen of the delivery and/or retrieval catheter 2382. FIG. 55D is an anterior side view of the delivery and/or retrieval catheter 2382 having the capture element 2308 encompassing the proximal end of the valve 2300 and nearly completing the compression, capture, and retrieval of the valve 2300 into the lumen of the delivery and/or retrieval catheter 2382.

Figure 56A:
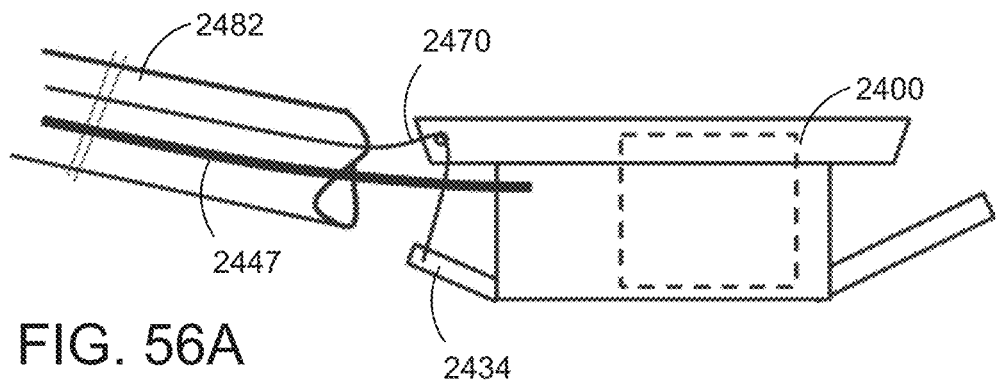
FIGS. 56A and 56B are schematic illustrations of an anterior side view of a delivery catheter and showing a pushing/pulling member extending from the delivery system and attaching to a proximal side of a prosthetic valve and a compression tether for at least partially compressing the proximal side of the prosthetic valve to allow for at least partial retrieval of the prosthetic valve into the delivery catheter, according to an embodiment.
Figure 56B:
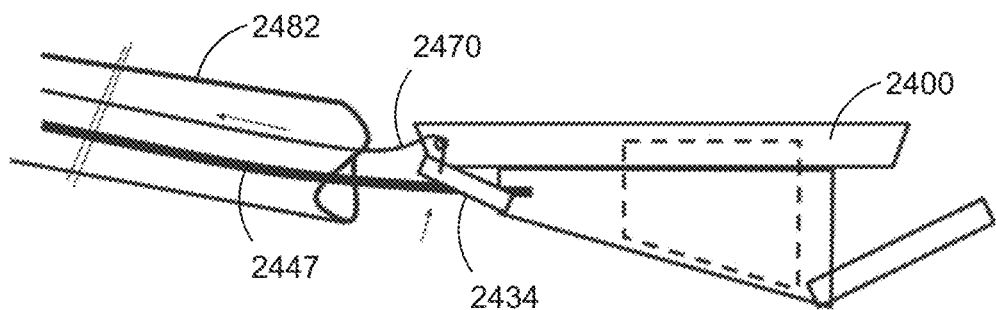

FIGS. 56A and 56B are a schematic illustrations of a prosthetic valve 2400 and distal end of a delivery and/or retrieval catheter 2482 having a push/pull cable 2447 attached to a proximal end of the valve 2400 and a compression mechanism and/or actuator 2470 to compress at least the proximal end of the valve 2400. For example, FIG. 56A shows a compression mechanism/actuator 2470 in the form of a suture(s), tether(s), cable(s), etc., configured to pull the proximal subannular anchoring element up against an underside of a supra-annular region of the valve 2400 (e.g., an underside of an atrial collar or the like). FIG. 56A shows the valve 2400 in a substantially uncompressed configuration. FIG. 56B shows the valve 2400 in a partially compressed configuration in response to a proximal force exerted on the compression mechanism/actuator 2470 (e.g., the suture(s), tether(s), cable(s), etc.), where the proximal subannular anchoring element 2434 is pulled in a supra-annular direction toward the supra-annular region of the valve 2400.

Figure 57A:
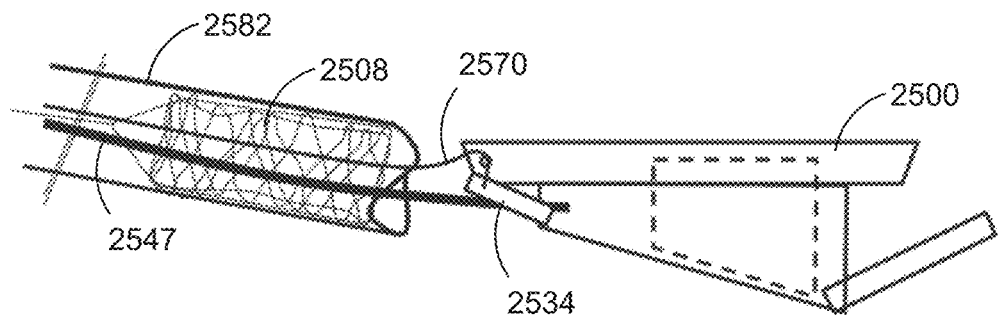
FIGS. 57A and 57B are schematic illustrations of an anterior side view of a delivery catheter and showing a pushing/pulling member extending from the delivery system and attaching to a proximal side of a prosthetic valve and (i) a compression tether and (ii) an extendable capture element for at least partially compressing the proximal side of the prosthetic valve to allow for at least partial retrieval of the prosthetic valve into the delivery catheter, according to an embodiment.
Figure 57B:
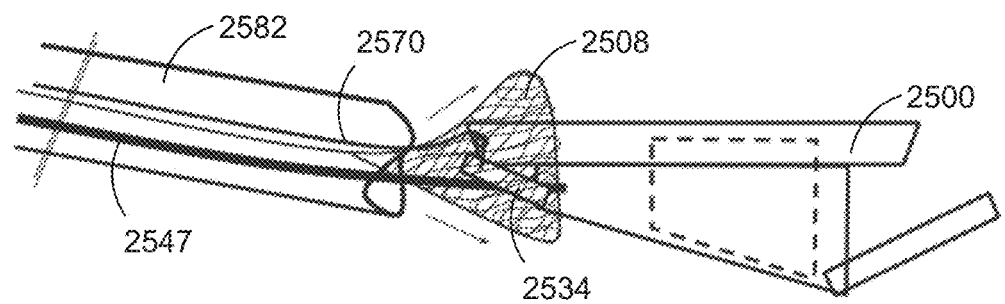

FIGS. 57A and 57B are a schematic illustrations of a prosthetic valve 2500 and distal end of a delivery and/or retrieval catheter 2582 having a push/pull cable 2547 attached to a proximal end of the valve 2500 and at least one compression mechanism/actuator 2570 to compress at least the proximal end of the valve 2500. For example, FIG. 57A shows a compression mechanism/actuator 2570 in the form of a suture(s), tether(s), cable(s), etc., configured to pull the proximal subannular anchoring element 2534 up against an underside of a supra-annular region of the valve 2500 (e.g., an underside of an atrial collar or the like) as well as a capture device 2508 loaded or pre-loaded within the lumen of the delivery and/or retrieval catheter 2582. The capture device 2508 can be extended from the delivery and/or retrieval catheter 2582 to encompass at least a proximal end of the valve 2500.

FIG. 57A shows the valve 2500 in a substantially uncompressed configuration. FIG. 57B shows the valve 2500 in a partially compressed configuration in response to a proximal force exerted on the compression mechanism (e.g., the suture(s), tether(s), cable(s), etc.), where the proximal subannular anchoring element is pulled in a supra-annular direction toward the supra-annular region of the valve 2500. FIG. 57B further shows the capture device extended from the delivery and/or retrieval catheter 2582 and encompassing at least the proximal end of the valve 2500. The capture device 2508 can facilitate a compression of the valve 2500 when a force exerted on the valve by the push/pull cable 2547 pulls the valve 2500 toward the delivery and/or retrieval catheter 2582.

Figure 58A:
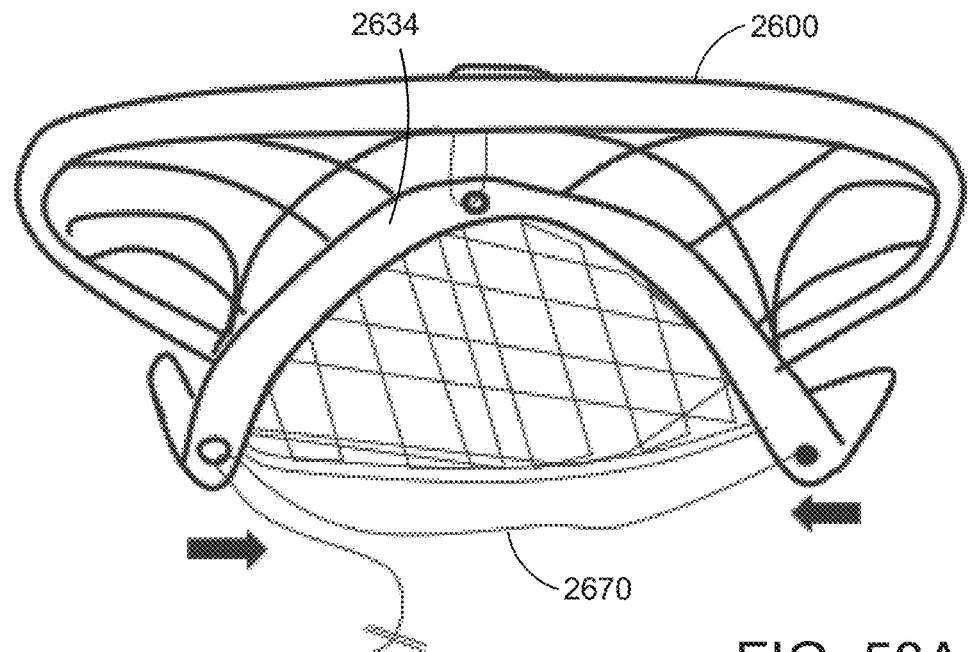
FIGS. 58A and 58B are proximal end schematic illustrations of a prosthetic valve, illustrating a compression tether routed through one or more portions of a proximal side of the prosthetic valve used to at least partially compress the proximal side of the prosthetic valve to facilitate a retrieval process, according to an embodiment.
Figure 58B:
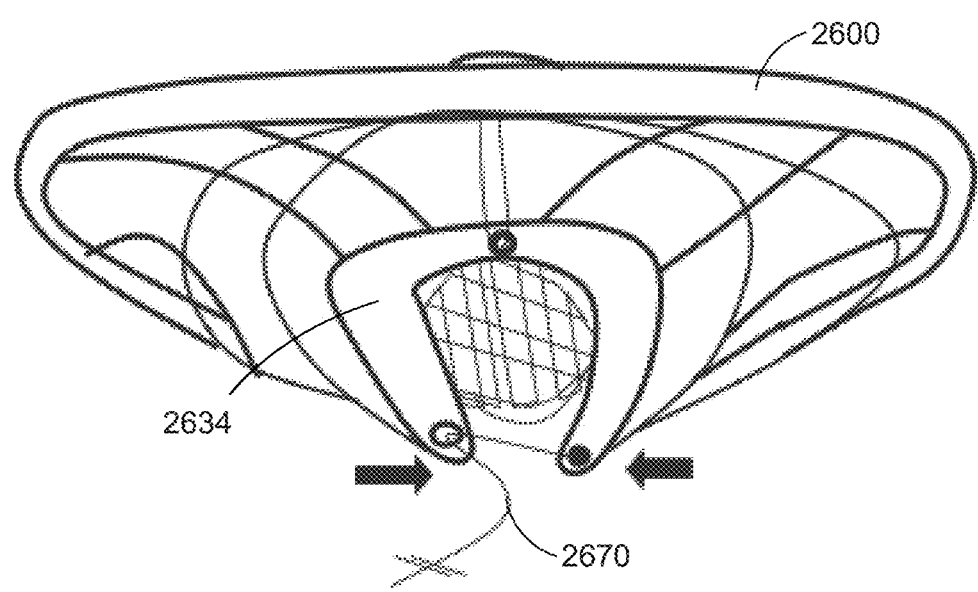

FIGS. 58A and 58B are proximal end views of a prosthetic valve 2600 in a first configuration and a second configuration, respectively, according to an embodiment. FIG. 58A shows a compression mechanism/actuator 2670 such as, for example, one or more suture(s), tether(s), tension member(s), cable(s), filament(s), etc., coupled to a proximal side of the valve 2600. More particularly, the compression mechanism/actuator 2670 can be routed around and/or through one or more proximal subannular sidewall portions, frame hips, anterior and/or posterior edges or wire frames, and/or any other suitable portion of the valve. In addition, the compression mechanism/actuator 2670 or a second compression mechanism can be coupled routed between and/or around a proximal anchoring element 2634 and a supra-annular region or collar of the valve 2600. FIG. 58A shows the proximal end of the valve 2600 in a substantially uncompressed or expanded configuration. FIG. 58B shows that the proximal anchoring element 2634 and/or the proximal subannular sidewall portions can be drawn inward and/or in a supra-annular direction toward the supra-annular region or collar of the valve 2600 to place the valve 2600 in the second configuration. The valve 2600 is shown at least partially compressed (or at least the proximal end of the valve 2600 is shown compressed) to allow for retrieval of the valve 2600 from a native annulus and, for example, into a lumen of a delivery and/or retrieval catheter.

Figure 59A:
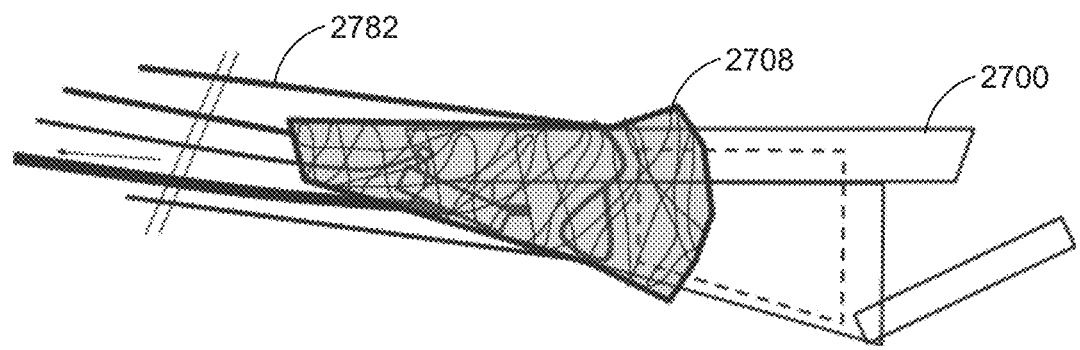
FIGS. 59A-59C are schematic illustration of an anterior side view of a delivery catheter and showing a process of retrieving a prosthetic valve into the delivery catheter using a pushing/pulling member, at least one compression tether, and an extendable capture element, according to an embodiment.
Figure 59B:
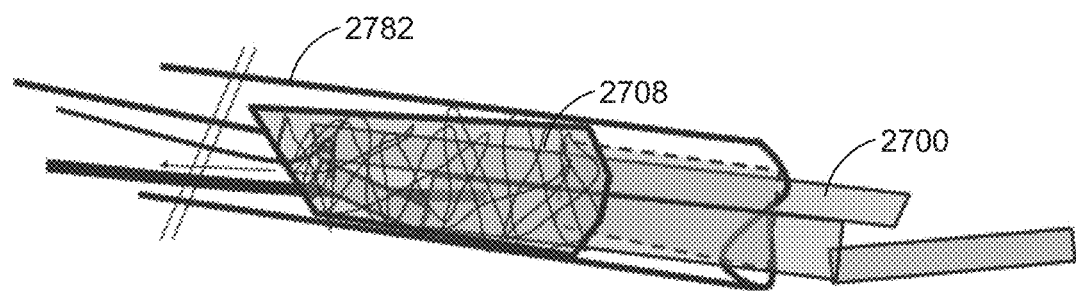
Figure 59C:
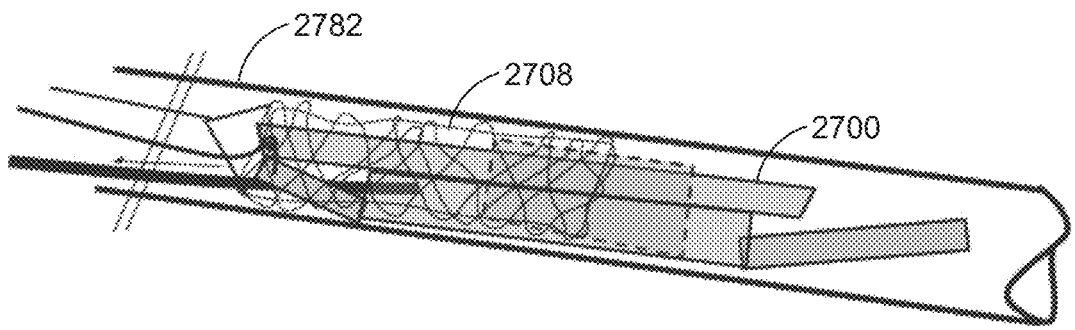

FIGS. 59A-59C are schematic illustrations of a prosthetic valve 2700 and show a process of retrieving the prosthetic valve into a delivery and/or retrieval catheter 2782, according to an embodiment. FIG. 59A is an anterior side view of the delivery and/or retrieval catheter 2782 having an extended capture element 2708 encompassing at least a proximal end of the valve 2700. The valve 2700 is shown at least partially compressed. A proximal end portion of the valve 2700 is shown pulled and/or retrieved into the delivery and/or retrieval catheter 2782. FIG. 59B shows the valve 2700 further compressed and nearly fully retracted and/or retrieved into the lumen of the delivery and/or retrieval catheter 2782 and the capture element 2708 and/or delivery and/or retrieval catheter 2782 further compressing a midsection and a distal portion of the valve 2700 as the valve 2700 is drawn into the lumen of the delivery and/or retrieval catheter 2782. FIG. 59C shows the valve 2700 fully compressed and retracted and/or retrieved into the lumen of the delivery and/or retrieval catheter 2782.

Figure 60A:
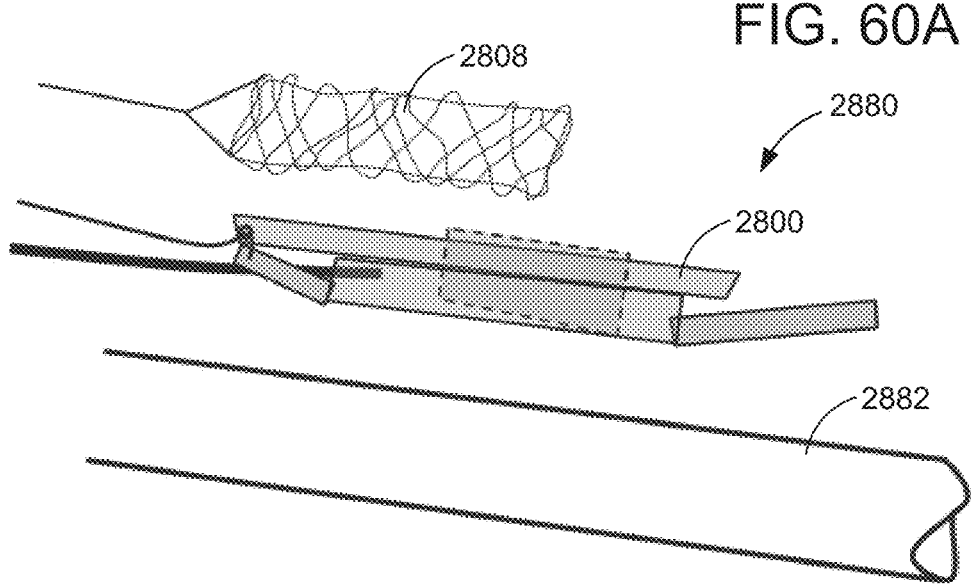
FIG. 60A is an exploded side view illustration of at least a portion of a delivery and/or retrieval system 180 including, for example, a capture element, a prosthetic valve, and a delivery catheter, according to an embodiment.
Figure 60B:
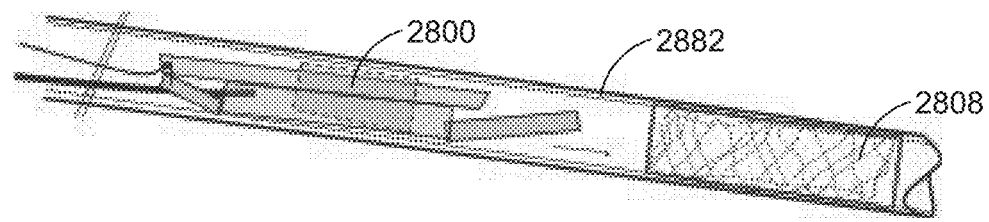
FIG. 60B is a side view of the portion of the delivery and/or retrieval system 180 of FIG. 60A showing each of the prosthetic valve in a compressed configuration and the capture element disposed in a lumen of the delivery catheter.
Figure 60C:
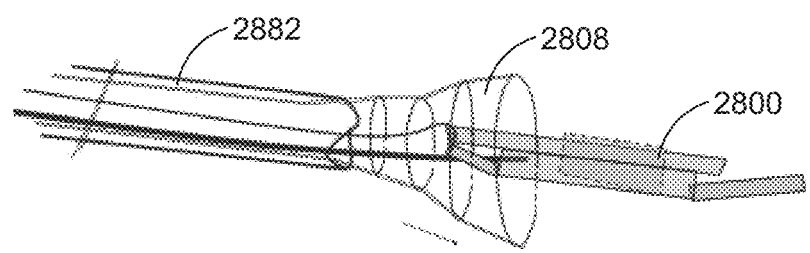
FIG. 60C is a side view of the portion of the delivery and/or retrieval system 180 of FIG. 60A showing the prosthetic valve distal to the delivery catheter and the capture element deployed from the delivery catheter and at least partially encompassing the prosthetic valve.

FIG. 60A is an exploded side view illustration of a delivery and/or retrieval system 2880 having a capture element 2808 and delivery and/or retrieval catheter 2882 and being configured to deliver and/or retrieve a valve 2800, according to an embodiment. FIG. 60B is a cross-sectional side view of the delivery and/or retrieval system 2880 showing the capture element 2808 integrated into a channel within the delivery and/or retrieval catheter 2882 or using an outer and inner sheathed delivery and/or retrieval catheter system with the capture element 2808 disposed between the inner and the outer sheath. FIG. 60C is a cross-sectional side view of delivery and/or retrieval system 2880 showing the capture element 2808 extended from the delivery and/or retrieval catheter 2882 after the valve 2800 has been deployed.

Figure 61A:
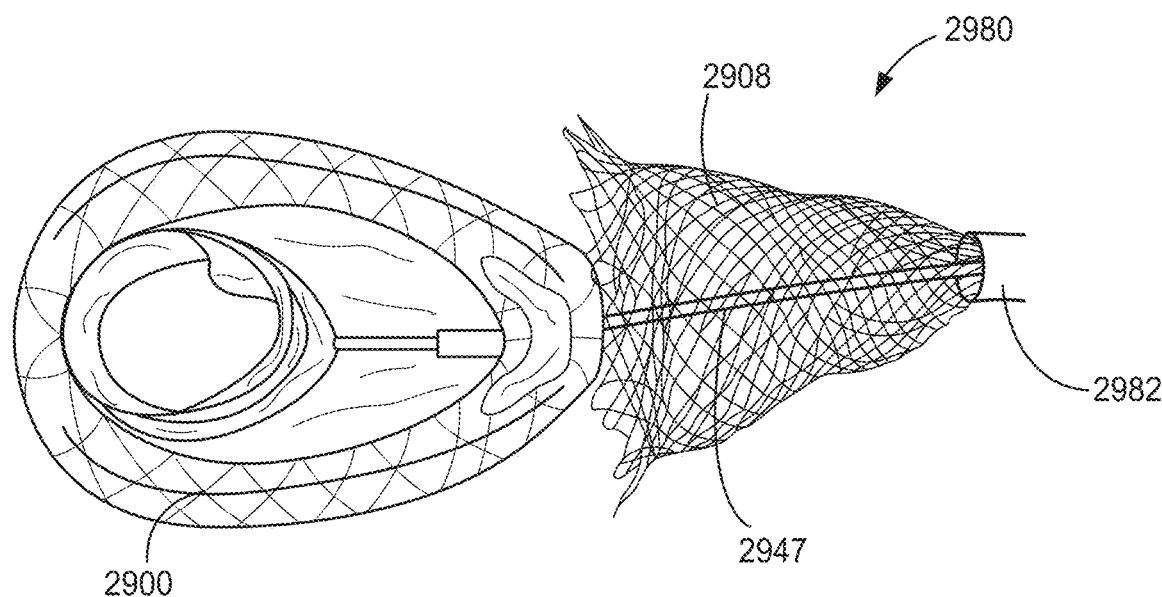
FIGS. 61A-61G are various views of at least a portion of a delivery and/or retrieval system 180 and showing a capture element being used to facilitate compression of a prosthetic valve to allow the prosthetic valve to be retrieved into a lumen of a delivery catheter, according to an embodiment.

FIGS. 61A-61G are various views of a delivery and/or retrieval system 2980 configured to deliver, deploy, and/or retrieve a prosthetic valve, according to an embodiment. FIG. 61A is a bottom view of a delivery and/or retrieval catheter 2982 having a capture element 2908 extending from a distal end of the catheter 2982 and encompassing at least a proximal end of the valve 2900. The capture element 2908 can be, for example, a self-expanding wire mesh, basket, net, and/or the like. In some embodiments, the capture element 2908 can be formed from a shape-memory alloy such as nitinol or the like. The capture element 2908 can be in a compressed configuration and, in response to being advanced out of the distal end of the catheter 2982 can automatically transition to an expanded configuration. In some implementations, the capture element 2908 can be included in or on a sheath, a capture element catheter, a control catheter, and/or any other suitable tube, member, rod, catheter, etc. In some implementations, the capture element 2908 can be disposed in the catheter 2982 during delivery of the valve 2900 into a heart. In other implementations, the capture element 2908 can be inserted into and advanced through the delivery catheter 2982 during deployment of the valve 2900 when it is desirable to at least partially retrieve the valve 2900 from the native annulus and/or the heart entirely.

Figure 61B:
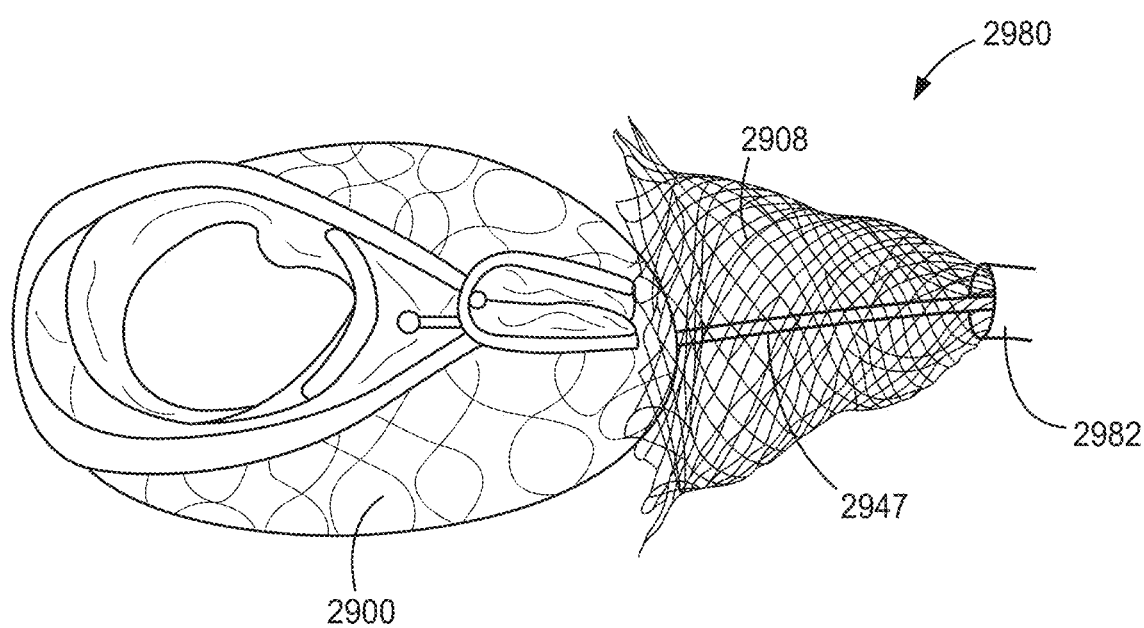
Figure 61C:
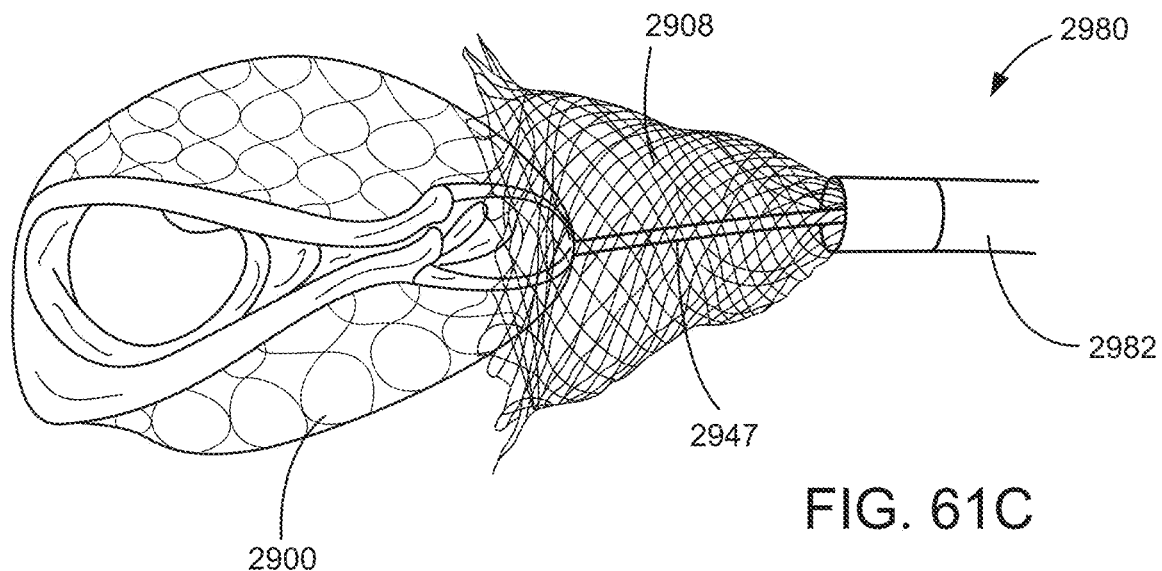

FIG. 61A is a bottom view showing the valve 2900 in a substantially uncompressed configuration with a push/pull cable 2947 attached to a proximal supra-annular portion of the valve 2900. The capture element 2908 is shown extending from the catheter 2982 but not yet encompassing the valve 2900. FIG. 61B is a bottom view showing the valve 2900 in a partially compressed configuration in which a proximal anchoring element and/or proximal subannular sidewalls are pulled inward and/or upward toward the supra-annular region of the valve 2900. The capture element 2908 is shown as beginning to extend over the proximal end of the valve 2900. FIG. 61C is a bottom view showing the valve 2900 in a further compressed configuration in which the proximal anchoring element and/or proximal subannular sidewalls are further pulled inward and/or upward. The valve 2900 is shown as being pulled into the extended capture element 2908 (e.g., in response to a force exerted by the push/pull cable 2947).

Figure 61D:
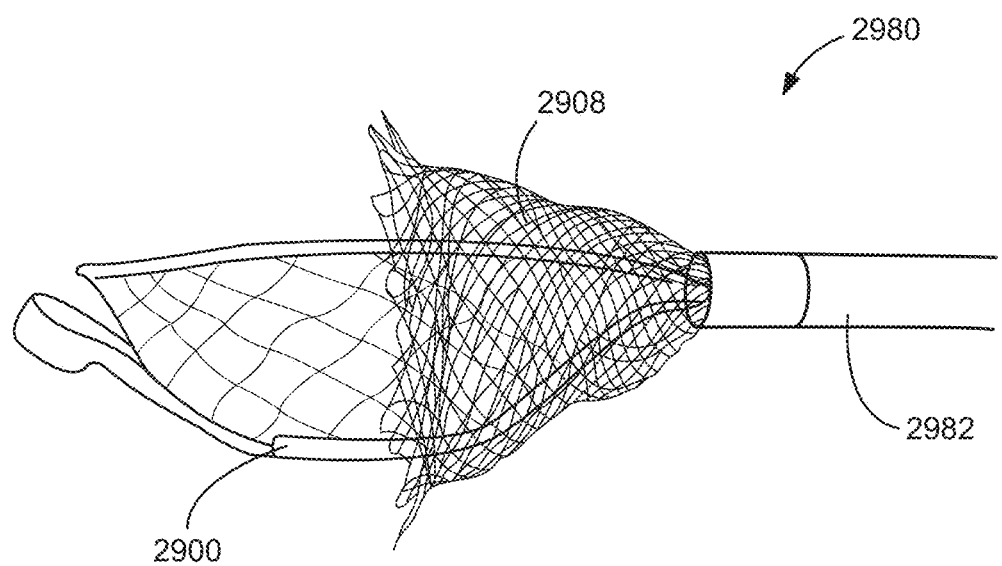
Figure 61E:
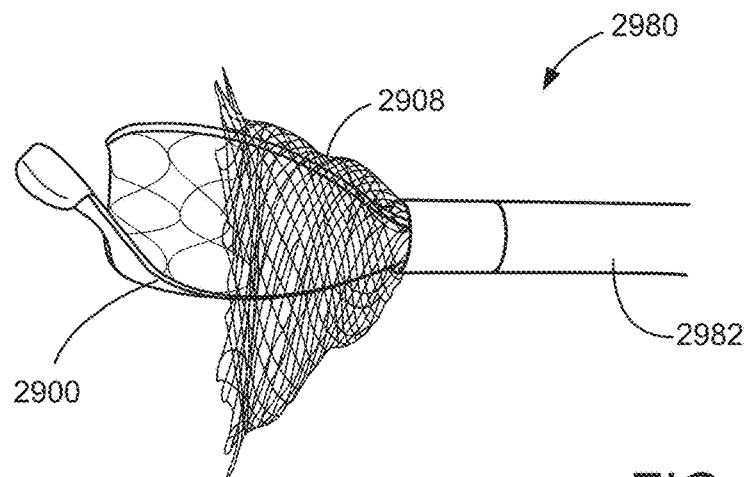

FIG. 61D is a septal-side view showing the proximal end of the valve 2900 in a compressed configuration and pulled adjacent to the delivery catheter 2982. The capture element 2908 is shown extending around and/or encompassing the proximal end of the valve 2900 to facilitate a compression of the valve 2900. FIG. 61E is a septal-side view showing the proximal end of the valve 2900 at least partially disposed in the delivery catheter 2982 and the capture element 2908 extending and/or encompassing more of the valve 2900 as the valve 2900 is pulled into the delivery catheter 2982 (e.g., in response to a force exerted by the push/pull cable 2947). The capture element 2908 is shown being pulled into the catheter 2982 along with the valve 2900.

Figure 61F:
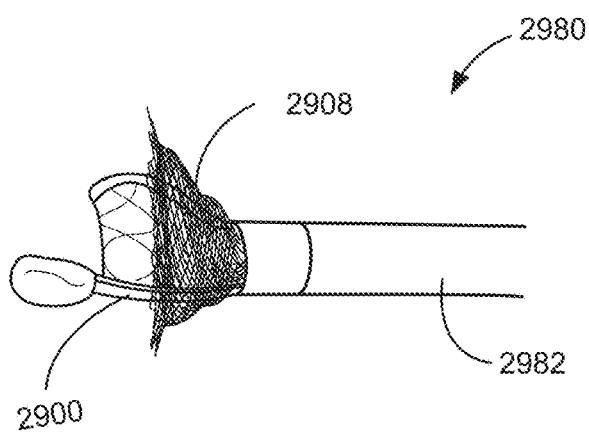
Figure 61G:
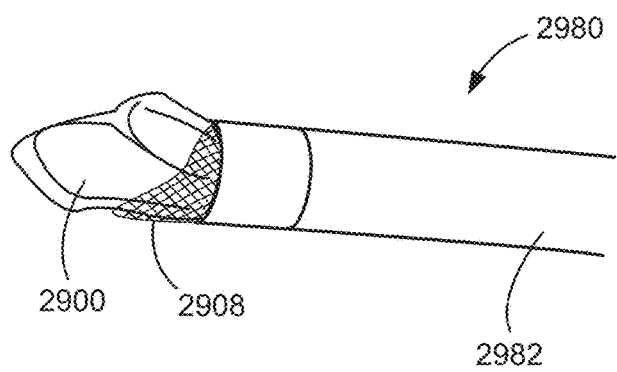

FIG. 61F is a septal-side view showing a mid-section of the valve 2900 pulled into the delivery catheter 2982. The valve 2900 is further compressed as it is pulled into the delivery catheter 2982 and the capture element 2908 is shown as encompassing a portion of the valve 2900 distal to delivery catheter 2982 while also being pulled into the delivery catheter 2982 with the valve 2900. FIG. 61G is a septal-side view showing the valve 2900 in a substantially compressed configuration and nearly entirely pulled and/or retrieved into the catheter 2982. Although not shown, the capture element 2908 encompasses the portion of the valve 2900 disposed in the delivery catheter 2982. In some instances, the compression of the valve 2900 can be sufficient to draw the remaining portion of the valve 2900 into the catheter 2982 substantially without the capture element 2908 facilitating a compression of the valve 2900.

Figure 62A:
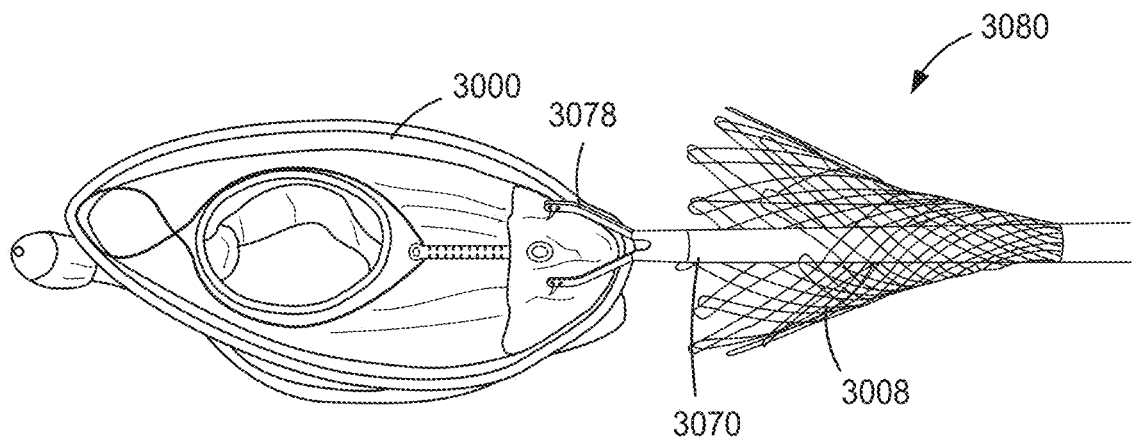
FIGS. 62A-62B are top views of at least a portion of a delivery and/or retrieval system 180 and showing a process of extending a capture element around a proximal side of a prosthetic valve and a portion of a control device having a control catheter and a yoke coupled to the proximal side of the prosthetic valve, according to an embodiment.
Figure 62B:
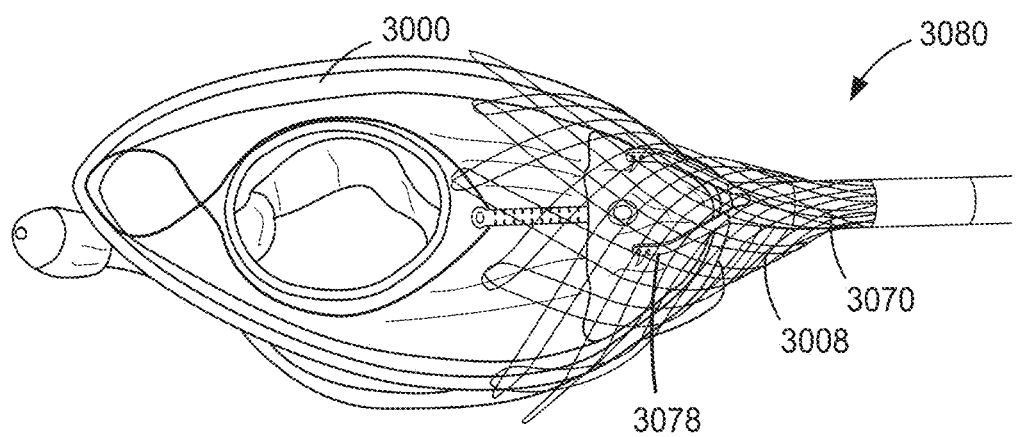

FIGS. 62A-62B are top views of at least a portion of a delivery and/or retrieval system 3080 and showing a process of extending a capture element 3008 around a proximal side of a prosthetic valve 3000 and a portion of a control device 3070 having a control catheter and a yoke 3078 coupled to the proximal side of the prosthetic valve 3000, according to an embodiment. FIG. 62A shows the capture element 3008 as a self-expanding wire mesh that is extended from a delivery catheter (not shown) and over a portion of the control device 3070 while being proximal to the valve 3000. The valve 3000 is shown having an offset flow control component mounted to an outer frame. The outer frame has an upper atrial collar component (e.g., a supra-annular member or region) and a lower subannular component, member, and/or region. The yoke 3078 is shown coupled to the upper atrial component. The valve 3000 and/or the control catheter can further include an actuation and/or compression system having one or more elements (e.g., sutures, tethers, tension members, etc.) for raising, lowering, and/or compressing a proximal anchoring element of the valve 3000 and for pinching or compressing, for example, subannular sidewall hips of the lower subannular component. FIG. 62B shows how the valve 3000 is brought within the funnel, mesh, basket, and/or structure of the capture element 3008, which guides the valve 3000 toward and/or into the delivery catheter and facilitates a compression of the valve 3000 in a height dimension and in a width dimension but not in a length dimension along a delivery axis.

FIGS. 63A-63E are various views of a portion of a delivery and/or retrieval system 3180 according to an embodiment. The delivery and/or retrieval system 3180 can be similar to any of the delivery and/or retrieval system 3180 described above with reference to FIGS. 55A-63A, or combinations thereof. The delivery and/or retrieval system 3180 is configured to deliver, deploy, and in some instances, retrieve a prosthetic valve 3100. The delivery and/or retrieval system 3180 includes a delivery and/or retrieval catheter 3182, a control device 3170 having a control catheter and a yoke 3178 mounted to a distal end of the control catheter, and a capture element 3108. In this embodiment, the delivery and/or retrieval system 3180 further includes an expansion element 3109 configured to facilitate an expansion of the capture element 3108 as the capture element 3108 extends from the delivery catheter 3182 and about at least a portion of the valve 3100.

Figure 63A:
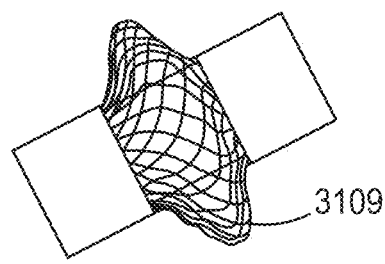
FIG. 63A is a perspective view of a portion of a capture element sheath with an expansion feature included in a delivery and retrieval system, according to an embodiment.

FIG. 63A is a perspective view of the expansion element 3109 included in the delivery and/or retrieval system 3180. The expansion element 3109 can be, for example, integrated into and/or a part of a distal end portion of the control catheter. In other embodiments, the expansion element 3109 can be integrated into and/or a part of a separate sheath, catheter, tube, and/or element that can be advanced through the delivery catheter 3182 (e.g., with or independent of the valve 3100). The expansion element 3109 is shown as an expandable frame, ramp, structure, and/or the like. The expansion element 3109 can be formed from, for example, a shape-memory allow such as nitinol and/or the like. The expansion element 3109 can be collapsible, allowing the expansion element 3109 to be advanced through the delivery catheter 3182, and can be expandable when released from a distal end of the delivery catheter 3182 (e.g., self-expanding, automatically expanding, and/or expanding in response to a force or other input).

Figure 63B:
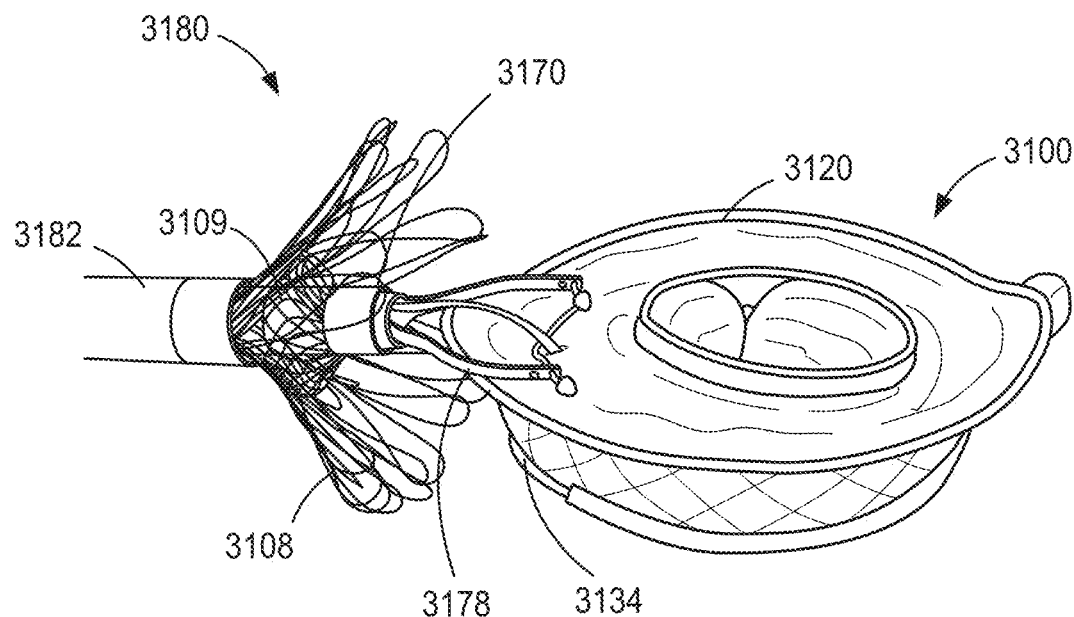
FIGS. 63B-63D are side perspective views of a prosthetic valve and a portion of the delivery and retrieval system showing a process of extending a delivery catheter, over the expansion feature of the capture element sheath, and about a portion of the prosthetic valve.

FIG. 63B is a perspective side view of the valve 3100 and shows a distal end of the delivery catheter 3182 proximal to the valve 3100, the yoke 3178 of the control device 3170 coupled to a supra-annular region 3120 of the valve 3100, and a tension member and/or actuation mechanism extending through a waypoint of the valve 3100, for example, to selectively engage a proximal anchoring element 3132 of a subannular region 3130 of the valve 3100. FIG. 63B shows the yoke 3178 removably secured to attachment points along the supra-annular region 3120 of the valve 3100. In some implementations, securement of the yoke 3178 to the supra-annular region 3120 can allow a distal force exerted on the control device to be transmitted, via the yoke 3178, to the valve 3100, which can be used during delivery and/or deployment of the valve 3100. Similarly, the securement of the yoke 3178 to the supra-annular region 3120 can allow a proximal force exerted on the control device to be transmitted, via the yoke 3178, to the valve 3100, which can be used during retrieval of the valve 3100.

Figure 63C:
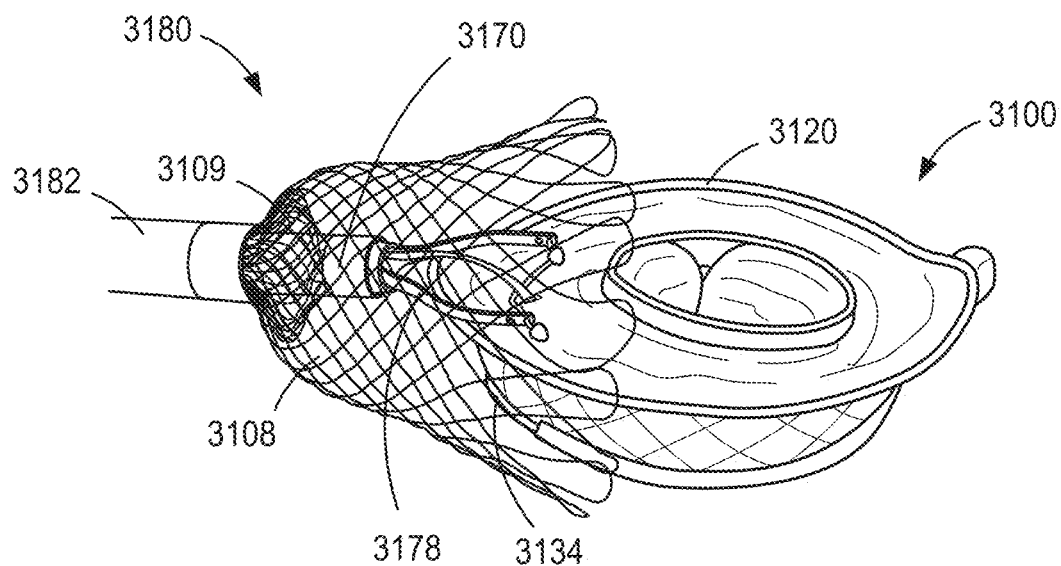

FIG. 63B further shows the expansion element 3109 in a distal position relative to the distal end of the delivery catheter 3182 (but in a proximal portion relative to the distal end of the control catheter). Moreover, the capture element 3108 is shown as being extended from the delivery catheter 3182 in a distal direction. The coaxial arrangement of the delivery and/or retrieval system 3180 is such that the capture element 3108 contacts at least a portion of the expansion element 3109 as the capture element 3108 extends from the delivery catheter 3182, which in turn, causes the capture element 3108 to expand radially relative to the common axis (e.g., a delivery axis). FIG. 63C shows the capture element 3108 further extended from the delivery catheter 3182 and shows that the arrangement of the expansion element 3109 prevents and/or reduces a likelihood of the capture element 3108 becoming entangled with the control device (e.g., the yoke 3178, the tension member, and/or any other suitable portion of the control device).

Figure 63D:
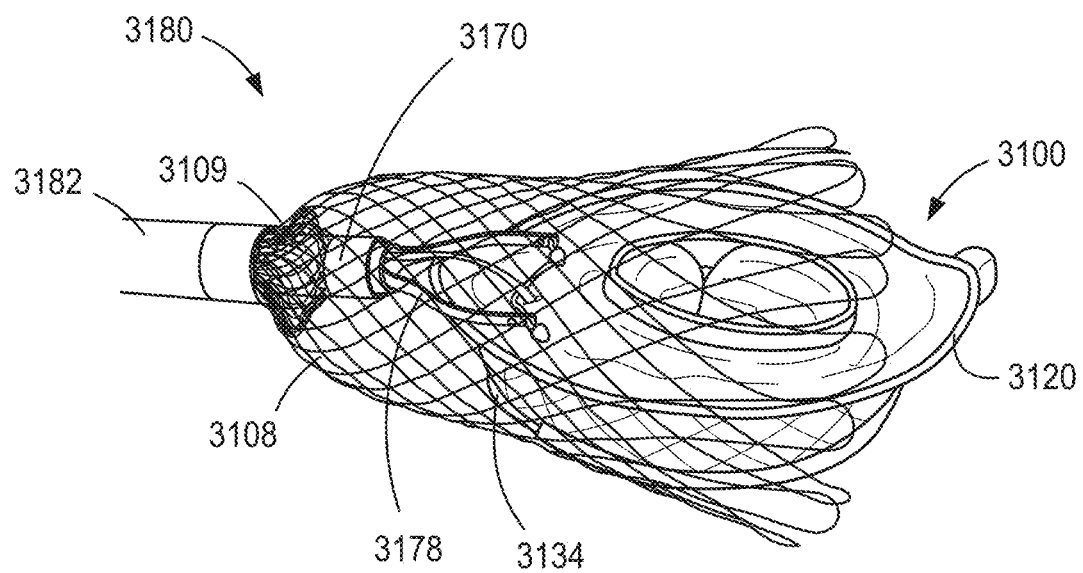
Figure 63E:
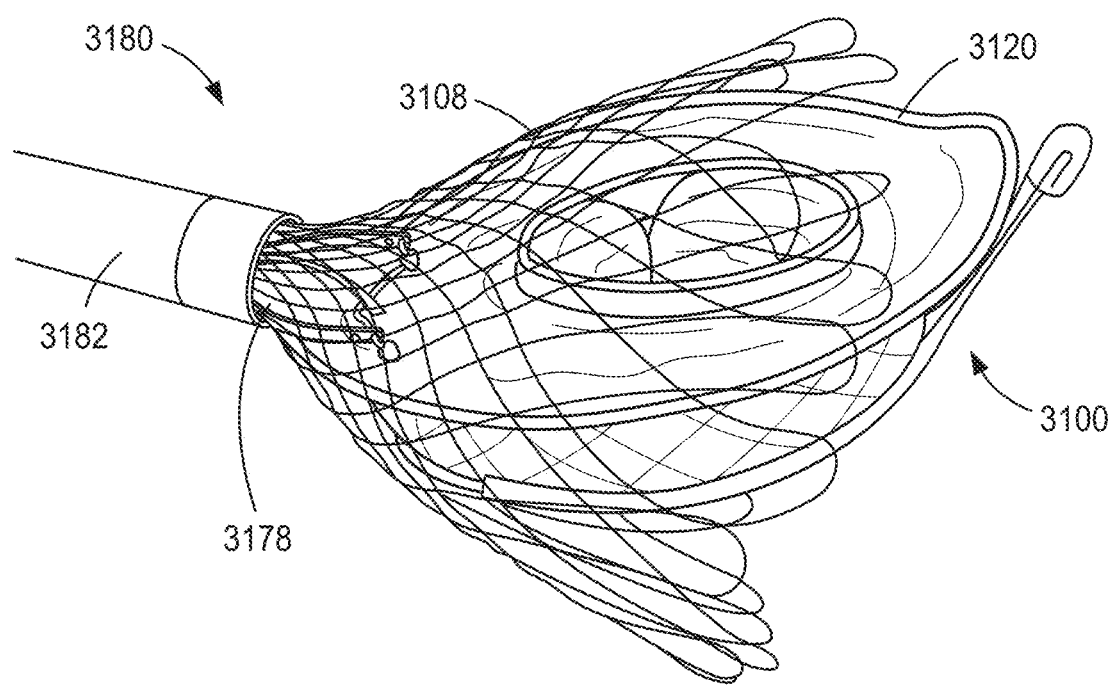
FIG. 63E is a side perspective view of the prosthetic valve and portion of the delivery and retrieval system of FIGS. 63B-63D showing the capture element facilitating a process of compressing and/or retrieving at least a portion of the prosthetic valve into the delivery catheter.

FIG. 63D shows the capture element 3108 in an extended configuration such that the capture element 3108 encompasses at least the proximal end of the valve 3100. FIG. 63E shows, the valve 3100 being pulled in a proximal direction in response to a proximally directed force exerted on the control device. The expansion element 3109 and the control catheter are retracted into the delivery catheter 3182 and thus, are not shown. The yoke 3178 is shown partially retracted into the delivery catheter 3182. The valve 3100 is shown pulled toward the delivery catheter 3182 and the proximal end of the valve 3100 is shown in a compressed configuration. The capture element 3108 encompassing at least the proximal end of the valve 3100 facilitates a compression of at least the proximal end. Moreover, the operator can manipulate a proximal end of the tension member (e.g., actuation mechanism) to transition the proximal end of the valve 3100 (or at least the proximal anchoring element 3134) from an expanded configuration to a compressed configuration. Thus, as the valve 3100 is pulled in a proximal direction toward the delivery catheter 3182, the control device and/or the capture element 3108 act to compress the valve. Although not shown in FIG. 63E, with the proximal end of the valve 3100 sufficiently compressed, further force in the proximal direction exerted by the control device can pull the valve 3100 into the delivery and/or retrieval catheter 3182.

As described above with reference to the control catheter shown in FIGS. 34A and 34B, any of the control catheters, delivery catheters, sheaths, tubes, etc., can be at least partially steerable and/or otherwise selectively movable, bendable, deformable, and/or the like. In some instances, a portion of an attachment device such as a yoke or the like integrated into a distal end of a control catheter can provide structural stiffness to the distal end of the control catheter allowing for a desired deflection, bending, and/or deformation without, for example, kinking, plastically (e.g., permanently) deforming, breaking, buckling, etc.

Figure 64A:
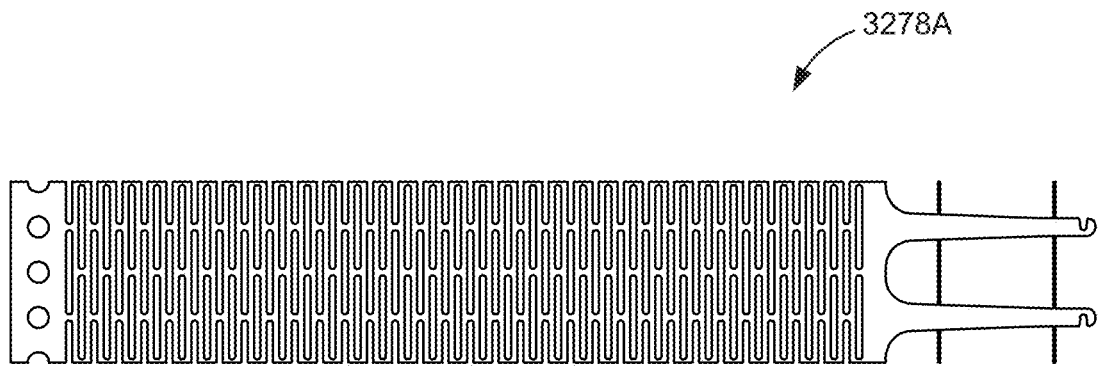
FIGS. 64A and 64B are each a top view of a laser-cut workpiece configured to be formed into at least a part of a distal end of a control device having, for example, a yoke, according to different embodiments.
Figure 64B:
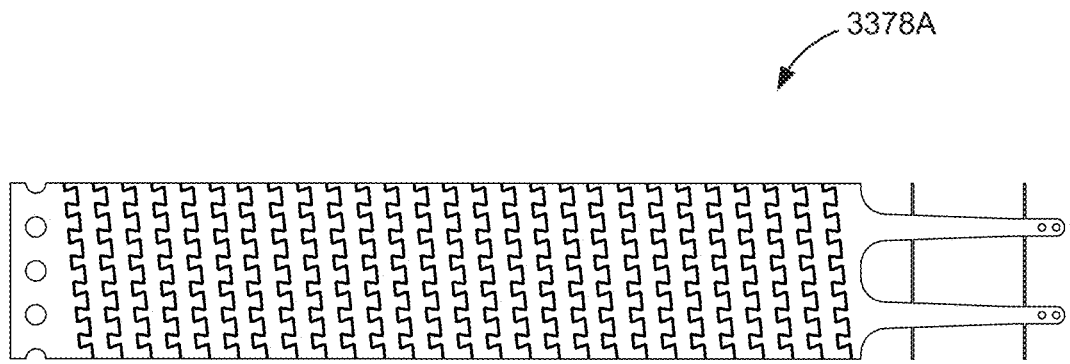

For example, FIGS. 64A and 64B are each a top view of a laser-cut workpiece configured to be formed into at least a part of a distal end of a control device having, for example, a yoke, according to different embodiments. FIG. 64A shows a laser-cut workpiece 3278A including multiple slots, slits, notches, cuts, and/or the like. Although shown as a flat pattern and/or otherwise as a flat sheet, the workpiece 3278A can be, for example, a laser cut cylinder or the like. In other embodiments, the workpiece 3278A can be laser-cut and then heat-set and/or otherwise formed into a substantially cylindrical shape with a yoke formed at a distal end thereof. In some implementations, the cylindrical workpiece 3278A can be integrated into a distal end of the control catheter and/or the like. In other implementations, the distal end of the control catheter can be over-molded and/or otherwise extruded over, around, and/or about a portion of the workpiece 3278A thereby forming an integrated distal end. Moreover, the pattern of slots, slits, notches, cuts, and/or the like can be selected to result in a desired flexibility and/or stiffness of the distal end of the control catheter and/or the like. In some implementations, for example, the desired flexibility and/or stiffness can allow a distal end of a control catheter to bend, flex, and/or deform in a manner similar to that shown in FIG. 34B.

FIG. 64B shows a laser-cut workpiece 3378A including multiple spiraled patterns forming a set of dovetails or the like. As described above with reference to the workpiece 3278A shown in FIG. 64A, the workpiece 3378A can be formed from a laser cut cylinder or can be formed from a laser-cut sheet that is subsequently heat-set and/or otherwise formed into a substantially cylindrical shape and integrated into a distal end portion of a control catheter and/or the like.

Figure 65:
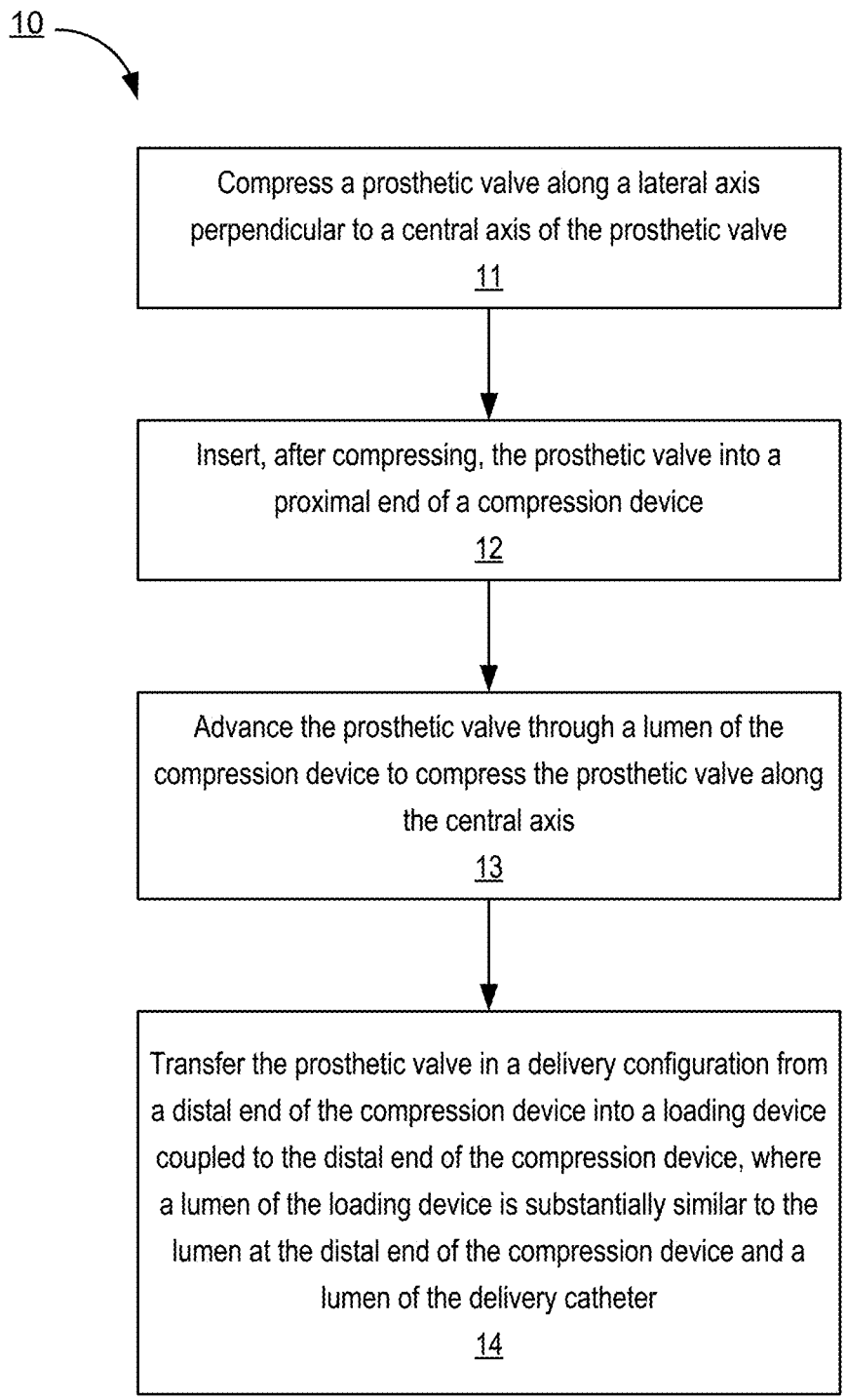
FIG. 65 is a flowchart illustrating a method of compressing a prosthetic valve into a delivery configuration for side-delivery to a patient via a delivery catheter, according to an embodiment.

FIG. 65 is a flowchart illustrating a method 10 of compressing a prosthetic valve into a delivery configuration for side-delivery to a patient via a delivery catheter, according to an embodiment. The valve can be substantially similar to any of those described herein such as the valves 100, 400, 500, 600, 700, 800, and/or 1000 and/or any of those described in the '957 PCT, the '010 PCT, the '231 PCT, the '390 PCT, the '108 PCT, the '327 Provisional, the '964 Provisional, the '345 Provisional, and/or the '807 Provisional incorporated by reference herein. For example, the valve can include an outer support frame and an (inner) flow control component that is mounted in and/or to the outer support frame. The outer support frame can include, for example, a supra-annular member or region, a subannular member or region, and a transannular member or region coupled therebetween. The flow control component is mounted to the outer support frame such that is extends through a portion of the transannular member or region, as described above. Moreover, the valve is compressible along a central axis parallel to a fluid flow direction through the valve and a lateral axis orthogonal and/or perpendicular to the central axis.

The method 10 includes compressing the prosthetic valve along the lateral axis of the valve perpendicular to the central axis, at 11. In some implementations, the valve is manually compressed along the lateral axis. For example, a user can exert a lateral force on the valve to compress, fold, and/or squeeze the valve into a laterally compressed configuration.

After laterally compressing the valve, the valve is inserted into a proximal end of a compression device that defines a lumen extending through the proximal end and a distal end, at 12. In some embodiments, a perimeter of the lumen at the proximal end is larger than a perimeter of the lumen at the distal end as described above with reference to the compression device 1090. Moreover, in some implementations, the valve can be inserted into the compression device while that the compression device and the valve are disposed in a fluid bath (e.g., a saline bath or the like). As described above, a distal end of the valve can be inserted into the compression device prior to a proximal end of the valve (e.g., a distal anchoring element can lead the valve through the compression device).

The prosthetic valve is advanced through the lumen of the compression device to compress the prosthetic valve along the central axis, at 13. In some implementations, the advancing of the valve can be in response to a control device and/or the like exerting a force on a proximal end of the valve to push the valve through the compression device, in response to a pulling device pulling the valve through the compression device (e.g., via a tether or the like attached to a distal end of the valve), or in response to a combination of pushing and/or pulling. As described above, a lumen of the compression device can be tapered in at least the axial direction as the lumen extends from the proximal end to the distal end of the compression device. The lumen at the distal end of the compression device can have a perimeter and/or diameter is associated with, for example, an axial-lateral extent of the valve in a compressed and/or delivery configuration. In other words, advancing the valve through the compression device places the valve in the delivery configuration.

The prosthetic valve in the delivery configuration is transferred from the distal end of the compression device into a loading device coupled to the distal end of the compression device, at 14. The loading device defines a lumen having a perimeter that is substantially similar to (i) the perimeter of the lumen at the distal end of the compression device and (ii) a perimeter of a lumen of the delivery catheter. As described above, the valve can be pushed and/or pulled through the compression device and into the loading device. Moreover, the perimeter of the lumen of the loading device is such that the valve is in the delivery configuration when disposed in the lumen of the loading device. With the valve compressed to the compressed and/or delivery configuration, the valve is ready to be advanced, for example, into and/or through the delivery catheter and into a target location in the patient (e.g., an annulus of a native heart valve).

Figure 66:
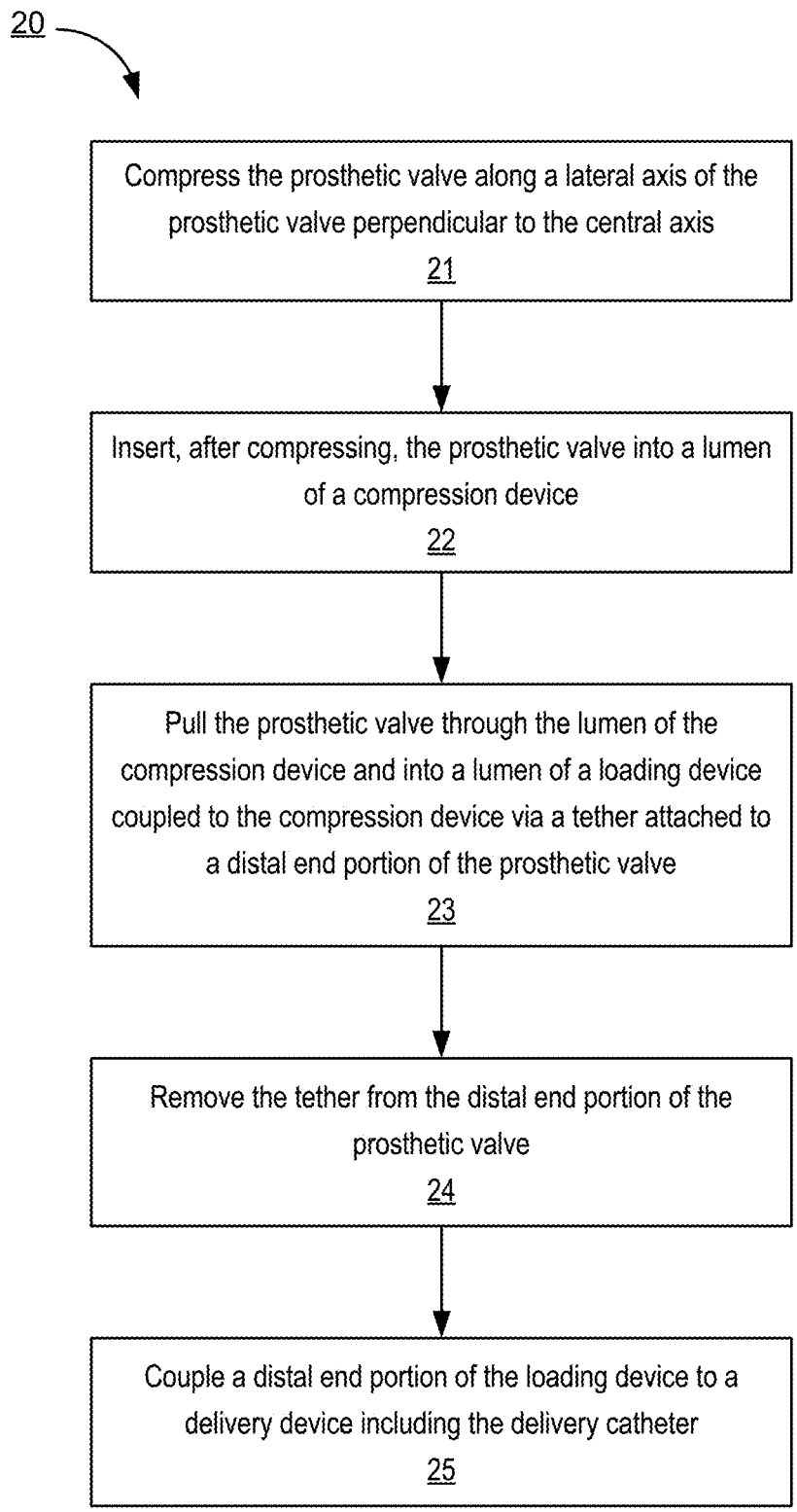
FIG. 66 is a flowchart illustrating a method of preparing a prosthetic valve for side-delivery to a patient via a delivery catheter, according to an embodiment.

FIG. 66 is a flowchart illustrating a method 20 of preparing a prosthetic valve for side-delivery to a patient via a delivery catheter, according to an embodiment. The valve can be substantially similar to any of those described herein such as the valves 100, 400, 500, 600, 700, 800, and/or 1000 and/or any of those described in the '957 PCT, the '010 PCT, the '231 PCT, the '390 PCT, the '108 PCT, the '327 Provisional, the '964 Provisional, the '345 Provisional, and/or the '807 Provisional incorporated by reference herein. For example, the valve can include an outer support frame and an (inner) flow control component that is mounted in and/or to the outer support frame. The outer support frame can include, for example, a supra-annular member or region, a subannular member or region, and a transannular member or region coupled therebetween. The flow control component is mounted to the outer support frame such that is extends through a portion of the transannular member or region, as described above. Moreover, the valve is compressible along a central axis parallel to a fluid flow direction through the valve and a lateral axis orthogonal and/or perpendicular to the central axis.

The method 20 includes compressing the prosthetic valve along the lateral axis of the valve perpendicular to the central axis, at 21. In some implementations, the valve is manually compressed along the lateral axis. For example, a user can exert a lateral force on the valve to compress, fold, and/or squeeze the valve into a laterally compressed configuration.

After laterally compressing the valve, the valve is inserted into a proximal end of a compression device that defines a lumen extending through the proximal end and a distal end, at 22. In some embodiments, a perimeter of the lumen at the proximal end is larger than a perimeter of the lumen at the distal end as described above with reference to the compression device 1090. Moreover, in some implementations, the valve can be inserted into the compression device while that the compression device and the valve are disposed in a fluid bath (e.g., a saline bath or the like). As described above, a distal end of the valve can be inserted into the compression device prior to a proximal end of the valve (e.g., a distal anchoring element can lead the valve through the compression device).

The prosthetic valve is pulled through the lumen of the compression device and into a loading device coupled to the compression device via a tether attached to a distal end portion of the valve such that the valve is compressed along the central axis to place the prosthetic valve in a delivery configuration when in the lumen of the loading device, at 23. In some embodiments, the tether can be included in a pulling device that is removably coupled to a distal end of the loading device. For example, the pulling device can be and/or can include a spool and/or winding device about which a portion of the tether is spooled or wound. In such embodiments, rotating the spool, winding, and/or any other suitable portion of the pulling device can increase a tension along the tether that can pull the tether through the compression device and into the loading device. As described in detail above, the compression device can have and/or can define a tapered lumen with a distal end thereof corresponding to a size of the valve in the delivery configuration. The lumen of the loading device can be substantially similar to the lumen at the distal end of the compression device and thus, the valve is in the delivery configuration when pulled into the lumen of the loading device.

The tether is removed from the distal end portion of the prosthetic valve, at 24. For example, the tether can be part of a pulling device and/or the like as described above, which in turn, can be decoupled from the distal end of the loading device. In some implementations, a user can, for example, pull on one end of the tether to withdraw the tether from the distal end portion the valve and the loading device. Moreover, the arrangement of the tether and valve is such that the tether can be removed from the distal end portion of the valve while the valve is in the delivery configuration and disposed in the lumen of the loading device.

The distal end of the loading device is coupled to a delivery device including the delivery catheter, at 25. The delivery device can be any suitable device such as, for example, the delivery device 1081 described above with reference to FIGS. 24-39. As such, the delivery device can include a handle and/or proximal portion that is coupled to the distal end of the loading device while the delivery catheter extends distally therefrom. In some implementations, at least one of the lumen of the loading device or the lumen of the delivery device can be flushed when the loading device is coupled to the delivery device and prior to advancing the valve from the loading device into the delivery device. In some implementations, the loading device and the delivery device can each include a gate or the like that is in a closed state until a flushing procedure has been performed and, after flushing, the gates can be transitioned to an open state to allow the valve to be transferred from the loading device into the delivery device for side-delivery via the delivery catheter.

FIG. 67 is a flowchart illustrating a method 30 of preparing a prosthetic valve for side-delivery to a patient through a lumen of a delivery catheter included in a delivery device, according to an embodiment. The valve can be substantially similar to any of those described herein such as the valves 100, 400, 500, 600, 700, 800, and/or 1000 and/or any of those described in the '957 PCT, the '010 PCT, the '231 PCT, the '390 PCT, the '108 PCT, the '327 Provisional, the '964 Provisional, the '345 Provisional, and/or the '807 Provisional incorporated by reference herein. For example, the valve can include an outer support frame and an (inner) flow control component that is mounted in and/or to the outer support frame. The outer support frame can include, for example, a supra-annular member or region, a subannular member or region, and a transannular member or region coupled therebetween. The flow control component is mounted to the outer support frame such that is extends through a portion of the transannular member or region, as described above. Moreover, the valve is compressible along a central axis parallel to a fluid flow direction through the valve and a lateral axis orthogonal and/or perpendicular to the central axis.

The method 30 includes compressing the prosthetic valve along the central axis and the lateral axis to transition the valve from an expanded configuration to a delivery configuration, at 31. In some implementations, the valve is manually compressed along the lateral axis. For example, a user can exert a lateral force on the valve to compress, fold, and/or squeeze the valve into a laterally compressed configuration. In some implementations, after laterally compressing the valve, the valve is advanced through a compression device to compress the valve along the central axis. In other implementations, the valve can be advanced through a compression device without manually compressing the valve along the lateral axis. For example, a first end of a compression device can have a size sufficient to receive an uncompressed valve and advancing the valve therethrough compresses the valve laterally and axially. In some implementations, the compression device can have an inner surface that defines a lumen and the size, shape, and/or configuration of the inner surface can at least partially define the way the valve is compressed as the valve is advanced therethrough. Moreover, a size and/or shape of the inner surface or lumen at a second end (e.g., a distal end) can be associated with a size, shape, and/or axial-lateral extent of the valve in the delivery configuration. Thus, the valve is transitioned from the expanded configuration to a delivery configuration.

The valve in the delivery configuration is advanced into a lumen of a loading device while a first gate at a distal end of the loading device is in a closed state to at least partially occlude the lumen of the loading device, at 32. For example, in some embodiments, the valve can be advanced through a compression device to be placed in the delivery configuration and then advanced into the lumen of the loading device, as described in detail above. In some implementations, the valve can be advanced into the lumen of the loading device to place a distal end or a distal subannular anchoring element in contact with and/or adjacent to a proximal side of the gate in the closed state. In some implementations, a hemostasis valve or the like can be coupled to the proximal end of the loading device when the valve is disposed therein to substantially seal the proximal end, with the prosthetic valve being disposed between the gate in the closed state and the hemostasis valve.

A distal end of the loading device is coupled to a handle of the delivery device while (i) the first gate is in the closed state and (ii) while a second gate at a proximal end of the handle is in a closed state to at least partially occlude a lumen of the handle, at 33. The lumen of the delivery catheter is in fluid communication with the lumen of the handle distal to the second gate. In some instances, a volume collectively defined by the lumens of the loading device and the delivery device between the first gate in the closed state and the second gate state can be flushed while the valve is proximal to the first gate. Each of the first gate and the second gate are transitioned from the closed state to an open state, at 34. For example, in some implementations, the gates are transitioned after flushing and/or the like. In some implementations, the gates can be opened in a substantially concurrent process. In other implementations, the first gate can be transitioned to the open state prior to the second gate, or vice versa. Moreover, transitioning the gates from the closed state to the open state can allow the valve to be advanced from the loading device and into a lumen of the delivery catheter for side-delivery of the valve to a target location in the patient (e.g., an annulus of a native heart valve).

FIG. 68 is a flowchart illustrating a method 40 of using a control device to selectively control a side-deliverable transcatheter prosthetic valve during at least one of delivery and deployment, according to an embodiment. The valve can be substantially similar to any of those described herein such as the valves 100, 400, 500, 600, 700, 800, and/or 1000 and/or any of those described in the '957 PCT, the '010 PCT, the '231 PCT, the '390 PCT, the '108 PCT, the '327 Provisional, the '964 Provisional, the '345 Provisional, and/or the '807 Provisional incorporated by reference herein. For example, the valve can include an outer support frame and an (inner) flow control component that is mounted in and/or to the outer support frame. The outer support frame can include, for example, a supra-annular member or region, a subannular member or region, and a transannular member or region coupled therebetween. The flow control component is mounted to the outer support frame such that is extends through a portion of the transannular member or region, as described above. Moreover, the valve is compressible along a central axis parallel to a fluid flow direction through the valve and a lateral axis orthogonal and/or perpendicular to the central axis.

The control device can be any suitable control device, actuator, delivery and/or retrieval system, and/or the like. For example, in some implementations, the control device can include at least a control catheter having a first tether, a second tether, and a tension member extending therethrough, and a yoke coupled to a distal end of the control catheter. In some embodiments, the control device can be similar to and/or substantially the same as the control devices 970 and/or 1070 described in detail above.

FIG. 68 is a flowchart illustrating a method 40 of using a control device to selectively control a side-deliverable transcatheter prosthetic valve during at least one of delivery and deployment, according to an embodiment. The valve can be substantially similar to any of those described herein such as the valves 100, 400, 500, 600, 700, 800, and/or 1000 and/or any of those described in the '957 PCT, the '010 PCT, the '231 PCT, the '390 PCT, the '108 PCT, the '327 Provisional, the '964 Provisional, the '345 Provisional, and/or the '807 Provisional incorporated by reference herein. For example, the valve can include an outer support frame and an (inner) flow control component that is mounted in and/or to the outer support frame. The outer support frame can include, for example, a supra-annular member or region, a subannular member or region, and a transannular member or region coupled therebetween. The flow control component is mounted to the outer support frame such that is extends through a portion of the transannular member or region, as described above. Moreover, the valve is compressible along a central axis parallel to a fluid flow direction through the valve and a lateral axis orthogonal and/or perpendicular to the central axis.

The control device can be any suitable control device, actuator, delivery and/or retrieval system, and/or the like. For example, in some implementations, the control device can include at least a control catheter having a first tether, a second tether, and a tension member extending therethrough, and a yoke coupled to a distal end of the control catheter. In some embodiments, the control device can be similar to and/or substantially the same as the control devices 970 and/or 1070 described in detail above.

The method 40 includes increasing a tension along the first tether and the second tether to secure the yoke against a surface of the prosthetic valve, at 41. As described above with reference to the control device 1070, the first tether and the second tether can be looped through a first portion and a second portion of the yoke, respectively, and a first attachment point and a second attachment point on the valve, respectively, to removably couple the yoke to the surface of the valve.

The valve is advanced through a lumen of a delivery catheter while the yoke is secured against the surface of the prosthetic valve, at 42. For example, in some implementations, a user and/or operator can exert a distally directed force on the control device and with the yoke secured against the surface of the valve, the control device can push the valve through the lumen of the delivery device (e.g., via a yoke-valve interface). In other implementations, the control device can include a pusher or the like that can extend through a portion of the valve to engage and/or contact a distal subannular anchoring element. As such, the distally directed force can be exerted on the distal subannular anchoring element, which in turn, can be operable to pull the valve through the lumen of the delivery catheter. In either implementation, when the valve reaches the distal end of the delivery catheter, valve is released from the distal end of the delivery catheter, at 43.

After releasing the valve, a tension along the tension member is increased to transition a proximal subannular anchoring element from a first configuration to a second configuration, at 44. For example, in some implementations, the arrangement of the control device and valve can be similar to and/or substantially the same as the arrangement described above with reference to the valves 600, 700, 800, and/or 1000. In some implementations, for example, the tension along the tension member can pull the proximal subannular anchoring element in a supra-annular direction toward the supra-annular region of the valve. In other implementations, the tension along the tension member can cause the proximal subannular anchoring element (or at least a portion thereof) to swing in one of an anterior direction or a posterior direction. As such, increasing the tension along the tension member can reduce reconfigure the proximal subannular anchoring element to, for example, reduce a perimeter of the subannular region of the valve.

The prosthetic valve is seated in an annulus of a native valve in response to a force exerted by the yoke on the surface of the prosthetic valve, at 45. For example, as described above, the yoke can be removably secured to a surface of the valve such that a distally directed force exerted on a proximal end of the control device results in the yoke exerting at least a portion of the distally directed force on the surface of the valve. In some implementations, a distal end of the control device can be steerable or the like such that at least a portion of the force exerted on the valve is in a subannular direction. In some implementations, the increasing the tension along the tension member can, for example, be operable to bow, bend, steer, deflect, and/or elastically (e.g., non-permanently) deform the distal end of the control device such that a distally directed force exerted along the control device results in the yoke exerting at least a portion of the force in the subannular direction, as described in detail above with reference to the control device 1070 shown in FIG. 34B.

The tension along the tension member is released to allow the proximal subannular anchoring element to transition from the second configuration toward the first configuration after the seating the prosthetic valve, at 46. For example, as described above with reference to the valves 600, 700, 800, and/or 1000, the proximal anchoring element can be configured to transition between the first configuration and the second configuration. The proximal anchoring element can be placed in the second configuration to reduce a perimeter of at least the subannular region of the valve as the valve is seated in the annulus. Once seated, the proximal anchoring element can be allowed to transition from the second configuration to the first configuration (e.g., an expanded configuration) to at least partially secure the valve in the annulus. In some instances, releasing the tension along the tension members can allow the proximal anchoring element to automatically transition from the second configuration to or toward the first configuration.

Once the valve is seated in the annulus, the control device is decoupled from the prosthetic valve, at 47. For example, as described above with reference to the valve 1000 and the control device 1070, the yoke can be releasably coupled to the valve via the tethers. The arrangement of the tethers can be such that pulling on one of a proximal end or a distal end of the tethers is operable to withdraw the tethers from the yoke and the attachment points of the valve. Thus, the yoke can be decoupled from the valve. Similarly, the tension member can be coupled to the proximal anchoring element in such a releasable manner. Accordingly, decoupling the control device from the valve can include releasing and withdrawing the tethers and the tension member. In addition, the guidewire catheter can be retracted from the valve. The control device can then be retracted through the delivery catheter while the valve remains seated in the annulus.

While various embodiments have been described above, it should be understood that they have been presented by way of example only, and not limitation. Likewise, it should be understood that the specific terminology used herein is for the purpose of describing particular embodiments and/or features or components thereof and is not intended to be limiting. Various modifications, changes, and/or variations in form and/or detail may be made without departing from the scope of the disclosure and/or without altering the function and/or advantages thereof unless expressly stated otherwise. Functionally equivalent embodiments, implementations, and/or methods, in addition to those enumerated herein, will be apparent to those skilled in the art from the foregoing descriptions and are intended to fall within the scope of the disclosure.

Where schematics, embodiments, and/or implementations described above indicate certain components arranged in certain orientations or positions, the arrangement of components may be modified. Although various embodiments have been described as having particular features and/or combinations of components, other embodiments are possible having a combination of any features and/or components from any of embodiments described herein, except mutually exclusive combinations. The embodiments described herein can include various combinations and/or sub-combinations of the functions, components, and/or features of the different embodiments described.

Where methods described above indicate certain events occurring in certain order, the ordering of certain events may be modified. Additionally, certain of the events may be performed concurrently in a parallel process when possible, as well as performed sequentially as described above. While methods have been described as having particular steps and/or combinations of steps, other methods are possible having a combination of any steps from any of methods described herein, except mutually exclusive combinations and/or unless the context clearly states otherwise.

What is claimed:

1. A method of using a control device to selectively control a side-deliverable transcatheter prosthetic valve during at least one of delivery and deployment, the control device including at least a control catheter and a yoke coupled to a distal end of the control catheter, the method comprising:

routing a distal end of a first tether through the control catheter, through a first side of the yoke, around a first attachment portion of an attachment tether on a supra-annular surface of the prosthetic valve, and back through the first side of the yoke and the control catheter such that each of a proximal end and the distal end of the first tether is proximal to a handle of the control device;

routing a distal end of a second tether through the control catheter, through a second side of the yoke, around a second attachment portion of the attachment tether, and back through the second side of the yoke and the control catheter such that each of a proximal end and the distal end of the second tether is proximal to the handle;

routing a distal end of a tension member through the control catheter, through a plurality of attachment points of a proximal subannular anchoring element, and back through the control catheter such that each of a proximal end and the distal end of the tension member is proximal to the handle;

increasing a tension along the first tether and the second tether to secure the yoke against the supra-annular surface of the prosthetic valve;

advancing the prosthetic valve through a lumen of a delivery catheter while the yoke is secured against the supra-annular surface of the prosthetic valve;

releasing the prosthetic valve from a distal end of the delivery catheter;

increasing a tension along the tension member to transition the proximal subannular anchoring element of the prosthetic valve from a first configuration to a second configuration after the releasing the prosthetic valve;

seating the prosthetic valve in an annulus of a native valve in response to a force exerted by the yoke on the supra-annular surface of the prosthetic valve;

releasing the tension along the tension member to allow the proximal subannular anchoring element to transition from the second configuration toward the first configuration after the seating the prosthetic valve; and decoupling the control device from the prosthetic valve.

2. The method of claim 1, wherein the advancing the prosthetic valve through the lumen of the delivery catheter includes pushing the prosthetic valve through the lumen of the delivery catheter in response to a distal force exerted by the yoke on the prosthetic valve while the yoke is secured against the supra-annular surface of the prosthetic valve.

3. The method of claim 1, wherein the advancing the prosthetic valve through the lumen of the delivery catheter includes advancing the prosthetic valve in a delivery configuration through the lumen of the delivery catheter such that a distal subannular anchoring element of the prosthetic valve is distal to a flow control component of the prosthetic valve.

4. The method of claim 1, wherein the control device further includes a guidewire catheter that extends through the control catheter, through the supra-annular surface of the prosthetic valve, and through a distal subannular anchoring element of the prosthetic valve.

5. The method of claim 4, wherein the guidewire catheter is disposable over a guidewire and has a stiffness greater than a stiffness of the guidewire, the stiffness of the guidewire catheter sufficient to limit the degrees of freedom associated with movement of the prosthetic valve during deployment.

6. The method of claim 5, wherein the guidewire catheter defines an axis, the seating the prosthetic valve in the annulus of the native valve includes the yoke exerting the force on the supra-annular surface of the prosthetic valve to move the prosthetic valve along the axis defined by the guidewire catheter or to rotate the prosthetic valve about the axis defined by the guidewire catheter.

7. The method of claim 1, wherein the increasing the tension along the tension member to transition the proximal subannular anchoring element from the first configuration to the second configuration is operable to bow a distal end of the control catheter in a supra-annular direction when the yoke is secured against the supra-annular surface of the prosthetic valve.

8. The method of claim 7, wherein the control catheter in a bowed configuration being oriented relative to the prosthetic valve such that a distally directed force exerted along the control catheter pushes a proximal end of the prosthetic valve in a subannular direction to seat at least the proximal end of the prosthetic valve in the annulus of the native valve.

9. The method of claim 1, wherein the increasing the tension along the tension member swings at least a portion of the proximal subannular anchoring element in at least one of a posterior direction or an anterior direction.

10. The method of claim 1, wherein:
the increasing the tension along the first tether and the second tether to secure the yoke against the surface of the prosthetic valve includes exerting a proximal force on each of the proximal end and the distal end of the first tether and each of the proximal end and the distal end of the second tether, and
the increasing the tension along the tension member to transition the proximal subannular anchoring element from the first configuration to the second configuration includes exerting a proximal force on each of the proximal end and the distal end of the tension member.

11. The method of claim 10, wherein the decoupling of the control device from the prosthetic valve includes:
exerting a proximal force on one of the proximal end or the distal end of the first tether to (i) release the first side of the yoke from the first portion of the attachment tether and (ii) withdraw the first tether from the first side of the yoke and at least a portion of the control catheter;
exerting a proximal force on one of the proximal end or the distal end of the second tether to (i) release the second side of the yoke from the second portion of the attachment tether and (ii) withdraw the second tether from the second side of the yoke and at least a portion of the control catheter; and
exerting a proximal force on one of the proximal end or the distal end of the tension member to withdraw the tension member from the plurality of attachment points of the proximal subannular anchoring element and at least a portion of the control catheter.

12. The method of claim 11, further comprising:
withdrawing the control device from the patient via the delivery catheter.

* * * * *